US012480140B2

(12) United States Patent
Baram et al.

(10) Patent No.: US 12,480,140 B2
(45) **Date of Patent: *Nov. 25, 2025**

(54) DIFFERENTIAL KNOCKOUT OF AN ALLELE OF A HETEROZYGOUS ELANE GENE

(71) Applicant: EMENDOBIO INC., Wilmington, DE (US)

(72) Inventors: David Baram, Tel Aviv (IL); Lior Izhar, Tel Aviv (IL); Asael Herman, Ness-Ziona (IL); Rafi Emmanuel, Ramla (IL); Michal Golan Mashiach, Ness-Ziona (IL); Joseph Georgeson, Rehovot (IL)

(73) Assignee: EMENDOBIO INC., Wilmington, DE (US)

( * ) Notice: Subject to any disclaimer, the term of this patent is extended or adjusted under 35 U.S.C. 154(b) by 958 days.

This patent is subject to a terminal disclaimer.

(21) Appl. No.: 17/053,629

(22) PCT Filed: May 6, 2019

(86) PCT No.: PCT/US2019/030874
§ 371 (c)(1),
(2) Date: Nov. 6, 2020

(87) PCT Pub. No.: WO2019/217294
PCT Pub. Date: Nov. 14, 2019

(65) Prior Publication Data

US 2021/0363547 A1 Nov. 25, 2021

Related U.S. Application Data

(60) Provisional application No. 62/743,309, filed on Oct. 9, 2018, provisional application No. 62/723,941, filed on Aug. 28, 2018, provisional application No. 62/667,536, filed on May 6, 2018.

(51) Int. Cl.
*A61K 35/28* (2015.01)
*C12N 9/22* (2006.01)
*C12N 15/11* (2006.01)
*C12N 15/90* (2006.01)
*C12Q 1/6883* (2018.01)

(52) U.S. Cl.
CPC ............ *C12N 15/907* (2013.01); *A61K 35/28* (2013.01); *C12N 9/22* (2013.01); *C12N 15/11* (2013.01); *C12Q 1/6883* (2013.01); *C12N 2310/20* (2017.05); *C12N 2800/80* (2013.01); *C12Q 2600/106* (2013.01)

(58) Field of Classification Search
None
See application file for complete search history.

(56) References Cited

U.S. PATENT DOCUMENTS

| | | | |
|---|---|---|---|
| 6,833,243 | B2 | 12/2004 | Rozen |
| 2011/0023143 | A1 | 1/2011 | Weinstein et al. |
| 2018/0155688 | A1 | 6/2018 | Seet et al. |
| 2019/0024086 | A1 | 1/2019 | Lande et al. |
| 2019/0255106 | A1 | 8/2019 | Lande |
| 2021/0130804 | A1 | 5/2021 | Baram |
| 2021/0155929 | A1 | 5/2021 | Baram |
| 2022/0387515 | A1 | 12/2022 | Baram |

FOREIGN PATENT DOCUMENTS

| | | | |
|---|---|---|---|
| WO | WO 2016/210292 | A1 | 12/2016 |
| WO | WO 2017/004616 | A1 | 1/2017 |
| WO | WO 2018/049073 | A1 | 3/2018 |

(Continued)

OTHER PUBLICATIONS

Nayak RC et al. J Clin Invest. Aug. 3, 2015;125(8):3103-16 (Year: 2015).*

NCBI XM_007731395.1 (NCBI BLAST database, Accession No. XM_007731395.1, published Dec. 22, 2014) (Year: 2014).*

Li D et al. Cell Biol Toxicol. Oct. 2019;35(5):403-406 (Year: 2019).*

(Continued)

*Primary Examiner* — Kimberly Chong
*Assistant Examiner* — Douglas Charles Ryan
(74) *Attorney, Agent, or Firm* — Potomac Law Group, PLLC; Jamaica Potts Szeliga

(57) ABSTRACT

Methods for inactivating in a cell a mutant allele of the elastase, neutrophil expressed gene (ELANE gene) gene having a mutation associated with severe congenital neutropenia (SCN) or cyclic neutropenia (CyN) and which cell is heterozygous at one or more polymorphic sites selected from the group consisting of: rs10414837, rs3761005, rs1683564, rs9749274, rs740021, rs201048029, rs199720952, rs28591229, rs71335276, rs58082177, rs3826946, rs10413889, rs761481944, rs3761008, rs10409474, rs3761007, rs17216649, rs10469327, rs8107095, rs10424470 and rs78302854, the method comprising introducing to the cell a composition comprising:
a CRISPR nuclease or a sequence encoding the CRISPR nuclease; and
a first RNA molecule comprising a guide sequence portion having 17-20 nucleotides,
wherein a complex of the CRISPR nuclease and the first RNA molecule affects a double strand break in the mutant allele of the ELANE gene
the method optionally further comprising introduction of a second RNA molecule comprising a guide sequence portion capable of complexing with a CRISPR nuclease, wherein the complex of the second RNA molecule and CRISPR nuclease affects a second double strand break in the ELANE gene.

12 Claims, 5 Drawing Sheets

Specification includes a Sequence Listing.

(56) References Cited

FOREIGN PATENT DOCUMENTS

| | | | |
|---|---|---|---|
| WO | WO 2018/085460 | A2 | 5/2018 |
| WO | WO 2019/217294 | A1 | 11/2019 |
| WO | WO 2020/112979 | A2 | 6/2020 |
| WO | WO 2023/281083 | A1 | 1/2023 |

OTHER PUBLICATIONS

Shu et al. Pediatr Infect Dis J. Feb. 2015;34(2):203-7 (Year: 2015).*
International Search Report issued Oct. 11, 2020 in connection with PCT International Application No. PCT/US2019/030874.
Kurnikova, M. et al. "Four novel ELANE mutations in patients with congenital neutropenia," Pediatric Blood & Cancer, Aug. 2011, vol. 57, No. 2, pp. 332-335.
Nayak, R. C. et al. "Pathogenesis of ELANE-mutant severe neutropenia revealed by induced pluripotent stem cells," Journal of Clinical Investigation, Jul. 20, 2015, vol. 125, No. 8, pp. 3103-3116.
Rs10414837, Reference SNP (rs) Report, Dec. 5, 2003.
Written Opinion (form PCT/ISA/237) issued Oct. 11, 2020 in connection with PCT International Application No. PCT/US2019/030874.
Blood, (2017), vol. 130, Supplement 1,p. 542.
Dewitt, Mark et al., "Selection-free genome editing of sickle mutation in human adult hematoietic stem/progenitor cells", Science Translational Medicine, 8, 2016.
Human Molecular Genetics, (2016), vol. 25, No. 20, pp. 4566-4576.
International Search Report issued Mar. 31, 2021 in connection with PCT International Application No. PCT/US2020/059186.
Written Opinion (form PCT/ISA/237) issued Mar. 31, 2021 in connection with PCT International Application No. PCT/US2020/059186.
Arun et al., "Spectrum of ELANE mutations in congenital neutropenia: a single-centre study in patients of Indian origin." Journal of Clinical Pathology, Aug. 31, 2018, vol. 71, iss. 12, pp. 1046-1051.
Extended European Search Report issued Feb. 21, 2022 in connection with European Application No. 19800445.9.
Nayak, Ramesh C. et al. "Pathogenesis of ELANE-mutant severe neutropenia revealed by induced pluripotent stem cells," Journal of Clinical Investigation, 2015, 125(8):3103-3116.
Dewitt, Mark A. et al. "Selection-free genome editing of the sickle mutation in human adult hematopoietic stem/progenitor cells," Science Translational Medicine, 2016, 8, 360ra134.
Ngoc Tung Tran, et al. "CRISPR-Cas9-Mediated ELANE Mutation Correction in Hematopoietic Stem and Progenitor Cells to Treat Severe Congenital Neutropenia," Molecular Therapy, 2020, vol. 28, No. 12, 2621-2634.
Nasri, Masoud et al. "Establishment of the Safe and Efficient CRISPR/Cas9-RNP Based Gene-Correction Platform of ELANE Mutations in iPSCs of Severe Congenital Neutropenia (CN) Patients with No Response to G-CSF and High Risk to Develop Leukemia," Blood, 2017, 130 (Supplement 1): 542.
Japanese Office Action issued Apr. 4, 2023 in connection with Japanese Application No. 2020-563637, including a concise English language explanation provided in the accompanying transmittal filed herewith.
International Preliminary Report on Patentability issued Nov. 10, 2020, including Written Opinion of the International Searching Authority issued Oct. 11, 2019, in connection with PCT International Application No. PCT/US2019/030874.
Matsushita, H. et al. "A Family of Severe Congenital Neutropenia with −199C to A Substitution in ELA2 Promoter." Am J Hematol. vol. 81, No. 12, pp. 985-986 (2006).
Office Action issued Aug. 22, 2023 in connection Japanese Patent Application No. 2020-563637, including an English-language translation.
Shin, Jun Wan, et al. "Permanent inactivation of Huntington's disease mutation by personalized allele-specific CRISPR/Cas9." Human Molecular Genetics, (2016) vol. 25, No. 20: 4566-4576.

* cited by examiner

| RSID | Heterozygous Frequency |
| --- | --- |
| rs10414837 | 33% |
| rs3761005 | 46% |
| rs1683564 | 42% |

DIFFERENTIAL KNOCKOUT OF AN ALLELE OF A HETEROZYGOUS ELANE GENE

CROSS-REFERENCE TO RELATED APPLICATIONS

This application is a § 371 national stage of PCT International Application No. PCT/US2019/03074, filed May 6, 2019, claiming the benefit of U.S. Provisional Application No. 62/743,309, filed Oct. 9, 2018, U.S. Provisional Application No. 62/723,941, filed Aug. 28, 2018, and U.S. Provisional Application No. 62/667,536, filed May 6, 2018 the contents of each of which are hereby incorporated by reference.

Throughout this application, various publications are referenced, including referenced in parenthesis. The disclosures of all publications mentioned in this application in their entireties are hereby incorporated by reference into this application in order to provide additional description of the art to which this invention pertains and of the features in the art which can be employed with this invention.

REFERENCE TO SEQUENCE LISTING

This application incorporates-by-reference nucleotide and/or amino acid sequences which are present in the file named "201106_90522-A-PCT_US_Substitute_Sequence_Listing_LMO.txt", which is 208,892 bytes in size, and which was created on Oct. 22, 2020 in the IBM-PC machine format, having an operating system compatibility with MS-Windows, which is contained in the text file filed Nov. 6, 2020 as part of this application.

BACKGROUND OF INVENTION

There are several classes of DNA variation in the human genome, including insertions and deletions, differences in the copy number of repeated sequences, and single nucleotide polymorphisms (SNPs). A SNP is a DNA sequence variation occurring when a single nucleotide (adenine (A), thymine (T), cytosine (C), or guanine (G)) in the genome differs between human subjects or paired chromosomes in an individual. Over the years, the different types of DNA variations have been the focus of the research community either as markers in studies to pinpoint traits or disease causation or as potential causes of genetic disorders. SNPs are usually considered benign and not causing disease.

A genetic disorder is caused by one or more abnormalities in the genome. Genetic disorders may be regarded as either "dominant" or "recessive." Recessive genetic disorders are those which require two copies (i.e., two alleles) of the abnormal/defective gene to be present. In contrast, a dominant genetic disorder involves a gene or genes which exhibit(s) dominance over a normal (functional/healthy) gene or genes. As such, in dominant genetic disorders only a single copy (i.e., allele) of an abnormal gene is required to cause or contribute to the symptoms of a particular genetic disorder. Such mutations include, for example, gain-of-function mutations in which the altered gene product possesses a new molecular function or a new pattern of gene expression. Gain-of-function mutations are generally dominant negative mutations. An example of a dominant negative mutation is haploinsufficiency where one allele is mutated and loses its function and the single wild type allele left does not generate enough protein to be sufficient for a specific cellular function. Other examples include dominant negative mutations which have a gene product that acts antagonistically to the wild-type allele.

Neutropenia

Neutropenia is defined as a reduction in the absolute number of neutrophils in the blood circulation and commonly diagnosed by measuring the absolute neutrophil count (ANC) in peripheral blood. The severity of neutropenia is characterized as mild with an ANC of 1000-1500/μL, moderate with an ANC of 500-1000/μL, or severe with an ANC of less than 500/sL (Boxer 2012).

Neutropenia can be classified as congenital (hereditary) or acquired. The two main types of the congenital condition, commonly of autosomal dominant inheritance, are cyclic neutropenia (CyN) and severe congenital neutropenia (SCN). Cyclic neutropenia is characterized by fluctuating neutrophil counts from normal levels to zero while severe congenital neutropenia (SCN) is characterized by very low ANC (500/μL) observed at birth, maturation arrest of the myelopoiesis in bone marrow at the promyelocyte/myelocyte stage, and early onset of bacterial infections (Carlsson et al. 2012; Horwitz et al. 2013).

SCN may be diagnosed by measuring a very low ANC in the blood and examining bone marrow aspirate to identify myeloid maturation arrest (Dale 2017). SCN is usually diagnosed before age 6 months, while diagnosis for CyN is generally raised during the second year of life, or later, and the main clinical manifestation is recurrent acute stomatologic disorders. Bone marrow examination is often necessary to rule out malignant hemopathies, determine cellularity, assess myeloid maturation, and detect signs of a precise etiology, with cytogenetic bone marrow studies now crucial when SCN is suspected. Antineutrophil antibody assay, immunoglobulin assay (Ig GAM), lymphocyte immunophenotyping, pancreatic markers (serum trypsinogen and fecal elastase) and liposoluble vitamin levels (vitamins A, E and D) are also of interest in assessing SCN and CyN (See Donadieu 2011).

SCN can be autosomal-recessive (HAX1, G6PC3), autosomal-dominant (ELANE, GFI1), or X-linked (WAS) forms of inheritance or occur sporadically (Carlsson et al. 2012; Boxer 2012).

Cyclic and congenital neutropenia are most frequently caused by mutations in the "elastase, neutrophil expressed gene" (ELANE gene)—the gene for neutrophil elastase. "ELANE gene mutations are identified in 40-55% of SCN patients and males and females are equally affected (Donadieu et al. 2011; Dale 2017). Mutations in the ELANE gene are associated with autosomal-dominant and sporadic cases of SCN (Carlsson et al. 2012). To date, more than 200 different ELANE mutations have been identified, which are randomly distributed over all exons as well as in intron 3 and intron 4 (Skokowa et al. 2017). More than 120 distinct ELANE gene mutations related to CyN and SCN are now known, for example C151 Y and G214R particularly associated with a poor prognosis. (See Makaryan et al. 2012; see also Germeshausen et al. 2013 for a comprehensive list of ELANE mutations related to CyN and SCN).

ELANE encodes neutrophil elastase (NE) which is involved in the function of neutrophil extracellular traps (networks of fibers that bind pathogens). Some studies suggest that the product of mutant ELANE acts to disrupt neutrophil production in the bone marrow and cause neutropenia. These studies indicate that mutations in NE initiate the unfolded protein response (UPR) leading to cell loss in the process of neutrophil formation in the marrow (Makaryan et al. 2017).

Current Treatments

Granulocyte colony-stimulating factor (G-CSF) is considered the first-line treatment for SCN (Connelly, Choi, and Levine 2012). G-CSF stimulates the production of more neutrophils and delays their apoptosis (Schdffer and Klein 2007). Overall survival is now estimated to exceed 80%, including patients developing malignancies, although 10% of SCN patients still die from severe bacterial infections or sepsis (Skokowa et al. 2017). Although G-CSF therapy is successful in preventing mortality from sepsis, long-term treatment was identified to be associated with an increased risk of developing myelodysplastic syndrome (MDS) or leukemia in SCN patients. The most common leukemia in SCN is AML, but acute lymphoid leukemia (ALL), juvenile myelomonocytic leukemia (JMML), chronic myelomonocytic leukemia (CMML), and bi-phenotypic leukemia are also reported in the literature (Connelly, Choi, and Levine 2012). It was previously demonstrated that patients who had a robust response to G-CSF (doses≤8 μg/kg/day) had a cumulative incidence of 15% for developing MDS/leukemia after 15 years on G-CSF, while an incidence of 34% was reported in patients with poor response to G-CSF despite high doses (Rosenberg et al. 2010).

Hematopoietic stem cell transplant (HSCT) is an alternative, curative therapy for patients who do not respond to G-CSF therapy or who develop AMI-MDS. However, patients with chronic neutropenia who undergo HCT are at increased risk of developing infectious complications such as fungal and graft-versus-host disease (Skokowa et al. 2017). Moreover, HCT requires a matched related donor for successful survival but most patients will not have an available matched donor (Connelly, Choi, and Levine 2012).

SUMMARY OF THE INVENTION

Disclosed is an approach for knocking out the expression of a dominant-mutant allele by disrupting the dominant-mutant allele or degrading the resulting mRNA.

The present disclosure provides a method for utilizing at least one naturally occurring heterozygous nucleotide difference or polymorphism (e.g., single nucleotide polymorphism (SNP)) for distinguishing/discriminating between two alleles of a gene, one allele bearing a mutation such that it encodes a mutated protein causing a disease phenotype ("mutant allele"), and the other allele encoding for a functional protein ("functional allele").

Embodiments of the present invention provide methods for utilizing at least one heterozygous SNP in a gene expressing a dominant mutant allele in a given cell or subject. In embodiments of the present invention, the SNP utilized may or may not be associated with a discase phenotype. In embodiments of the present invention, an RNA molecule comprising a guide sequence targets the mutant allele of the gene by targeting the nucleotide base present at a heterozygous SNP in the mutant allele of the gene and therefore having a different nucleotide base from the functional allele of the gene.

In some embodiments, the method further comprises the step of knocking out expression of the mutated protein and allowing expression of the functional protein.

The present invention provides a method for inactivating in a cell a mutant allele of the elastase, neutrophil expressed gene (ELANE gene) gene having a mutation associated with severe congenital neutropenia (SCN) or cyclic neutropenia (CyN) and which cell is heterozygous at one or more polymorphic sites selected from the group consisting of: rs10414837, rs3761005, rs1683564, rs9749274, rs740021, rs201048029, rs199720952, rs28591229, rs71335276, rs58082177, rs3826946, rsI0413889, rs761481944, rs3761008, rs10409474, rs3761007, rs17216649, rs10469327, rs8107095, rs10424470 and rs78302854, the method comprising introducing to the cell a composition comprising:

a CRISPR nuclease or a sequence encoding the CRISPR nuclease; and a first RNA molecule comprising a guide sequence portion having 17-20 nucleotides, wherein a complex of the CRISPR nuclease and the first RNA molecule affects a double strand break in the mutant allele of the ELANE gene.

The present invention provides for a modified cell obtained by the methods of the present invention.

The present invention provides for a modified cell lacking at least a portion of one allele of the ELANE gene.

The present invention provides for a composition comprising modified cells and a pharmaceutically acceptable carrier.

The present invention provides for an in vitro or ex vivo method of preparing a composition, comprising mixing the cells of the present invention with the pharmaceutically acceptable carrier.

The present invention provides for a method of preparing in vitro or ex vivo a composition comprising modified cells, the method comprising:

a) isolating HSPCs from cells obtained from a subject with an ELANE gene mutation related to SCN or CyN and/or suffering from SCN or CyN and which subject is heterozygous at one or more polymorphic sites selected from the group consisting of: rs10414837, rs3761005, rs1683564, rs9749274, rs740021, rs201048029, rs199720952, rs28591229, rs71335276, rs58082177, rs3826946, rs10413889, rs761481944, rs3761008, rs10409474, rs3761007, rs17216649, rs10469327, rs8107095, rs10424470 and rs78302854, and obtaining the cell from the subject;

b) introducing to the cells of step (a) a composition comprising:

a CRISPR nuclease or a sequence encoding the CRISPR nuclease; and a first RNA molecule comprising a guide sequence portion having 17-20 nucleotides, wherein a complex of the CRISPR nuclease and the first RNA molecule affects a double strand break in the mutant allele of the ELANE gene in one or more cells, optionally, introducing to the cells a second RNA molecule comprising a guide sequence portion capable of complexing with a CRISPR nuclease, wherein the complex of the second RNA molecule and CRISPR nuclease affects a second double strand break in the ELANE gene in the one or more cells so as to inactive the mutant allele of the ELANE gene in one or more cells thereby obtaining modified cells; optionally c) culture expanding the modified cells of step (b), wherein the modified cells are capable of engraftnent and giving rise to progeny cells after engraftnent.

The present invention provides for use of a composition prepared in vitro by a method comprising:

a) isolating HSPCs from cells obtained from a subject with an ELANE gene mutation related to SCN or CyN and/or suffering from SCN or CyN and which subject is heterozygous at one or more polymorphic sites selected from the group consisting of: rs10414837, rs3761005, rs1683564, rs9749274, rs740021, rs201048029, rs199720952, rs28591229, rs71335276, rs58082177, rs3826946, rs10413889, rs761481944, rs3761008, rs10409474, rs3761007, rs17216649, rs10469327, rs8107095, rs10424470 and rs78302854;

b) introducing to the cells of step (a) a composition comprising:

a CRISPR nuclease or a sequence encoding the CRISPR nuclease; and a first RNA molecule comprising a guide sequence portion having 17-20 nucleotides, wherein a complex of the CRISPR nuclease and the first RNA molecule affects a double strand break in the mutant allele of the ELANE gene in one or more cells, optionally, introducing to the cells a second RNA molecule comprising a guide sequence portion capable of complexing with a CRISPR nuclease, wherein the complex of the second RNA molecule and CRISPR nuclease affects a second double strand break in the ELANE gene in the one or more cells so as to inactive the mutant allele of the ELANE gene in one or more cells thereby obtaining modified cells; optionally;

c) culture expanding the cells of step (b) wherein the modified cells are capable of engraftment and giving rise to progeny cells after engraftment; and d) administering to the subject the cells of step (b) or step (c)

for treating the SCN or CyN in the subject.

The present invention provides for a method of treating a subject afflicted with SCN or CyN, comprising administration of a therapeutically effective amount of the modified cells, compositions, or the compositions prepared by the methods of the instant invention The present invention provides for a method for treating SCN or CyN in a subject with an ELANE gene mutation relating to SCN or CYN in need thereof and which subject is heterozygous at one or more polymorphic sites selected from the group consisting of: rs10414837, rs3761005, rs1683564, rs9749274, rs740021, rs201048029, rs199720952, rs28591229, rs71335276, rs58082177, rs3826946, rs10413889, rs761481944, rs3761008, rs10409474, rs3761007, rs17216649, rs10469327, rs8107095, rs10424470 and rs78302854, the method comprising:

a) isolating HSPCs from cells obtained from the subject;

b) introducing to the cells of step (a) a composition comprising:

a CRISPR nuclease or a sequence encoding the CRISPR nuclease; and a first RNA molecule comprising a guide sequence portion having 17-20 nucleotides, wherein a complex of the CRISPR nuclease and the first RNA molecule affects a double strand break in the mutant allele of the ELANE gene in one or more cells, optionally, introducing to the cells a second RNA molecule comprising a guide sequence portion capable of complexing with a CRISPR nuclease, wherein the complex of the second RNA molecule and CRISPR nuclease affects a second double strand break in the ELANE gene in the one or more cells so as to inactive the mutant allele of the ELANE gene in one or more cells thereby obtaining modified cells; optionally;

c) culture expanding the cells of step (b) wherein the modified cells are capable of engraftment and giving rise to progeny cells after engraftment; and d) administering to the subject the cells of step (b) or step (c) thereby treating the SCN or CyN in the subject.

The present invention provides for a method for treating SCN or CyN in a subject with an ELANE gene mutation relating to SCN or CYN in need thereof and which subject is heterozygous at one or more polymorphic sites selected from the group consisting of: rs10414837, rs3761005, rs1683564, rs9749274, rs740021, rs201048029, rs199720952, rs28591229, rs71335276, rs58082177, rs3826946, rs10413889, rs761481944, rs3761008, rs10409474, rs3761007, rs17216649, rs10469327, rs8107095, rs10424470 and rs78302854, the method comprising administering to the subject autologous modified cells or progeny of autologous modified cells, wherein the autologous modified cells are modified so as to have a double strand break in the mutant allele of the ELANE gene, wherein said double strand break results from introduction to the cells of a composition comprising a CRISPR nuclease or a sequence encoding the CRISPR nuclease and a first RNA molecule wherein a complex of the CRISPR nuclease and the first RNA molecule affects a double strand break in the mutant allele of the ELANE gene so as to inactive the mutant allele of the ELANE gene in the cell, thereby treating the SCN or CyN in the subject.

The present invention provides for a method of selecting a subject for treatment from a pool of subjects diagnosed with SCN or CyN, comprising the steps of:

a) obtaining cells from each subject in the pool of subjects;

b) screening each subject's cells for an ELANE gene mutation related to SCN or CyN, and selecting only subjects with an ELANE gene mutation related to SCN or CyN;

c) screening by sequencing the cells of the subjects selected in step (b) for heterozygosity at one or more polymorphic sites selected from the group consisting of: rs10414837, rs3761005, rs1683564, and d) selecting for treatment only subjects with cells heterozygous at the one of more polymorphic sites.

Embodiments of the present invention further comprise treating SCN or CyN in a selected subject, comprising:

e) obtaining hematopoetic stein and progenitor cells (HSPC) cells from the bone marrow of the subject either by aspiration or by mobilization and apheresis of peripheral blood;

f) introducing to the HSPC cells of step (e):

one or more CRISPR nucleases or sequences encoding the one or more CRISPR nuclease;

a first RNA molecule comprising a guide sequence portion having 17-20 nucleotides in a sequence of 17-20 contiguous nucleotides set forth in any one of SEQ ID NOs: 1-1192 targeting the nucleotide base of the heterozygous allele of the one or more polymorphic sites present on the mutant allele of the ELANE gene, and a second RNA molecule comprising a guide sequence portion targeting a sequence in intron 3, intron 4 or 3' UTR of the ELANE gene, wherein a complex of the first RNA molecule and a CRISPR nuclease affects a first double strand break in the mutant allele of the ELANE gene in one or more of the HSPC cells and a complex of the second RNA molecule and a CRISPR nuclease affect a second double strand break in intron 3, intron 4, or 3' U' TR of both alleles of the ELANE gene in the one or more HSPC cells in which the complex of the first RNA molecule and the CRISPR nuclease affected a first double strand break, thereby obtaining modified cells;

g) administering to the subject the modified cells of step (f), thereby treating SCN or CyN in the subject.

The present invention provides an RNA molecule comprising a guide sequence portion having 17-20 nucleotides in the sequence of 17-20 contiguous nucleotides set forth in any one of SEQ ID NOs: 1-1192.

The present invention provides a method for inactivating in a cell a mutant ELANE allele, the method comprising delivering to the cell the RNA molecules or compositions of the present invention.

The present invention provides use of the RNA molecules, the compositions, or the composition prepared by the method of the present invention for inactivating in a cell a mutant ELANE allele.

The present invention provides a medicament comprising the RNA molecules, compositions, or the compositions prepared by the methods of the instant invention for use in inactivating in a cell a mutant ELANE allele, wherein the medicament is administered by dclivcring to the cell the RNA molecules, compositions, or the compositions prepared by the methods of the instant invention.

The present invention provides for use of the methods, the modified cells, the compositions, or the compositions prepared by the methods, or the RNA molecules of the instant invention for treating ameliorating or preventing SCN or CyN in to a subject having or at risk of having SCN or CyN.

The present invention provides for a medicament comprising the RNA molecules, compositions, compositions prepared by the methods of the instant invention, or the modified cells of the instant invention, for use in treating ameliorating or preventing SCN or CyN, wherein the medicament is administered by delivering to a subject having or at risk of having SCN or CyN the RNA molecules, compositions, compositions prepared by the methods of the instant invention, or the modified cells of the instant invention.

The present invention provides for a kit for inactivating a mutant ELANE allele in a cell, comprising the RNA molecules of the instant invention, a CRISPR nuclease or a sequence encoding the CRISPR nuclease, and/or a tracrRNA molecule or a sequence encoding the tracrRNA; and instructions for delivering the RNA molecule; CRISPR nuclease or sequence encoding the CRISPR nuclease, and/or tracrRNA molecule or sequence encoding the tracrRNA to the cell to inactivate the mutant ELANE allele in the cell.

The present invention provides for a kit for treating SCN or CyN in a subject, comprising the RNA molecules of the instant invention, a CRISPR nuclease or sequence encoding the CRISPR nuclease, and/or a tracrRNA molecule or sequence encoding the tracrRNA molecule; and instructions for delivering the RNA molecule; CRISPR nuclease, and/or the tracrRNA to a subject having or at risk of having SCN or CyN so as to treat the SCN or CyN.

The present invention provides a kit for inactivating a mutant ELANE allele in a cell, comprising the compositions, the composition prepared by the methods of the instant invention, or the modified cells of the instant invention, and instructions for delivering the composition to the cell so as to inactivate the ELANE gene in the cell.

The present invention provides a kit for treating SCN or CyN in a subject, comprising the composition, the compositions prepared by the methods of the instant invention, or the modified cells of the instant invention, and instructions for delivering the compositions, the compositions prepared by the methods of the instant invention, or the modified cells of the instant invention, to a subject having or at risk of having SCN or CyN so as to treat SCN or CyN.

DETAILED DESCRIPTION

Figure 1:
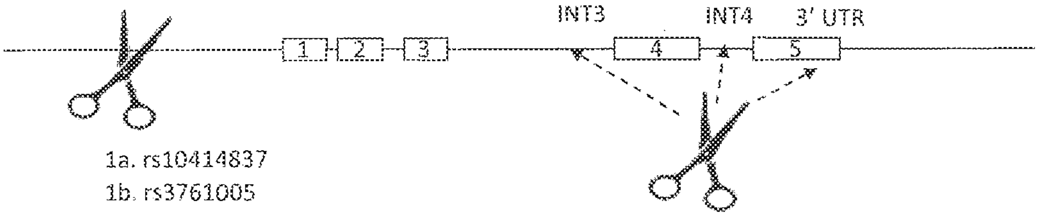
FIG. 1: excising the promoter region from an upstream SNP position until intron 3 or intron 4 or the 3' UTR. In one example, a first guide sequence targets a specific sequence of a heterozygous SNP position in an upstream region of the mutant allele (strategy 1a-rs10414837, strategy 1b-rs3761005) and a second guide sequence targets a sequence in intron 4 which is common to two alleles of the gene.

Embodiments of the present invention provide a method for inactivating in a cell a mutant allele of the elastase, neutrophil expressed gene (ELANE gene) gene having a mutation associated with severe congenital neutropenia (SCN) or cyclic neutropenia (CyN) and which cell is heterozygous at one or more polymorphic sites selected from the group consisting of: rs10414837, rs3761005, rs1683564, rs9749274. rs740021, rs201048029, rs199720952, rs28591229, rs71335276, rs58082177, rs3826946, rs10413889, rs761481944, rs3761008, rs10409474, rs3761007, rs17216649, rs10469327, rs8107095, rs10424470 and rs78302854, the method comprising introducing to the cell a composition comprising:

- a CRISPR nuclease or a sequence encoding the CRISPR nuclease; and
- a first RNA molecule comprising a guide sequence portion having 17-20 nucleotides, wherein a complex of the CRISPR nuclease and the first RNA molecule affects a double strand break in the mutant allele of the ELANE gene.

In embodiments of the present invention, the CRISPR nuclease and the first RNA molecule affects a double strand break in the mutant allele of the ELANE gene, which mutant allele is targeted for the double strand break based on the one or more polymorphic sites.

In embodiments of the present invention, the CRISPR nuclease and the first RNA molecule affects a double strand break in the mutant allele of the ELANE gene, which mutant allele is targeted for the double strand break based on a sequence of the mutant allele at the one or more polymorphic sites.

In embodiments of the present invention, the CRISPR nuclease and the first RNA molecule affects a double strand break in the mutant allele of the ELANE based on the nucleotide base of the one or more polymorphic sites present on the mutant allele of the ELANE gene.

Embodiments of the present invention further comprise introduction of a second RNA molecule comprising a guide sequence portion capable of complexing with a CRISPR nuclease, wherein the complex of the second RNA molecule and CRISPR nuclease affects a second double strand break in the ELANE gene.

In embodiments of the present invention, a composition may comprise 1, 2, 3 or more CRISPR nucleases or sequencing encoding the CRISPR nucleases. In ebodiments of the present invention, introducing a composition to the cell may comprise introducing 1, 2, 3, or more compositions to the cell. In embodiments of the present invention, each composition may comprise a different CRISPR nuclease or sequence encoding the CRISPR nucleases or the same CRISPR nuclease or sequence encoding the CRISPR nuclease. In embodiments of the present invention involving two RNA molecules, the second RNA molecule may form a complex with the same CRISPR nuclease as the first RNA molecule, or may form a complex with another CRISPR nuclease.

In embodiments of the present invention, the second double strand break is within a non-coding region of the ELANE gene. In embodiments of the present invention, the non-coding region of the ELANE gene is selected an intron or an untranslated region (UTR). In embodiments of the present invention, the non-coding region is in intron 3 or intron 4. In an embodiments of the present invention the UTR is the 3'UTR.

In embodiments of the present invention, the guide sequence portion of the first RNA molecule comprises 17-20 contiguous nucleotides as set forth in any one of SEQ ID NOs: 1-1192.

According to embodiments of the present invention, the guide sequence portion of the second RNA molecule comprises 17-20 nucleotides in the sequence of 17-20 contiguous nucleotides set forth in any one of SEQ ID NOs: 1-1192, or any one of SEQ ID NOs 1193-2000.

In embodiments of the present invention, the second double strand break is within a non-coding region of the ELANE gene.

In embodiments of the present invention, the cell is heterozygous at rs10414837 or rs3761005 and the complex of the second RNA molecule and CRISPR nuclease affects a double strand break in intron 4 of the ELANE gene.

In embodiments of the present invention, the cell is heterozygous at rs10414837 or rs3761005 and the complex of the second RNA molecule and CRISPR nuclease affects a double strand break in intron 3 of the ELANE gene.

In embodiments of the present invention, the cell is heterozygous at rs10414837 or rs3761005 and the complex of the second RNA molecule and CRISPR nuclease affects a double strand break in the 3' UTR region of the ELANE gene.

In embodiments of the present invention, the cell is heterozygous at rs1683564 and the complex of the second RNA molecule and CRISPR nuclease affects a double strand break in intron 4 of the ELANE gene.

In embodiments of the present invention, the cell is heterozygous at rs1683564 and the complex of the second RNA molecule and CRISPR nuclease affects a double strand break in intron 3 of the ELANE gene.

In embodiments of the present invention, the cell is heterozygous at rs1683564 and the complex of the second RNA molecule and CRISPR nuclease affects a double strand break in the 3' UTR region of the ELANE gene.

In some embodiments, the cell is heterozygous at the polymorphic sites in the ELANE rs10414837, and a complex of a first RNA molecule comprising a guide sequence portion having 17-20 nucleotides and a CRISPR nuclease affects a double strand break in the mutant allele of the ELANE gene and not in the functional allele of the ELANE gene. In such embodiments the guide sequence portion of the first RNA molecule comprises having 17-20 nucleotides may comprise a sequence of 17-20 contiguous nucleotides as set forth in any one of SEQ ID NOs: 82, 86, 93, 94, 115, 119,135, 173, 180, 213, 215, 224, 225, 262, 263, 307, 308.319, 323, 351, 352, 374, 461, 462, 466, 467, 474, 477, 478, 491, 504, 505, 533, 537, 538, 550, 556, 569, 570, 583, 584, 684, 685, 714, 745, 790, 791, 845, 846, 854, 857, 858, 861, 863, 864, 880, 881, 886, 890, 891, 901, 911, 912, 936, 937, 939, 940, 960, 961, 972, 978, 979, 983, 984, 1018, 1034, 1035, 1040, 1086, 1110, 1111, 1135, 1144, and 1145.

In some embodiments, the cell is heterozygous at the polymorphic sites in the ELANE rs3761005, and a complex of a first RNA molecule comprising a guide sequence portion having 17-20 nucleotides and a CRISPR nuclease affects a double strand break in the mutant allele of the ELANE gene and not in the functional allele of the ELANE gene. In such embodiments the guide sequence portion of the first RNA molecule comprises having 17-20 nucleotides may comprise a sequence of 17-20 contiguous nucleotides as set forth in any one of SEQ ID NOs: 26, 57, 65, 66, 70, 187, 188, 191, 206, 220, 221, 243, 245, 261, 275, 356, 357, 392, 417, 418, 431, 441, 442, 447, 488, 513, 514, 545, 546, 548, 598, 599, 604, 607, 608, 612, 613, 639, 648, 658, 659, 660, 680, 681, 742, 743, 755, 756, 759, 762,763, 767, 771, 772, 773, 786, 787, 815, 816, 818, 819, 820, 831, 836, 849, 850, 870, 871, 898, 899, 907, 908, 1009, 1010, 1013, 1023, 1029, 1030, 1082, 1083, 1093, 1099, 1100, 1101, 1107, 1108, and 1182.

In some embodiments, the cell is heterozygous at the polymorphic sites in the ELANE rs1683564, and a complex of a first RNA molecule comprising a guide sequence portion having 17-20 nucleotides and a CRISPR nuclease affects a double strand break in the mutant allele of the ELANE gene and not in the functional allele of the ELANE gene. In such embodiments the guide sequence portion of the first RNA molecule comprises having 17-20 nucleotides may comprise a sequence of 17-20 contiguous nucleotides as set forth in any one of SEQ ID NOs: 52, 87, 122, 164, 175, 199, 214, 290, 326, 345, 346, 373, 404,412, 436, 437, 451, 452, 483, 484, 517, 520, 525, 617, 618, 621, 641, 661, 676, 722, 736, 806, 855, 856, 878, 879, 888, 889, 896, 903, 905, 913, 914, 929, 933, 934, 935, 982, 998, 1021, 1022, 1026, 1046, 1047, 1053, 1097, 1121, 1122, 1124, 1126, 1127, 1131, 1134, 1175, 1176, 1183, and 1190.

Embodiments of the present invention comprise obtaining the cell with an ELANE gene mutation associated with severe congenital neutropenia (SCN) or CyN from a subject with an ELANE gene mutation related to SCN or CyN and/or suffering from SCN or CyN and which subject is heterozygous at one or more polymorphic sites selected from the group consisting of: rs10414837, rs3761005, rs1683564, rs9749274, rs740021, rs201048029, rs199720952, rs28591229, rs71335276, rs58082177, rs3826946, rs10413889, rs761481944, rs3761008, rs10409474, rs3761007, rs17216649, rs10469327, rs8107095, rs10424470 and rs78302854.

Embodiments of the present invention comprise first selecting a subject with an ELANE gene mutation related to SCN or CyN and/or suffering from SCN or CyN and which subject is heterozygous at one or more polymorphic sites selected from the group consisting of: rs10414837, rs3761005, rs1683564, rs9749274, rs740021, rs201048029, rs199720952, rs28591229, rs71335276, rs58082177, rs3826946, rs10413889, rs761481944, rs3761008, rs10409474, rs3761007, rs17216649, rs10469327, rs8107095, rs10424470 and rs78302854, and obtaining the cell from the subject.

Embodiments of the present invention comprise obtaining the cell from the subject by mobilization and/or by apheresis.

Embodiments of the present invention comprise obtaining the cell from the subject by bone marrow aspiration.

In embodiments of the present invention, the cell is prestimulated prior to introducing the composition to the cell.

Embodiments of the present invention comprise culture expanding the cell to obtain cells.

In embodiments of the present invention, the cells are cultured with one or more of: stem cell factor (SCF), IL-3, and GM-CSF.

In embodiments of the present invention, the cells are cultured with at least one cytokine.

In embodiments of the present invention, the at least one cytokine is a recombinant human cytokine.

In embodiments of the present invention, the cell is among a plurality of cells, wherein the composition comprising the first RNA molecule or both the first and the second RNA molecule is introduced into at least the cell as well as other cells among the plurality of cells, and the mutant allele of the ELANE gene is inactivated in at least the cell as well as in the other cells among the plurality of cells, thereby obtaining multiple modified cells.

In embodiments of the present invention, introducing the composition comprising the first RNA molecule or introduction of the second RNA molecule comprises electroporation of the cell or cells.

Embodiments of the present invcntion provide for a modified cell obtained by the methods of the present invention.

In embodiments of the present invention, the modified cells are further culture expanded.

In embodiments of the present invention, the modified cells are capable of engraftment.

In embodiments of the invention, modified cells are capable of long-term engraftment when infused into a patient, giving rise to differentiated hematopoietic cells for at least 12 months after infusion, preferably at least 24 months and even, more preferably at least 30 months after infusion. In a further embodiment, the modified cells are capable of long-term engraftment when infused into an autologous subject. In a further embodiment, the modified cells are capable of long-term engraftment when infused into a subject without myeloablation. In an embodiment of the present invention, the modified cells are delivered to a subject in sufficient numbers that, when engrafted into a human subject, provide long term engraftment.

In embodiments of the present invention, the modified cell or cells are capable of giving rise to progeny cells.

In embodiments of the present invention, the modified cell or cells are capable of giving rise to progeny cells after engraftment.

In embodiments of the present invention, the modified cell or cells are capable of giving rise to progeny cells after an autologous engraftment.

In embodiments of the present invention, the modified cell or cells are capable of giving rise to progeny cells for at least 12 months or at least 24 months after engraftment.

In one embodiment, the cell or cells are stem cells. In one embodiment, the cell is an embryonic stem cell. In some embodiment, the stem cell is a hematopoietic stem/progenitor cell (HSPC).

In embodiments of the present invention, the modified cell or cells are CD34+ hematopoietic stem cells.

In embodiments of the present invention, the modified cell or cells are bone marrow cells or peripheral mononucleated cells (PMCs).

Embodiments of the present invention provide for a modified cell lacking at least a portion of one allele of the ELANE gene.

In embodiments of the present invention, the modified cell was modified from a cell heterozygous at one or more polymorphic sites selected from the group consisting of: rs10414837, rs3761005, rs1683564, rs9749274, rs740021, rs201048029, rs199720952, rs28591229, rs71335276, rs58082177, rs3826946, rs10413889, rs761481944, rs3761008, rs10409474, rs3761007, rs17216649, rs10469327, rs8107095, rs10424470 and rs78302854.

Embodiments of the present invention provide for a composition comprising modified cells and a pharmaceutically acceptable carrier.

Embodiments of the present invention provide for an in vitro or ex vivo method of preparing a composition, comprising mixing the cells of the present invention with the pharmaceutically acceptable carrier.

Embodiments of the present invention provide for a method of preparing in vitro or ex vivo a composition comprising modified cells, the method comprising:

a) isolating HSPCs from cells obtained from a subject with an ELANE gene mutation related to SCN or CyN and/or suffering from SCN or CyN and which subject is heterozygous at one or more polymorphic sites selected from the group consisting of: rs10414837, rs3761005, rs1683564, rs9749274, rs740021, rs201048029, rs199720952, rs28591229, rs71335276, rs58082177, rs3826946, rs10413889, rs761481944, rs3761008, rs10409474, rs3761007, rs17216649, rs10469327, rs8107095, rs10424470 and rs78302854, and obtaining the cell from the subject;

b) introducing to the cells of step (a) a composition comprising:

a CRISPR nuclease or a sequence encoding the CRISPR nuclease; and a first RNA molecule comprising a guide sequence portion having 17-20 nucleotides, wherein a complex of the CRISPR nuclease and the first RNA molecule affects a double strand break in the mutant allele of the ELANE gene in one or more cells, optionally, introducing to the cells a second RNA molecule comprising a guide sequence portion capable of complexing with a CRISPR nuclease, wherein the complex of the second RNA molecule and CRISPR nuclease affects a second double strand break in the ELANE gene in the one or more cells so as to inactive the mutant allele of the ELANE gene in one or more cells thereby obtaining modified cells; optionally c) culture expanding the modified cells of step (b), wherein the modified cells are capable of engraftment and giving rise to progeny cells after engraftment.

Embodiments of the present invention provide for use of a composition prepared in vitro by a method comprising:

a) isolating HSPCs from cells obtained from a subject with an ELANE gene mutation related to SCN or CyN and/or suffering from SCN or CyN and which subject is heterozygous at one or more polymorphic sites selected from the group consisting of: rs10414837, rs3761005, rs1683564, rs9749274, rs740021, rs201048029, rs199720952, rs28591229, rs71335276, rs58082177, rs3826946, rs10413889, rs761481944, rs3761008, rs10409474, rs3761007, rs17216649, rs10469327, rs8107095, rs10424470 and rs78302854;

b) introducing to the cells of step (a) a composition comprising:

a CRISPR nuclease or a sequence encoding the CRISPR nuclease; and a first RNA molecule comprising a guide sequence portion having 17-20 nucleotides, wherein a complex of the CRISPR nuclease and the first RNA molecule affects a double strand break in the mutant allele of the ELANE gene in one or more cells, optionally, introducing to the cells a second RNA molecule comprising a guide sequence portion capable of complexing with a CRISPR nuclease, wherein the complex of the second RNA molecule and CRISPR nuclease affects a second double strand break in the ELANE gene in the one or more cells so as to inactive the mutant allele of the ELANE gene in one or more cells thereby obtaining modified cells; optionally;

c) culture expanding the cells of step (b) wherein the modified cells are capable of engraftment and giving rise to progeny cells after engraftment; and d) administering to the subject the cells of step (b) or step (c) for treating the SCN or CyN in the subject.

Embodiments of the present invention provide for a method of treating a subject afflicted with SCN or CyN, comprising administration of a therapeutically effective amount of the modified cells, compositions, or the compositions prepared by the methods of the instant invention Embodiments of the present invention provide for a method for treating SCN or CyN in a subject with an ELANE gene mutation relating to SCN or CYN in need thereof and which subject is heterozygous at one or more polymorphic sites selected from the group consisting of: rs10414837, rs3761005, rs1683564, rs9749274, rs740021, rs201048029, rs199720952, rs28591229, rs71335276, rs58082177, rs3826946, rs10413889, rs761481944, rs3761008, rs10409474, rs3761007, rs17216649, rs10469327, rs8107095, rs10424470 and rs78302854, the method comprising:

a) isolating HSPCs from cells obtained from the subject;

b) introducing to the cells of step (a) a composition comprising:

a CRISPR nuclease or a sequence encoding the CRISPR nuclease; and a first RNA molecule comprising a guide sequence portion having 17-20 nucleotides, wherein a complex of the CRISPR nuclease and the first RNA molecule affects a double strand break in the mutant allele of the ELANE gene in one or more cells, optionally, introducing to the cells a second RNA molecule comprising a guide sequence portion capable of complexing with a CRISPR nuclease, wherein the complex of the second RNA molecule and CRISPR nuclease affects a second double strand break in the ELANE gene in the one or more cells so as to inactive the mutant allele of the ELANE gene in one or more cells thereby obtaining modified cells; optionally;

c) culture expanding the cells of step (b) wherein the modified cells are capable of engraftment and giving rise to progeny cells after engraftment; and d) administering to the subject the cells of step (b) or step (c) thereby treating the SCN or CyN in the subject.

Embodiments of the present invention provide for a method for treating SCN or CyN in a subject with an ELANE gene mutation relating to SCN or CYN in need thereof and which subject is heterozygous at one or more polymorphic sites selected from the group consisting of: rs10414837, rs3761005, rs1683564, rs9749274, rs740021, rs201048029, rs199720952, rs28591229, rs71335276, rs58082177, rs3826946, rs10413889, rs761481944, rs3761008, rs10409474, rs3761007, rs17216649, rs10469327, rs8107095, rs10424470 and rs78302854, the method comprising administering to the subject autologous modified cells or progeny of autologous modified cells. wherein the autologous modified cells are modified so as to have a double strand break in the mutant allele of the ELANE gene, wherein said double strand break results from introduction to the cells of a composition comprising a CRISPR nuclease or a sequence encoding the CRISPR nuclease and a first RNA molecule wherein a complex of the CRISPR nuclease and the first RNA molecule affects a double strand break in the mutant allele of the ELANE gene so as to inactive the mutant allele of the ELANE gene in the cell, thereby treating the SCN or CyN in the subject.

Embodiments of the present invention provide for a method of selecting a subject for treatment from a pool of subjects diagnosed with SCN or CyN, comprising the steps of:

a) obtaining cells from each subject in the pool of subjects;

b) screening each subject's cells for an ELANE gene mutation related to SCN or CyN, and selecting only subjects with an ELANE gene mutation related to SCN or CyN;

c) screening by sequencing the cells of the subjects selected in step (b) for heterozygosity at one or more polymorphic sites selected from the group consisting of: rs10414837, rs3761005, rs1683564, and d) selecting for treatment only subjects with cells heterozygous at the one of more polymorphic sites.

Embodiments of the present invention further comprise treating SCN or CyN in a selected subject, comprising:

e) obtaining HSPC cells from the bone marrow of the subject either by aspiration or by mobilization and apheresis of peripheral blood;

f) introducing to the HSPC cells of step (e):

one or more CRISPR nucleases or sequences encoding the one or more CRISPR nucleases a first RNA molecule comprising a guide sequence portion having 17-20 nucleotides in a sequence of 17-20 contiguous nucleotides set forth in any one of SEQ ID NOs: 1-1192 targeting the nucleotide base of the heterozygous allele of the one or more polymorphic sites present on the mutant allele of the ELANE gene, and a second RNA molecule comprising a guide sequence portion targeting a sequence in intron 3, intron 4 or 3' UTR of the ELANE gene, wherein a complex of the first RNA molecule and a CRISPR nuclease affects a first double strand break in the mutant allele of the ELANE gene in one or more of the HSPC cells and a complex of the second RNA molecule and a CRISPR nuclease affect a second double strand break in intron 3, intron 4, or 3' UTR of both alleles of the ELANE gene in the one or more HSPC cells in which the complex of the first RNA molecule and the CRISPR nuclease affected a first double strand break, thereby obtaining modified cells;

g) administering to the subject the modified cells of step (f), thereby treating SCN or CyN in the subject.

Embodiments of the present invention provide an RNA molecule comprising a guide sequence portion having 17-20 nucleotides in the sequence of 17-20 contiguous nucleotides set forth in any one of SEQ ID NOs: 1-1192.

Embodiments of the present invention further comprise a second RNA molecule comprising a guide sequence portion.

In embodiments of the present invention, the second RNA molecule targets a non-coding region of the ELANE gene.

In embodiments of the present invention, the nucleotide sequence of the guide sequence portion of the second RNA molecule is a different nucleotide sequence from the sequence of the guide sequence portion of the first RNA molecule.

In embodiments of the present invention, the first RNA molecule further comprise a portion having a sequence which binds to a CRISPR nuclease. In embodiments of the present invention, the second RNA molecule further comprise a portion having a sequence which binds to a CRISPR nuclease.

In embodiments of the present invention, the sequence which binds to a CRISPR nuclease is a tracrRNA sequence.

In embodiments of the present invention, the first RNA molecule further comprises a portion having a tracr mate sequence. In embodiments of the present invention, the second RNA molecule further comprises a portion having a tracr mate sequence.

In embodiments of the present invention, the first RNA molecule further comprises one or more linker portions. In embodiments of the present invention, the second RNA molecule further comprises one or more linker portions.

In embodiments of the present invention, the first RNA molecule is up to 300 nucleotides in length. In embodiments of the present invention, the second RNA molecule is up to 300 nucleotides in length.

In embodiments of the present invention, the composition further comprises one or more CRISPR nucleases or sequences encoding the one or more CRISPR nucleases. In embodiments of the present invention, the composition further comprises one or more tracrRNA molecules or sequences encoding the one or more tracrRNA molecules.

Embodiments of the present invention provide a method for inactivating in a cell a mutant ELANE allele, the method comprising delivering to the cell the RNA molecules or compositions of the present invention.

In embodiments of the present invention, the one or more CRISPR nuclease or sequences encoding the one or more CRISPR nucleases and the RNA molecule or RNA molecules are delivered to the subject and/or cells substantially at the same time or at different times.

In embodiments of the present invention, the tracrRNA molecules or sequences encoding the one or more tracrRNA molecules and the RNA molecule or RNA molecules are delivered to the subject and/or cells substantially at the same time or at different times.

In embodiments of the present invention, the method comprises removing an exon containing a disease-causing mutation from a mutant allele, wherein the first RNA molecule or the first and the second RNA molecules target regions flanking an entire exon or a portion of the exon.

In embodiments of the present invention, the method comprises removing multiple exons, the entire open reading frame of a gene, or removing the entire gene.

In embodiments of the present invention, the first RNA molecule or the first and the second RNA molecules target an alternative splicing signal sequence between an exon and an intron of a mutant allele.

In embodiments of the present invention, the second RNA molecule targets a sequence present in both a mutant allele and a functional allele.

In embodiments of the present invention, the second RNA molecule targets an intron.

In embodiments of the present invention, the method results in subjecting the mutant allele to insertion or deletion by an error prone non-homologous end joining (NHEJ) mechanism, generating a frameshift in the mutant allele's sequence.

In embodiments of the present invention, the frameshift results in inactivation or knockout of the mutant allele.

In embodiments of the present invention, the frameshift creates an early stop codon in the mutant allele or the frameshift results in nonsense-mediated mRNA decay of the transcript of the mutant allele.

In embodiments of the present invention, inactivating or treating results in a truncated protein encoded by the mutant allele and a functional protein encoded by the functional allele.

In embodiments of the present invention, the cells or the subject is heterozygous at rs10414837 or rs3761005 and wherein the complex of the second RNA molecule and CRISPR nuclease affects a double strand break in intron 4 of the ELANE gene.

In embodiments of the present invention, the cells or the subject is heterozygous at rs10414837 or rs3761005 and the complex of the second RNA molecule and CRISPR nuclease affects a double strand break in intron 3 of the ELANE gene.

In embodiments of the present invention, the cells or the subject is heterozygous at rs10414837 or rs3761005 and wherein the complex of the second RNA molecule and CRISPR nuclease affects a double strand break in the 3' UTR region of the ELANE gene.

In embodiments of the present invention, the cells or the subject is heterozygous at rs1683564 and wherein the complex of the second RNA molecule and CRISPR nuclease affects a double strand break in intron 4 of the ELANE gene.

In embodiments of the present invention, the cells or the subject is heterozygous at rs1683564 and wherein the complex of the second RNA molecule and CRISPR nuclease affects a double strand break in intron 3 of the ELANE gene.

In embodiments of the present invention, the cells or the subject is heterozygous at rs1683564 and wherein the complex of the second RNA molecule and CRISPR nuclease affects a double strand break in the 3' UTR region of the ELANE gene.

Embodiments of the present invention provide use of the RNA molecules, the compositions, or the composition prepared by the method of the present invention for inactivating in a cell a mutant ELANE allele.

Embodiments of the present invention provide a medicament comprising the RNA molecules, compositions, or the compositions prepared by the methods of the instant invention for use in inactivating in a cell a mutant ELANE allele, wherein the medicament is administered by delivering to the cell the RNA molecules, compositions, or the compositions prepared by the methods of the instant invention.

Embodiments of the present invention provide for use of the methods, the modified cells, the compositions, or the compositions prepared by the methods, or the RNA molecules of the instant invention for treating ameliorating or preventing SCN or CyN in to a subject having or at risk of having SCN or CyN.

Embodiments of the present invention provide for a medicament comprising the RNA molecules, compositions, compositions prepared by the methods of the instant invention, or the modified cells of the instant invention, for use in treating ameliorating or preventing SCN or CyN, wherein the medicament is administered by delivering to a subject having or at risk of having SCN or CyN the RNA molecules, compositions, compositions prepared by the methods of the instant invention, or the modified cells of the instant invention.

Embodiments of the present invention provide for a kit for inactivating a mutant ELANE allele in a cell, comprising the RNA molecules of the instant invention, a CRISPR nuclease or sequence encoding the CRISPR nuclease, and/or a tracrRNA molecule or sequence encoding the tracrRNA molecule; and instructions for delivering the RNA molecule; CRISPR nuclease or sequence encoding the CRISPR nuclease, and/or the tracrRNA or sequence encoding the tracrRNA molecule to the cell to inactivate the mutant ELANE allele in the cell.

Embodiments of the present invention provide for a kit for treating SCN or CyN in a subject, comprising the RNA molecules of the instant invention, a CRISPR nuclease or sequence encoding the CRISPR nuclease, and/or a tracrRNA molecule or sequence encoding the tracrRNA molecule; and instructions for delivering the RNA molecule; CRISPR nuclease or sequence encoding the CRISPR nuclease, and/or the tracrRNA or sequence encoding the tracrRNA molecule to a subject having or at risk of having SCN or CyN so as to treat the SCN or CyN.

Embodiments of the present invention provide for a kit for inactivating a mutant ELANE allele in a cell, comprising the compositions, the composition prepared by the methods of the instant invention, or the modified cells of the instant invention, and instructions for delivering the composition to the cell so as to inactivate the ELANE gene in the cell.

Embodiments of the present invention provide for a kit for treating SCN or CyN in a subject, comprising the composition, the compositions prepared by the methods of the instant invention, or the modified cells of the instant invention, and instructions for delivering the compositions, the compositions prepared by the methods of the instant invention, or the modified cells of the instant invention, to a subject having or at risk of having SCN or CyN so as to treat SCN or CyN.

Definitions

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

It should be understood that the terms "a" and "an" as used above and elsewhere herein refer to "one or more" of the enumerated components. It will be clear to one of ordinary skill in the art that the use of the singular includes the plural unless specifically stated otherwise. Therefore, the terms "a," "an" and "at least one" are used interchangeably in this application.

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

Unless otherwise stated, adjectives such as "substantially" and "about" modifying a condition or relationship characteristic of a feature or features of an embodiment of the invention, are understood to mean that the condition or characteristic is defined to within tolerances that are acceptable for operation of the embodiment for an application for which it is intended. Unless otherwise indicated, the word "or" in the specification and claims is considered to be the inclusive "or" rather than the exclusive or, and indicates at least one of, or any combination of items it conjoins.

In the description and claims of the present application, each of the verbs, "comprise," "include" and "have" and conjugates thereof, are used to indicate that the object or objects of the verb are not necessarily a complete listing of components, elements or parts of the subject or subjects of the verb. Other terms as used herein are meant to be defined by their well-known meanings in the art.

As used herein, the term "heterozygous single nucleotide polymorphism" or "SNP" refers to a single nucleotide position in a genome that differs between paired chromosomes within a population. As used herein the most common or most prevalent nucleotide base at the position is referred to as the reference (REF), wild-type (WT), common, or major form. Less prevalent nucleotide bases at the position are referred to as the alternative (ALT), minor, rare, or variant forms.

The "guide sequence portion" of an RNA molecule refers to a nucleotide sequence that is capable of hybridizing to a specific target DNA sequence, e.g., the guide sequence portion has a nucleotide sequence which is fully complementary to the DNA sequence being targeted along the length of the guide sequence portion. In some embodiments, the guide sequence portion is 17, 18, 19, 20, 21, 22, 23, or 24 nucleotides in length, or approximately 17-24, 18-22, 19-22, 18-20, or 17-nucleotides in length. The entire length of the guide sequence portion is fully complementary to the DNA sequence being targeted along the length of the guide sequence portion. The guide sequence portion may be part of an RNA molecule that can form a complex with a CRISPR nuclease with the guide sequence portion serving as the DNA targeting portion of the CRISPR complex. When the DNA molecule having the guide sequence portion is present contemporaneously with the CRISPR molecule the RNA molecule is capable of targeting the CRISPR nuclease to the specific target DNA sequence. Each possibility represents a separate embodiment. An RNA molecule can be custom designed to target any desired sequence.

The term "targets" as used herein, refers to the guide sequence portion of the RNA molecule's preferential hybridization to a nucleic acid having a targeted nucleotide sequence. It is understood that the term "targets" encompasses variable hybridization efficiencies, such that there is preferential targeting of the nucleic acid having the targeted nucleotide sequence, but unintentional off-target hybridization in addition to on-target hybridization might also occur. It is understood that where an RNA molecule targets a sequence, a complex of the RNA molecule and a CRISPR nuclease molecule targets the sequence for nuclease activity.

In the context targeting a DNA sequence that is present in a plurality of cells, it is understood that the targeting encompasses hybridization of the guide sequence portion of the RNA molecule with the sequence in one or more of the cells, and also encompasses hybridization of the RNA molecule with the target sequence in fewer than all of the cells in the plurality of cells. Accordingly, it is understood that where an RNA molecule targets a sequence in a plurality of cells, a complex of the RNA molecule and a CRISPR nuclease is understood to hybridize with the target sequence in one or more of the cells, and also may hybridize with the target sequence in fewer than all of the cells. Accordingly, it is understood that the complex of the RNA molecule and the CRISPR nuclease introduces a double strand break in relation to hybridization with the target sequence in one or more cells and may also introduce a double strand break in relation to hybridization with the target sequence in fewer than all of the cells. As used herein, the term "modified cells" refers to cells in which a double strand break is effected by a complex of an RNA molecule and the CRISPR nuclease as a result of hybridization with the target sequence, i.e. on-target hybridization.

In embodiments of the present invention, RNA guide molecule may target the mutant allele based on the nucleotide base present in the polymorphic site on the mutant allele.

In embodiments of the present invention, an RNA molecule comprises a guide sequence portion having 17-20 nucleotides in the sequence of 17-20 contiguous nucleotides set forth in any one of SEQ ID NOs: 1-1192; or set forth in the following group SEQ ID NOs: 6, 75, 76, 252, 253, 287, 295, 296, 311, 536, 592, 595, 596, 597, 695, 729, 737, 812, 839, 915, 947, 1048, 1049, 1070, 1071, 1169, or set forth in the following group SEQ ID NOs: 6, 75, 76, 93, 94, 97, 98, 148, 149, 171, 173, 180, 182, 183, 184, 187, 188, 213, 232, 234, 249, 252, 253, 264, 272, 287, 291, 295, 296, 305, 306, 307, 308, 311, 326, 333, 334, 337, 338, 339, 340, 351, 352, 358, 359, 378, 379, 385, 388, 399, 408, 410, 419, 420, 426, 427, 428, 429, 430, 436, 437, 449, 450, 465, 468, 476, 477, 478, 480, 495, 497, 499, 500, 508, 511, 521, 522, 523, 524, 529, 530, 532, 536, 542, 545, 546, 564, 565, 566, 573, 574, 583, 584, 591, 592, 595, 596, 597, 598, 599, 601, 602, 604, 612, 613, 616, 622, 623, 634, 644, 645, 658, 659, 661, 670, 671, 678, 680, 681, 684, 685, 688, 689, 694, 695, 714, 715, 716, 722, 723, 724, 729, 736, 737, 739, 740, 745, 755, 756, 760, 761, 769, 770, 771, 772, 775, 776, 786, 787, 806, 809, 812, 818, 819, 821, 822, 826, 829, 830, 833, 834, 839, 845, 846, 861, 862, 874, 875, 876, 877, 884, 888, 889, 890, 891, 893, 894, 911, 912, 913, 914, 915, 925, 928, 930, 931, 939, 940, 942, 946, 947, 948, 949, 950, 957, 972, 974, 982, 994, 998, 1006, 1007, 1008, 1021, 1022, 1026, 1027, 1028, 1031, 1032, 1034, 1035, 1039, 1046, 1047, 1048, 1049, 1057, 1070, 1071, 1072, 1074, 1075, 1076, 1079, 1084, 1090, 1091, 1093, 1094, 1095, 1112, 1113, 1116, 1117, 1118, 1119, 1121, 1122, 1124, 1140, 1168, 1169, 1170, 1171, 1179; or sct forth in the following group SEQ ID NOs: 6, 10, 13, 14, 19, 21, 22, 23, 24, 25, 26, 29, 30, 34, 35, 36, 39, 42, 43, 44, 45, 46, 47, 48, 49, 50, 52, 53, 54, 55, 57, 58, 61, 62, 64, 65, 66, 67, 68, 69, 70, 71, 72, 73, 74, 75, 76, 82, 86, 87, 88, 89, 91, 92, 93, 94, 95, 96, 97, 98, 99, 100, 101, 102, 103, 107, 108, 109, 115, 119, 122, 123, 124, 125, 126, 127, 128, 130, 133, 134, 135, 136, 137, 138, 139, 140, 141, 142, 143, 144, 148, 149, 150, 152, 153, 155, 156, 158, 159, 160, 161, 162, 163, 164, 167, 168, 169, 170, 171, 172, 173, 175, 176, 177, 178, 179, 180, 181, 182, 183, 184, 187, 188, 189, 190, 191, 192, 195, 196, 198, 199, 201, 203, 206, 209, 211, 212, 213, 214, 215, 216, 217, 219, 220, 221, 223, 224, 225, 226, 227, 232, 233, 234, 236, 237, 238, 240, 241, 242, 243, 244, 245, 246, 247, 248, 249, 250, 251, 252, 253, 254, 255, 256, 261, 262, 263, 264, 265, 266, 267, 269, 270, 271, 272, 273, 274, 275, 276, 277, 281, 282, 285, 286, 287, 290, 291, 292, 293, 294, 295, 296, 302, 303, 305, 306, 307, 308, 310, 311, 314, 319, 323, 326, 327, 328, 329, 331, 332, 333, 334, 335, 336, 337, 338, 339, 340, 341, 343, 344, 345, 346, 349, 350, 351, 352, 353, 354, 356, 357, 358, 359, 360, 363, 364, 366, 370, 371, 372, 373, 374, 375, 376, 377, 378, 379, 380, 381, 382, 385, 386, 387, 388, 389, 390, 391, 392, 393, 394, 395, 396, 397, 399, 400, 404, 405, 406, 407, 408, 410, 411, 412, 415, 417, 418, 419, 420, 422, 423, 424, 425, 426, 427, 428, 429, 430, 431, 432, 433, 435, 436, 437, 440, 441, 442, 443, 444, 445, 446, 447, 449, 450, 451, 452, 454, 455, 456, 457, 460, 461, 462, 464, 465, 466, 467, 468, 469, 470, 471, 474, 475, 476, 477, 478, 479, 480, 483, 484, 485, 486, 488, 489, 491, 492, 493, 494, 495, 496, 497, 498, 499, 500, 501, 502, 504, 505, 506, 508, 509, 510, 511, 513, 514, 517, 518, 519, 520, 521, 522, 523, 524, 525, 526, 527, 528, 529, 530, 531, 532, 533, 536, 537, 538, 539, 540, 541, 542, 543, 544, 545, 546, 547, 548, 549, 550, 552, 553, 554, 555, 556, 557, 558, 559, 560, 561, 562, 563, 564, 565, 566, 567, 568, 569, 570, 571, 573, 574, 577, 579, 580, 582, 583, 584, 586, 587, 588, 590, 591, 592, 593, 595, 596, 597, 598, 599, 600, 601, 602, 604, 605, 606, 607, 608, 609, 610, 612, 613, 614, 615, 616, 617, 618, 619, 620, 621, 622, 623, 624, 625, 628, 629, 630, 633, 634, 635, 636, 637, 638, 639, 640, 641, 644, 645, 648,650, 651, 652, 653, 654, 655, 658, 659, 660, 661, 663, 664, 665, 667, 670, 671, 672, 673, 675, 676,678, 680, 681, 683, 684, 685, 686, 688, 689, 690, 691, 692, 694, 695, 698, 700, 701, 702, 703, 704, 705, 706, 707,708, 709, 712, 713, 714, 715, 716, 718, 719, 720, 722, 723, 724, 727, 728, 729, 730, 731, 732, 733, 734, 735, 736, 737, 738, 739, 740, 742, 743, 744, 745, 746, 747, 748, 749, 753, 754, 755, 756, 757, 758, 759, 760, 761, 762, 763, 764, 767, 769, 770, 771, 772, 773, 775, 776, 778, 779, 780, 781, 786, 787, 788, 789, 790, 791, 792, 794, 795, 798, 800, 801, 805, 806, 807, 808, 809, 811, 812, 813, 814, 815, 816, 818, 819, 820, 821, 822, 823, 826, 829, 830, 831, 832, 833, 834, 835, 836, 837, 838, 839, 843, 844, 845, 846, 849, 850, 852, 853, 854, 855, 856, 857, 858, 861, 862, 863, 864, 865, 866, 867, 868, 870, 871, 872, 874, 875, 876, 877, 878, 879, 880, 881, 882, 883, 884, 886, 887, 888, 889, 890, 891, 893, 894, 895, 896, 897, 898, 899, 901, 902, 903, 905, 906, 907, 908, 909, 910,911, 912, 913, 914, 915, 916, 917,920, 921, 925, 926, 927, 928,929, 930, 931, 932, 933, 934, 935, 936, 937, 939, 940, 942, 943, 945, 946, 947, 948, 949, 950, 951, 952, 953, 954, 955, 956, 957, 958, 960, 961, 962, 963, 964, 965, 966, 967, 968, 969, 972, 974, 975, 976, 978, 979, 982, 983, 984, 988,989, 990, 991, 992, 993, 994, 996, 997, 998, 1001, 1002, 1003, 1004, 1005, 1006, 1007, 1008, 1009, 1010, 1011, 1012, 1013, 1014, 1015, 1017, 1018, 1019, 1020, 1021, 1022, 1023, 1024, 1026, 1027, 1028, 1029, 1030, 1031, 1032, 1033, 1034, 1035, 1036, 1037, 1038, 1039, 1040, 1042, 1043, 1044, 1045, 1046, 1047, 1048, 1049, 1050, 1051, 1052, 1053, 1054, 1055, 1056, 1057, 1058, 1061, 1062, 1063, 1064, 1069, 1070, 1071, 1072, 1073, 1074, 1075, 1076, 1077, 1078, 1079, 1080, 1081, 1082, 1083, 1084, 1086, 1090, 1091, 1093, 1094, 1095, 1097, 1099, 1100, 1101, 1102, 1103, 1104, 1105, 1107, 1108, 1110, 1111, 1112, 1113, 1114, 1115, 1116, 1117, 1118, 1119, 1120, 1121, 1122, 1123, 1124, 1126, 1127, 1128, 1131, 1132, 1133, 1134, 1135, 1136, 1137, 1138, 1139, 1140, 1142, 1143, 1144, 1145, 1147, 1148, 1149, 1151, 1152, 1153, 1154, 1155, 1156, 1158, 1159, 1160, 1162, 1164, 1165, 1166, 1167, 1168, 1169, 1170, 1171, 1172, 1173, 1175, 1176, 1179, 1180, 1181, 1182, 1183. It is understood that in any of the embodiments of the present invention the guide sequence portion of an RNA molecule may comprise 17-20 contiguous nucleotides set forth in any single sequence of SEQ ID NOs: 1-1192, or in any single sequence from the above groups of sequences.

As used herein, "contiguous nucleotides" set forth in a SEQ ID NO refers to nucleotides in a sequence of nucleotides in the order set forth in the SEQ ID NO without any intervening nucleotides.

In embodiments of the present invention, the guide sequence portion may be 20 nucleotides in length and consists of 20 nucleotides in the sequence of 20 contiguous nucleotides set forth in any one of SEQ ID NOs: 1-1192. In embodiments of the present invention, the guide sequence portion may be less than 20 nucleotides in length. For example, in embodiments of the present invention the guide sequence portion may be 17, 18, or 19 nucleotides in length. In such embodiments the guide sequence portion may consist of 17, 18, or 19 nucleotides, respectively, in the sequence of 17-20 contiguous nucleotides set forth in any one of SEQ ID NOs: 1-1192. For example, a guide sequence portion having 17 nucleotides in the sequence of 17 contiguous nucleotides set forth in SEQ ID NO: I may consist of any one of the following nucleotide sequences (nucleotides excluded from the contiguous sequence are marked in strike-through):

SEQ ID NO: 1
AAAAAAACACAAUGUGGGGA 17 nucleotide guide sequence 1:
(SEQ ID NO: 1201)
~~AAA~~AAAACACAAUGUGGGGA 17 nucleotide guide sequence 2:
(SEQ ID NO: 1202)
~~AA~~AAAAACACAAUGUGGGGA~~A~~

17 nucleotide guide sequence 3:
(SEQ ID NO: 1203)
~~A~~AAAAAAACACAAUGUGGG~~GA~~

17 nucleotide guide sequence 4:
(SEQ ID NO: 1204)
AAAAAAACACAAUGUGG~~GGA~~

In embodiments of the present invention, the guide sequence portion may be greater than nucleotides in length. For example, in embodiments of the present invention the guide sequence portion may be 21, 22, 23. or 24 nucleotides in length. In such embodiments the guide sequence portion comprises 20 nucleotides in the sequence of 20 contiguous nucleotides set forth in any one of SEQ ID NOs: 1-1192 and additional nucleotides fully complimentary to a nucleotide or sequence of nucleotides adjacent to the 3' end of the target sequence, 5' end of the target sequence, or both.

In embodiments of the present invention, a CRISPR nuclease and an RNA molecule comprising a guide sequence portion form a CRISPR complex that binds to a target DNA sequence to effect cleavage of the target DNA sequence. CRISPR nucleases, e.g. Cpf1, may form a CRISPR complex comprising a CRISPR nuclease and RNA molecule without a further tracrRNA molecule. Alternatively, CRISPR nucleases, e.g. Cas9, may form a CRISPR complex between the CRISPR nuclease, an RNA molecule, and a tracrRNA molecule.

In embodiments of the present invention, the RNA molecule may further comprise the sequence of a tracrRNA molecule. Such embodiments may be designed as a synthetic fusion of the guide portion of the RNA molecule and the trans-activating crRNA (tracrRNA). (See Jinek (2012) Science). Embodiments of the present invention may also form CRISPR complexes utilizing a separate tracrRNA molecule and a separate RNA molecule comprising a guide sequence portion. In such embodiments the tracrRNA molecule may hybridize with the RNA molecule via base pairing and may be advantageous in certain applications of the invention described herein.

The term "tracr mate sequence" refers to a sequence sufficiently complementary to a tracrRNA molecule so as to hybridize to the tracrRNA via basepairing and promote the formation of a CRISPR complex. (See U.S. Pat. No. 8,906,616). In embodiments of the present invention, the RNA molecule may further comprise a portion having a tracr mate sequence.

According to embodiments of the present invention, an RNA molecule may be up to 300, 290, 280, 270, 260, 250, 240, 230, 220, 210, 200, 190, 180, 170, 160, 150, 140, 130, 120, 110, or 100 nucleotides in length. Each possibility represents a separate embodiment. In embodiments of the present invention, the RNA molecule may be 17 up to 300 nucleotides in length, 100 up to 300 nucleotides in length, 150 up to 300 nucleotides in length, 200 up to 300 nucleotides in length, 100 to 200 nucleotides in length, or 150 up to 250 nucleotides in length. Each possibility represents a separate embodiment.

A "gene," for the purposes of the present disclosure, includes a DNA region encoding a gene product, as well as all DNA regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions.

"Eukaryotic" cells include, but are not limited to, fungal cells (such as yeast), plant cells, animal cells, mammalian cells and human cells.

As used herein, the term HSPC refers to both hematopoietic stem cells and hematopoietic stem progenitor cells. Non-limiting examples of stem cells include a bone marrow cell, a myeloid progenitor cell, a multipotent progenitor cell, a lineage restricted progenitor cell.

As used herein, "progenitor cell" refers to a lineage cell that is derived from stem cell and retains mitotic capacity and multipotency (e.g., can differentiate or develop into more than one but not all types of mature lineage of cell). As used herein "hematopoiesis" or "hemopoiesis" refers to the formation and development of various types of blood cells (e.g., red blood cells, megakaryocytcs, myceloid cells (e.g., monocytes, macrophages and neutrophil), and lymphocytes) and other formed elements in the body (e.g., in the bone marrow).

The term "nuclease" as used herein refers to an enzyme capable of cleaving the phosphodiester bonds between the nucleotide subunits of nucleic acid. A nuclease may be isolated or derived from a natural source. The natural source may be any living organism. Alternatively, a nuclease may be a modified or a synthetic protein which retains the phosphodiester bond cleaving activity. Gene modification can be achieved using a nuclease, for example a CRISPR nuclease.

In embodiments of the present invention, an RNA molecule is designed to target a heterozygous polymorphic site present in the mutant allele of the ELANE gene, wherein the RNA molecule targets the nucleotide base, REF or ALT, of the heterozygous polymorphic site present in the mutant allele of the ELANE gene The present disclosure provides a method for utilizing at least one naturally occurring nucleotide difference or polymorphism (e.g., single nucleotide polymorphism (SNP)) for distinguishing/discriminating between two alleles of a gene, one allele bearing a mutation such that it encodes a mutated protein causing a disease phenotype ("mutant allele"), and the other allele encoding for a functional protein ("functional allele"). The method further comprises the step of knocking out expression of the mutated protein and allowing expression of the functional protein. In some embodiments, the method is for treating, ameliorating, or preventing a dominant negative genetic disorder.

Embodiments of the present invention provide methods for utilizing at least one heterozygous SNP in a gene expressing a dominant mutant allele in a given cell or subject. In embodiments of the present invention, the SNP utilized may or may not be associated with a disease phenotype. In embodiments of the present invention, an RNA molecule comprising a guide sequence targets the mutant allele of the gene by targeting the nucleotide base present at a heterozygous SNP in the mutant allele of the gene and therefore having a different nucleotide base in the functional allele of the gene.

According to embodiments of the present invention, the first RNA molecule targets a first heterozygous SNP present in an exon or promoter of the ELANE gene wherein the first RNA molecule targets the nucleotide base, REF or ALT, of the first SNP present in the mutant allele of the ELANE gene, and wherein the second RNA molecule targets a second heterozygous SNP present in the same or a different exon or an intron of the ELANE gene wherein the second RNA molecule targets the nucleotide base, REF or ALT, of the second SNP present in the mutant allele of the ELANE gene, or a the second RNA molecule targets a sequence in a non-coding region present in both the mutant or functional allele.

According to embodiments of the present invention, the first RNA molecule or the first and the second RNA molecules target a heterozygous SNP present in the promoter region, the start codon, or the untranslated region (UTR) of the ELANE gene wherein the RNA molecule targets the nucleotide base, REF or ALT, of the SNP present in the mutant allele of the ELANE gene.

According to embodiments of the present invention, the first RNA molecule or the first and the second RNA molecules targets at least a portion of the promoter and/or the start codon and/or a portion of the UTR of the mutant allele of the ELANE gene.

According to embodiments of the present invention, the first RNA molecule targets a portion of the promoter, a first heterozygous SNP present in the promoter of the ELANE gene, or a heterozygous SNP present upstream to the promoter of the ELANE gene and the second RNA molecule targets a second heterozygous SNP, which is present in the ELANE gene downstream of the first heterozygous SNP, and is in the promoter, in the UTR, or in an intron or in an exon of the ELANE gene, wherein the first RNA molecule targets the nucleotide base, REF or ALT, of the first SNP present in the mutant allele of the of the ELANE gene, wherein the second RNA molecule targets the nucleotide base, REF or ALT, of the second SNP present in the mutant allele of the ELANE gene.

According to embodiments of the present invention, the first RNA molecule targets a heterozygous SNP present in the promoter, upstream of the promoter, or the JTR of a the ELANE gene wherein the RNA molecule targets the nucleotide base, REF or ALT, of the SNP present in the mutant allele of the ELANE gene and the second RNA molecule is designed to target a sequence which is present in an intron of both the mutant allele and the functional allele of the ELANE gene.

According to embodiments of the present invention, the first RNA molecule targets a sequence upstream of the promotor which is present in both a mutant and functional allele of the ELANE gene and the second RNA molecule targets a heterozygous SNP present in any location of the of the ELANE gene wherein the second RNA molecule targets the nucleotide base, REF or ALT, of the SNP present in the mutant allele of the ELANE gene.

According to embodiments of the present invention, there is provided a method comprising removing an exon containing a disease-causing mutation from a mutant allele, wherein the first RNA molecule or the first and the second RNA molecules target regions flanking an entire exon or a portion of the exon.

According to embodiments of the present invention, there is provided a method comprising removing multiple exons, the entire open reading frame of a gene, or removing the entire gene.

According to embodiments of the present invention, the first RNA molecule targets a first heterozygous SNP present in an exon or promoter of the ELANE gene, and wherein the second RNA molecule targets a second heterozygous SNP present in the same or a different exon or in an intron of the ELANE gene wherein the second RNA molecule targets the nucleotide base, REF or ALT, of the second SNP present in the mutant allele of the ELANE gene, or the second RNA molecule targets a sequence in an intron present in both the mutant and functional allele of the ELANE gene.

According to embodiments of the present invention, the first RNA molecule or the first and the second RNA molecules target an alternative splicing signal sequence between an exon and an intron of a mutant allele.

According to embodiments of the present invention, the second RNA molecule targets a sequence present in both a mutant allele and a functional allele of the ELANE gene.

According to embodiments of the present invention, the second RNA molecule targets an intron.

According to embodiments of the present invention, there is provided a method comprising subjecting the mutant allele to insertion or deletion by an error prone non-homologous end joining (NHEJ) mechanism, generating a frameshift in the mutant allele's sequence.

According to embodiments of the present invention, the frameshift results in inactivation or knockout of the mutant allele.

According to embodiments of the present invention, the frameshift creates an early stop codon in the mutant allele.

According to embodiments of the present invention, the frameshift results in nonsense-mediated mRNA decay of the transcript of the mutant allele.

According to embodiments of the present invention, the inactivating or treating results in a truncated protein encoded by the mutant allele and a functional protein encoded by the functional allele.

The compositions and methods of the present disclosure may be utilized for treating, preventing, ameliorating, or slowing progression of SCN or CyN.

In some embodiments, a mutant allele is deactivated by delivering to a cell an RNA molecule which targets a heterozygous SN1P present in the promoter region, the start codon, or the untranslated region (UTR) of the ELANE gene wherein the RNA molecule targets the nucleotide base, REF or ALT, of the SNP present in the mutant allele of the ELANE gene.

In some embodiments, a mutant allele is inactivated by removing at least a portion of the promoter and/or removing the start codon and/or a portion of the UTR. In some embodiments, the method of deactivating a mutant allele comprises removing at least a portion of the promoter. In such embodiments one RNA molecule may be designed for targeting a first heterozygous SNP present in the promoter or upstream to the promoter of the ELANE gene and another RNA molecule is designed to target a second heterozygous SNP, which is downstream of the first SNP, and is present in the promoter, in the UTR, or in an intron or in an exon of the ELANE gene. Alternatively, one RNA molecule may be designed for targeting a heterozygous SNP present in the promoter, or upstream of the promoter, or the UTR of the ELANE gene and another RNA molecule is designed to target a sequence which is present in an intron of both the mutant allele and the functional allele of the ELANE gene. Alternatively, one RNA molecule may be designed for targeting a sequence upstream of the promotor which is present in both the mutant and functional allele and the other guide is designed to target a heterozygous SNP present in any location of the ELANE gene e.g., in an exon, intron, UTR, or downstream of the promoter of the ELANE gene wherein the RNA molecule targets the nucleotide base, REF or ALT, of the SNP present in the mutant allele of the ELANE gene.

In some embodiments, the method of deactivating a mutant allele comprises an exon skipping step comprising removing an exon containing a disease-causing mutation from the mutant allele. Removing an exon containing a disease-causing mutation in the mutant allele requires two RNA molecules which target regions flanking the entire exon or a portion of the exon. Removal of an exon containing the disease-causing mutation may be designed to eliminate the disease-causing action of the protein while allowing for expression of the remaining protein product which retains some or all of the wild-type activity. As an alternative to single exon skipping, multiple exons, the entire open reading frame or the entire gene can be excised using two RNA molecules flanking the region desired to be excised.

In some embodiments, the method of deactivating a mutant allele comprises delivering two RNA molecules to a cell, wherein one RNA molecule targets a first heterozygous SNP present in an exon or promoter of the ELANE gene wherein the RNA molecule targets the nucleotide base, REF or ALT, of the first SNP present in the mutant allele of the ELANE gene, and wherein the other RNA molecule targets a second heterozygous SNP present in the same or a different exon or in an intron of the ELANE gene wherein the RNA molecule targets the nucleotide base, REF or ALT, of the second SNP present in the mutant allele of the ELANE gene, or the second RNA molecule targets a sequence in an intron present in both the mutant or functional allele.

In some embodiments, an RNA molecule is used to target a CRISPR nuclease to an alternative splicing signal sequence between an exon and an intron of a mutant allele, thereby destroying the alternative splicing signal sequence in the mutant allele.

Any one of, or combination of, the above-mentioned strategies for deactivating a mutant allele may be used in the context of the invention.

Additional strategies may be used to deactivate a mutant allele. For example, in embodiments of the present invention, an RNA molecule is used to direct a CRISPR nuclease to an exon or a splice site of a mutant allele in order to create a double-stranded break (DSB), leading to insertion or deletion of nucleotides by an error-prone non-homologous end-joining (NHEJ) mechanism and formation of a frameshift mutation in the mutant allele. The frameshift mutation may result in: (1) inactivation or knockout of the mutant allele by generation of an early stop codon in the mutant allele, resulting in generation of a truncated protein; or (2) nonsense mediated mRNA decay of the transcript of the mutant allele. In further embodiments, one RNA molecule is used to direct a CRISPR nuclease to a promotor of a mutant allele.

In some embodiments, the method of deactivating a mutant allele further comprises enhancing activity of the functional protein such as by providing a protein/peptide, a nucleic acid encoding a protein/peptide, or a small molecule such as a chemical compound, capable of activating/enhancing activity of the functional protein.

According to some embodiments, the present disclosure provides an RNA molecule which binds to/associates with and/or directs the RNA guided DNA nuclease e.g., CRISPR nuclease to a sequence comprising at least one nucleotide which differs between a mutant allele and a functional allele (e.g., heterozygous SNP) of a gene of interest (i.e., a sequence of the mutant allele which is not present in the functional allele).

In some embodiments, the method comprises the steps of: contacting a mutant allele of a gene of interest with an allele-specific RNA molecule and a CRISPR nuclease e.g., a Cas9 protein, wherein the allele-specific RNA molecule and the CRISPR nuclease e.g., Cas9 associate with a nucleotide sequence of the mutant allele of the gene of interest which differs by at least one nucleotide from a nucleotide sequence of a functional allele of the gene of interest, thereby modifying or knocking-out the mutant allele.

In some embodiments, the allele-specific RNA molecule and a CRISPR nuclease is introduced to a cell encoding the gene of interest. In some embodiments, the cell encoding the gene of interest is in a mammalian subject. In some embodiments, the cell encoding the gene of interest is in a plant.

In some embodiments, the cleaved mutant allele is further subjected to insertion or deletion (indel) by an error prone non-homologous end joining (NHEJ) mechanism, generating a frameshift in the mutant allele's sequence. In some embodiments, the generated frameshift results in inactivation or knockout of the mutant allele. In some embodiments, the generated frameshift creates an early stop codon in the mutant allele and results in generation of a truncated protein. In such embodiments, the method results in the generation of a truncated protein encoded by the mutant allele and a functional protein encoded by the functional allele. In some embodiments, a frameshift generated in a mutant allele using the methods of the invention results in nonsense-mediated mRNA decay of the transcript of the mutant allele.

In some embodiments, the mutant allele is an allele of the "elastase, neutrophil expressed" gene (ELANE gene). In some embodiments, the RNA molecule targets a heterozygous SNP of the ELANE gene which co-exists with/is genetically linked to the mutated sequence associated with SCN or CyN genetic disorder. In some embodiments, the RNA molecule targets a heterozygous SNP of the ELANE gene, wherein the heterozygosity of said SNP is highly prevalent in the population. In embodiments of the present invention, the REF nucleotide is prevalent in the mutant allele and not in the functional allele of an individual subject to be treated. In embodiments of the present invention, the ALT nucleotide is prevalent in the mutant allele and not in the functional allele of an individual subject to be treated. In some embodiments, a disease-causing mutation within a mutant ELANE allele is targeted.

In embodiments of the present invention, the heterozygous SNP may or may not be associated with an ELANE related disease phenotype. In embodiments of the present invention, the heterozygous SNP is associated with an ELANE related disease phenotype. In embodiments of the present invention, the SNP is not associated with an ELANE related disease phenotype In some embodiments, the heterozygous SNP is within an exon of the gene of interest. In such embodiments, a guide sequence portion of an RNA molecule may be designed to target the exon of the gene of interest.

In some embodiments, a heterozygous SNP is within an intron or an exon of the gene of interest. In some embodiments, a heterozygous SNP is in a splice site between the intron and the exon. In some embodiments a heterozygous SNP is in a PAM site of the genc of interest.

A skilled artisan will appreciate that in each of the embodiments of the present invention, individually, each of the RNA molecules of the present invention are capable of complexing with a nuclease, e.g. a CRISPR nuclease, such as to associate with a target genomic DNA sequence of interest next to a protospacer adjacent motif (PAM). The nuclease then mediates cleavage of target DNA to create a double-stranded break within the protospacer. Accordingly, in embodiments of the present invention, the guide sequences and RNA molecules of the present invention may target a location 1, 2, 3, 4, 5, 6, 7, 8, 9, 10, 11, 12, 13, 14, 15, 16, 17, 18, 19, 20, 21, 22, 23, 24, 25, 26, 27, or 28 nucleotides upstream or downstream from a PAM site.

Therefore, in embodiments of the present invention, the RNA molecules of the present invention in complex with a nuclease, e.g., a CRISPR nuclease, may affect a double strand break in an allele of a gene 1, 2, 3, 4, 5, 6, 7, 8, 9, 10, 11, 12, 13, 14, 15, 16, 17, 18, 19, 20, 21, 22, 23, 24, 25, 26, 27, 28 upstream or downstream from a target site. A skilled artisan will appreciate that where a heterozygous polymorphic site is present and is used to define the target, an RNA molecule may be designed to target and affect a double stranded break in only the REF or ALT nucleotide base of the heterozygous polymorphic site.

Where the heterozygous polymorphic site is within the PAM site, it is understood that the RNA molecule may be designed to target a sequence 1, 2, 3, 4, 5, 6, 7, 8, 9, 10, 11, 12, 13, 14, 15, 16, 17, 18, 19, 20, 21, 22, 23, 24, 25, 26, 27, or 28 nucleotides upstream or downstream from the PAM site, and a complex of the RNA molecule and nuclease is designed to target only one of the REF or ALT nucleotide base of the heterozygous polymorphic site in the PAM site and effect a break in the PAM site, e.g, the tracrRNA is designed to target one of the REF or ALT nucleotide base of the heterozygous polymorphic site.

In embodiments of the present invention, an RNA molecule is designed to target a heterozygous polymorphic site present in the ELANE gene, wherein the RNA molecule and/or the complex of the RNA molecule and a CRISPR nuclease targets the nucleotide base, REF or ALT, of the heterozygous polymorphic site present in the mutant allele of the ELANE gene In embodiments of the present invention, the RNA molecules, compositions, methods, cells, kits, or medicaments are utilized for treating a subject having a disease phenotype resulting from the heterozygote ELANE gene. In embodiments of the present invention, the disease is SCN or CyN. In such embodiments, the method results in improvement, amelioration or prevention of the disease phenotype.

In embodiments of the present invention, the RNA molecules, compositions, methods, cells, kits, or medicaments of the present invention are utilized in combination with a second therapy for SCN or CyN to treat the subject. In embodiments of the present invention, the RNA molecules, compositions, methods, kits, or medicaments of the present invention are administered prior to administration of the second therapy, during administration of the second therapy, and/or after administration of the second therapy.

In embodiments of the present invention, the RNA molecules, compositions, methods, cells, kits, or medicaments of the present invention are administered in combination with Granulocyte colony-stimulating factor (G-CSF) therapy.

Embodiments referred to above refer to a CRISPR nuclease, RNA molecule(s), and tracrRNA being effective in a subject or cells at the same time. The CRISPR, RNA molecule(s), and tracrRNA can be delivered substantially at the same time or can be delivered at different times but have effect at the same time. For example, this includes delivering the CRISPR nuclease to the subject or cells before the RNA molecule and/or tracr RNA is substantially extant in the subject or cells.

According to embodiments of the present invention, there is provided a method for inactivating in a cell a mutant allele of the ELANE gene, the method comprising the steps of:

a) selecting a cell with an ELANE gene mutation associated with SCN or CyN and who is heterozygous at one or more polymorphic sites in the ELANE gene selected from the group consisting of: rs10414837, rs3761005, rs1683564, rs9749274, rs740021, rs201048029, rs199720952, rs28591229, rs71335276, rs58082177, rs3826946, rs10413889, rs761481944, rs3761008, rs10409474, rs3761007, rs17216649, rs10469327, rs8107095, rs10424470 and rs78302854;

b) introducing to the cell a composition comprising:

a CRISPR nuclease or sequence encoding the CRISPR nuclease, and a first RNA molecule comprising a guide sequence portion having 17-20 nucleotides, wherein a complex of the CRISPR nuclease and the first RNA molecule affects a double strand break in the mutant allele of the ELANE gene and not in the functional allele of the ELANE gene in the cell;

thereby inactivating the mutant allele of the ELANE gene in the cell.

According to embodiments of the present invention, there is provided a method for inactivating in a cell a mutant allele of the ELANE gene, the method comprising the steps of:

a) selecting a cell with an ELANE gene mutation associated with SCN or CyN and who is heterozygous at one or more polymorphic sites in the ELANE gene selected from the group consisting of: rs10414837, rs3761005, rs1683564, rs9749274, rs740021, rs201048029, rs199720952, rs28591229, rs71335276, rs58082177, rs3826946, rs10413889, rs761481944, rs3761008, rs10409474, rs3761007, rs17216649, rs10469327, rs8107095, rs10424470 and rs78302854;

b) introducing to the cell a composition comprising:

a CRISPR nuclease or sequence encoding the CRISPR nuclease, and a first RNA molecule comprising a guide sequence portion having 17-20 nucleotides, wherein a complex of the CRISPR nuclease and the first RNA molecule affects a double strand break in the mutant allele of the ELANE gene and not in the functional allele of the ELANE gene in the cell;

and wherein the method further comprises introduction of a second RNA molecule comprising a guide sequence portion capable of complexing with a CRISPR nuclease, wherein the complex of the second RNA molecule and the CRISPR nuclease affects a second double strand break in the ELANE gene;

thereby inactivating the mutant allele of the ELANE gene in the cell.

According to embodiments of the present invention, there is provided a method for inactivating in a cell a mutant allele of the ELANE gene having a mutation associated with SCN or CyN and which cell is heterozygous at one or more polymorphic sites in the ELANE gene selected from the group consisting of: rs10414837, rs3761005, rs1683564, rs9749274, rs740021, rs201048029, rs199720952, rs28591229, rs71335276, rs58082177, rs3826946, rs10413889, rs761481944, rs3761008, rs10409474, rs3761007, rs17216649, rs10469327, rs8107095, rs10424470 and rs78302854, the method comprising introducing to the cell a composition comprising:

a CRISPR nuclease or sequence encoding the CRISPR nuclease, and a first RNA molecule comprising a guide sequence portion having 17-20 nucleotides, wherein a complex of the CRISPR nuclease and the first RNA molecule affects a double strand break in the mutant allele of the ELANE gene;

thereby inactivating the mutant allele of the ELANE gene in the cell.

According to embodiments of the present invention, there is provided a method for inactivating in a cell a mutant allele of the ELANE gene with an ELANE gene mutation associated with SCN or CyN and heterozygous at one or more polymorphic sites in the ELANE gene selected from the group consisting of: rs10414837, rs3761005, rs1683564, rs9749274, rs740021, rs201048029, rs199720952, rs28591229, rs71335276, rs58082177, rs3826946, rs10413889, rs761481944, rs3761008, rs10409474, rs3761007, rs17216649, rs10469327, rs8107095, rs10424470 and rs78302854, the method comprising:

introducing to the cell a composition comprising:

a CRISPR nuclease or sequence encoding the CRISPR nuclease, and a first RNA molecule comprising a guide sequence portion having 17-20 nucleotides, wherein a complex of the CRISPR nuclease and the first RNA molecule affects a double strand break in the mutant allele of the ELANE gene;

and wherein the method further comprises introduction of a second RNA molecule comprising a guide sequence portion capable of complexing with a CRISPR nuclease, wherein the complex of the second RNA molecule and CRISPR nuclease affects a second double strand break in the ELANE gene;

thereby inactivating the mutant allele of the ELANE gene in the cell.

In embodiments of the present invention, a complex of the CRISPR nuclease and the first RNA molecule affects a double strand break in the mutant allele of the ELANE gene and not in the functional allele of the ELANE gene in the cell.

In embodiments of the present invention, the cell is also heterozygous at least one additional polymorphic site in the ELANE gene selected from the group consisting of: rs10414837, rs3761005, rs1683564, rs9749274, rs740021, rs201048029, rs199720952, rs28591229, rs71335276, rs58082177, rs3826946, rs10413889, rs761481944, rs3761008, rs10409474, rs3761007, rs17216649, rs10469327, rs8107095, rs10424470 and rs78302854.

In embodiments of the present invention, a cell with an ELANE gene mutation associated with SCN or CyN may be from a subject with the ELANE gene mutation and/or afflicted with SCN or CyN. Accordingly, selecting a cell with an ELANE gene mutation may comprise selecting a subject with the ELANE gene mutation. In further embodiments of the present invention, selecting a cell may comprise selecting a cell from a subject with the ELANE gene mutation. In embodiments of the present invention, introducing the compositions of the subject invention to the cell may comprise introducing the compositions of the invention to the cell of a subject afflicted with the ELANE gene mutation.

Accordingly, in embodiments of the present invention, there is provided a method for inactivating in a cell a mutant allele of the ELANE gene of a subject, the method comprising the step of selecting a subject with an ELANE gene mutation resulting in SCN or CyN and who is heterozygous at one or more polymorphic sites in the ELANE gene selected from the group consisting of: rs10414837, rs3761005, rs1683564, rs9749274, rs740021, rs201048029, rs199720952, rs28591229, rs71335276, rs58082177, rs3826946, rs10413889, rs761481944, rs3761008, rs10409474, rs3761007, rs17216649, rs10469327, rs8107095, rs10424470 and rs78302854n.

Accordingly, embodiments of the present invention encompass the screening of subjects or cells for the ELANE gene. A person having ordinary skill in the art would readily understand methods of screening for mutations within the ELANE gene in the art, by way of non-limiting examples, e.g., sequencing-by-synthesis, Sanger sequencing, karyotyping, Fluorescence In situ Hybridization, and/or microarray testing. In embodiments of the present invention, mutations within the ELANE gene are screened by exon sequencing.

In embodiments of the present invention, the subject is or has been diagnosed with SCN or CyN by measuring the absolute neutrophil count (ANC) in peripheral blood. In embodiments of the present invention, SCN is or was diagnosed before the subject reaches the age 6 months. In embodiments of the present invention, CyN is or was diagnosed between the ages of 12 and 24 months, or after the age of 24 months. In embodiments of the present invention, SCN or Cyn is diagnosed by one or more of recurrent acute stomatologic disorders. In embodiments of the present invention, SCN or CyN is diagnosed by bone marrow examination, preferably the bone marrow examination is a cytogenetic bone marrow study. In embodiments of the present invention, SCN or CyN is diagnosed by one or more of: antineutrophil antibody assay, immunoglobulin assay (Ig GAM), lymphocyte immunophenotyping, pancreatic markers (serum trypsinogen and fecal elastase) and liposoluble vitamin levels (vitamins A, E and D). It is understood that any diagnostic method may be used with any other diagnostic method.

In embodiments of the present invention, a subject diagnosed with SCN or CyN is screened by Exon sequencing to identify an ELANE pathogenic mutation in the ELANE gene. In further embodiments the subject is screened by Sanger sequencing to confirm heterozygosity of at least one SNP in Table 1. In embodiments of the present invention, the SNP is one of rs1683564, rs10414837, and rs3761005. In embodiments of the present invention, the nucleotide of the heterozygous SNP on the mutant allele of the ELANE gene determined using BAC bio. In embodiments of the present invention, appropriate guides are selected according to Table 2. In embodiments of the present invention, the guides selected are introduced to cells, e.g. PBMCs, obtained from the subject and reduction in the pathogenic ELANE mutation in the cells is measured by, e.g. Next Generation Sequencing.

It is understood that the CRISPR/Cas9 gene editing system enables targeting the nuclease to a target site in a sequence specific manner to address disease-causing mutations. Hematopoietic stem and progenitor cells (HSPCs) have therapeutic potential because of their ability to both self-renew and differentiate (Yu, Natanson, and Dunbar 2016). Accordingly, embodiments of the present invention apply genome editing to HSPCs.

In embodiments of the present invention, an autologous therapy and utilizes autologous CD34+ hematopoietic stem cells from patients diagnosed with SCN or CyN which are edited with CRISPR/Cas9. In embodiments of the present invention, CD34+ cells are isolated from bone marrow or peripheral blood mononucleated cells (PBMCs) following patient apheresis.

In the case of dominant negative (or compound heterozygous) indications, such as SCN or CyN, the strategy is to edit the mutant allele and avoid cleavage in the non-mutant allele or other off targets by targeting a heterozygous SNP sequence.

Embodiments of the present invention may include the following steps:

- Selection of a patient diagnosed with SCN or CyN identified as exhibiting heterozygosity in at least one of the SNPs of Table 1 hereinbelow. In embodiments of the present invention, the subject is heterozygous at rs10414837, rs3761005, or rs1683564;
- Selection of a therapeutic strategy based on the identified heterozygous SNP position of the candidate patient;
- Obtaining HSPC cells from the bone marrow of the subject either by aspiration or by mobilization and apheresis of peripheral blood, optionally, the HSPC cells are processed (e.g., enriched, stimulated, both);
- Introducing into the HSPC cells (e.g., by ex vivo electroporation) a composition comprising:
  - a CRISPR nuclease or a sequence encoding the same (e.g., mRNA),
  - a discriminatory RNA molecule that targets a particular sequence in the identified heterozygous SNP position of the mutant allele (REF/ALT sequence), and
  - a non-discriminatory RNA molecule targeting a sequence in intron 3, intron 4 or 3' UTR, which is common to both the mutant allele and the other allele,
  - thereby editing the HSPC cells to knockout expression of mutant ELANE allele; and
- Introducing the edited HSPC to the candidate patient.

In embodiments of the present invention, CD34+ cells may be isolated from bone marrow or peripheral blood mononucleated cells (PBMCs) following patient apheresis. Bone marrow or PBMCs may be collected from the patient by apheresis following HSPC mobilization. In embodiments of the invention the apheresis product may be washed to remove platelets and a CD34+ cell population may be enriched via purification using, e.g. a CliniMACS system (Miltenyi Biotec). In embodiments of the present invention, the selected cells may be prestimulated ex vivo, e.g. with a mixture of recombinant human cytokines. In embodiments of the present invention, the cells may undergo electroporation. In embodiments of the present invention, prior to electroporation, stimulated cells (e.g. CD34+ cells), the CRISPR nuclease mRNA and gRNA may be preincubated under defined conditions. In embodiments of the present invention, the cells are electroporated ex vivo with the CRISPR nuclease mRNA/gRNA mixture or with a preassembled RNPs (Ribonuclease protein of the CRISPR nuclease protein and gRNA), followed by cell washing. In embodiments of the present invention, the cells are suspended into a final formulation. In embodiments of the present invention, the cells may be resuspended. In embodiments of the present invention, the resuspended cells may be filled into bags for infusion. In embodiments of the present invention, the bags may be frozen using a freeze down step in a controlled rate freezer and/or stored in the vapor phase of liquid nitrogen. In embodiments of the present invention, the product may be administered by intravenous (IV) administration to a patient.

Dominant Genetic Disorders

One of skill in the art will appreciate that all subjects with any type of heterozygote genetic disorder (e.g., dominant genetic disorder) may be subjected to the methods described herein. In one embodiment, the present invention may be used to target a gene involved in, associated with, or causative of dominant genetic disorders such as, for example, SCN or CyN. In some embodiments, the dominant genetic disorder is SCN or CyN. In some embodiments, the target gene is the ELANE gene (Entrez Gene, gene ID No: 335).

CRISPR Nucleases and PAM Recognition

In some embodiments, the sequence specific nuclease is selected from CRISPR nucleases, or a functional variant thereof. In some embodiments, the sequence specific nuclease is an RNA guided DNA nuclease. In such embodiments, the RNA sequence which guides the RNA guided DNA nuclease (e.g., Cpf1) binds to and/or directs the RNA guided DNA nuclease to the sequence comprising at least one nucleotide which differs between a mutant allele and its counterpart functional allele (e.g., SNP). In some embodiments, the CRISPR complex does not further comprise a tracrRNA. In a non-limiting example, in which the RNA guided DNA nuclease is a CRISPR protein, the at least one nucleotide which differs between the dominant mutant allele and the functional allele may be within the PAM site and/or proximal to the PAM site within the region that the RNA molecule is designed to hybridize to. A skilled artisan will appreciate that RNA molecules can be engineered to bind to a target of choice in a genome by commonly known methods in the art.

In embodiments of the present invention, a type II CRISPR system utilizes a mature crRNA:tracrRNA complex directs a CRISPR nuclease, e.g. Cas9, to the target DNA via Watson-Crick base-pairing between the crRNA and the protospacer on the target DNA next to the protospacer adjacent motif (PAM), an additional requirement for target recognition. The CRISPR nuclease then mediates cleavage of target DNA to create a double-stranded break within the protospacer. A skilled artisan will appreciate that each of the engineered RNA molecule of the present invention is further designed such as to associate with a target genomic DNA sequence of interest next to a protospacer adjacent motif (PAM), e.g., a PAM matching the sequence relevant for the type of CRISPR nuclease utilized, such as for a non-limiting example, NGG or NAG, wherein "N" is any nucleobase, for *Streptococcus pyogenes* Cas9 WT (SpCAS9); NNGRRT for *Staphylococcus aureus* (SaCas9); NNNVRYM for *Jejuni* Cas9 WT; NGAN or NGNG for SpCas9-VQR variant; NGCG for SpCas9-VRER variant; NGAG for SpCas9-EQR variant; NNNNGATT for *Neisseria meningitidis* (NmCas9); or TTTV for Cpf1. RNA molecules of the present invention are each designed to form complexes in conjunction with one or more different CRISPR nucleases and designed to target polynucleotide sequences of interest utilizing one or more different PAM sequences respective to the CRISPR nuclease utilized.

In some embodiments, an RNA-guided DNA nuclease e.g., a CRISPR nuclease, may be used to cause a DNA break at a desired location in the genome of a cell. The most commonly used RNA-guided DNA nucleases are derived from CRISPR systems, however, other RNA-guided DNA nucleases are also contemplated for use in the genome editing compositions and methods described herein. For instance, see U.S. Patent Publication No. 2015-0211023, incorporated herein by reference.

CRISPR systems that may be used in the practice of the invention vary greatly. CRISPR systems can be a type I, a type II, type III, or type V system. Non-limiting examples of suitable CRISPR proteins include Cas3, Cas4, Cas5, Cas5e (or CasD), Cas6, Cas6e, Cas6f, Cas7, Cas8a1, Cas8a2, Cas8b, Cas8c, Cas9, Cas10, Cas12a, Cas12b, Cas12c, Cas12d, Cas12d, Cas1 Od, CasF, CasG, CasH, Csy1, Csy2, Csy3, Cse1 (or CasA), Cse2 (or CasB), Cse3 (or CasE), Cse4 (or CasC), Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csxl7, Csxl4, Csx10, Csxl6, CsaX, Csx3, Csz1, Csx15, Csf1, Csf2, Csf3, Csf4, and Cu1966. (See, e.g., Koonin 2017).

In some embodiments, the RNA-guided DNA nuclease is a CRISPR nuclease derived from a type 11 CRISPR system (e.g., Cas9). The CRISPR nuclease may be derived from *Streptococcus pyogenes, Streptococcus thermophilus, Streptococcus* sp., *Staphylococcus aureus, Neisseria meningitidis, Treponema denticola, Nocardiopsis dassonvillei, Streptomyces pristinaespiralis, Streptomyces viridochromogenes, Streptomyces viridochromogenes, Streptosporangium roseum, Streptosporangium roseum, Alicyclobacillus acidocaldarius, Bacillus* pseudomycoides, *Bacillus selenitireducens, Exiguobacterium sibiricum, Lactobacillus delbrueckii, Lactobacillus salivarius, Microscilla marina, Burkholderiales bacterium, Polaromonas naphihalenivorans, Polaromonas* sp., *Crocosphaera watsonii, Cyanothece* sp., *Microcystis aeruginosa, Synechococcus* sp., *Acetohalobium arabaticum, Ammonifex degensii, Caldicelulosiruptor becscii, Candidatus Desulforudis, Clostridium botulinum, Clostridium diffjicile, Finegoldia magna, Natranaerobius thermophilus, Pelotomaculumthermopropionicum, Acidithiobacillus caldus, Acidithiobacillus ferrooxidans, Allochromatium vinosum, Marinobacter* sp., *Nitrosococcus halophilus, Nitrosococcus watsoni, Pseudoalteromonas haloplanktis, Ktedonobacter racemifer, Methanohalobium evestigatum, Anabaena variabilis, Nodularia spumigena, Nostoc* sp., *Arthrospira maxima, Arthrospira*

*platensis, Arthrospira* sp., *Lyngbya* sp., *Microcoleus chthonoplastes, Oscillatoria* sp., *Petrotoga mobilis, Thermosipho africanus, Acaryochloris marina, Francisella* cf. *novicida* Fxl, *Alicyclobacillus acidoterrestris, Oleiphilus* sp., Bacterium CG09_39_24, Deltaproteobacteria bacterium, or any species which encodes a CRISPR nuclease with a known PAM sequence. CRISPR nucleases encoded by uncultured bacteria may also be used in the context of the invention. (See Burstein et al. Nature, 2017). Variants of CRIPSR proteins having known PAM sequences e.g., spCas9 DI 135E variant, spCas9 VQR variant, spCas9 EQR variant, or spCas9 VRER variant may also be used in the context of the invention.

Thus, an RNA guided DNA nuclease of a CRISPR system, such as a Cas9 protein or modified Cas9 or homolog or ortholog of Cas9, or other RNA guided DNA nucleases belonging to other types of CRISPR systems, such as Cpf1 and its homologs and orthologs, may be used in the compositions of the present invention.

In certain embodiments, the CRIPSR nuclease may be a "functional derivative" of a naturally occurring Cas protein. A "functional derivative" of a native sequence polypeptide is a compound having a qualitative biological property in common with a native sequence polypeptide. "Functional derivatives" include, but are not limited to, fragments of a native sequence and derivatives of a native sequence polypeptide and its fragments, provided that they have a biological activity in common with a corresponding native sequence polypeptide. A biological activity contemplated herein is the ability of the functional derivative to hydrolyze a DNA substrate into fragments. The term "derivative" encompasses both amino acid sequence variants of polypeptide, covalent modifications, and fusions thereof. Suitable derivatives of a Cas polypeptide or a fragment thereof include but are not limited to mutants, fusions, covalent modifications of Cas protein or a fragment thereof. Cas protein, which includes Cas protein or a fragment thereof, as well as derivatives of Cas protein or a fragment thereof, may be obtainable from a cell or synthesized chemically or by a combination of these two procedures. The cell may be a cell that naturally produces Cas protein, or a cell that naturally produces Cas protein and is genetically engineered to produce the endogenous Cas protein at a higher expression level or to produce a Cas protein from an exogenously introduced nucleic acid, which nucleic acid encodes a Cas that is same or different from the endogenous Cas. In some cases, the cell does not naturally produce Cas protein and is genetically engineered to produce a Cas protein.

In some embodiments, the CRISPR nuclease is Cpf1. Cpf1 is a single RNA-guided endonuclease which utilizes a T-rich protospacer-adjacent motif. Cpf1 cleaves DNA via a staggered DNA double-stranded break. Two Cpf1 enzymes from Acidaminococcus and Lachnospiraceae have been shown to carry out efficient genome-editing activity in human cells. (See Zetsche et al. (2015) Cell.).

Thus, an RNA guided DNA nuclease of a Type 11 CRISPR System, such as a Cas9 protein or modified Cas9 or homologs, orthologues, or variants of Cas9, or other RNA guided DNA nucleases belonging to other types of CRISPR systems, such as Cpf1 and its homologs, orthologues, or variants, may be used in the present invention.

In some embodiments, the guide molecule comprises one or more chemical modifications which imparts a new or improved property (e.g., improved stability from degradation, improved hybridization energetics, or improved binding properties with an RNA guided DNA nuclease). Suitable chemical modifications include, but are not limited to one or more of: modified bases, modified sugar moieties, or modified inter-nucleoside linkages. Non-limiting examples of suitable chemical modifications include: 4-acetylcytidine, 5-(carboxyhydroxymethyl)uridine, 2'-O-methylcytidine, 5-carboxymethylaminomethyl-2-thiouridine, 5-carboxymethylaminomethyluridine, dihydrouridine, 2'-O-methylpseudouridine, "beta, D-galactosylqueuosine", 2'-O-methylguanosine, inosine, N6-isopentenyladenosine, 1-methyladenosine, 1-methylpseudouridine, 1-methylguanosine, 1-methylinosine, "2,2-dimethylguanosine", 2-methyladenosine, 2-methylguanosine, 3-methylcytidine, 5-methylcytidine, N6-methyladenosine, 7-methylguanosine, 5-methylaminomethyluridine, 5-methoxyaminomethyl-2-thiouridine, "beta, D-mannosylqueuosine", 5-methoxycarbonylmethyl-2-thiouridine, 5-methoxycarbonylmethyluridine, 5-methoxyuridine, 2-methylthio-N6-isopentenyladenosine, N-((9-beta-D-ribofuranosyl-2-methylthiopurine-6-yl)carbamoyl)threonine, N-((9-beta-D-ribofuranosylpurine-6-yl) N-methylcarbamoyl)threonine, uridine-5-oxyacetic acid-methylester, uridine-5-oxyacetic acid, wybutoxosine, queuosine, 2-thiocytidine, 5-methyl-2-thiouridine, 2-thiouridine, 4-thiouridine, 5-methyluridine, N-((9-beta-D-ribofuranosylpurine-6-yl)-carbamoyl)thrmonine, 2'-O-methyl-5-methyluridine, 2'-O-methyluridine, wybutosine, "3-(3-amino-3-carboxy-propyl)uridine, (acp3) u", 2'-O-methyl (M), 3'-phosphorothioate (MS), 3'-thioPACE (MSP), pseudouridine, or 1-methyl pseudo-uridine. Each possibility represents a separate embodiment of the present invention.

Further non-limiting examples of suitable chemical modifications include: $m^1A$ (1-methyladenosine); $m^2A$ (2-methyladenosine); Am (2'-O-methyladenosine); $ms^2m^6A$ (2-methylthio-$N^6$-methyladenosine); $i^6A$ ($N^6$-isopentenyladenosine); $ms^2i^6A$ (2-methylthio-$N^6$isopentenyladeno sine); $io^6A$ ($N^6$-(cis-hydroxyisopentenyl)adenosine); $ms^2io^6A$ (2-methylthio-$N^b$-(cis-hydroxyisopentenyl) adenosine); $g^6A$ ($N^6$-glycinylcarbamoyladenosine); $t^6A$ ($N^6$-threonylcarbamoyladenosine); $ms^2t^6A$ (2-methylthio-$N^6$-threonyl carhamoyladenosine); $m^6t^6A$ ($N^6$-methyl-$N^6$-threonylcarbamoyladenosine); $hn^6A$ ($N^6$-hydroxynorvalylcarbamoyladenosine); $ms^2hn^6A$ (2-methylthio-$N^6$-hydroxynorvalyl carbamoyladenosine); Ar(p) (2'-O-ribosyladenosine (phosphate)); I (inosine); $m^1I$ (1-methylinosine); $m^1Im$ (1,2'-O-dimethylinosine); $m^3C$ (3-methylcytidine); Cm (2'-O-methylcytidine); $s^2C$ (2-thiocytidine); $ac^4C$ ($N^4$-acetylcytidine); $f^5C$ (5-formylcytidine); $m^5Cm$ (5,2'-O-dimethylcytidine); $ac^4Cm$ ($N^4$-acetyl-2'-O-methylcytidine); $k^2C$ (lysidine); $m^1G$ (1-methylguanosine); $m^2G$ ($N^2$-methylguanosine); $m^7G$ (7-methylguanosine); Gm (2'-O-methylguanosine); $m^2$ 2G ($N^2$,$N^2$-dimethylguanosine); $m^2Gm$ ($N^2$,2'-O-dimethylguanosine); $m^2{}_2Gm$ ($N^2$,$N^2$,2'-O-trimethylguanosine); Gr(p) (2'-O-ribosylguanosine (phosphate)); yW (wybutosine); $o_2yW$ (peroxywybutosine); OHyW (hydroxywybutosine); OHyW* (undermodified hydroxywybutosine); imG (wyosine); mimG (methylwyosinc); Q (queuosine); oQ (epoxyqucuosine); galQ (galactosyl-queuosine); manQ (mannosyl-queuosine); $preQ_0$ (7-cyano-7-deazaguanosine); $preQ_1$ (7-aminomethyl-7-deazaguanosine); $G^4$ (archaeosine); D (dihydrouridine); $m^5Um$ (5,2'-O-dimethyluridine); $s^4U$ (4-thiouridine); $m^5s^2U$ (5-methyl-2-thiouridine); $s^2Um$ (2-thio-2'-O-methyluridine); $acp^3U$ (3-(3-amino-3-carboxypropyl)uridine); $ho^5U$ (5-hydroxyuridine); $mo^5U$ (5-methoxyuridine); $cmo^5U$ (uridine 5-oxyacetic acid); $mCmo^5U$ (uridine 5-oxyacetic acid methyl ester); $chm^5U$ (5-(carboxyhydroxymethyl)uridine)); $mchm^5U$ (5-(carboxyhydroxymethyl)uridine methyl ester); $mcm^5U$ (5-methoxycarbonylmethyluridine); $mcm^3Um$ (5-methuxycarbonylmethyl-2'-O-methyluridine); mcm$^5$s$^2$U (5-methoxycarbonylmcthyl-2-thiouridine); nm$^5$S$^2$U (5-aminomethyl-2-thiouridine); mnm$^5$-U (5-methylaminomethyluridine); mnm$^5$s$^2$U (5-methylaminomethyl-2-thiouridine); mnm$^5$se$^2$U (5-methylaminomethyl-2-selenouridine); ncm$^5$U (5-carbamoylmethyluridine); ncm$^5$Um (5-carbamoylmethyl-2'-O-methyluridine); cmnm$^5$U (5-carboxymethylaminomethyluridine); cmnm$^5$Um (5-carboxymethylaminomethyl-2'-O-methyluridine); cmmm$^3$s$^2$U (5-carboxymethylaminomethyl-2-thiouridine); dimethyladenosine); Im (2'-O-methylinosine); m$^4$C (N$^4$-methylcytidine); m$^4$Cm (N$^4$,2'-O-dimethylcytidine); hm$^5$C (5-hydroxymethylcytidine); m$^3$U (3-methyluridine); cm$^5$U (5-carboxymethyluridine); m$^6$An (N$^6$,2'-O-dimethyladenosine); m$^6$ $_2$Am (N$^6$,N$^6$,O-2'-trimethyladenosine); m$^{2,7}$G (N$^2$, 7-dimethylguanosine); m2,2,7G (N$^2$,N$^2$,7-trimethylguanosine); m$^3$Um (3,2'-O-dimethyluridine); m$^5$D (5-methyldihydrouridine); f$^5$Cm (5-formyl-2'-O-methylcytidine); m$^1$ Gm (1,2'-O-dimethylguanosine); m$^1$Am (1,2'-O-dimethyladenosine); τm$^5$-U (5-taurinomethyluridine); τm$^5$s$^2$U (5-taurinomethyl-2-thiouridine)); imG-14 (4-demethylwyosine); imG2 (isowyosine); or ac$^6$A (N$^6$-acetyladenosine). Each possibility represents a separate embodiment of the present invention. (See e.g. U.S. Pat. No. 9,750,824).

Guide Sequences which Specifically Target a Mutant Allele

A given gene may contain thousands of SNPs. Utilizing a 24 base pair target window for targeting each SNP in a gene would require hundreds of thousands of guide sequences. Any given guide sequence when utilized to target a SNP may result in degradation of the guide sequence, limited activity, no activity, or off-target effects. Accordingly, suitable guide sequences are necessary for targeting a given gene. By the present invention, a novel set of guide sequences have been identified for knocking out expression of a mutated protein, inactivating a mutant ELANE gene allele, and treating SCN or CyN.

The present disclosure provides guide sequences capable of specifically targeting a mutant allele for inactivation while leaving the functional allele unmodified. The guide sequences of the present invention are designed to, and are most likely to, specifically differentiate between a mutant allele and a functional allele. Of all possible guide sequences which target a mutant allele desired to be inactivated, the specific guide sequences disclosed herein are specifically effective to function with the disclosed embodiments.

Briefly, the guide sequences may have properties as follows: (1) target a heterozygous SNP/insertion/deletion/indel with a high prevalence in the general population, in a specific ethnic population or in a patient population is above 1% and the SNP/insertion/deletion/indel heterozygosity rate in the same population is above 1%; (2) target a location of a SNP/insertion/deletion/indel proximal to a portion of the gene e.g., within 5k bases of any portion of the gene, for example, a promoter, a UTR, an exon or an intron; and (3) target a mutant allele using an RNA molecule which targets a founder or common pathogenic mutations for the disease/gene. In some embodiments, the prevalence of the SNP/insertion/deletion/indel in the general population, in a specific ethnic population or in a patient population is above 1%, 2%, 3%, 4%, 5%, 6%, 7%, 8%, 9%, 10%, 11%, 12%, 13%, 14%, or 15% and the SNP/insertion/deletion/indel heterozygosity rate in the same population is above 1%, 2%, 3%, 4%, 5%, 6%, 7%, 8%, 9%, 10%, 11%, 12%, 13%, 14%, or 15%. Each possibility represents a separate embodiment and may be combined at will.

For each gene, according to SNP/insertion/deletion/indel any one of the following strategies may be used to deactivate the mutant allele: (1) Knockout strategy using one RNA molecule—one RNA molecule is utilized to direct a CRISPR nuclease to a mutant allele and create a double-strand break (DSB) leading to formation of a frameshift mutation in an exon or in a splice site region of the mutant allele; (2) Knockout strategy using two RNA molecules—two RNA molecules are utilized. A first RNA molecule targets a region in the promoter or an upstream region of a mutant allele and another RNA molecule targets downstream of the first RNA molecule in a promoter, exon, or intron of the mutant allele; (3) Exon(s) skipping strategy—one RNA molecule may be used to target a CRISPR nuclease to a splice site region, either at the 5'end of an intron (donor sequence) or the 3' end of an intron (acceptor sequence), in order to destroy the splice site. Alternatively, two RNA molecules may be utilized such that a first RNA molecule targets an upstream region of an exon and a second RNA molecule targets a region downstream of the first RNA molecule, thereby excising the exon(s). Based on the locations of identified SNPs/insertions/deletions/indels for each mutant allele, any one of, or a combination of, the above-mentioned methods to deactivate the mutant allele may be utilized.

When only one RNA molecule is used is that the location of the SNP is in an exon or in close proximity (e.g., within 20 basepairs) to a splice site between the intron and the exon. When two RNA molecules are used, guide sequences may target two SNPs such that the first SNP is upstream of exon 1 e.g., within the 5' untranslated region, or within the promoter or within the first 2 kilobases 5' of the transcription start site, and the second SNP is downstream of the first SNP e.g., within the first 2 kilobases 5' of the transcription start site, or within intron 1, 2 or 3, or within exon 1, exon 2, or exon 3.

Guide sequences of the present invention may target a SNP in the upstream portion of the targeted gene, preferably upstream of the last exon of the targeted gene. Guide sequences may target a SNP upstream to exon 1, for example within the 5' untranslated region, or within the promoter or within the first 4-5 kilobases 5' of the transcription start site.

Guide sequences of the present invention may also target a SNP within close proximity (e.g., within 50 basepairs, more preferably with 20 basepairs) to a known protospacer adjacent motif (PAM) site.

Guide sequences of the present invention also may target: (1) a heterozygous SNP for the targeted gene; (2) a heterozygous SNPs upstream and downstream of the gene; (3) a SNPs with a prevalence of the SNP/insertion/deletion/indel in the general population, in a specific ethnic population, or in a patient population above 1%; (4) have a guanine-cytosine content of greater than 30% and less than 85%; (5) have no repeat of 4 or more thymine/uracil or 8 or more guanine, cytosine, or adenine; (6) having no off-target identified by off-target analysis; and (7) preferably target Exons over Introns or be upstream of a SNP rather than downstream of a SNP.

In embodiments of the present invention, the SNP may be upstream or downstream of the gene. In embodiments of the present invention, the SNP is within 4,000 base pairs upstream or downstream of the gene.

The at least one nucleotide which differs between the mutant allele and the functional allele, may be upstream, downstream or within the sequence of the disease-causing mutation of the gene of interest. The at least one nucleotide which differs between the mutant allele and the functional allele, may be within an exon or within an intron of the gene of interest. In some embodiments, the at least one nucleotide which differs between the mutant allele and the functional allele is within an exon of the gene of interest. In some embodiments, the at least one nucleotide which differs between the mutant allele and the functional allele is within an intron or an exon of the gene of interest, in close proximity to a splice site between the intron and the exon e.g., 1, 2, 3, 4, 5, 6, 7, 8, 9, 10, 11, 12, 13, 14, 15, 16, 17, 18, 19, or 20 nucleotides upstream or downstream to the splice site.

In some embodiments, the at least one nucleotide is a single nucleotide polymorphisms (SNPs). In some embodiments, each of the nucleotide variants of the SNP may be expressed in the mutant allele. In some embodiments, the SNP may be a founder or common pathogenic mutation.

Guide sequences may target a SNP which has both (1) a high prevalence in the general population e.g., above 1% in the population; and (2) a high heterozygosity rate in the population, e.g., above 1%. Guide sequences may target a SNP that is globally distributed. A SNP may be a founder or common pathogenic mutation. In some embodiments, the prevalence in the general population is above 1%, 2%, 3%, 4%, 5%, 6%, 7%, 8%, 9%, 10%, 11%, 12%, 13%, 14%, or 15%. Each possibility represents a separate embodiment. In some embodiments, the heterozygosity rate in the population is above 1%, 2%, 3%, 4%, 5%, 6%, 7%, 8%, 9%, 10%, 11%, 12%, 13%, 14%, or 15%. Each possibility represents a separate embodiment.

In some embodiments, the at least one nucleotide which differs between the mutant allele and the functional allele is linked to/co-exists with the disease-causing mutation in high prevalence in a population. In such embodiments, "high prevalence" refers to at least 92%, 93%, 94%, 95%, 96%, 97%, 98%, 99%, or 100%. Each possibility represents a separate embodiment of the present invention. In one embodiment, the at least one nucleotide which differs between the mutant allele and the functional allele, is a disease-associated mutation. In some embodiments, the SNP is highly prevalent in the population. In such embodiments, "highly prevalent" refers to at least 10%, 11%, 12%, 13%, 14%, 15%, 20%, 30%, 40%, 50%, 60%, or 70% of a population. Each possibility represents a separate embodiment of the present invention.

Guide sequences of the present invention may satisfy any one of the above criteria and are most likely to differentiate between a mutant allele from its corresponding functional allele.

In some embodiments the RNA molecule targets a heterozygous SNP present in the ELANE gene from the SNPs as shown in Table 1 below. The SNP details are indicated in the 1$^{st}$ column and include: SNP ID No. (based on NCBI's 2018 database of Single Nucleotide Polymorphisms (dbSNP)). For variants with no available rs number variants characteristic are indicated based on gnomAD 2018 browser database. The 2$^{nd}$ column indicates an assigned identifier for each SNP. The 3$^{rd}$ column indicates the location of each SNP on the ELANE gene.

TABLE 1

| ELANE gene SNPs | | |
|---|---|---|
| RSID | SNP No. | SNP location in the gene |
| rs9749274 | s1 | downstream +972bp |
| rs740021 | s2 | upstream −198bp |
| rs201048029 | s3 | upstream −2614bp |
| rs199720952 | s4 | downstream +173bp |
| rs28591229 | s5 | downstream +2053bp |
| rs71335276 | s6 | downstream +3125bp |
| rs58082177 | s7 | upstream −2840bp |
| rs3826946 | s8 | upstream −2103bp |
| rs10413889 | s9 | upstream −2003bp |
| rs3761005 | s10 | upstream −1509bp |
| rs761481944 | s11 | downstream +2824bp |
| rs3761008 | s12 | upstream −2279bp |
| rs10409474 | s13 | upstream −1569bp |
| rs3761007 | s14 | upstream −1728bp |
| rs1683564 | s15 | downstream +2971bp |
| rs17216649 | s16 | Exon_5 of 5 |
| rs10469327 | s17 | downstream +2133bp |
| rs8107095 | s18 | downstream +3588bp |
| rs10414837 | s19 | upstream −2684bp |
| rs10424470 | s20 | upstream −3504bp |
| rs78302854 | s21 | downstream +862bp |

Figure 5:
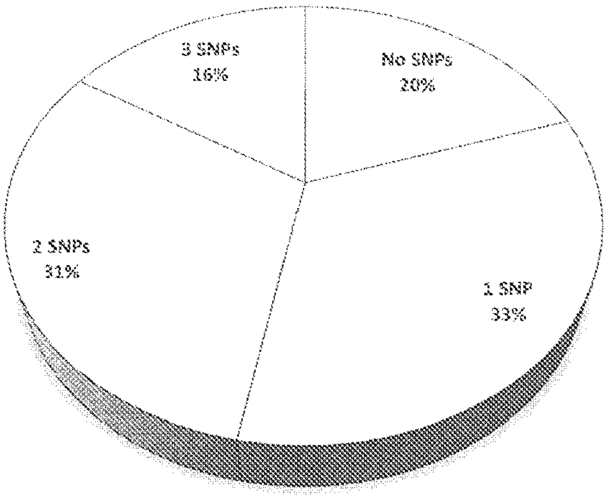
FIG. 5: The expected coverage in the population based on heterozygotes frequency and overlap/linkage between select heterozygous SNPs. Designing alternative solutions for the three therapeutic strategies may enable a coverage of about 80% of the population. It is evaluated that 80% of the population bear one or more heterozygous SNPs from the list above. From which 33% bear one heterozygous SNP, 31% two heterozygous SNPs from the list, 16% bear three heterozygous SNPs. Whereas 20% don't bear any of the SNPs listed above.

FIG. 5 discloses the heterogenicity of given selections of SNPs from Table 1 in the human population.

Figure 2:
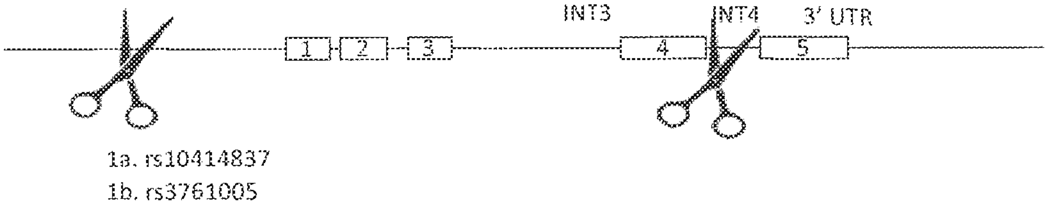
FIG. 2: excising the promoter region from an upstream SNP position until intron 3 or intron 4 or the 3' UTR. In one example, a first guide sequence targets a specific sequence of a heterozygous SNP position in an upstream region of the mutant allele (strategy 1a-rs10414837, strategy 1b-rs3761005) and a second guide sequence targets a sequence in intron 3 which is common to two alleles of the gene. In another, a first guide sequence targets a specific sequence of a heterozygous SNP position in an upstream region of the mutant allele (strategy 1a-rs10414837, strategy 1b-rs3761005) and a second guide sequence targets a sequence in 3' UTR which is common to two alleles of the gene.

Embodiments of the present invention may include excising the promoter region from an upstream SNP position until intron 3 or intron 4 or the 3' UTR. In an embodiment, a first guide sequence targets a specific sequence of a heterozygous SNP position in an upstream region of the mutant allele (strategy 1a-rs10414837, strategy 1b-rs3761005) and a second guide sequence targets a sequence in intron 4 which is common to two alleles of the gene. (FIG. 1). In a further embodiment, a first guide sequence targets a specific sequence of a heterozygous SNP position in an upstream region of the mutant allele (strategy 1a-rs10414837, strategy 1b-rs3761005) and a second guide sequence targets a sequence in intron 3 which is common to two alleles of the gene. In another, a first guide sequence targets a specific sequence of a heterozygous SNP position in an upstream region of the mutant allele (strategy 1a-rs10414837, strategy 1 b-rs3761005) and a second guide sequence targets a sequence in 3' UTR which is common to two alleles of the gene. (FIG. 2).

Figure 3:
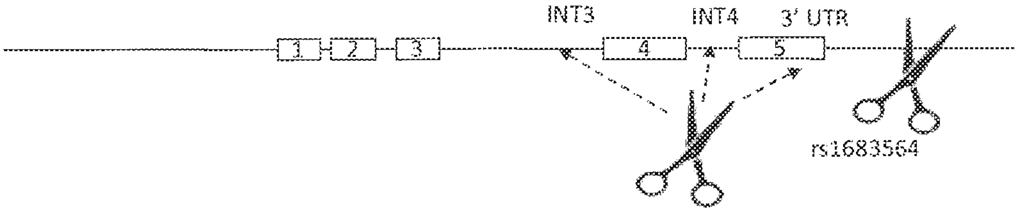
FIG. 3: excising from intron 3 or intron 4 or 3' UTR to regions downstream to the 3' UTR. In one example, a first guide sequence targets a specific sequence of a heterozygous SNP position in an upstream region of the mutant allele (strategy 2-rs1683564) and a second guide sequence targets a sequence in intron 4 which is common to two alleles of the gene. In another, a first guide sequence targets a specific sequence of a heterozygous SNP position in an upstream region of the mutant allele (strategy 2-rs1683564) and a second guide sequence targets a sequence in intron 3 which is common to two alleles of the gene. In a further, a first guide sequence targets a specific sequence of a heterozygous SNP position in an upstream region of the mutant allele (strategy 2-rs1683564) and a second guide sequence targets a sequence in 3' UTR which is common to two alleles of the gene.

Embodiments of the present invention may include excising from intron 3 or intron 4 or 3' UTR to regions downstream to the 3' UTR. In an embodiment, a first guide sequence targets a specific sequence of a heterozygous SNP position in an upstream region of the mutant allele (strategy 2-rs1683564) and a second guide sequence targets a sequence in intron 4 which is common to two alleles of the gene. In a further embodiment, a first guide sequence targets a specific sequence of a heterozygous SNP position in an upstream region of the mutant allele (strategy 2-rs1683564) and a second guide sequence targets a sequence in intron 3 which is common to two alleles of the gene. In a further, a first guide sequence targets a specific sequence of a heterozygous SNP position in an upstream region of the mutant allele (strategy 2-rs1683564) and a second guide sequence targets a sequence in 3' UTR which is common to two alleles of the gene. (FIG. 3).

Figure 4:
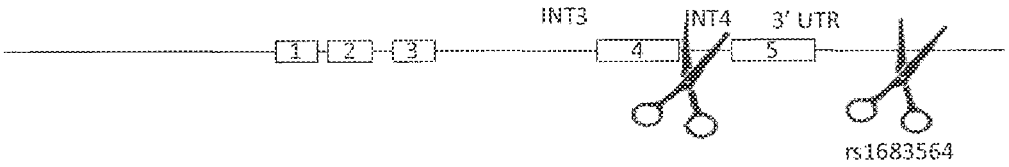
FIG. 4: excising from intron 3 or intron 4 or 3' UTR to regions downstream to the 3' UTR. The strategy is designed such as to specifically knock-out the disease-causing allele ('mutant allele'), while leaving the healthy allele intact. Allele specific editing is achieved by using guides that target discriminating (heterozygous) SNP positions with relatively high heterozygosity frequency in the population.

Embodiments of the present invention excising from intron 3 or intron 4 or 3' UI'R to regions downstream to the 3' UTR. The strategy is designed such as to specifically knock-out the disease-causing allele ('mutant allele'), while leaving the healthy allele intact. Allele specific editing is achieved by using guides that target discriminating (heterozygous) SNP positions with relatively high heterozygosity frequency in the population. (FIG. 4).

Delivery to Cells

It is understood that in the methods embodied, the RNA molecules and compositions described herein may be delivered to a target cell or subject by any suitable means. The following embodiments provide non-limiting examples of methods of delivery of the RNA molecules and composition of the present invention.

In some embodiments, RNA molecule compositions of the present invention may be targeted to any cell which contains and/or expresses a dominant negative allele, including any mammalian or plant cell. For example, in one embodiment the RNA molecule specifically targets a mutant ELANE allele and the target cell is a hepatocyte cell.

Any suitable viral vector system may be used to deliver nucleic acid compositions e.g., the RNA molecule compositions of the subject invention. Conventional viral and non-viral based gene transfer methods can be used to introduce nucleic acids and target tissues. In certain embodiments, nucleic acids are administered for in vivo or ex vivo gene therapy uses. Non-viral vector delivery systems include naked nucleic acid, and nucleic acid complexed with a delivery vehicle such as a liposome or poloxamer. For a review of gene therapy procedures, see Anderson (1992) Science 256:808-813; Nabel & Felgner (1993) TIBTECH 11:211-217; Mitani & Caskey (1993) TIBTECH 11:162-166; Dillon (1993) TIBTECH 11:167-175; Miller (1992) Nature 357:455-460; Van Brunt (1988) Biotechnology 6(10):1149-1154; Vigne (1995) Restorative Neurology and Neuroscience 8:35-36; Kremer & Perricaudet (1995) British Medical Bulletin 51(1):31-44; Haddada et al. (1995) in Current Topics in Microbiology and Immunology Doerfler and Bohm (eds.); and Yu et al. (1994) Gene Therapy 1:13-26.

Methods of non-viral delivery of nucleic acids and/or proteins include electroporation, lipofection, microinjection, biolistics, particle gun acceleration, virosomes, liposomes, immunoliposomes, lipid nanoparticles (LNPs), polycation or lipid:nucleic acid conjugates, artificial virions, and agent-enhanced uptake of nucleic acids or can be delivered to plant cells by bacteria or viruses (e.g., *Agrobacterium, Rhizobium* sp. NGR234*, Sinorhizoboiummeliloti, Mesorhizobium loti*, tobacco mosaic virus, potato virus X, cauliflower mosaic virus and cassava vein mosaic virus). (See, e.g., Chung et al. (2006) Trends Plant Sci. 11 (1):1-4). Sonoporation using, e.g., the Sonitron 2000 system (Rich-Mar), can also be used for delivery of nucleic acids. Cationic-lipid mediated delivery of proteins and/or nucleic acids is also contemplated as an in vivo or in vitro delivery method. (See Zuris et al. (2015) Nat. Biotechnol. 33(1):73-80; see also Coelho et al. (2013) N. Engl. J. Med. 369, 819-829; Judge et al. (2006) Mol. Ther. 13, 494-505; and Basha et al. (2011) Mol. Ther. 19, 2186-2200).

Additional exemplary nucleic acid delivery systems include those provided by Amaxa® Biosystems (Cologne, Germany), Maxcyte, Inc. (Rockville, Md.), BTX Molecular Delivery Systems (Holliston, Mass.) and Copernicus Therapeutics Inc., (see, e.g., U.S. Pat. No. 6,008,336). Lipofection is described in e.g., U.S. Pat. Nos. 5,049,386, 4,946,787; and 4,897,355, and lipotection reagents are sold commercially (e.g., Transfectan™, Lipofectin™, and Lipofectamine™, RNA iMAX). Cationic and neutral lipids that are suitable for efficient receptor-recognition lipofection of polynucleotides include those of Felgner, WO 91/17424, WO 91/16024. Delivery can be to cells (ex vivo administration) or target tissues (in vivo administration).

The preparation of lipid:nucleic acid complexes, including targeted liposomes such as immunolipid complexes, is well known to one of skill in the art (See, e.g., Crystal (1995) Science 270:404-410; Blaese et al. (1995) Cancer Gene Ther. 2:291-297; Behr et al. (1994) Bioconjugate Chem. 5:382-389; Remy et al. (1994) Bioconjugate Chem. 5:647-654; Gao et al. (1995) Gene Therapy 2:710-722; Ahmad et al. (1992) Cancer Res. 52:4817-4820; U.S. Pat. Nos. 4,186,183, 4,217,344, 4,235,871, 4,261,975, 4,485,054, 4,501,728, 4,774,085, 4,837,028, and 4,946,787).

Additional methods of delivery include the use of packaging the nucleic acids to be delivered into EnGeneIC delivery vehicles (EDVs). These EDVs are specifically delivered to target tissues using bispecific antibodies where one arm of the antibody has specificity for the target tissue and the other has specificity for the EDV. The antibody brings the EDVs to the target cell surface and then the EDV is brought into the cell by endocytosis. Once in the cell, the contents are released (See MacDiarmid et al (2009) Nature Biotechnology 27(7):643).

The use of RNA or DNA viral based systems for viral mediated delivery of nucleic acids take advantage of highly evolved processes for targeting a virus to specific cells in the body and trafficking the viral payload to the nucleus. Viral vectors can be administered directly to patients (in vivo) or they can be used to treat cells in vitro and the modified cells are administered to patients (ex vivo). Conventional viral based systems for the delivery of nucleic acids include, but are not limited to, retroviral, lentivirus, adenoviral, adeno-associated, vaccinia and herpes simplex virus vectors for gene transfer.

The tropism of a retrovirus can be altered by incorporating foreign envelope proteins, expanding the potential target population of target cells. Lentiviral vectors are retroviral vectors that are able to transduce or infect non-dividing cells and typically produce high viral titers. Selection of a retroviral gene transfer system depends on the target tissue. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the therapeutic gene into the target cell to provide permanent transgene expression. Widely used retroviral vectors include those based upon murine leukemia virus (MuLV), gibbon ape leukemia virus (GaLV), Simian Immunodeficiency virus (SIV), human immunodeficiency virus (HIV), and combinations thereof (See, e.g., Buchscher et al. (1992) J. Virol. 66:2731-2739; Johann et al. (1992) J. Virol. 66:1635-1640; Sommerfelt et al. (1990) Virol. 176:58-59; Wilson et al. (1989) J. Virol. 63:2374-2378; Miller et al. (1991) J. Virol. 65:2220-2224; PCT/US94/05700).

At least six viral vector approaches are currently available for gene transfer in clinical trials, which utilize approaches that involve complementation of defective vectors by genes inserted into helper cell lines to generate the transducing agent.

pLASN and MFG-S are examples of retroviral vectors that have been used in clinical trials (Dunbar et al. (1995) Blood 85:3048-305; Kohn et al. (1995) Nat. Med. 1:1017-102; Malech et al. (1997) PNAS 94:22 12133-12138). PA317/pLASN was the first therapeutic vector used in a gene therapy trial. (Blaese et al. (1995). Transduction efficiencies of 50% or greater have been observed for MFG-S packaged vectors. (Ellem et al. (1997) Immunol Immunother. 44(1):10-20; Dranoff et al. (1997) Hum. Gene Ther. 1:111-2).

Packaging cells are used to form virus particles that are capable of infecting a host cell. Such cells include 293 cells, which package adenovirus, AAV, and Psi-2 cells or PA317 cells, which package retrovirus. Viral vectors used in gene therapy are usually generated by a producer cell line that packages a nucleic acid vector into a viral particle. The vectors typically contain the minimal viral sequences required for packaging and subsequent integration into a host (if applicable), other viral sequences being replaced by an expression cassette encoding the protein to be expressed. The missing viral functions are supplied in trans by the packaging cell line. For example, AAV vectors used in gene therapy typically only possess inverted terminal repeat (ITR) sequences from the AAV genome which are required for packaging and integration into the host genome. Viral DNA is packaged in a cell line, which contains a helper plasmid encoding the other AAV genes, namely rep and cap, but lacking ITR sequences. The cell line is also infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV. Additionally, AAV can be produced at clinical scale using baculovirus systems (see U.S. Pat. No. 7,479,554).

In many gene therapy applications, it is desirable that the gene therapy vector be delivered with a high degree of specificity to a particular tissue type. Accordingly, a viral vector can be modified to have specificity for a given cell type by expressing a ligand as a fusion protein with a viral coat protein on the outer surface of the virus. The ligand is chosen to have affinity for a receptor known to be present on the cell type of interest. For example, Han et al. (1995) Proc. Natl. Acad. Sci. USA 92:9747-9751, reported that Moloney murine leukemia virus can be modified to express human heregulin fused to gp70, and the recombinant virus infects certain human breast cancer cells expressing human epidermal growth factor receptor. This principle can be extended to other virus-target cell pairs, in which the target cell expresses a receptor and the virus expresses a fusion protein comprising a ligand for the cell-surface receptor. For example, filamentous phage can be engineered to display antibody fragments (e.g., FAB or Fv) having specific binding affinity for virtually any chosen cellular receptor. Although the above description applies primarily to viral vectors, the same principles can be applied to nonviral vectors. Such vectors can be engineered to contain specific uptake sequences which favor uptake by specific target cells.

Gene therapy vectors can be delivered in vivo by administration to an individual patient, typically by systemic administration (e.g., intravitreal, intravenous, intraperitoneal, intramuscular, subdermal, or intracranial infusion) or topical application, as described below. Alternatively. vectors can be delivered to cells ex vivo, such as cells explanted from an individual patient (e.g., lymphocytes, bone marrow aspirates, tissue biopsy) or universal donor hematopoietic stem cells, followed by reimplantation of the cells into a patient, usually after selection for cells which have incorporated the vector.

Ex vivo cell transfection for diagnostics, research, or for gene therapy (e.g., via re-infusion of the transfected cells into the host organism) is well known to those of skill in the art. In a preferred embodiment, cells are isolated from the subject organism, transfected with a nucleic acid composition, and re-infused back into the subject organism (e.g., patient). Various ccli types suitable for ex vivo transfection are well known to those of skill in the art (See, e.g., Freshney et al. (1994) Culture of Animal Cells, A Manual of Basic Technique, 3rd ed, and the references cited therein for a discussion of how to isolate and culture cells from patients).

Suitable cells include, but are not limited to, eukaryotic cells and/or cell lines. Non-limiting examples of such cells or cell lines generated from such cells include COS, CHO (e.g., CHO-S, CHO-K1, CHO-DG44, CHO-DLJXB11, CHO-DUKX, CHOK1SV), VERO, MDCK, W138, V79, B14AF28-G3, BHK, HaK, NSO, SP2/0-Agl4, HeLa, HEK293 (e.g., HEK293-F, IIEK293-H, HEK293-T), perC6 cells, any plant cell (differentiated or undifferentiated), as well as insect cells such as *Spodopterafugiperda* (Sf), or fungal cells such as *Saccharomyces, Pichia* and *Schizosaccharomyces*. In certain embodiments, the cell line is a CHO-K1, MDCK or HEK293 cell line. Additionally, primary cells may be isolated and used ex vivo for reintroduction into the subject to be treated following treatment with a guided nuclease system (e.g. CRISPR/Cas). Suitable primary cells include peripheral blood mononuclear cells (PBMC), and other blood cell subsets such as, but not limited to, CD4+ T cells or CD8+ T cells. Suitable cells also include stem cells such as, by way of example, embryonic stem cells, induced pluripotent stem cells, hematopoietic stem cells (CD34+), neuronal stem cells and mesenchymal stem cells.

In one embodiment, stem cells are used in ex vivo procedures for cell transfection and gene therapy. The advantage to using stem cells is that they can be differentiated into other cell types in vitro, or can be introduced into a mammal (such as the donor of the cells) where they will engraft in the bone marrow. Methods for differentiating CD34+ cells in vitro into clinically important immune cell types using cytokines such a GM-CSF, IFN-gamma, and TNF-alpha are known (as a non-limiting example see, Inaba et al., J. Exp. Med. 176:1693-1702 (1992)).

Stem cells are isolated for transduction and differentiation using known methods. For example, stem cells are isolated from bone marrow cells by panning the bone marrow cells with antibodies which bind unwanted cells, such as CD4+ and CD8+ (T cells), CD45+(panB cells), GR-1 (granulocytes), and lad (differentiated antigen presenting cells) (as a non-limiting example see Inaba et al. (1992) J. Exp. Med. 176:1693-1702). Stem cells that have been modified may also be used in some embodiments.

Typically, the cells are administered in a pharmaceutical composition comprising at least one pharmaceutically-acceptable carrier. The phrase "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. The phrase "pharmaceutically acceptable carrier" as used herein means a pharmaceutically-acceptable material, composition or vehicle, such as a liquid or solid filler, diluent, excipient, or solvent encapsulating material.

Any one of the RNA molecule compositions described herein is suitable for genome editing in post-mitotic cells or any cell which is not actively dividing, e.g., arrested cells. Examples of post-mitotic cells which may be edited using an RNA molecule composition of the present invention include, but are not limited to, a hepatocyte cell.

Vectors (e.g., retroviruses, liposomes, etc.) containing therapeutic nucleic acid compositions can also be administered directly to an organism for transduction of cells in vivo. Administration is by any of the routes normally used for introducing a molecule into ultimate contact with blood or tissue cells including, but not limited to, injection, infusion, topical application (e.g., eye drops and cream) and electroporation. Suitable methods of administering such nucleic acids are available and well known to those of skill in the art, and, although more than one route can be used to administer a particular composition, a particular route can often provide a more immediate and more effective reaction than another route. According to some embodiments, the composition is delivered via IV injection.

Vectors suitable for introduction of transgenes into immune cells (e.g., T-cells) include non-integrating lentivirus vectors. See, e.g., U.S. Patent Publication No. 2009-0117617.

Pharmaceutically acceptable carriers are determined in part by the particular composition being administered, as well as by the particular method used to administer the composition. Accordingly, there is a wide variety of suitable formulations of pharmaceutical compositions available, as described below (See, e.g., Remington's Pharmaceutical Sciences, 17th ed., 1989).

In accordance with some embodiments, there is provided an RNA molecule which binds to/associates with and/or directs the RNA guided DNA nuclease to a sequence comprising at least one nucleotide which differs between a mutant allele and a functional allele (e.g., SNP) of a gene of interest (i.e., a sequence of the mutant allele which is not present in the functional allele). The sequence may be within the disease associated mutation. The sequence may be upstream or downstream to the disease associated mutation. Any sequence difference between the mutant allele and the functional allele may be targeted by an RNA molecule of the present invention to inactivate the mutant allele, or otherwise disable its dominant disease-causing effects, while preserving the activity of the functional allele.

The disclosed compositions and methods may also be used in the manufacture of a medicament for treating dominant genetic disorders in a patient.

Mechanisms of Action for Several Embodiments Disclosed Herein

Mutations in ELANE that were demonstrated to lead to SCN or CyN, mediate translation from alternative in frame ORF (open reading frame) that generate truncated N-terminus protein thus causing ER and protein misfolding stress.

Without being bound by any theory or mechanism, the instant invention may be utilized to apply a CRISPR nuclease to process the mutated pathologic ELANE allele and not the functional ELANE allele, such as to prevent expression of the mutated pathologic allele or to produce a truncated non-pathologic peptide from the mutated pathologic allele, or to repair/correct the mutated pathologic ELANE allele in order to prevent ameliorate or treat SCN or CyN.

Several alternative editing strategies utilizing SNPs located upstream and downstream to the ORF may be applied. The strategies include exclusion of the whole gene, truncation of the gene to exclude the C-terminus of the gene, and attenuation of the expression of the gene.

In some embodiments, two guides (e.g., guides disclosed in Table 2) may be utilized to remove the entire gene (i.e., exons 1, 2, 3, 4, and 5) to knockout the mutant protein. In some embodiments, a first guide RNA is utilized to mediate an allele specific DSB by targeting a SNP/WT sequence located upstream to the ORF of the mutated allele of the ELANE gene, and a second guide RNA may be utilized to mediate DSB in a SNP/WT sequence located in exon 5 or downstream to the mutated allele of the ELANE gene, or a sequence located in intron 4, 3' UTR or downstream to the alleles of the ELANE gene, or a SNP/WT sequence located in intron 4, 3'UTR or downstream to the alleles of the ELANE gene.

There are records of healthy individuals harboring frameshift mutation that result in gain of stop codon located till exon 3. Therefore, a potential strategy may be to truncate the mutated allele such that to include at most exons 1 till 3. In some embodiments, two guides (e.g., guides disclosed in Table 2) may be utilized to truncate the c-terminus of the mutated allele of the ELANE gene. In some embodiments, a first guide RNA may be utilized to mediate an allele specific DSB by targeting a SNP/WT sequence in exon 5 or downstream of the mutated allele, and a second guide RNA may be utilized to mediate DSB in a sequence located in intron 1, 2 or 3 of the ELANE gene, or a SNP/WT sequence. A peptide/protein encoded by the truncated mutated allele may exhibit no pathological effect. Alternatively, a nonsense-mediated mRNA decay may be triggered resulting in knockout of the expression of the mutated allele. Results may be verified by examining mRNA and protein expression.

In some embodiments, the expression of the mutated allele may be attenuated by excising elements from the proximal promoter and enhancer regions using the SNPs located upstream to the ORF. In a non-limiting example, a significant reduction may be achieved by excising most of the enhancer region by targeting a SNP.

Examples of RNA Guide Sequences which Specifically Target Mutant Alleles of ELANE Gene Although a large number of guide sequences can be designed to target a mutant allele, the nucleotide sequences described in Tables 2 identified by SEQ ID NOs: 1-1192 below were specifically selected to effectively implement the methods set forth herein and to effectively discriminate between alleles.

Referring to columns 1-4, each of SEQ TI) NOs: 1-1192 indicated in column 1 corresponds to an engineered guide sequence. The corresponding SNP details are indicated in column 2. The SNP details indicated in the 2nd column include the assigned identifier for each SNP corresponding to a SNP ID indicated in Table 1. Column 3 indicates whether the target of each guide sequence is the ELANE gene polymorph or wild type sequence where indicated. Column 4 indicates the guanine-cytosine content of each guide sequence where indicated.

Table 2 shows guide sequences designed for use as described in the embodiments above to associate with different SNPs within a sequence of a mutant ELANE allele. Each engineered guide molecule is further designed such as to associate with a target genomic DNA sequence of interest that lies next to a protospacer adjacent motif (PAM), e.g., a PAM matching the sequence NGG or NAG, where "N" is any nucleobase. The guide sequences were designed to work in conjunction with one or more different CRISPR nucleases, including, but not limited to, e.g. SpCas9WT (PAM SEQ: NGG), SpCas9.VQR.1 (PAM SEQ: NGAN), SpCas9.VQR.2 (PAM SEQ: NGNG), SpCas9.EQR (PAM SEQ: NGAG), SpCas9.VRER (PAM SEQ: NGCG), SaCas9WT (PAM SEQ: NNGRRT), NmCas9WT (PAM SEQ: NNNNGATT), Cpf1 (PAM SEQ: TTTV), or JeCas9WT (PAM SEQ: NNNVRYM). RNA molecules of the present invention are each designed to form complexes in conjunction with one or more different CRISPR nucleases and designed to target polynucleotide sequences of interest utilizing one or more different PAM sequences respective to the CRISPR nuclease utilized.

TABLE 2

| Guide sequences designed to associate with specific SNPs of the ELANE gene | | | |
|---|---|---|---|
| SEQ ID NO: | SNP ID (Table 1) | Target (ALT/REF) | % GC |
| 1 | s1 | REF | 35% |
| 2 | s1 | ALT | 30% |
| 3 | s1 | REF | 35% |
| 4 | s1 | ALT | 30% |
| 5 | s1 | REF | 40% |
| 6 | s2 | BOTH | 30% |
| 7 | s3 | BOTH | 30% |
| 8 | s1 | ALT | 35% |
| 9 | s1 | REF | 40% |
| 10 | s2 | REF | 30% |
| 11 | s4 | BOTH | 45% |
| 12 | s3 | BOTH | 30% |
| 13 | s5 | ALT | 55% |
| 14 | s5 | REF | 60% |
| 15 | s1 | ALT | 35% |
| 16 | s1 | REF | 45% |
| 17 | s6 | REF | 60% |
| 18 | s6 | ALT | 55% |
| 19 | s2 | BOTH | 35% |
| 20 | s7 | ALT | 30% |
| 21 | s8 | ALT | 45% |
| 22 | s9 | ALT | 55% |
| 23 | s9 | REF | 60% |
| 24 | s5 | ALT | 60% |
| 25 | s5 | REF | 65% |
| 26 | s10 | REF | 55% |
| 27 | s11 | REF | 55% |
| 28 | s1 | ALT | 40% |
| 29 | s12 | ALT | 30% |
| 30 | s2 | ALT | 35% |
| 31 | s1 | REF | 45% |
| 32 | s6 | REF | 65% |
| 33 | s6 | ALT | 60% |
| 34 | s13 | REF | 60% |
| 35 | s13 | ALT | 60% |
| 36 | s2 | BOTH | 35% |
| 37 | s4 | BOTH | 45% |
| 38 | s6 | ALT | 50% |
| 39 | s12 | ALT | 30% |
| 40 | s1 | REF | 30% |
| 41 | s3 | BOTH | 35% |
| 42 | s12 | ALT | 35% |
| 43 | s12 | REF | 30% |
| 44 | s14 | ALT | 65% |
| 45 | s8 | ALT | 45% |
| 46 | s5 | ALT | 50% |
| 47 | s5 | REF | 55% |
| 48 | s9 | ALT | 60% |
| 49 | s9 | REF | 65% |
| 50 | s5 | ALT | 60% |
| 51 | s11 | REF | 60% |
| 52 | s15 | REF | 70% |
| 53 | s9 | ALT | 45% |
| 54 | s9 | REF | 50% |
| 55 | s5 | REF | 65% |
| 56 | s11 | REF | 55% |
| 57 | s10 | REF | 60% |
| 58 | s16 | REF | 75% |
| 59 | s1 | BOTH | 45% |
| 60 | s11 | REF | 55% |
| 61 | s8 | ALT | 40% |
| 62 | s8 | REF | 40% |
| 63 | s1 | ALT | 40% |
| 64 | s17 | REF | 60% |
| 65 | s10 | ALT | 60% |
| 66 | s10 | REF | 60% |
| 67 | s2 | REF | 35% |
| 68 | s2 | ALT | 30% |
| 69 | s8 | REF | 45% |
| 70 | s10 | ALT | 55% |
| 71 | s2 | REF | 30% |
| 72 | s12 | REF | 30% |
| 73 | s12 | ALT | 35% |
| 74 | s2 | ALT | 35% |
| 75 | s2 | REF | 35% |

TABLE 2-continued

| Guide sequences designed to associate with specific SNPs of the ELANE gene | | | |
|---|---|---|---|
| SEQ ID NO: | SNP ID (Table 1) | Target (ALT/REF) | % GC |
| 76 | s2 | ALT | 30% |
| 77 | s1 | REF | 50% |
| 78 | s7 | ALT | 35% |
| 79 | s6 | ALT | 65% |
| 80 | s6 | REF | 70% |
| 81 | s18 | ALT | 70% |
| 82 | s19 | REF | 55% |
| 83 | s6 | REF | 70% |
| 84 | s6 | ALT | 65% |
| 85 | s11 | REF | 60% |
| 86 | s19 | ALT | 50% |
| 87 | s15 | REF | 50% |
| 88 | s5 | REF | 65% |
| 89 | s5 | ALT | 60% |
| 90 | s18 | BOTH | 70% |
| 91 | s8 | ALT | 35% |
| 92 | s8 | REF | 35% |
| 93 | s19 | ALT | 55% |
| 94 | s19 | REF | 60% |
| 95 | s9 | ALT | 70% |
| 96 | s16 | REF | 75% |
| 97 | s13 | REF | 60% |
| 98 | s13 | ALT | 60% |
| 99 | s8 | REF | 45% |
| 100 | s8 | ALT | 45% |
| 101 | s2 | REF | 40% |
| 102 | s16 | REF | 70% |
| 103 | s16 | ALT | 65% |
| 104 | s6 | ALT | 60% |
| 105 | s6 | REF | 65% |
| 106 | s20 | REF | 65% |
| 107 | s13 | ALT | 55% |
| 108 | s2 | ALT | 35% |
| 109 | s2 | REF | 40% |
| 110 | s6 | ALT | 65% |
| 111 | s6 | REF | 70% |
| 112 | s6 | ALT | 50% |
| 113 | s4 | BOTH | 45% |
| 114 | s18 | ALT | 70% |
| 115 | s19 | REF | 55% |
| 116 | s6 | REF | 70% |
| 117 | s6 | ALT | 65% |
| 118 | s11 | REF | 60% |
| 119 | s19 | ALT | 50% |
| 120 | s18 | REF | 70% |
| 121 | s18 | ALT | 75% |
| 122 | s15 | REF | 50% |
| 123 | s12 | ALT | 30% |
| 124 | s5 | REF | 60% |
| 125 | s5 | ALT | 55% |
| 126 | s13 | REF | 55% |
| 127 | s9 | REF | 55% |
| 128 | s9 | ALT | 50% |
| 129 | s18 | BOTH | 75% |
| 130 | s9 | REF | 75% |
| 131 | s18 | ALT | 75% |
| 132 | s18 | REF | 70% |
| 133 | s14 | ALT | 60% |
| 134 | s14 | REF | 65% |
| 135 | s19 | BOTH | 65% |
| 136 | s8 | REF | 35% |
| 137 | s8 | ALT | 35% |
| 138 | s12 | REF | 35% |
| 139 | s12 | ALT | 40% |
| 140 | s17 | BOTH | 40% |
| 141 | s8 | BOTH | 45% |
| 142 | s16 | REF | 70% |
| 143 | s8 | ALT | 35% |
| 144 | s8 | REF | 35% |
| 145 | s6 | BOTH | 55% |
| 146 | s1 | ALT | 35% |
| 147 | s1 | REF | 40% |
| 148 | s14 | BOTH | 55% |
| 149 | s12 | ALT | 30% |
| 150 | s12 | BOTH | 30% |

TABLE 2-continued

Guide sequences designed to associate with specific SNPs of the ELANE gene

| SEQ ID NO: | SNP ID (Table 1) | Target (ALT/REF) | % GC |
|---|---|---|---|
| 151 | s1 | REF | 35% |
| 152 | s5 | ALT | 55% |
| 153 | s5 | REF | 60% |
| 154 | s3 | BOTH | 40% |
| 155 | s12 | ALT | 35% |
| 156 | s12 | REF | 30% |
| 157 | s1 | BOTH | 45% |
| 158 | s16 | REF | 70% |
| 159 | s14 | ALT | 70% |
| 160 | s8 | ALT | 45% |
| 161 | s5 | ALT | 55% |
| 162 | s5 | REF | 60% |
| 163 | s14 | BOTH | 70% |
| 164 | s15 | REF | 60% |
| 165 | s6 | ALT | 55% |
| 166 | s6 | REF | 60% |
| 167 | s9 | ALT | 65% |
| 168 | s9 | REF | 70% |
| 169 | s5 | REF | 70% |
| 170 | s5 | ALT | 65% |
| 171 | s5 | BOTH | 65% |
| 172 | s5 | ALT | 65% |
| 173 | s19 | ALT | 60% |
| 174 | s11 | REF | 65% |
| 175 | s15 | ALT | 65% |
| 176 | s9 | ALT | 50% |
| 177 | s9 | REF | 55% |
| 178 | s5 | REF | 70% |
| 179 | s14 | REF | 70% |
| 180 | s19 | REF | 65% |
| 181 | s9 | ALT | 65% |
| 182 | s8 | BOTH | 45% |
| 183 | s12 | ALT | 40% |
| 184 | s12 | REF | 35% |
| 185 | s20 | ALT | 55% |
| 186 | s20 | ALT | 70% |
| 187 | s10 | REF | 60% |
| 188 | s10 | ALT | 60% |
| 189 | s13 | REF | 60% |
| 190 | s13 | ALT | 60% |
| 191 | s10 | BOTH | 70% |
| 192 | s14 | REF | 70% |
| 193 | s20 | ALT | 60% |
| 194 | s20 | REF | 55% |
| 195 | s12 | ALT | 30% |
| 196 | s2 | BOTH | 45% |
| 197 | s6 | BOTH | 50% |
| 198 | s16 | ALT | 65% |
| 199 | s15 | REF | 60% |
| 200 | s11 | REF | 55% |
| 201 | s14 | REF | 60% |
| 202 | s20 | REF | 65% |
| 203 | s17 | ALT | 60% |
| 204 | s20 | ALT | 70% |
| 205 | s11 | REF | 60% |
| 206 | s10 | REF | 65% |
| 207 | s20 | REF | 60% |
| 208 | s18 | REF | 75% |
| 209 | s5 | ALT | 65% |
| 210 | s20 | ALT | 70% |
| 211 | s9 | REF | 70% |
| 212 | s9 | ALT | 65% |
| 213 | s19 | BOTH | 55% |
| 214 | s15 | BOTH | 65% |
| 215 | s19 | ALT | 65% |
| 216 | s5 | REF | 60% |
| 217 | s5 | ALT | 55% |
| 218 | s6 | ALT | 55% |
| 219 | s8 | REF | 40% |
| 220 | s10 | REF | 65% |
| 221 | s10 | ALT | 65% |
| 222 | s6 | REF | 60% |
| 223 | s14 | REF | 60% |
| 224 | s19 | REF | 60% |
| 225 | s19 | ALT | 55% |
| 226 | s14 | ALT | 55% |
| 227 | s8 | ALT | 40% |
| 228 | s1 | ALT | 45% |
| 229 | s1 | REF | 50% |
| 230 | s11 | REF | 55% |
| 231 | s20 | REF | 50% |
| 232 | s8 | ALT | 40% |
| 233 | s12 | ALT | 30% |
| 234 | s8 | REF | 40% |
| 235 | s1 | ALT | 45% |
| 236 | s9 | ALT | 65% |
| 237 | s9 | REF | 70% |
| 238 | s8 | ALT | 40% |
| 239 | s11 | REF | 40% |
| 240 | s5 | BOTH | 40% |
| 241 | s17 | ALT | 60% |
| 242 | s17 | REF | 65% |
| 243 | s10 | ALT | 65% |
| 244 | s17 | BOTH | 60% |
| 245 | s10 | REF | 65% |
| 246 | s17 | REF | 65% |
| 247 | s17 | ALT | 60% |
| 248 | s2 | REF | 35% |
| 249 | s13 | REF | 60% |
| 250 | s13 | ALT | 55% |
| 251 | s13 | REF | 55% |
| 252 | s2 | ALT | 30% |
| 253 | s2 | REF | 35% |
| 254 | s12 | ALT | 30% |
| 255 | s8 | REF | 45% |
| 256 | s2 | ALT | 35% |
| 257 | s11 | ALT | 65% |
| 258 | s20 | REF | 50% |
| 259 | s20 | ALT | 55% |
| 260 | s11 | REF | 45% |
| 261 | s10 | ALT | 60% |
| 262 | s19 | ALT | 50% |
| 263 | s19 | REF | 55% |
| 264 | s5 | REF | 50% |
| 265 | s17 | ALT | 60% |
| 266 | s17 | REF | 65% |
| 267 | s2 | REF | 35% |
| 268 | s11 | REF | 60% |
| 269 | s17 | ALT | 45% |
| 270 | s17 | REF | 50% |
| 271 | s2 | REF | 30% |
| 272 | s8 | REF | 45% |
| 273 | s12 | REF | 30% |
| 274 | s12 | ALT | 35% |
| 275 | s10 | ALT | 65% |
| 276 | s8 | REF | 40% |
| 277 | s8 | ALT | 40% |
| 278 | s20 | ALT | 45% |
| 279 | s6 | REF | 55% |
| 280 | s6 | ALT | 50% |
| 281 | s2 | ALT | 30% |
| 282 | s9 | BOTH | 65% |
| 283 | s4 | REF | 30% |
| 284 | s4 | BOTH | 50% |
| 285 | s9 | ALT | 55% |
| 286 | s9 | REF | 60% |
| 287 | s2 | REF | 30% |
| 288 | s6 | ALT | 55% |
| 289 | s11 | REF | 65% |
| 290 | s15 | REF | 70% |
| 291 | s9 | REF | 50% |
| 292 | s16 | REF | 75% |
| 293 | s2 | REF | 40% |
| 294 | s2 | ALT | 35% |
| 295 | s2 | REF | 40% |
| 296 | s2 | ALT | 35% |
| 297 | s1 | REF | 50% |
| 298 | s7 | ALT | 35% |
| 299 | s6 | ALT | 65% |
| 300 | s6 | REF | 70% |

TABLE 2-continued

Guide sequences designed to associate with specific SNPs of the ELANE gene

| SEQ ID NO: | SNP ID (Table 1) | Target (ALT/REF) | % GC |
|---|---|---|---|
| 301 | s11 | REF | 60% |
| 302 | s5 | REF | 70% |
| 303 | s5 | ALT | 65% |
| 304 | s18 | BOTH | 70% |
| 305 | s8 | ALT | 35% |
| 306 | s8 | REF | 35% |
| 307 | s19 | ALT | 60% |
| 308 | s19 | REF | 65% |
| 309 | s7 | ALT | 30% |
| 310 | s16 | REF | 75% |
| 311 | s2 | REF | 30% |
| 312 | s6 | ALT | 65% |
| 313 | s6 | REF | 70% |
| 314 | s13 | ALT | 55% |
| 315 | s6 | ALT | 65% |
| 316 | s6 | REF | 70% |
| 317 | s6 | ALT | 50% |
| 318 | s18 | REF | 70% |
| 319 | s19 | REF | 55% |
| 320 | s6 | REF | 70% |
| 321 | s6 | ALT | 65% |
| 322 | s11 | REF | 65% |
| 323 | s19 | ALT | 50% |
| 324 | s18 | REF | 70% |
| 325 | s18 | ALT | 75% |
| 326 | s15 | BOTH | 55% |
| 327 | s5 | REF | 65% |
| 328 | s5 | ALT | 60% |
| 329 | s13 | REF | 55% |
| 330 | s18 | BOTH | 75% |
| 331 | s14 | ALT | 60% |
| 332 | s14 | REF | 65% |
| 333 | s8 | REF | 40% |
| 334 | s8 | ALT | 40% |
| 335 | s12 | REF | 35% |
| 336 | s12 | ALT | 40% |
| 337 | s17 | BOTH | 45% |
| 338 | s8 | ALT | 40% |
| 339 | s8 | REF | 40% |
| 340 | s14 | BOTH | 60% |
| 341 | s12 | BOTH | 35% |
| 342 | s1 | BOTH | 50% |
| 343 | s16 | REF | 70% |
| 344 | s16 | ALT | 65% |
| 345 | s15 | ALT | 60% |
| 346 | s15 | REF | 65% |
| 347 | s6 | ALT | 55% |
| 348 | s6 | REF | 60% |
| 349 | s5 | REF | 70% |
| 350 | s5 | ALT | 65% |
| 351 | s19 | ALT | 60% |
| 352 | s19 | REF | 65% |
| 353 | s9 | ALT | 70% |
| 354 | s8 | BOTH | 50% |
| 355 | s3 | BOTH | 45% |
| 356 | s10 | REF | 60% |
| 357 | s10 | ALT | 60% |
| 358 | s13 | REF | 65% |
| 359 | s13 | ALT | 65% |
| 360 | s14 | REF | 70% |
| 361 | s20 | ALT | 60% |
| 362 | s20 | REF | 55% |
| 363 | s14 | REF | 65% |
| 364 | s14 | ALT | 60% |
| 365 | s20 | REF | 70% |
| 366 | s17 | ALT | 65% |
| 367 | s20 | ALT | 75% |
| 368 | s11 | REF | 65% |
| 369 | s20 | REF | 65% |
| 370 | s5 | ALT | 65% |
| 371 | s9 | REF | 75% |
| 372 | s9 | ALT | 70% |
| 373 | s15 | BOTH | 65% |
| 374 | s19 | ALT | 65% |
| 375 | s8 | REF | 40% |
| 376 | s8 | ALT | 40% |
| 377 | s12 | REF | 30% |
| 378 | s17 | REF | 65% |
| 379 | s17 | ALT | 60% |
| 380 | s13 | REF | 60% |
| 381 | s13 | ALT | 60% |
| 382 | s13 | REF | 60% |
| 383 | s20 | REF | 50% |
| 384 | s20 | ALT | 55% |
| 385 | s5 | REF | 50% |
| 386 | s17 | ALT | 60% |
| 387 | s17 | REF | 65% |
| 388 | s13 | ALT | 60% |
| 389 | s17 | ALT | 50% |
| 390 | s17 | REF | 55% |
| 391 | s8 | REF | 45% |
| 392 | s10 | ALT | 65% |
| 393 | s8 | REF | 45% |
| 394 | s8 | ALT | 45% |
| 395 | s2 | REF | 40% |
| 396 | s9 | ALT | 60% |
| 397 | s9 | REF | 65% |
| 398 | s6 | ALT | 55% |
| 399 | s9 | BOTH | 50% |
| 400 | s16 | REF | 75% |
| 401 | s6 | ALT | 65% |
| 402 | s6 | REF | 70% |
| 403 | s11 | REF | 60% |
| 404 | s15 | REF | 55% |
| 405 | s16 | REF | 75% |
| 406 | s2 | ALT | 30% |
| 407 | s2 | REF | 35% |
| 408 | s13 | ALT | 55% |
| 409 | s18 | REF | 75% |
| 410 | s13 | REF | 55% |
| 411 | s14 | BOTH | 60% |
| 412 | s15 | ALT | 60% |
| 413 | s6 | ALT | 60% |
| 414 | s6 | REF | 65% |
| 415 | s8 | BOTH | 55% |
| 416 | s3 | BOTH | 50% |
| 417 | s10 | REF | 60% |
| 418 | s10 | ALT | 60% |
| 419 | s14 | REF | 65% |
| 420 | s14 | ALT | 60% |
| 421 | s20 | REF | 70% |
| 422 | s17 | REF | 65% |
| 423 | s17 | ALT | 60% |
| 424 | s13 | ALT | 60% |
| 425 | s13 | REF | 60% |
| 426 | s5 | ALT | 45% |
| 427 | s5 | REF | 50% |
| 428 | s17 | ALT | 60% |
| 429 | s17 | REF | 65% |
| 430 | s13 | ALT | 60% |
| 431 | s10 | ALT | 65% |
| 432 | s2 | REF | 40% |
| 433 | s13 | ALT | 60% |
| 434 | s18 | REF | 75% |
| 435 | s13 | REF | 60% |
| 436 | s15 | ALT | 65% |
| 437 | s15 | REF | 70% |
| 438 | s6 | ALT | 65% |
| 439 | s6 | REF | 70% |
| 440 | s8 | BOTH | 60% |
| 441 | s10 | REF | 65% |
| 442 | s10 | ALT | 65% |
| 443 | s17 | REF | 70% |
| 444 | s17 | ALT | 65% |
| 445 | s13 | ALT | 60% |
| 446 | s13 | REF | 60% |
| 447 | s10 | ALT | 70% |
| 448 | s1 | REF | 40% |
| 449 | s13 | ALT | 65% |
| 450 | s13 | REF | 65% |

TABLE 2-continued

Guide sequences designed to associate with specific SNPs of the ELANE gene

| SEQ ID NO: | SNP ID (Table 1) | Target (ALT/REF) | % GC |
|---|---|---|---|
| 451 | s15 | ALT | 65% |
| 452 | s15 | REF | 70% |
| 453 | s6 | REF | 55% |
| 454 | s17 | REF | 70% |
| 455 | s17 | ALT | 65% |
| 456 | s13 | ALT | 65% |
| 457 | s13 | REF | 65% |
| 458 | s6 | REF | 55% |
| 459 | s4 | BOTH | 45% |
| 460 | s5 | REF | 60% |
| 461 | s19 | REF | 70% |
| 462 | s19 | ALT | 65% |
| 463 | s18 | ALT | 75% |
| 464 | s17 | REF | 55% |
| 465 | s5 | REF | 60% |
| 466 | s19 | REF | 70% |
| 467 | s19 | ALT | 65% |
| 468 | s5 | ALT | 55% |
| 469 | s9 | ALT | 55% |
| 470 | s9 | REF | 60% |
| 471 | s17 | REF | 55% |
| 472 | s18 | ALT | 75% |
| 473 | s4 | ALT | 35% |
| 474 | s19 | REF | 60% |
| 475 | s13 | BOTH | 70% |
| 476 | s5 | REF | 55% |
| 477 | s19 | REF | 70% |
| 478 | s19 | ALT | 65% |
| 479 | s17 | ALT | 50% |
| 480 | s5 | ALT | 50% |
| 481 | s6 | REF | 70% |
| 482 | s6 | ALT | 65% |
| 483 | s15 | REF | 70% |
| 484 | s15 | ALT | 65% |
| 485 | s9 | ALT | 50% |
| 486 | s9 | REF | 55% |
| 487 | s18 | REF | 70% |
| 488 | s10 | REF | 70% |
| 489 | s17 | REF | 50% |
| 490 | s18 | ALT | 75% |
| 491 | s19 | REF | 60% |
| 492 | s16 | REF | 75% |
| 493 | s16 | REF | 75% |
| 494 | s13 | BOTH | 70% |
| 495 | s5 | REF | 50% |
| 496 | s5 | REF | 70% |
| 497 | s9 | REF | 55% |
| 498 | s16 | BOTH | 65% |
| 499 | s13 | REF | 60% |
| 500 | s13 | ALT | 60% |
| 501 | s16 | ALT | 70% |
| 502 | s16 | REF | 75% |
| 503 | s18 | REF | 75% |
| 504 | s19 | REF | 65% |
| 505 | s19 | ALT | 60% |
| 506 | s13 | REF | 65% |
| 507 | s11 | REF | 65% |
| 508 | s14 | REF | 60% |
| 509 | s16 | ALT | 70% |
| 510 | s17 | ALT | 50% |
| 511 | s5 | ALT | 45% |
| 512 | s18 | REF | 75% |
| 513 | s10 | ALT | 65% |
| 514 | s10 | REF | 65% |
| 515 | s6 | REF | 70% |
| 516 | s6 | ALT | 65% |
| 517 | s15 | REF | 70% |
| 518 | s14 | ALT | 55% |
| 519 | s14 | REF | 60% |
| 520 | s15 | ALT | 65% |
| 521 | s9 | ALT | 50% |
| 522 | s9 | REF | 55% |
| 523 | s17 | REF | 65% |
| 524 | s17 | ALT | 60% |
| 525 | s15 | REF | 55% |

TABLE 2-continued

Guide sequences designed to associate with specific SNPs of the ELANE gene

| SEQ ID NO: | SNP ID (Table 1) | Target (ALT/REF) | % GC |
|---|---|---|---|
| 526 | s12 | ALT | 30% |
| 527 | s5 | REF | 65% |
| 528 | s5 | ALT | 60% |
| 529 | s13 | REF | 60% |
| 530 | s17 | REF | 45% |
| 531 | s2 | REF | 35% |
| 532 | s9 | REF | 60% |
| 533 | s19 | REF | 60% |
| 534 | s11 | REF | 55% |
| 535 | s18 | REF | 75% |
| 536 | s16 | REF | 75% |
| 537 | s19 | REF | 65% |
| 538 | s19 | ALT | 60% |
| 539 | s8 | ALT | 40% |
| 540 | s8 | REF | 40% |
| 541 | s16 | REF | 70% |
| 542 | s13 | BOTH | 65% |
| 543 | s9 | REF | 75% |
| 544 | s5 | REF | 50% |
| 545 | s10 | REF | 60% |
| 546 | s10 | ALT | 60% |
| 547 | s17 | REF | 70% |
| 548 | s10 | BOTH | 70% |
| 549 | s5 | REF | 70% |
| 550 | s19 | REF | 70% |
| 551 | s18 | REF | 75% |
| 552 | s12 | ALT | 35% |
| 553 | s9 | REF | 50% |
| 554 | s14 | ALT | 65% |
| 555 | s14 | REF | 70% |
| 556 | s19 | BOTH | 65% |
| 557 | s8 | ALT | 45% |
| 558 | s8 | REF | 45% |
| 559 | s8 | REF | 40% |
| 560 | s8 | ALT | 40% |
| 561 | s13 | REF | 65% |
| 562 | s12 | ALT | 40% |
| 563 | s16 | REF | 65% |
| 564 | s13 | REF | 55% |
| 565 | s13 | ALT | 55% |
| 566 | s17 | BOTH | 45% |
| 567 | s12 | ALT | 40% |
| 568 | s12 | REF | 35% |
| 569 | s19 | REF | 55% |
| 570 | s19 | ALT | 50% |
| 571 | s8 | BOTH | 50% |
| 572 | s6 | BOTH | 45% |
| 573 | s8 | REF | 40% |
| 574 | s8 | ALT | 40% |
| 575 | s20 | REF | 50% |
| 576 | s20 | ALT | 55% |
| 577 | s16 | REF | 75% |
| 578 | s18 | REF | 70% |
| 579 | s13 | ALT | 65% |
| 580 | s13 | REF | 65% |
| 581 | s20 | ALT | 55% |
| 582 | s16 | REF | 70% |
| 583 | s19 | REF | 65% |
| 584 | s19 | ALT | 60% |
| 585 | s3 | BOTH | 40% |
| 586 | s13 | ALT | 65% |
| 587 | s13 | REF | 65% |
| 588 | s2 | ALT | 35% |
| 589 | s11 | REF | 60% |
| 590 | s2 | REF | 40% |
| 591 | s14 | REF | 60% |
| 592 | s16 | ALT | 70% |
| 593 | s17 | ALT | 45% |
| 594 | s18 | REF | 75% |
| 595 | s16 | REF | 75% |
| 596 | s16 | BOTH | 70% |
| 597 | s16 | ALT | 70% |
| 598 | s10 | REF | 60% |
| 599 | s10 | ALT | 60% |
| 600 | s5 | ALT | 45% |

TABLE 2-continued

Guide sequences designed to associate with specific SNPs of the ELANE gene

| SEQ ID NO: | SNP ID (Table 1) | Target (ALT/REF) | % GC |
|---|---|---|---|
| 601 | s13 | REF | 60% |
| 602 | s13 | ALT | 60% |
| 603 | s18 | REF | 75% |
| 604 | s10 | ALT | 70% |
| 605 | s14 | REF | 60% |
| 606 | s14 | ALT | 55% |
| 607 | s10 | ALT | 60% |
| 608 | s10 | REF | 60% |
| 609 | s14 | REF | 70% |
| 610 | s14 | ALT | 65% |
| 611 | s6 | REF | 70% |
| 612 | s10 | ALT | 60% |
| 613 | s10 | REF | 60% |
| 614 | s17 | REF | 65% |
| 615 | s17 | ALT | 60% |
| 616 | s9 | ALT | 50% |
| 617 | s15 | REF | 70% |
| 618 | s15 | REF | 65% |
| 619 | s14 | ALT | 55% |
| 620 | s14 | REF | 60% |
| 621 | s15 | ALT | 60% |
| 622 | s8 | ALT | 40% |
| 623 | s8 | REF | 40% |
| 624 | s12 | ALT | 35% |
| 625 | s12 | REF | 30% |
| 626 | s6 | ALT | 55% |
| 627 | s6 | REF | 60% |
| 628 | s9 | ALT | 50% |
| 629 | s9 | REF | 55% |
| 630 | s13 | REF | 60% |
| 631 | s1 | REF | 40% |
| 632 | s20 | REF | 55% |
| 633 | s17 | REF | 65% |
| 634 | s14 | ALT | 55% |
| 635 | s14 | ALT | 55% |
| 636 | s14 | REF | 60% |
| 637 | s12 | ALT | 30% |
| 638 | s8 | ALT | 45% |
| 639 | s10 | REF | 65% |
| 640 | s12 | ALT | 30% |
| 641 | s15 | REF | 55% |
| 642 | s1 | REF | 40% |
| 643 | s1 | ALT | 35% |
| 644 | s5 | ALT | 60% |
| 645 | s5 | REF | 65% |
| 646 | s6 | REF | 60% |
| 647 | s6 | ALT | 55% |
| 648 | s10 | REF | 60% |
| 649 | s11 | REF | 55% |
| 650 | s12 | ALT | 30% |
| 651 | s2 | ALT | 35% |
| 652 | s13 | REF | 60% |
| 653 | s12 | ALT | 35% |
| 654 | s12 | REF | 30% |
| 655 | s5 | REF | 55% |
| 656 | s11 | REF | 60% |
| 657 | s1 | BOTH | 50% |
| 658 | s10 | ALT | 60% |
| 659 | s10 | REF | 60% |
| 660 | s10 | ALT | 60% |
| 661 | s15 | ALT | 50% |
| 662 | s11 | REF | 45% |
| 663 | s16 | REF | 70% |
| 664 | s9 | REF | 55% |
| 665 | s9 | ALT | 50% |
| 666 | s18 | REF | 75% |
| 667 | s16 | REF | 70% |
| 668 | s1 | ALT | 40% |
| 669 | s1 | REF | 45% |
| 670 | s5 | ALT | 55% |
| 671 | s5 | REF | 60% |
| 672 | s5 | BOTH | 65% |
| 673 | s14 | BOTH | 75% |
| 674 | s20 | ALT | 55% |
| 675 | s12 | BOTH | 35% |

TABLE 2-continued

Guide sequences designed to associate with specific SNPs of the ELANE gene

| SEQ ID NO: | SNP ID (Table 1) | Target (ALT/REF) | % GC |
|---|---|---|---|
| 676 | s15 | REF | 65% |
| 677 | s18 | REF | 75% |
| 678 | s5 | REF | 60% |
| 679 | s6 | ALT | 55% |
| 680 | s10 | REF | 65% |
| 681 | s10 | ALT | 65% |
| 682 | s6 | REF | 60% |
| 683 | s14 | REF | 60% |
| 684 | s19 | REF | 60% |
| 685 | s19 | ALT | 55% |
| 686 | s14 | ALT | 55% |
| 687 | s20 | REF | 50% |
| 688 | s9 | ALT | 70% |
| 689 | s9 | REF | 75% |
| 690 | s5 | BOTH | 40% |
| 691 | s12 | ALT | 30% |
| 692 | s2 | ALT | 40% |
| 693 | s11 | REF | 60% |
| 694 | s13 | REF | 60% |
| 695 | s2 | REF | 30% |
| 696 | s6 | REF | 55% |
| 697 | s6 | ALT | 50% |
| 698 | s9 | BOTH | 65% |
| 699 | s4 | BOTH | 55% |
| 700 | s2 | REF | 40% |
| 701 | s2 | ALT | 35% |
| 702 | s5 | REF | 75% |
| 703 | s5 | ALT | 70% |
| 704 | s8 | ALT | 40% |
| 705 | s8 | REF | 40% |
| 706 | s16 | REF | 75% |
| 707 | s5 | BOTH | 70% |
| 708 | s13 | REF | 65% |
| 709 | s13 | ALT | 65% |
| 710 | s20 | ALT | 60% |
| 711 | s20 | REF | 55% |
| 712 | s17 | ALT | 65% |
| 713 | s5 | ALT | 70% |
| 714 | s19 | ALT | 65% |
| 715 | s8 | REF | 40% |
| 716 | s8 | ALT | 40% |
| 717 | s11 | ALT | 45% |
| 718 | s17 | ALT | 50% |
| 719 | s17 | REF | 55% |
| 720 | s9 | BOTH | 55% |
| 721 | s11 | REF | 65% |
| 722 | s15 | REF | 55% |
| 723 | s14 | REF | 70% |
| 724 | s14 | ALT | 65% |
| 725 | s18 | ALT | 75% |
| 726 | s18 | REF | 75% |
| 727 | s9 | ALT | 55% |
| 728 | s9 | REF | 60% |
| 729 | s16 | REF | 75% |
| 730 | s5 | REF | 75% |
| 731 | s9 | REF | 60% |
| 732 | s13 | REF | 60% |
| 733 | s13 | ALT | 60% |
| 734 | s16 | ALT | 70% |
| 735 | s16 | REF | 75% |
| 736 | s15 | REF | 70% |
| 737 | s16 | ALT | 70% |
| 738 | s14 | REF | 75% |
| 739 | s14 | ALT | 60% |
| 740 | s14 | REF | 65% |
| 741 | s11 | REF | 55% |
| 742 | s10 | REF | 65% |
| 743 | s10 | ALT | 65% |
| 744 | s17 | REF | 70% |
| 745 | s19 | REF | 70% |
| 746 | s8 | ALT | 45% |
| 747 | s8 | REF | 45% |
| 748 | s12 | ALT | 40% |
| 749 | s12 | REF | 35% |
| 750 | s20 | BOTH | 55% |

TABLE 2-continued

Guide sequences designed to associate with specific SNPs of the ELANE gene

| SEQ ID NO: | SNP ID (Table 1) | Target (ALT/REF) | % GC |
|---|---|---|---|
| 751 | s20 | ALT | 55% |
| 752 | s3 | BOTH | 45% |
| 753 | s16 | REF | 75% |
| 754 | s16 | ALT | 70% |
| 755 | s10 | REF | 65% |
| 756 | s10 | ALT | 65% |
| 757 | s13 | REF | 65% |
| 758 | s13 | ALT | 65% |
| 759 | s10 | BOTH | 75% |
| 760 | s14 | REF | 65% |
| 761 | s14 | ALT | 60% |
| 762 | s10 | ALT | 65% |
| 763 | s10 | REF | 65% |
| 764 | s9 | ALT | 55% |
| 765 | s20 | REF | 55% |
| 766 | s20 | ALT | 60% |
| 767 | s10 | REF | 60% |
| 768 | s11 | REF | 55% |
| 769 | s13 | REF | 60% |
| 770 | s13 | ALT | 60% |
| 771 | s10 | ALT | 60% |
| 772 | s10 | REF | 60% |
| 773 | s10 | ALT | 60% |
| 774 | s11 | REF | 50% |
| 775 | s9 | REF | 55% |
| 776 | s9 | ALT | 50% |
| 777 | s18 | REF | 75% |
| 778 | s16 | ALT | 70% |
| 779 | s14 | REF | 75% |
| 780 | s16 | REF | 75% |
| 781 | s5 | BOTH | 65% |
| 782 | s20 | ALT | 60% |
| 783 | s20 | ALT | 70% |
| 784 | s18 | REF | 75% |
| 785 | s20 | ALT | 75% |
| 786 | s10 | REF | 65% |
| 787 | s10 | ALT | 65% |
| 788 | s16 | REF | 70% |
| 789 | s14 | REF | 60% |
| 790 | s19 | REF | 60% |
| 791 | s19 | ALT | 55% |
| 792 | s14 | ALT | 55% |
| 793 | s20 | REF | 55% |
| 794 | s12 | BOTH | 30% |
| 795 | s2 | BOTH | 45% |
| 796 | s11 | REF | 60% |
| 797 | s6 | BOTH | 55% |
| 798 | s9 | BOTH | 65% |
| 799 | s4 | BOTH | 60% |
| 800 | s8 | ALT | 40% |
| 801 | s8 | REF | 40% |
| 802 | s20 | ALT | 65% |
| 803 | s20 | REF | 60% |
| 804 | s11 | ALT | 50% |
| 805 | s9 | BOTH | 60% |
| 806 | s15 | REF | 60% |
| 807 | s14 | REF | 70% |
| 808 | s14 | ALT | 65% |
| 809 | s13 | BOTH | 60% |
| 810 | s11 | REF | 55% |
| 811 | s9 | REF | 70% |
| 812 | s16 | REF | 75% |
| 813 | s14 | REF | 65% |
| 814 | s14 | ALT | 60% |
| 815 | s10 | BOTH | 70% |
| 816 | s10 | REF | 60% |
| 817 | s20 | REF | 65% |
| 818 | s10 | ALT | 65% |
| 819 | s10 | REF | 65% |
| 820 | s10 | ALT | 60% |
| 821 | s9 | REF | 55% |
| 822 | s9 | ALT | 50% |
| 823 | s16 | REF | 75% |
| 824 | s20 | ALT | 70% |
| 825 | s11 | REF | 65% |

TABLE 2-continued

Guide sequences designed to associate with specific SNPs of the ELANE gene

| SEQ ID NO: | SNP ID (Table 1) | Target (ALT/REF) | % GC |
|---|---|---|---|
| 826 | s9 | BOTH | 65% |
| 827 | s20 | ALT | 70% |
| 828 | s20 | REF | 65% |
| 829 | s14 | REF | 70% |
| 830 | s14 | ALT | 65% |
| 831 | s10 | BOTH | 70% |
| 832 | s17 | REF | 65% |
| 833 | s9 | REF | 60% |
| 834 | s9 | ALT | 55% |
| 835 | s16 | REF | 75% |
| 836 | s10 | BOTH | 70% |
| 837 | s9 | REF | 65% |
| 838 | s9 | ALT | 60% |
| 839 | s16 | ALT | 75% |
| 840 | s6 | REF | 70% |
| 841 | s20 | ALT | 75% |
| 842 | s20 | REF | 70% |
| 843 | s9 | REF | 75% |
| 844 | s9 | ALT | 70% |
| 845 | s19 | ALT | 55% |
| 846 | s19 | REF | 60% |
| 847 | s20 | ALT | 70% |
| 848 | s20 | REF | 65% |
| 849 | s10 | ALT | 60% |
| 850 | s10 | REF | 60% |
| 851 | s6 | ALT | 65% |
| 852 | s9 | REF | 70% |
| 853 | s9 | ALT | 65% |
| 854 | s19 | REF | 70% |
| 855 | s15 | ALT | 65% |
| 856 | s15 | REF | 70% |
| 857 | s19 | ALT | 55% |
| 858 | s19 | REF | 60% |
| 859 | s20 | ALT | 70% |
| 860 | s20 | REF | 65% |
| 861 | s19 | BOTH | 55% |
| 862 | s17 | BOTH | 55% |
| 863 | s19 | ALT | 55% |
| 864 | s19 | REF | 60% |
| 865 | s14 | ALT | 60% |
| 866 | s14 | REF | 65% |
| 867 | s17 | REF | 60% |
| 868 | s17 | ALT | 55% |
| 869 | s18 | REF | 75% |
| 870 | s10 | ALT | 60% |
| 871 | s10 | REF | 60% |
| 872 | s5 | REF | 60% |
| 873 | s6 | ALT | 60% |
| 874 | s17 | ALT | 60% |
| 875 | s17 | REF | 65% |
| 876 | s9 | REF | 65% |
| 877 | s9 | ALT | 60% |
| 878 | s15 | ALT | 65% |
| 879 | s15 | REF | 70% |
| 880 | s19 | ALT | 55% |
| 881 | s19 | REF | 60% |
| 882 | s5 | REF | 60% |
| 883 | s5 | ALT | 55% |
| 884 | s12 | ALT | 30% |
| 885 | s20 | REF | 65% |
| 886 | s19 | REF | 50% |
| 887 | s17 | BOTH | 55% |
| 888 | s15 | ALT | 60% |
| 889 | s15 | REF | 65% |
| 890 | s19 | ALT | 55% |
| 891 | s19 | REF | 60% |
| 892 | s6 | ALT | 55% |
| 893 | s14 | ALT | 60% |
| 894 | s14 | REF | 65% |
| 895 | s2 | REF | 40% |
| 896 | s15 | BOTH | 65% |
| 897 | s8 | REF | 40% |
| 898 | s10 | REF | 70% |
| 899 | s10 | ALT | 70% |
| 900 | s6 | REF | 60% |

TABLE 2-continued

Guide sequences designed to associate with specific SNPs of the ELANE gene

| SEQ ID NO: | SNP ID (Table 1) | Target (ALT/REF) | % GC |
|---|---|---|---|
| 901 | s19 | BOTH | 65% |
| 902 | s17 | ALT | 50% |
| 903 | s15 | REF | 75% |
| 904 | s18 | ALT | 75% |
| 905 | s15 | ALT | 65% |
| 906 | s14 | REF | 65% |
| 907 | s10 | ALT | 60% |
| 908 | s10 | REF | 60% |
| 909 | s8 | ALT | 40% |
| 910 | s8 | REF | 40% |
| 911 | s19 | REF | 60% |
| 912 | s19 | ALT | 55% |
| 913 | s15 | REF | 65% |
| 914 | s15 | ALT | 60% |
| 915 | s16 | BOTH | 70% |
| 916 | s14 | ALT | 60% |
| 917 | s8 | ALT | 40% |
| 918 | s6 | REF | 60% |
| 919 | s6 | ALT | 55% |
| 920 | s5 | ALT | 55% |
| 921 | s5 | REF | 60% |
| 922 | s6 | ALT | 55% |
| 923 | s1 | ALT | 45% |
| 924 | s1 | REF | 50% |
| 925 | s17 | ALT | 60% |
| 926 | s8 | REF | 35% |
| 927 | s8 | ALT | 35% |
| 928 | s17 | REF | 65% |
| 929 | s15 | REF | 65% |
| 930 | s9 | REF | 60% |
| 931 | s9 | ALT | 55% |
| 932 | s14 | REF | 60% |
| 933 | s15 | ALT | 60% |
| 934 | s15 | REF | 65% |
| 935 | s15 | ALT | 60% |
| 936 | s19 | ALT | 50% |
| 937 | s19 | REF | 55% |
| 938 | s11 | ALT | 40% |
| 939 | s19 | ALT | 50% |
| 940 | s19 | REF | 55% |
| 941 | s11 | REF | 60% |
| 942 | s12 | REF | 30% |
| 943 | s5 | REF | 55% |
| 944 | s20 | REF | 50% |
| 945 | s13 | REF | 60% |
| 946 | s12 | ALT | 35% |
| 947 | s16 | REF | 65% |
| 948 | s13 | REF | 55% |
| 949 | s13 | ALT | 55% |
| 950 | s17 | BOTH | 45% |
| 951 | s8 | ALT | 40% |
| 952 | s12 | ALT | 30% |
| 953 | s12 | ALT | 35% |
| 954 | s12 | REF | 30% |
| 955 | s8 | ALT | 40% |
| 956 | s8 | REF | 40% |
| 957 | s17 | REF | 60% |
| 958 | s8 | REF | 40% |
| 959 | s1 | ALT | 45% |
| 960 | s19 | REF | 50% |
| 961 | s19 | ALT | 45% |
| 962 | s9 | ALT | 70% |
| 963 | s8 | REF | 45% |
| 964 | s8 | ALT | 45% |
| 965 | s12 | ALT | 30% |
| 966 | s9 | REF | 75% |
| 967 | s8 | BOTH | 45% |
| 968 | s12 | ALT | 35% |
| 969 | s12 | REF | 30% |
| 970 | s6 | BOTH | 45% |
| 971 | s20 | REF | 65% |
| 972 | s19 | REF | 50% |
| 973 | s11 | REF | 35% |
| 974 | s17 | BOTH | 55% |
| 975 | s2 | ALT | 30% |

TABLE 2-continued

Guide sequences designed to associate with specific SNPs of the ELANE gene

| SEQ ID NO: | SNP ID (Table 1) | Target (ALT/REF) | % GC |
|---|---|---|---|
| 976 | s2 | REF | 35% |
| 977 | s11 | REF | 40% |
| 978 | s19 | ALT | 50% |
| 979 | s19 | REF | 55% |
| 980 | s3 | BOTH | 30% |
| 981 | s11 | BOTH | 60% |
| 982 | s15 | REF | 65% |
| 983 | s19 | ALT | 55% |
| 984 | s19 | REF | 60% |
| 985 | s6 | ALT | 60% |
| 986 | s6 | REF | 65% |
| 987 | s6 | ALT | 50% |
| 988 | s14 | ALT | 55% |
| 989 | s14 | REF | 60% |
| 990 | s8 | REF | 35% |
| 991 | s8 | ALT | 35% |
| 992 | s12 | REF | 30% |
| 993 | s12 | ALT | 35% |
| 994 | s14 | REF | 70% |
| 995 | s11 | REF | 60% |
| 996 | s9 | REF | 75% |
| 997 | s9 | ALT | 70% |
| 998 | s15 | ALT | 60% |
| 999 | s20 | REF | 50% |
| 1000 | s20 | ALT | 55% |
| 1001 | s8 | REF | 40% |
| 1002 | s9 | ALT | 55% |
| 1003 | s9 | REF | 60% |
| 1004 | s16 | REF | 70% |
| 1005 | s14 | BOTH | 60% |
| 1006 | s5 | BOTH | 45% |
| 1007 | s17 | ALT | 60% |
| 1008 | s17 | REF | 65% |
| 1009 | s10 | REF | 65% |
| 1010 | s10 | ALT | 65% |
| 1011 | s13 | ALT | 60% |
| 1012 | s13 | REF | 60% |
| 1013 | s10 | ALT | 65% |
| 1014 | s17 | REF | 65% |
| 1015 | s17 | ALT | 60% |
| 1016 | s6 | REF | 55% |
| 1017 | s5 | REF | 55% |
| 1018 | s19 | BOTH | 65% |
| 1019 | s17 | REF | 50% |
| 1020 | s17 | ALT | 45% |
| 1021 | s15 | REF | 70% |
| 1022 | s15 | ALT | 65% |
| 1023 | s10 | REF | 65% |
| 1024 | s16 | REF | 70% |
| 1025 | s18 | ALT | 75% |
| 1026 | s15 | ALT | 65% |
| 1027 | s13 | REF | 60% |
| 1028 | s14 | REF | 60% |
| 1029 | s10 | ALT | 60% |
| 1030 | s10 | REF | 60% |
| 1031 | s17 | REF | 65% |
| 1032 | s17 | ALT | 60% |
| 1033 | s2 | REF | 35% |
| 1034 | s19 | REF | 60% |
| 1035 | s19 | ALT | 55% |
| 1036 | s8 | ALT | 40% |
| 1037 | s8 | REF | 40% |
| 1038 | s12 | ALT | 35% |
| 1039 | s13 | REF | 60% |
| 1040 | s19 | REF | 55% |
| 1041 | s3 | BOTH | 35% |
| 1042 | s8 | REF | 40% |
| 1043 | s8 | ALT | 40% |
| 1044 | s13 | ALT | 60% |
| 1045 | s13 | REF | 60% |
| 1046 | s15 | REF | 60% |
| 1047 | s15 | ALT | 55% |
| 1048 | s2 | ALT | 30% |
| 1049 | s2 | REF | 35% |
| 1050 | s16 | BOTH | 65% |

TABLE 2-continued

| Guide sequences designed to associate with specific SNPs of the ELANE gene | | | |
|---|---|---|---|
| SEQ ID NO: | SNP ID (Table 1) | Target (ALT/REF) | % GC |
| 1051 | s17 | REF | 65% |
| 1052 | s17 | ALT | 60% |
| 1053 | s15 | ALT | 60% |
| 1054 | s12 | ALT | 35% |
| 1055 | s13 | ALT | 60% |
| 1056 | s13 | REF | 60% |
| 1057 | s14 | ALT | 55% |
| 1058 | s8 | ALT | 40% |
| 1059 | s6 | REF | 60% |
| 1060 | s6 | ALT | 55% |
| 1061 | s12 | ALT | 30% |
| 1062 | s2 | ALT | 30% |
| 1063 | s5 | ALT | 50% |
| 1064 | s5 | REF | 55% |
| 1065 | s11 | REF | 55% |
| 1066 | s6 | ALT | 55% |
| 1067 | s1 | ALT | 40% |
| 1068 | s1 | REF | 45% |
| 1069 | s16 | ALT | 65% |
| 1070 | s2 | REF | 40% |
| 1071 | s2 | ALT | 35% |
| 1072 | s17 | ALT | 40% |
| 1073 | s16 | REF | 70% |
| 1074 | s13 | REF | 60% |
| 1075 | s13 | ALT | 60% |
| 1076 | s17 | ALT | 60% |
| 1077 | s8 | REF | 35% |
| 1078 | s8 | ALT | 35% |
| 1079 | s17 | ALT | 45% |
| 1080 | s14 | ALT | 55% |
| 1081 | s14 | REF | 60% |
| 1082 | s10 | REF | 60% |
| 1083 | s10 | ALT | 60% |
| 1084 | s17 | REF | 65% |
| 1085 | s20 | BOTH | 55% |
| 1086 | s19 | ALT | 55% |
| 1087 | s20 | REF | 55% |
| 1088 | s20 | ALT | 60% |
| 1089 | s11 | REF | 50% |
| 1090 | s13 | REF | 55% |
| 1091 | s13 | ALT | 55% |
| 1092 | s18 | REF | 70% |
| 1093 | s10 | BOTH | 65% |
| 1094 | s14 | REF | 60% |
| 1095 | s14 | ALT | 55% |
| 1096 | s21 | ALT | 30% |
| 1097 | s15 | REF | 65% |
| 1098 | s18 | ALT | 75% |
| 1099 | s10 | ALT | 60% |
| 1100 | s10 | REF | 60% |
| 1101 | s10 | ALT | 65% |
| 1102 | s14 | REF | 70% |
| 1103 | s14 | ALT | 65% |
| 1104 | s9 | REF | 60% |
| 1105 | s9 | ALT | 55% |
| 1106 | s6 | REF | 65% |
| 1107 | s10 | ALT | 55% |
| 1108 | s10 | REF | 55% |
| 1109 | s6 | ALT | 60% |
| 1110 | s19 | ALT | 55% |
| 1111 | s19 | REF | 60% |
| 1112 | s14 | ALT | 55% |
| 1113 | s14 | REF | 60% |
| 1114 | s17 | REF | 60% |
| 1115 | s17 | ALT | 55% |
| 1116 | s5 | ALT | 50% |
| 1117 | s5 | REF | 55% |
| 1118 | s17 | ALT | 60% |
| 1119 | s17 | REF | 65% |
| 1120 | s9 | ALT | 45% |
| 1121 | s15 | ALT | 60% |
| 1122 | s15 | REF | 65% |
| 1123 | s2 | REF | 40% |
| 1124 | s15 | REF | 70% |
| 1125 | s11 | REF | 65% |
| 1126 | s15 | ALT | 60% |
| 1127 | s15 | ALT | 55% |
| 1128 | s16 | BOTH | 65% |
| 1129 | s6 | REF | 60% |
| 1130 | s6 | ALT | 55% |
| 1131 | s15 | REF | 65% |
| 1132 | s14 | ALT | 55% |
| 1133 | s14 | REF | 60% |
| 1134 | s15 | ALT | 60% |
| 1135 | s19 | REF | 55% |
| 1136 | s8 | ALT | 35% |
| 1137 | s8 | REF | 35% |
| 1138 | s17 | ALT | 50% |
| 1139 | s17 | REF | 55% |
| 1140 | s12 | ALT | 30% |
| 1141 | s11 | BOTH | 35% |
| 1142 | s2 | ALT | 30% |
| 1143 | s2 | REF | 35% |
| 1144 | s19 | ALT | 45% |
| 1145 | s19 | REF | 50% |
| 1146 | s6 | REF | 60% |
| 1147 | s12 | REF | 30% |
| 1148 | s12 | ALT | 35% |
| 1149 | s2 | ALT | 35% |
| 1150 | s11 | REF | 55% |
| 1151 | s9 | REF | 75% |
| 1152 | s9 | ALT | 70% |
| 1153 | s9 | ALT | 50% |
| 1154 | s9 | REF | 55% |
| 1155 | s13 | ALT | 60% |
| 1156 | s13 | REF | 60% |
| 1157 | s1 | REF | 35% |
| 1158 | s5 | REF | 55% |
| 1159 | s5 | ALT | 50% |
| 1160 | s13 | REF | 60% |
| 1161 | s18 | ALT | 75% |
| 1162 | s12 | ALT | 30% |
| 1163 | s20 | REF | 55% |
| 1164 | s8 | REF | 40% |
| 1165 | s8 | ALT | 40% |
| 1166 | s17 | REF | 65% |
| 1167 | s12 | ALT | 30% |
| 1168 | s14 | ALT | 55% |
| 1169 | s16 | REF | 65% |
| 1170 | s17 | ALT | 40% |
| 1171 | s17 | REF | 45% |
| 1172 | s14 | ALT | 55% |
| 1173 | s14 | REF | 60% |
| 1174 | s20 | BOTH | 50% |
| 1175 | s15 | REF | 60% |
| 1176 | s15 | ALT | 55% |
| 1177 | s6 | REF | 55% |
| 1178 | s6 | ALT | 50% |
| 1179 | s8 | ALT | 45% |
| 1180 | s9 | REF | 70% |
| 1181 | s9 | ALT | 65% |
| 1182 | s10 | REF | 65% |
| 1183 | s15 | REF | 55% |
| 1184 | s4 | BOTH | 45% |
| 1185 | s4 | BOTH | 45% |
| 1186 | s4 | BOTH | 45% |
| 1187 | s4 | BOTH | 45% |
| 1188 | s4 | BOTH | 35% |
| 1189 | s4 | ALT | 30% |
| 1190 | s15 | REF | 65% |
| 1191 | s2 | REF | 25% |
| 1192 | s13 | REF | 55% |

For the foregoing embodiments, each embodiment disclosed herein is contemplated as being applicable to each of the other disclosed embodiment. For example, it is understood that any of the RNA molecules or compositions of the present invention may be utilized in any of the methods of the present invention.

As used herein, all headings are simply for organization and are not intended to limit the disclosure in any manner. The content of any individual section may be equally applicable to all sections.

Examples are provided below to facilitate a more complete understanding of the invention. The following examples illustrate the exemplary modes of making and practicing the invention. However, the scope of the invention is not limited to specific embodiments disclosed in these Examples, which are for purposes of illustration only.

Further, the examples herein below disclose methods utilizing SpCas9 and guide sequences suitable to target the SpCas9 to the disclosed SNP positions. The examples demonstrate the feasibility of the strategies disclosed. A person having ordinary skill in the art would understand that the same guides sequences may be used with different CRISPR nuclease to target the disclosed SNPs to apply each of the specified strategies. Further, different guide sequences that target other CRISPR nucleases to the same SNPs may be used together with the other nucleases to apply each of the specified strategies.

EXPERIMENTAL DETAILS

Figure 6:
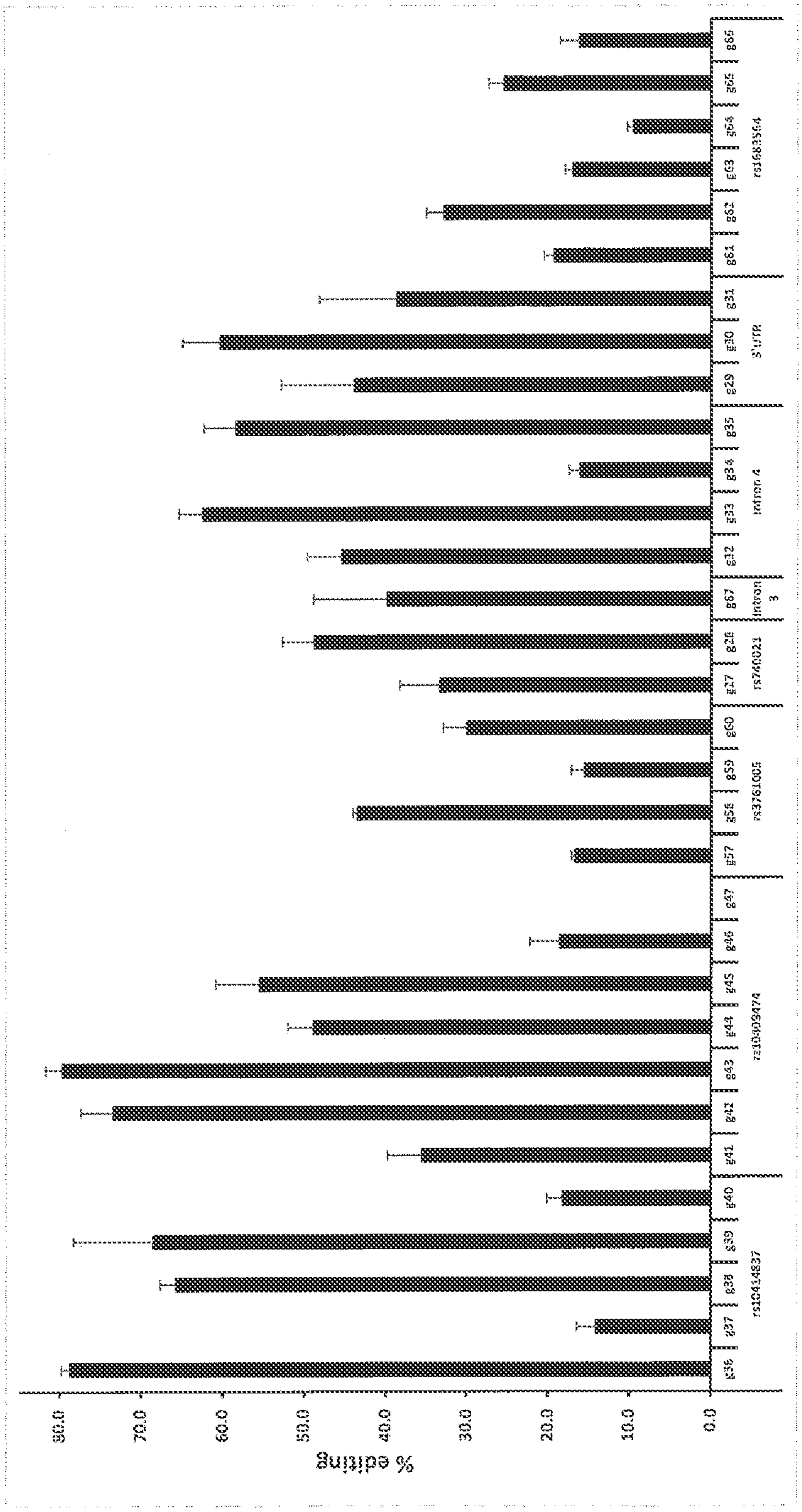
FIG. 6: HeLa cells seeded into 96 well-plate (3K/well). 24 h later were co-transfected with either 65 ng of WT-Cas9 or Dead-Cas9 and 20 ng of gRNA plasmids, identified as g36 through g66, targeting the different regions and SNPs in ELANE using Turbofect reagent (Thermo Scientific). Percent of editing was calculated according the following formula: 100%-(Intensity not edited band/Intensity total bands)*100. The mean activity of each gRNA following subtraction of the Dead-Cas9 background activity±SD of three independent experiment is shown.

Example 1: Screening Guide Sequences Suitable to Work in Conjunction with SpCas9 and Targeting SNPs and Sequences Complying with the Disclosed Strategies HeLa cells were seeded into 96 well-plate (3K/well). 24 h later, cells were co-transfected with either 65 rig of WT-Cas9 or Dead-Cas9 and 20 ng of gRNA plasmids, identified as g36 through g66, targeting the different regions and SNPs in ELANE using Turbofect reagent (Thermo Scientific). 12 hours later, fresh media was added, and 72 hours post transfection, genomic DNA were extracted, and the expected region targeted by the Cas9 was amplified and the product size was analyzed by capillary electrophoreses with a DNA ladder. The intensity of the bands was analyzed using the Peak Scanner software v1.0. The percent of editing was calculated according the following formula: 100%−(Intensity not edited band/Intensity total bands)*100. FIG. 6 represents the mean activity of each gRNA following subtraction of the De-ad-Cas9 background activity±SD of three independent experiment.

TABLE 3 guides sg36 through sg66 of Example 1 as identified by SEQ ID NO.

| Guide sequence | Example 1 gID | SEQ ID NO: | SNP location |
|---|---|---|---|
| UAGGGGUGUUAUGGUCACAG | g36 | 972 | upstream -2590 bp |
| CACAGCGGGUGUAGACUCCG | g37 | 308 | upstream -2590 bp |
| ACAGCGGGUGUAGACUCCGA | g38 | 94 | upstream -2590 bp |
| CAGCGGGUGUAGACUCCGAG | g39 | 352 | upstream -2590 bp |
| AGCGGGUGUAGACUCCGAGG | g40 | 180 | upstream -2590 bp |
| CCGUUGCAGCUGGAACAUCG | g41 | 499 | upstream -1475 bp |
| CGUUGCAGCUGGAACAUCGU | g42 | 564 | upstream -1475 bp |
| GUUGCAGCUGGAACAUCGUG | g43 | 948 | upstream -1475 bp |
| UUGCAGCUGGAACAUCGUGG | g44 | 1192 | upstream -1475 bp |
| CUGGAACAUCGUGGGGGAGA | g45 | 601 | upstream -1475 bp |
| UGGAACAUCGUGGGGGAGAU | g46 | 1090 | upstream -1475 bp |
| AUCGUGGGGGAGAUGGGAAG | g47 | 249 | upstream -1475 bp |
| GGAGUCCCAGCUGCGGGAAA | g57 | 786 | upstream -1415 bp |
| GCUGCGGGAAAGGGAUUCCC | g58 | 755 | upstream -1415 bp |
| GGGAAUCCCUUUCCCGCAGC | g59 | 819 | upstream -1415 bp |
| GGAAUCCCUUUCCCGCAGCU | g60 | 772 | upstream -1415 bp |
| CAAAUGUCAGAUAAUCAAUG | g27 | 287 | upstream |
| AAAUGUCAGAUAAUCAAUGU | g28 | 1191 | upstream |
| ACCAAGGCUCAGGGCGUUGG | g67 | 1193 | Int3 |
| CCUGUUGCUGCAGUCCGGGC | g32 | 1194 | Int4 |
| CCAGCCCGGACUGCAGCAAC | g33 | 1195 | Int4 |
| UCCCUCCUAGGGUCUAGCCA | g34 | 1196 | Int4 |
| AGUCCGGGCUGGGAGCGGGU | g35 | 1197 | Int4 |

TABLE 3-continued

| guides sg36 through sg66 of Example 1 as identified by SEQ ID NO. | | | |
|---|---|---|---|
| Guide sequence | Example 1 gID | SEQ ID NO: | SNP location |
| AUGUUUAUUGUGCCAGAUGC | g29 | 1198 | 3UTR |
| GUGGGCAGCUGAGGUGACCC | g30 | 1199 | 3UTR |
| CACCCACACUCUCCAGCAUC | g31 | 1200 | 3UTR |
| UGUCAAGCCCCAGAGGCCAC | g61 | 1122 | downstream +2968 bp |
| GUCAAGCCCCAGAGGCCACA | g62 | 889 | downstream +2968 bp |
| GUCUCUGUCCCUGUGGCCUC | g63 | 913 | downstream +2968 bp |
| UCUCUGUCCCUGUGGCCUCU | g64 | 1046 | downstream +2968 bp |
| CUCUGUCCCUGUGGCCUCUG | g65 | 1190 | downstream +2968 bp |
| UGUCAAGCCCCAGAGGCCAC | g66 | 1122 | downstream +2968 bp |

Example 2: Demonstrating the Feasibility of the Excision Strategies

HeLa cells were co-transfected with spCas9-WT and RNA pairs; sg35 (INT 4) with either g39 (rs10414837), g58 (rs3761005) or g62 (rs1683564) for strategies 1a, 1b and 2, respectively. 72 h post-transfection, gDNA was extracted and excision efficiency was assessed by measuring the decrease in copy number of exon 1 (strategy 1) or exon 5 (strategy 2), using droplet digital PCR (ddPCR) kits (10042958 and 10031228, Bio-Rad Laboratories). In addition. exon 1 was used to normalize the excision rate of strategy 2 while exon 5 was used to normalize the excision rate of strategy 1. The results disclosed in Table 4 represent the mean % excision+SD (standard deviation) of 2 independent experiments.

TABLE 4

| Tested excision rate for each strategy | | |
|---|---|---|
| Strategy | Guide-RNA pair | Excision rate (%) |
| 1.a | g39 + g35 | 49 ± 2 |
| 1.b | g58 + g35 | 45 ± 9.6 |
| 2 | g62 + g35 | 41 ± 12.6 |

Example 3: Assessing allele discriminating editing with the different sgRNAs

Ribonucleoprotein complexes (RNPs) were assembled from the relevant gRNAs, targeting the reference sequence, and WT-Cas9 (#1081058) or HiFi Cas9 (#1081060) purchased from Integrated DNA Technology (IDT) according to the manufacturer instructions. The RNPs were then nucleofected into iPSCs harboring the relevant SNPs using the 4D-Nucleofecor (R) System (Lonza). 721 h later, gDNA is extracted and the SNPs regions were amplified and sent to NGS analysis. Allele discrimination were assessed according to % of editing detected in the reference and the alternative alleles. The Indels frequency in each site was calculated using Cas-Analyzer software. Results are summarized in Table 5.

TABLE 5

| % Editing using indicated guide sequences | | | | | | |
|---|---|---|---|---|---|---|
| | % of Editing | | | | | |
| | rs10414837 (g39) | | rs3761005 (g58) | | rs1683564 (g62) | |
| spCas9 Varaint | Reference Allele | Alternative Allele | Reference Allele | Alternative Allele | Reference Allele | Alternative Allele |
| WT-Cas9 | 65.3 | 34.7 | 50 | 50 | 100 | 0 |
| HiFi-Cas9 | 94.3 | 5.7 | 49 | 51 | 100 | 0 |

Example 4: Editing Efficiency in HSCs

Figure 7:
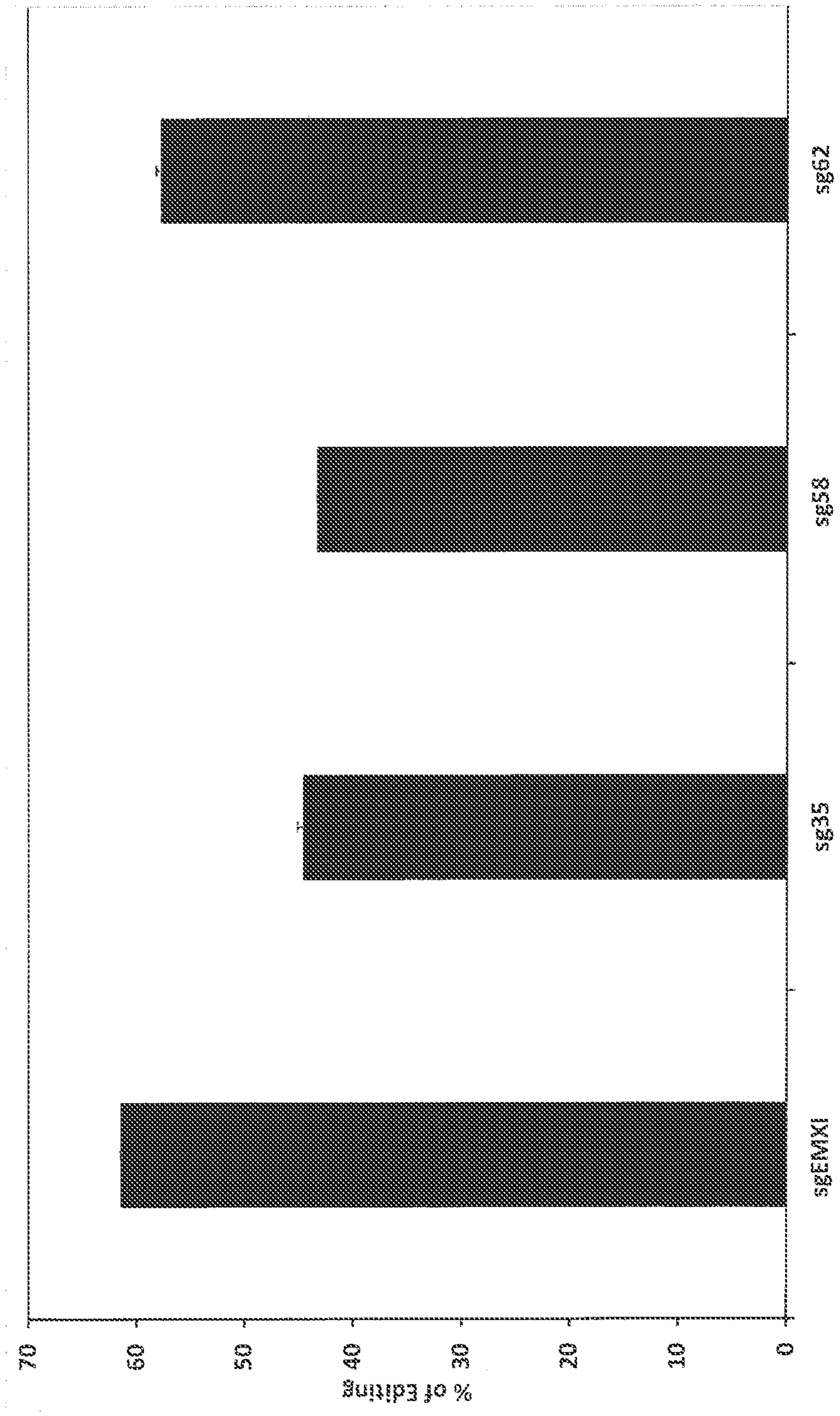
FIG. 7: HSCs from healthy donors were nucleofected with RNA components of spCas9-WT and gRNAs targeting either EMX1 (sgEMX1) or ELANE (g35: INT 4; g58: rs3761005; g62: rs1683564). 72 h post nucleofection gDNA was extracted and editing levels were assayed by IDAA. The mean % of editing±SD of 2 independent experiments performed in duplicates is shown.

HSCs from healthy donors were nucleofected with RNA components of spCas9-WT and gRNAs targeting either EMX1 (sgEMX1) or ELANE (g35: INT 4; g58: rs3761005; g62: rs1683564). 72 h post nucleofection gDNA was extracted and editing levels were assayed by IDAA. FIG. 7 represents the mean % of editing i SD of 2 independent experiments performed in duplicates.

Example 5: Functional Maturation Assay

To prove the rescue of the phenotype in corrected cells, a maturation assay starting from patient-derived induced pluripotent cells (iPSC), is prepared from reprogrammed somatic cells. The cells provide a renewable source of patient-derived cells and are shown to accurately replicate the disease phenotype. Briefly, patient PBMCs are transfected with episomal constructs expressing the reprogramming genes, Oct4, Sox2, Nanog, Lin28, L-Myc, Klf4, and SV40LT. Patient-derived iPSC and normal iPSCs harboring the same SNPs genotype are differentiated into hematopoietic progenitor cells using a commercial kit (STEMdiffrm Hematopoietic Kit, STEMCELL Technologies). After 12 days the differentiation efficiency is estimated by analyzing the cells for their expression of progenitor markers CD34 and CD45, by Flow cytometry analysis. Normal and SCN differentiated progenitor cells are be subjected to gene editing and are grown for 5 days in conditioned media containing stem cell factor (SCF), IL-3, and GM-CSF that promotes the differentiation into neutrophils. Normal unedited and edited cells, SCN edited cells differentiate into neutrophils while unedited SCN-derived cells arrest at earlier differentiation stages. The efficiency of differentiation into neutrophils is measured by detecting neutrophils surface markers (e.g. upregulation of CD16, CD66b and the pan myeloid marker CD33) by Flow cytometry.

Example 6: In Vivo Pilot Dose-Range Finding and Biodistribution Study in Immunodeficient Mice The dosing schedule, dose range, and route of administration, are studied to determine the presence and number of HSCs with self-renewal and multilineage capacity in immunodeficient NSG mice, following G-CSF administration. A repopulation assay is conducted to determine the presence and number of HSCs that are able to regenerate a functional immune system to establish long term engraftment. For such verification, the NSG strain is used, which is highly supportive of human engraftment and hematopoietic repopulation. The NSG mouse is a NOD SCID mouse lacking mature T cells, B cells, and natural killer (NK) cells, in addition to being deficient in multiple cytokine signaling pathways and having many defects in innate immunity. Engraftment is assessed 16 weeks after primary transplantation (analysis after 12 weeks post-transplant).

The 16-week pilot biodistribution study in NSG mice investigates dose and maximum duration and is conducted at several cell dose levels. The study includes three dose levels plus a group of mice receiving unedited SCN cells. Duration of the pilot study is 16 weeks; however, one of two high dose groups continues for up to 6 months. Mice survive for 6 months in the pilot study, and the duration of the pivotal biodistribution study is 6 months. During the study, persistence of expression via qPCR and immune histochemistry is studied.

Example 7: Pivotal Biodistribution Study in Immunodeficient Mice

The pivotal biodistribution study utilizes NSG mice and follows the pilot dose-range findings of Example 6. This study is conducted in compliance with Good Laboratory Practice (GLP) and is a pivotal nonclinical pharmacokinetics, pharmacodynamics, and toxicology study. Assessment of toxicity is based on mortality, clinical observations, body and organ weights, and clinical and anatomic pathology following HSC infusion.

Transplantation of gene-edited CD34+ cells into NSG mice requires conditioning in order to provide depletion of endogenous bone marrow and to allow the engraftment of donor cells. Accordingly, Busulfan-conditioning is employed to mimic the clinical situation. Three groups (gene edited cells, unedited cells and busulfan vehicle only controls) of 10 male and female mice per group are utilized.

Although the NSG mouse model is not completely similar to the human neutrophil depleted situation, this does not affect the validity of the model for use in the biodistribution study of the gene-edited CD34+ cells, since the mice at any rate are treated with busulfan, depleting the bone marrow function, before the in vivo injection of ex vivo gene edited cells. An available neutrophil-depleted mouse strain, myeloid cell leukemia 1 (Mcl-1) antiapoptotic protein in Lyz2$^{Cre/Cre}$Mcl-1$^{flox/flox}$ (Mel-1$^{\Delta Myelo}$) shows that myeloid-specific deletion of Mcl-1 lead to very severe neutropenia (Csepregi et al. 2018). Mcl-1$^{\Delta Myelo}$ mice are able to breed and their survival is close to normal both under specific pathogen-free and conventional housing conditions. However, in contrast to the NSG mouse, there is limited experience with the Mcl-1$^{\Delta Myelo}$ mouse model.

Example 8: A Correction Analysis

Guide sequences comprising 17-20 nucleotides in the sequences of 17-20 contiguous nucleotides set forth in SEQ ID NOs: 1-1192 are screened for high on target activity. On target activity is determined by DNA capillary electrophoresis analysis.

According to DNA capillary electrophoresis analysis, guide sequences comprising 17-20 nucleotides in the sequences of 17-20 contiguous nucleotides set forth in SEQ ID NOs: 1-1192 are found to be suitable for correction of the ELANE gene.

Example 9: Efficacy of Allele Specific Knockout of ELANE

Figure 8:
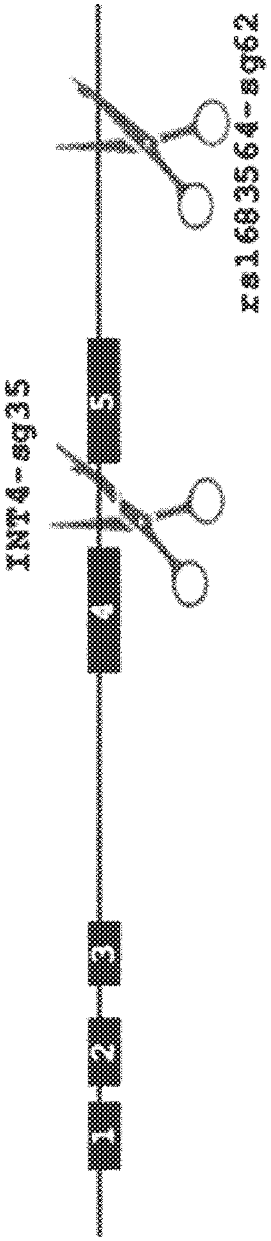
FIG. 8: Specific knock-out of the mutated allele of the ELANE gene is mediated by excising intron 4 and exon5 of the mutant allele of the ELANE gene. This is achieved by mediating a DSB in intron 4 and utilizing SNP rs1683564 for mediating an allele specific DSB.

Specific knock-out of the mutated allele of the ELANE gene is mediated by excising intron 4 and exon5 of the mutant allele of the ELANE gene. This is achieved by mediating a DSB in intron 4 and utilizing SNP rs1683564 for mediating an allele specific DSB as described in FIG. 8. To demonstrate that this strategy effectively enables HSCs to differentiate into mature and functional neutrophils, healthy donors are nucleofected with HSCs (Lonza) with RNPs containing g35 and g62 targeting the respective SNP of intron 4 (See Table 1). Unedited cells are used as a positive control. Forty-eight (48) hours following nucleofection, HSCs are differentiated towards neutrophils according to a published protocol (Zhenwang Jie, et al. PlosOne 2017). The differentiation efficiency of the edited and unedited cells is measured by FACS following staining with the neutrophils specific markers CD66b and CD177. To assess the function of the HSCs-mediated neutrophils, the following assays are performed:

1. Phagocytosis: is assayed using the EZCell™ Phagocytosis Assay Kit (BioVision). The kit utilizes pre-labeled Zymosan particles as a tool for rapid and accurate detection and quantification of in vitro phagocytosis by flow cytometry.
2. A killing assay is conducted by incubating the HSCs-derived neutrophils with *E. coli*, with the bacteria then seeded on agar plate for colonies formation. Untreated bacteria or bacteria that were incubated with undifferentiated HSCs are used as controls. The killing efficiency is calculated as follows: (#of colonies$_{Neutrophils}$/#of colonies$_{Control}$)×100.

3. Chemotaxis is assayed using the EZCell™ Cell Migration/Chemotaxis Assay Kit (Biovision).

Example 10: Subject Selection for Treatment

Step 1: Four patients A-D diagnosed with SCN or CyN are screened by Exon sequencing to identify an ELANE pathogenic mutation in the ELANE gene. Step 2: Subjects with an identified mutation are then screened by Sanger sequencing to confirm heterozygosity of at least one of rs1683564, rs10414837 and rs3761005. Step 3: For each subject determined to be heterozygous at at least one of of rs1683564, rs10414837 and rs3761005, the nucleotide of the heterozygous SNP on the mutant allele of the ELANE gene is determined using BAC bio. Step 4: Appropriate guides are selected according to Table 6.

TABLE 6

Guides Designed for Discriminating SNPs and used for the Editing Strategy

| gRNA | SEQ ID NO: | Target SNP | DNA Sequence | Location | Mechanism |
|---|---|---|---|---|---|
| g39 REF | 352 | rs10414837 | CAGCGGGTGTAGACTCCGAG | Promoter region | Excision, allele knock out |
| ALT | 351 | | CAGCAGGTGTAGACTCCGAG | | |
| g58 REF | 755 | rs3761005 | GCTGCGGGAAAGGGATTCCC | Promoter region | Excision, allele knock out |
| ALTt | 756 | | GCTGCGGGAATGGGATTCCC | | |
| g62 REF | 889 | rs1683564 | GTCAAGCCCCAGAGGCCACA | Downstream to 3'UTR | Excision, allele knock out |
| ALT | 888 | | GTCAAGCCCCAGAGGACACA | | |
| g35 | 1197 | | AGTCCGGGCTGGGAGCGGGT | Intron 4 | Excision, allele knock out |

Step 5: The guides selected are introduced to PBMCs obtained from each respective subject and reduction in the pathogenic ELANE mutation in the PBMCs is verified by Next Generation Sequencing. The methodology for patients A-D is illustrated below:

1. Patient A is screened according to step 1 and found to have a known pathogenic mutation in his ELANE gene, in agreement with his phenotype and clinical condition. Patient A is screened according to step 2, around the SNPs of interest, and is found to be homozygous for all three SNP-rs10414837, rs1683564 and rs3761005. Patient A is determined to not eligible for treatment.
2. Patient B is verified for a known pathogenic ELANE mutation. Patient B is screened according to step 2 and is found to be homozygous for SNPs rs1683564 and rs10414837. Patient B is found to be heterozygous for rs3761005 in the promotor region. Patient B is determined to be eligible for treatment. According to step 3, the nucleotide of the SNP residing on the same allele as the pathogenic ELANE mutation (linkage determination) is determined. Patent B is found to have the reference nucleotide base in the rs3761005 SNP position on the same allele as the ELANE pathogenic mutation. g58ref is fully complementary to this SNP presentation and is selected in combination with g35 directed at the non-coding region of intron 4. According to step 4, the chosen guide composition includes a pair of guides g58ref and g35. Successful excision of the mutated allele using the selected pair of guides is verified according to step 5 on the patient PMBCs using NGS readout.
3. Patient C suffers from Severe Neutropenia since early childhood. Screening according to step A, no pathogenic mutation is found in his ELANE gene. Patient C is determined to not eligible for treatment.
4. Patient D is verified to have a known pathogenic mutation in ELANE gene, and when genotyping his SNPs according to step 2, he is found to be heterozygous at 2 out of 3 SNPs—both rs10414837 and rs1683564 are found to be heterozygous while rs3761005 is found to be homozygous. A selection between two possible SNPs to use for the gene manipulation is made. In order to make the selection, step 3 is performed to determine the linkage between the SNPs and the pathogenic mutation, i.e. determination of which nucleotide of the SNP (reference or alternative) resides on the same allele as the ELANE pathogenic mutation (SNP presentation). Patient D is determined to have the reference presentation of rs10414837 and sg39ref is determined to be appropriate for use. Referring to the rs1683564 SNP, the alternative presentation is found to be linked to the ELANE pathogenic mutation, sg62alt is determined to be the appropriate guide for use. Each of these guides is used in combination with g35. According to Step 4, two pairs of possible guides compositions are identified: sg39ref+g35, and g62alt+g35. To determine which of the guide pairs is preferable, a database of editing properties and characterization of each of the guides and guide pairs is assessed to determine off-target and editing efficiencies A guide pair is selected based on the database assessment, and is utilized according to step 5 on PBCS providing an NGS readout.

REFERENCES

1. Ahmad and Allen (1992) "Antibody-mediated Specific Binging and Cytotoxicity of Lipsome-entrapped Doxorubicin to Lung Cancer Cells in Vitro", Cancer Research 52:4817-20
2. Anders (1992) "Human gene therapy", Science 256:808-13

3. Basha et al. (2011) "Influence of Cationic Lipid Composition on Gene Silencing Properties of Lipid Nanoparticle Formulations of siRNA in Antigen-Presenting Cells", Mol. Ther. 19(12):2186-200
4. Behr (1994) Gene transfer with synthetic cationic amphiphiles: Prospects for gene therapy", Bioconjuage Chem 5:382-89
5. Blaese (1995) "Vectors in cancer therapy: how will they deliver", Cancer Gene Ther. 2:291-97
6. Blaese et al. (1995) "T lymphocyte-directed gene therapy for ADA-SCID: initial trial results after 4 years", Science 270(5235):475-80
7. Boxer, L. A. (2012) "How to approach neutropenia", Hematology Am Soc Hematol Educ Program 2012: 174-182
8. Buchschacher and Panganiban (1992) "Human immunodeficiency virus vectors for inducible expression of foreign genes", J. Virol. 66:2731-39
9. Burstein et al. (2017) "New CRISPR-Cas systems from uncultivated microbes", Nature 542:237-41
10. Carlsson, G et al. (2012) "Incidence of severe congenital neutropenia in Sweden and risk of evolution to myelodysplastic syndrome/leukaemia", Br J Hacmatol 158(3): 363-369
11. Chung et al. (2006) "*Agrobacterium* is not alone: gene transfer to plants by viruses and other bacteria", Trends Plant Sci. 11(1):1-4
12. Connelly, J. A. et al. (2012) "Hematopoietic stem cell transplantation for severe congenital neutropenia", Curr Opin Hematol 19(1): 44-51
13. Crystal (1995) "Transfer of genes to humans: early lessons and obstacles to success", Science 270(5235): 404-10
14. Dale, D. C. (2017) "How 1 manage children with neutropenia", Br J Haematol 178(3): 351-363
15. Dillon (1993) "Regulation gene expression in gene therapy" Trends in Biotechnology 11(5):167-173
16. Donadieu, J. et al. (2011) "Congenital neutropenia: diagnosis, molecular bases and patient management", Orphanet J Rare Dis 6: 26.
17. Dranoff et al. (1997) "A phase I study of vaccination with autologous, irradiated melanoma cells engineered to secrete human granulocyte macrophage colony stimulating factor", Hum. Gene Ther. 8(1):111-23
18. Donadieu et al. (2011) "Congenital neutropenia: diagnosis, molecular bases and patient management", Orphanet J Rare Dis. 6:26
19. Dunbar et al. (1995) "Retrovirally marked CD34-enriched peripheral blood and bone marrow cells contribute to long-term engraftment after autologous transplantation", Blood 85:3048-57
20. Ellem et al. (1997) "A case report: immune responses and clinical course of the first human use of granulocyte/macrophage-colony-stimulating-factor-transduced autologous melanoma cells for immunotherapy", Cancer Immunol Immunother 44:10-20
21. Gao and Huang (1995) "Cationic liposome-mediated gene transfer" Gene Ther. 2(10):710-22
22. Germeshausen et al. (2013) "The spectrum of ELANE mutations and their implications in severe congenital and cyclic neutropenia", Hum Mutat. 34(6):905-14
23. Haddada et al. (1995) "Gene Therapy Using Adenovirus Vectors", in: The Molecular Repertoire of Adenoviruses III: Biology and Pathogenesis, ed. Doerfler and BBhm, pp. 297-306
24. Han et al. (1995) "Ligand-directed retro-viral targeting of human breast cancer cells", Proc Natl Acad Sci U.S.A. 92(21):9747-51
25. Horwitz, M. S. et al. (2013) "ELANE mutations in cyclic and severe congenital neutropenia: genetics and pathophysiology", Hematol Oncol Clin North Am 27(1): 19-41, vii.
26. Inaba et al. (1992) "Generation of large numbers of dendritic cells from mouse bone marrow cultures supplemented with granulocyte/macrophage colony-stimulating factor", J Exp Med. 176(6):1693-702
27. Jinek et al. (2012) "A programmable dual-RNA-guided DNA endonuclease in adaptive bacterial immunity," Science 337(6096):816-21
28. Johan et al. (1992) "GLVR1, a receptor for gibbon ape leukemia virus, is homologous to a phosphate permease of *Neurospora crassa* and is expressed at high levels in the brain and thymus", J Virol 66(3):1635-40
29. Judge et al. (2006) "Design of noninflammatory synthetic siRNA mediating potent gene silencing in vivo", Mol Ther. 13(3):494-505
30. Kohn et al. (1995) "Engraftment of gene-modified umbilical cord blood cells in neonates with adnosine deaminase deficiency", Nature Medicine 1:1017-23
31. Koonen et al. (2017) "Diversity, classification and evolution of CRIPR-Cas systems", Current Opinion in Microbiology 37:67-78
32. Kremer and Perricaudet (1995) "Adenovirus and adeno-associated virus mediated gene transfer", Br. Med. Bull. 51(1):31-44
33. Macdiarmid et al. (2009) "Sequential treatment of drug-resistant tumors with targeted minicells containing siRNA or a cytotoxic drug", Nat Biotchcnol. 27(7):643-51
34. Malech et al. (1997) "Prolonged production of NADPH oxidase-corrected granulocytes after gene therapy of chronic granulomatous disease", PNAS 94(22):12133-38
35. Makaran et al. (2015) "The diversity of mutations and clinical outcomes for ELANE-associated neutropenia", Curr Opin Hematol. 22(1):3-11
36. Miller et al. (1991) "Construction and properties of retrovirus packaging cells based on gibbon ape leukemia virus", J Virol. 65(5):2220-24
37. Miller (1992) "Human gene therapy comes of age", Nature 357:455-60
38. Mitani and Caskey (1993) "Delivering therapeutic genes—matching approach and application", Trends in Biotechnology 11(5):162-66
39. Nabel and Felgner (1993) "Direct gene transfer for immunotherapy and immunization", Trends in Biotechnology 11(5):211-15
40. Remy et al. (1994) "Gene Transfer with a Series of Lipphilic DNA-Binding Molecules", Bioconjugate Chem. 5(6):647-54
41. Rosenberg, P. S. et al. (2010) "Stable long-term risk of leukaemia in patients with severe congenital neutropenia maintained on G-CSF therapy", Br J Haematol 150(2): 196-199.
42. Schaffer, A et al. (2007) "Genetic heterogeneity in severe congenital neutropenia: how many aberrant pathways can kill a neutrophil?" Curr Opin Allergy Clin Immunol 7(6): 481-494
43. Sentmanat et al. (2018) "A Survey of Validation Strategies for CRISPR-Cas9 Editing", Scientific Reports 8:888, doi:10.1038/s41598-018-19441-8
44. Skokowa, J. et al. (2017) "Severe congenital neutropenias", Nat Rev Dis Primers 3: 17032

45. Sommerfelt et al. (1990) "Localization of the receptor gene for type D simian retroviruses on human chromosome 19", J. Virol. 64(12):6214-20
46. Van Brunt (1988) "Molecular framing: transgenic animals as bioactors" Biotechnology 6:1149-54
47. Vigne et al. (1995) "Third-generation adenovectors for gene therapy", Restorative Neurology and Neuroscience 8(1,2): 35-36
48. Wilson et al. (1989) "Formation of infectious hybrid virion with gibbon ape leukemia virus and human T-cell leukemia virus retroviral envelope glycoproteins and the gag and po/proteins of Moloney murine leukemia virus", J. Virol. 63:2374-78
49. Yu et al. (1994) "Progress towards gene therapy for HIV infection", Gene Ther. 1(1):13-26
50. Yu, K et al. (2016) "Gene Editing of Human Hematopoietic Stem and Progenitor Cells: Promise and Potential Hurdles", Hum Gene Ther 27(10): 729-740
51. Zetsche et al. (2015) "Cpf1 is a single RNA-guided endonuclease of a class 2 CRIPSR-Cas system" Cell 163(3):759-71
52. Zhenwang et al. (2017) "Large-scale ex vivo generation of human neutrophils from cord blood $CD34^+$ cells", PLOS ONE, available at <https://doi.org/i0.1371/journal-.pone.0180832>
53. Zuris et al. (2015) "Cationic lipid-mediated delivery of proteins enables efficient protein based genome editing in vitro and in vivo" Nat Biotechnol. 33(1):73-80

The invention claimed is:

1. A method for inactivating in a cell a mutant allele of the elastase neutrophil expressed gene (ELANE gene) having a mutation associated with severe congenital neutropenia (SCN) or cyclic neutropenia (CyN), the method comprising (a) delivering to an isolated human cell that comprises a mutant ELANE allele and a functional ELANE allele a composition comprising: a CRISPR nuclease or a sequence encoding the CRISPR nuclease; and an isolated guide RNA molecule (gRNA) that targets the mutant ELANE allele, wherein the gRNA comprises a CRISPR RNA (crRNA) comprising a nucleic acid sequence of 17-20 nucleotides which comprise 17-20 contiguous nucleotides set forth in SEQ ID NOs: 889 or 888; and, (b) culturing the cell obtained in step (a) such that the mutant ELAINE ELANE allele is inactivated and the functional ELANE allele remains intact.

2. The method of claim 1, further comprising introduction of an isolated second gRNA, wherein the gRNA comprises a CRISPR RNA (crRNA) that complexes with a CRISPR nuclease to affect a second double strand break in the ELANE gene, wherein the second double strand break is within intron 4 of the ELANE gene.

3. The method of claim 2, wherein the isolated second gRNA molecule comprises a nucleic acid sequence of 17-20 nucleotides which comprise 17-20 contiguous nucleotides set forth in SEQ ID NO: 1197.

4. The method of claim 1, wherein the isolated human cell is obtained from a subject with an ELANE gene mutation related to SCN or CyN and/or suffering from SCN or CyN and wherein the subject has a mutant ELANE allele and a functional ELANE allele.

5. The method of claim 4, comprising obtaining the isolated human cell from the subject by mobilization and/or by apheresis, or by bone marrow aspiration.

6. The method of claim 4, wherein the isolated human cell is prestimulated prior to introducing the composition to the cell.

7. The method of claim 4, further comprising culture expanding the isolated human cell to obtain multiple isolated human cells.

8. The method of claim 7, wherein the isolated human cells are cultured with one or more of: stem cell factor (SCF), IL-3, and GM-CSF;

wherein the cells are cultured with at least one cytokine; and/or wherein the at least one cytokine is a recombinant human cytokine.

9. A composition comprising a cell obtained by the method of claim 1, wherein the mutant ELANE allele is inactivated and the functional ELANE allele remains intact ("the modified cell") and a pharmaceutically acceptable carrier.

10. The composition of claim 9, wherein the modified cell is a hematopoietic stem cell and/or progenitor cell (HSPC);

wherein the modified cell is a CD34+ hematopoietic stem cell; or wherein the modified cell is a bone marrow cell or peripheral mononucleated cell (PMC).

11. The composition of claim 9, wherein the modified cell is lacking at least a portion of one allele of the ELANE gene.

12. An isolated gRNA that targets a mutant ELANE allele, wherein the gRNA comprises a CRISPR RNA (crRNA) consisting of the nucleic acid sequence of SEQ ID NOs: 888, or 889.

* * * * *

SEQUENCE LISTING

<160> NUMBER OF SEQ ID NOS: 1204

<210> SEQ ID NO 1
<211> LENGTH: 20
<212> TYPE: RNA
<213> ORGANISM: Artificial Sequence
<220> FEATURE:
<223> OTHER INFORMATION: Seynthetic

<400> SEQUENCE: 1
aaaaaaacac aaugugggga 20

<210> SEQ ID NO 2
<211> LENGTH: 20
<212> TYPE: RNA
<213> ORGANISM: Artificial Sequence
<220> FEATURE:
<223> OTHER INFORMATION: Seynthetic

<400> SEQUENCE: 2
aaaaaaauac aaugugggga 20

<210> SEQ ID NO 3
<211> LENGTH: 20
<212> TYPE: RNA
<213> ORGANISM: Artificial Sequence
<220> FEATURE:
<223> OTHER INFORMATION: Seynthetic

<400> SEQUENCE: 3
aaaaaacaca augugggga 20

<210> SEQ ID NO 4
<211> LENGTH: 20
<212> TYPE: RNA
<213> ORGANISM: Artificial Sequence
<220> FEATURE:
<223> OTHER INFORMATION: Seynthetic

<400> SEQUENCE: 4
aaaaaauaca augugggga 20

<210> SEQ ID NO 5
<211> LENGTH: 20
<212> TYPE: RNA
<213> ORGANISM: Artificial Sequence
<220> FEATURE:
<223> OTHER INFORMATION: Seynthetic

<400> SEQUENCE: 5
aaaaacacaa uguggggaag 20

<210> SEQ ID NO 6
<211> LENGTH: 20
<212> TYPE: RNA
<213> ORGANISM: Artificial Sequence
<220> FEATURE:
<223> OTHER INFORMATION: Seynthetic

<400> SEQUENCE: 6
aaaaacccac auugauuauc 20

<210> SEQ ID NO 7
<211> LENGTH: 20
<212> TYPE: RNA
<213> ORGANISM: Artificial Sequence
<220> FEATURE:
<223> OTHER INFORMATION: Seynthetic

<400> SEQUENCE: 7
aaaaagaaag uguugcuuug 20

<210> SEQ ID NO 8
<211> LENGTH: 20
<212> TYPE: RNA
<213> ORGANISM: Artificial Sequence
<220> FEATURE:
<223> OTHER INFORMATION: Seynthetic

<400> SEQUENCE: 8
aaaaauacaa uguggggaag 20

<210> SEQ ID NO 9
<211> LENGTH: 20
<212> TYPE: RNA
<213> ORGANISM: Artificial Sequence
<220> FEATURE:
<223> OTHER INFORMATION: Seynthetic

<400> SEQUENCE: 9
aaaacacaau guggggaagu 20

<210> SEQ ID NO 10
<211> LENGTH: 20
<212> TYPE: RNA
<213> ORGANISM: Artificial Sequence
<220> FEATURE:
<223> OTHER INFORMATION: Seynthetic

<400> SEQUENCE: 10
aaaacccaca uugauuaucu 20

<210> SEQ ID NO 11
<211> LENGTH: 20
<212> TYPE: RNA
<213> ORGANISM: Artificial Sequence
<220> FEATURE:
<223> OTHER INFORMATION: Seynthetic

<400> SEQUENCE: 11
aaaacccccg cuccauuaaa 20

<210> SEQ ID NO 12
<211> LENGTH: 20
<212> TYPE: RNA
<213> ORGANISM: Artificial Sequence
<220> FEATURE:
<223> OTHER INFORMATION: Seynthetic

<400> SEQUENCE: 12
aaaagaaagu guugcuuuga 20

<210> SEQ ID NO 13
<211> LENGTH: 20
<212> TYPE: RNA
<213> ORGANISM: Artificial Sequence
<220> FEATURE:
<223> OTHER INFORMATION: Seynthetic

<400> SEQUENCE: 13
aaaagcaggg ggaaccucgu 20

<210> SEQ ID NO 14
<211> LENGTH: 20
<212> TYPE: RNA
<213> ORGANISM: Artificial Sequence
<220> FEATURE:
<223> OTHER INFORMATION: Seynthetic

<400> SEQUENCE: 14
aaaagccggg ggaaccucgu 20

<210> SEQ ID NO 15
<211> LENGTH: 20
<212> TYPE: RNA
<213> ORGANISM: Artificial Sequence
<220> FEATURE:
<223> OTHER INFORMATION: Seynthetic

<400> SEQUENCE: 15
aaaauacaau guggggaagu 20

<210> SEQ ID NO 16
<211> LENGTH: 20
<212> TYPE: RNA
<213> ORGANISM: Artificial Sequence
<220> FEATURE:
<223> OTHER INFORMATION: Seynthetic

<400> SEQUENCE: 16
aaacacaaug uggggaaguc 20

<210> SEQ ID NO 17
<211> LENGTH: 20
<212> TYPE: RNA
<213> ORGANISM: Artificial Sequence
<220> FEATURE:
<223> OTHER INFORMATION: Seynthetic

<400> SEQUENCE: 17
aaacacccug ggggacucug 20

<210> SEQ ID NO 18
<211> LENGTH: 20
<212> TYPE: RNA
<213> ORGANISM: Artificial Sequence
<220> FEATURE:
<223> OTHER INFORMATION: Seynthetic

<400> SEQUENCE: 18
aaacacccug ggugacucug 20

<210> SEQ ID NO 19
<211> LENGTH: 20
<212> TYPE: RNA
<213> ORGANISM: Artificial Sequence
<220> FEATURE:
<223> OTHER INFORMATION: Seynthetic

<400> SEQUENCE: 19
aaacccacau ugauuaucug 20

<210> SEQ ID NO 20
<211> LENGTH: 20
<212> TYPE: RNA
<213> ORGANISM: Artificial Sequence
<220> FEATURE:
<223> OTHER INFORMATION: Seynthetic

<400> SEQUENCE: 20
aaacuaagaa aauagcugug 20

<210> SEQ ID NO 21
<211> LENGTH: 20
<212> TYPE: RNA
<213> ORGANISM: Artificial Sequence
<220> FEATURE:
<223> OTHER INFORMATION: Seynthetic

<400> SEQUENCE: 21
aaagacugca cgugagaaug 20

<210> SEQ ID NO 22
<211> LENGTH: 20
<212> TYPE: RNA
<213> ORGANISM: Artificial Sequence
<220> FEATURE:
<223> OTHER INFORMATION: Seynthetic

<400> SEQUENCE: 22
aaagauacag cguccccac 20

<210> SEQ ID NO 23
<211> LENGTH: 20
<212> TYPE: RNA
<213> ORGANISM: Artificial Sequence
<220> FEATURE:
<223> OTHER INFORMATION: Seynthetic

<400> SEQUENCE: 23
aaagauacgg cguccccac 20

<210> SEQ ID NO 24
<211> LENGTH: 20
<212> TYPE: RNA
<213> ORGANISM: Artificial Sequence
<220> FEATURE:
<223> OTHER INFORMATION: Seynthetic

<400> SEQUENCE: 24
aaagcagggg gaaccucgug 20

<210> SEQ ID NO 25
<211> LENGTH: 20
<212> TYPE: RNA
<213> ORGANISM: Artificial Sequence
<220> FEATURE:
<223> OTHER INFORMATION: Seynthetic

<400> SEQUENCE: 25
aaagccgggg gaaccucgug 20

<210> SEQ ID NO 26
<211> LENGTH: 20
<212> TYPE: RNA
<213> ORGANISM: Artificial Sequence
<220> FEATURE:
<223> OTHER INFORMATION: Seynthetic

<400> SEQUENCE: 26
aaagggauuc ccaggaccca 20

<210> SEQ ID NO 27
<211> LENGTH: 20
<212> TYPE: RNA
<213> ORGANISM: Artificial Sequence
<220> FEATURE:
<223> OTHER INFORMATION: Seynthetic

<400> SEQUENCE: 27
aaaguucagg gauguccgcc 20

<210> SEQ ID NO 28
<211> LENGTH: 20
<212> TYPE: RNA
<213> ORGANISM: Artificial Sequence
<220> FEATURE:
<223> OTHER INFORMATION: Seynthetic

<400> SEQUENCE: 28
aaauacaaug uggggaaguc 20

<210> SEQ ID NO 29
<211> LENGTH: 20
<212> TYPE: RNA
<213> ORGANISM: Artificial Sequence
<220> FEATURE:
<223> OTHER INFORMATION: Seynthetic

<400> SEQUENCE: 29
aaauucacgu ucguaaaguu 20

<210> SEQ ID NO 30
<211> LENGTH: 20
<212> TYPE: RNA
<213> ORGANISM: Artificial Sequence
<220> FEATURE:
<223> OTHER INFORMATION: Seynthetic

<400> SEQUENCE: 30
aaauuugaau gcgauugugc 20

<210> SEQ ID NO 31
<211> LENGTH: 20
<212> TYPE: RNA
<213> ORGANISM: Artificial Sequence
<220> FEATURE:
<223> OTHER INFORMATION: Seynthetic

<400> SEQUENCE: 31
aacacaaugu ggggaaguca 20

<210> SEQ ID NO 32

<211> LENGTH: 20
<212> TYPE: RNA
<213> ORGANISM: Artificial Sequence
<220> FEATURE:
<223> OTHER INFORMATION: Seynthetic

<400> SEQUENCE: 32
aacacccugg gggacucugg 20

<210> SEQ ID NO 33
<211> LENGTH: 20
<212> TYPE: RNA
<213> ORGANISM: Artificial Sequence
<220> FEATURE:
<223> OTHER INFORMATION: Seynthetic

<400> SEQUENCE: 33
aacacccugg gugacucugg 20

<210> SEQ ID NO 34
<211> LENGTH: 20
<212> TYPE: RNA
<213> ORGANISM: Artificial Sequence
<220> FEATURE:
<223> OTHER INFORMATION: Seynthetic

<400> SEQUENCE: 34
aacaucgugg gggagauggg 20

<210> SEQ ID NO 35
<211> LENGTH: 20
<212> TYPE: RNA
<213> ORGANISM: Artificial Sequence
<220> FEATURE:
<223> OTHER INFORMATION: Seynthetic

<400> SEQUENCE: 35
aacauggugg gggagauggg 20

<210> SEQ ID NO 36
<211> LENGTH: 20
<212> TYPE: RNA
<213> ORGANISM: Artificial Sequence
<220> FEATURE:
<223> OTHER INFORMATION: Seynthetic

<400> SEQUENCE: 36
aacccacauu gauuaucuga 20

<210> SEQ ID NO 37
<211> LENGTH: 20
<212> TYPE: RNA
<213> ORGANISM: Artificial Sequence
<220> FEATURE:
<223> OTHER INFORMATION: Seynthetic

<400> SEQUENCE: 37
aacccccgcu ccauuaaaaa 20

<210> SEQ ID NO 38
<211> LENGTH: 20
<212> TYPE: RNA
<213> ORGANISM: Artificial Sequence
<220> FEATURE:
<223> OTHER INFORMATION: Seynthetic

<400> SEQUENCE: 38
aacuucacca cacccagagu 20

<210> SEQ ID NO 39
<211> LENGTH: 20
<212> TYPE: RNA
<213> ORGANISM: Artificial Sequence
<220> FEATURE:
<223> OTHER INFORMATION: Seynthetic

<400> SEQUENCE: 39
aacuuuacga acgugaauuu 20

<210> SEQ ID NO 40
<211> LENGTH: 20
<212> TYPE: RNA
<213> ORGANISM: Artificial Sequence
<220> FEATURE:
<223> OTHER INFORMATION: Seynthetic

<400> SEQUENCE: 40
aagaaaaaaa cacaaugugg 20

<210> SEQ ID NO 41
<211> LENGTH: 20
<212> TYPE: RNA
<213> ORGANISM: Artificial Sequence
<220> FEATURE:
<223> OTHER INFORMATION: Seynthetic

<400> SEQUENCE: 41
aagaaagugu ugcuuugaga 20

<210> SEQ ID NO 42
<211> LENGTH: 20
<212> TYPE: RNA
<213> ORGANISM: Artificial Sequence
<220> FEATURE:
<223> OTHER INFORMATION: Seynthetic

<400> SEQUENCE: 42
aagaacuuua cgaacgugaa 20

<210> SEQ ID NO 43
<211> LENGTH: 20
<212> TYPE: RNA
<213> ORGANISM: Artificial Sequence
<220> FEATURE:
<223> OTHER INFORMATION: Seynthetic

<400> SEQUENCE: 43
aagaacuuua ugaacgugaa 20

<210> SEQ ID NO 44
<211> LENGTH: 20
<212> TYPE: RNA
<213> ORGANISM: Artificial Sequence
<220> FEATURE:
<223> OTHER INFORMATION: Seynthetic

<400> SEQUENCE: 44
aagacuccag ccuggcccag 20

<210> SEQ ID NO 45
<211> LENGTH: 20
<212> TYPE: RNA

<213> ORGANISM: Artificial Sequence
<220> FEATURE:
<223> OTHER INFORMATION: Seynthetic

<400> SEQUENCE: 45
aagacugcac gugagaaugu 20

<210> SEQ ID NO 46
<211> LENGTH: 20
<212> TYPE: RNA
<213> ORGANISM: Artificial Sequence
<220> FEATURE:
<223> OTHER INFORMATION: Seynthetic

<400> SEQUENCE: 46
aagagaaaag caggggaac 20

<210> SEQ ID NO 47
<211> LENGTH: 20
<212> TYPE: RNA
<213> ORGANISM: Artificial Sequence
<220> FEATURE:
<223> OTHER INFORMATION: Seynthetic

<400> SEQUENCE: 47
aagagaaaag ccgggggaac 20

<210> SEQ ID NO 48
<211> LENGTH: 20
<212> TYPE: RNA
<213> ORGANISM: Artificial Sequence
<220> FEATURE:
<223> OTHER INFORMATION: Seynthetic

<400> SEQUENCE: 48
aagauacagc gucccccacc 20

<210> SEQ ID NO 49
<211> LENGTH: 20
<212> TYPE: RNA
<213> ORGANISM: Artificial Sequence
<220> FEATURE:
<223> OTHER INFORMATION: Seynthetic

<400> SEQUENCE: 49
aagauacggc gucccccacc 20

<210> SEQ ID NO 50
<211> LENGTH: 20
<212> TYPE: RNA
<213> ORGANISM: Artificial Sequence
<220> FEATURE:
<223> OTHER INFORMATION: Seynthetic

<400> SEQUENCE: 50
aagcaggggg aaccucgugu 20

<210> SEQ ID NO 51
<211> LENGTH: 20
<212> TYPE: RNA
<213> ORGANISM: Artificial Sequence
<220> FEATURE:
<223> OTHER INFORMATION: Seynthetic

<400> SEQUENCE: 51
aagccacacc ugaaggcgga 20

<210> SEQ ID NO 52
<211> LENGTH: 20
<212> TYPE: RNA
<213> ORGANISM: Artificial Sequence
<220> FEATURE:
<223> OTHER INFORMATION: Seynthetic

<400> SEQUENCE: 52
aagccccaga ggccacaggg 20

<210> SEQ ID NO 53
<211> LENGTH: 20
<212> TYPE: RNA
<213> ORGANISM: Artificial Sequence
<220> FEATURE:
<223> OTHER INFORMATION: Seynthetic

<400> SEQUENCE: 53
aagccccuuc caaagauaca 20

<210> SEQ ID NO 54
<211> LENGTH: 20
<212> TYPE: RNA
<213> ORGANISM: Artificial Sequence
<220> FEATURE:
<223> OTHER INFORMATION: Seynthetic

<400> SEQUENCE: 54
aagccccuuc caaagauacg 20

<210> SEQ ID NO 55
<211> LENGTH: 20
<212> TYPE: RNA
<213> ORGANISM: Artificial Sequence
<220> FEATURE:
<223> OTHER INFORMATION: Seynthetic

<400> SEQUENCE: 55
aagccggggg aaccucgugu 20

<210> SEQ ID NO 56
<211> LENGTH: 20
<212> TYPE: RNA
<213> ORGANISM: Artificial Sequence
<220> FEATURE:
<223> OTHER INFORMATION: Seynthetic

<400> SEQUENCE: 56
aaggcggaca ucccugaacu 20

<210> SEQ ID NO 57
<211> LENGTH: 20
<212> TYPE: RNA
<213> ORGANISM: Artificial Sequence
<220> FEATURE:
<223> OTHER INFORMATION: Seynthetic

<400> SEQUENCE: 57
aagggauucc caggacccag 20

<210> SEQ ID NO 58
<211> LENGTH: 20
<212> TYPE: RNA
<213> ORGANISM: Artificial Sequence
<220> FEATURE:

<223> OTHER INFORMATION: Seynthetic

<400> SEQUENCE: 58
aaggggcugc cggagucccc 20

<210> SEQ ID NO 59
<211> LENGTH: 20
<212> TYPE: RNA
<213> ORGANISM: Artificial Sequence
<220> FEATURE:
<223> OTHER INFORMATION: Seynthetic

<400> SEQUENCE: 59
aagugacuuc cccacauugu 20

<210> SEQ ID NO 60
<211> LENGTH: 20
<212> TYPE: RNA
<213> ORGANISM: Artificial Sequence
<220> FEATURE:
<223> OTHER INFORMATION: Seynthetic

<400> SEQUENCE: 60
aaguucaggg auguccgccu 20

<210> SEQ ID NO 61
<211> LENGTH: 20
<212> TYPE: RNA
<213> ORGANISM: Artificial Sequence
<220> FEATURE:
<223> OTHER INFORMATION: Seynthetic

<400> SEQUENCE: 61
aauaaagacu gcacgugaga 20

<210> SEQ ID NO 62
<211> LENGTH: 20
<212> TYPE: RNA
<213> ORGANISM: Artificial Sequence
<220> FEATURE:
<223> OTHER INFORMATION: Seynthetic

<400> SEQUENCE: 62
aauaaugacu gcacgugaga 20

<210> SEQ ID NO 63
<211> LENGTH: 20
<212> TYPE: RNA
<213> ORGANISM: Artificial Sequence
<220> FEATURE:
<223> OTHER INFORMATION: Seynthetic

<400> SEQUENCE: 63
aauacaaugu ggggaaguca 20

<210> SEQ ID NO 64
<211> LENGTH: 20
<212> TYPE: RNA
<213> ORGANISM: Artificial Sequence
<220> FEATURE:
<223> OTHER INFORMATION: Seynthetic

<400> SEQUENCE: 64
aauccauggu gcggggacca 20

<210> SEQ ID NO 65
<211> LENGTH: 20
<212> TYPE: RNA
<213> ORGANISM: Artificial Sequence
<220> FEATURE:
<223> OTHER INFORMATION: Seynthetic

<400> SEQUENCE: 65
aaucccauuc ccgcagcugg 20

<210> SEQ ID NO 66
<211> LENGTH: 20
<212> TYPE: RNA
<213> ORGANISM: Artificial Sequence
<220> FEATURE:
<223> OTHER INFORMATION: Seynthetic

<400> SEQUENCE: 66
aaucccuuuc ccgcagcugg 20

<210> SEQ ID NO 67
<211> LENGTH: 20
<212> TYPE: RNA
<213> ORGANISM: Artificial Sequence
<220> FEATURE:
<223> OTHER INFORMATION: Seynthetic

<400> SEQUENCE: 67
aaucgcauuc aaaugucaga 20

<210> SEQ ID NO 68
<211> LENGTH: 20
<212> TYPE: RNA
<213> ORGANISM: Artificial Sequence
<220> FEATURE:
<223> OTHER INFORMATION: Seynthetic

<400> SEQUENCE: 68
aaucgcauuc aaauuucaga 20

<210> SEQ ID NO 69
<211> LENGTH: 20
<212> TYPE: RNA
<213> ORGANISM: Artificial Sequence
<220> FEATURE:
<223> OTHER INFORMATION: Seynthetic

<400> SEQUENCE: 69
aaugacugca cgugagaaug 20

<210> SEQ ID NO 70
<211> LENGTH: 20
<212> TYPE: RNA
<213> ORGANISM: Artificial Sequence
<220> FEATURE:
<223> OTHER INFORMATION: Seynthetic

<400> SEQUENCE: 70
aaugggauuc ccaggaccca 20

<210> SEQ ID NO 71
<211> LENGTH: 20
<212> TYPE: RNA
<213> ORGANISM: Artificial Sequence
<220> FEATURE:
<223> OTHER INFORMATION: Seynthetic

<400> SEQUENCE: 71
aaugucagau aaucaaugug 20

<210> SEQ ID NO 72
<211> LENGTH: 20
<212> TYPE: RNA
<213> ORGANISM: Artificial Sequence
<220> FEATURE:
<223> OTHER INFORMATION: Seynthetic

<400> SEQUENCE: 72
aauucacguu cauaaaguuc 20

<210> SEQ ID NO 73
<211> LENGTH: 20
<212> TYPE: RNA
<213> ORGANISM: Artificial Sequence
<220> FEATURE:
<223> OTHER INFORMATION: Seynthetic

<400> SEQUENCE: 73
aauucacguu cguaaaguuc 20

<210> SEQ ID NO 74
<211> LENGTH: 20
<212> TYPE: RNA
<213> ORGANISM: Artificial Sequence
<220> FEATURE:
<223> OTHER INFORMATION: Seynthetic

<400> SEQUENCE: 74
aauuugaaug cgauugugca 20

<210> SEQ ID NO 75
<211> LENGTH: 20
<212> TYPE: RNA
<213> ORGANISM: Artificial Sequence
<220> FEATURE:
<223> OTHER INFORMATION: Seynthetic

<400> SEQUENCE: 75
acaaucgcau ucaaauguca 20

<210> SEQ ID NO 76
<211> LENGTH: 20
<212> TYPE: RNA
<213> ORGANISM: Artificial Sequence
<220> FEATURE:
<223> OTHER INFORMATION: Seynthetic

<400> SEQUENCE: 76
acaaucgcau ucaaauuuca 20

<210> SEQ ID NO 77
<211> LENGTH: 20
<212> TYPE: RNA
<213> ORGANISM: Artificial Sequence
<220> FEATURE:
<223> OTHER INFORMATION: Seynthetic

<400> SEQUENCE: 77
acacaaugug gggaagucac 20

<210> SEQ ID NO 78
<211> LENGTH: 20

<212> TYPE: RNA
<213> ORGANISM: Artificial Sequence
<220> FEATURE:
<223> OTHER INFORMATION: Seynthetic

<400> SEQUENCE: 78
acacacagcu auuuucuuag 20

<210> SEQ ID NO 79
<211> LENGTH: 20
<212> TYPE: RNA
<213> ORGANISM: Artificial Sequence
<220> FEATURE:
<223> OTHER INFORMATION: Seynthetic

<400> SEQUENCE: 79
acacccagag ucacccaggg 20

<210> SEQ ID NO 80
<211> LENGTH: 20
<212> TYPE: RNA
<213> ORGANISM: Artificial Sequence
<220> FEATURE:
<223> OTHER INFORMATION: Seynthetic

<400> SEQUENCE: 80
acacccagag ucccccaggg 20

<210> SEQ ID NO 81
<211> LENGTH: 20
<212> TYPE: RNA
<213> ORGANISM: Artificial Sequence
<220> FEATURE:
<223> OTHER INFORMATION: Seynthetic

<400> SEQUENCE: 81
acacccccuu ccugcccacc 20

<210> SEQ ID NO 82
<211> LENGTH: 20
<212> TYPE: RNA
<213> ORGANISM: Artificial Sequence
<220> FEATURE:
<223> OTHER INFORMATION: Seynthetic

<400> SEQUENCE: 82
acacccgcug ugaccauaac 20

<210> SEQ ID NO 83
<211> LENGTH: 20
<212> TYPE: RNA
<213> ORGANISM: Artificial Sequence
<220> FEATURE:
<223> OTHER INFORMATION: Seynthetic

<400> SEQUENCE: 83
acacccuggg ggacucuggg 20

<210> SEQ ID NO 84
<211> LENGTH: 20
<212> TYPE: RNA
<213> ORGANISM: Artificial Sequence
<220> FEATURE:
<223> OTHER INFORMATION: Seynthetic

<400> SEQUENCE: 84
acacccuggg ugacucuggg 20

<210> SEQ ID NO 85
<211> LENGTH: 20
<212> TYPE: RNA
<213> ORGANISM: Artificial Sequence
<220> FEATURE:
<223> OTHER INFORMATION: Seynthetic

<400> SEQUENCE: 85
acaccugaag gcggacaucc 20

<210> SEQ ID NO 86
<211> LENGTH: 20
<212> TYPE: RNA
<213> ORGANISM: Artificial Sequence
<220> FEATURE:
<223> OTHER INFORMATION: Seynthetic

<400> SEQUENCE: 86
acaccugcug ugaccauaac 20

<210> SEQ ID NO 87
<211> LENGTH: 20
<212> TYPE: RNA
<213> ORGANISM: Artificial Sequence
<220> FEATURE:
<223> OTHER INFORMATION: Seynthetic

<400> SEQUENCE: 87
acaccuuugu cucugucccu 20

<210> SEQ ID NO 88
<211> LENGTH: 20
<212> TYPE: RNA
<213> ORGANISM: Artificial Sequence
<220> FEATURE:
<223> OTHER INFORMATION: Seynthetic

<400> SEQUENCE: 88
acacgagguu cccccggcuu 20

<210> SEQ ID NO 89
<211> LENGTH: 20
<212> TYPE: RNA
<213> ORGANISM: Artificial Sequence
<220> FEATURE:
<223> OTHER INFORMATION: Seynthetic

<400> SEQUENCE: 89
acacgagguu cccccugcuu 20

<210> SEQ ID NO 90
<211> LENGTH: 20
<212> TYPE: RNA
<213> ORGANISM: Artificial Sequence
<220> FEATURE:
<223> OTHER INFORMATION: Seynthetic

<400> SEQUENCE: 90
acacggacgg uccuccagcc 20

<210> SEQ ID NO 91
<211> LENGTH: 20
<212> TYPE: RNA
<213> ORGANISM: Artificial Sequence
<220> FEATURE:
<223> OTHER INFORMATION: Seynthetic

<400> SEQUENCE: 91
acacuuaaua aagacugcac 20

<210> SEQ ID NO 92
<211> LENGTH: 20
<212> TYPE: RNA
<213> ORGANISM: Artificial Sequence
<220> FEATURE:
<223> OTHER INFORMATION: Seynthetic

<400> SEQUENCE: 92
acacuuaaua augacugcac 20

<210> SEQ ID NO 93
<211> LENGTH: 20
<212> TYPE: RNA
<213> ORGANISM: Artificial Sequence
<220> FEATURE:
<223> OTHER INFORMATION: Seynthetic

<400> SEQUENCE: 93
acagcaggug uagacuccga 20

<210> SEQ ID NO 94
<211> LENGTH: 20
<212> TYPE: RNA
<213> ORGANISM: Artificial Sequence
<220> FEATURE:
<223> OTHER INFORMATION: Seynthetic

<400> SEQUENCE: 94
acagcgggug uagacuccga 20

<210> SEQ ID NO 95
<211> LENGTH: 20
<212> TYPE: RNA
<213> ORGANISM: Artificial Sequence
<220> FEATURE:
<223> OTHER INFORMATION: Seynthetic

<400> SEQUENCE: 95
acagcguccc ccaccccuga 20

<210> SEQ ID NO 96
<211> LENGTH: 20
<212> TYPE: RNA
<213> ORGANISM: Artificial Sequence
<220> FEATURE:
<223> OTHER INFORMATION: Seynthetic

<400> SEQUENCE: 96
acagggggac uccggcagcc 20

<210> SEQ ID NO 97
<211> LENGTH: 20
<212> TYPE: RNA
<213> ORGANISM: Artificial Sequence
<220> FEATURE:
<223> OTHER INFORMATION: Seynthetic

<400> SEQUENCE: 97
acaucguggg ggagauggga 20

<210> SEQ ID NO 98
<211> LENGTH: 20
<212> TYPE: RNA
<213> ORGANISM: Artificial Sequence
<220> FEATURE:
<223> OTHER INFORMATION: Seynthetic

<400> SEQUENCE: 98 acauggugggg ggagauggga 20

<210> SEQ ID NO 99
<211> LENGTH: 20
<212> TYPE: RNA
<213> ORGANISM: Artificial Sequence
<220> FEATURE:
<223> OTHER INFORMATION: Seynthetic

<400> SEQUENCE: 99
acauucucac gugcagucau 20

<210> SEQ ID NO 100
<211> LENGTH: 20
<212> TYPE: RNA
<213> ORGANISM: Artificial Sequence
<220> FEATURE:
<223> OTHER INFORMATION: Seynthetic

<400> SEQUENCE: 100
acauucucac gugcagucuu 20

<210> SEQ ID NO 101
<211> LENGTH: 20
<212> TYPE: RNA
<213> ORGANISM: Artificial Sequence
<220> FEATURE:
<223> OTHER INFORMATION: Seynthetic

<400> SEQUENCE: 101
acauuugaau gcgauugugc 20

<210> SEQ ID NO 102
<211> LENGTH: 20
<212> TYPE: RNA
<213> ORGANISM: Artificial Sequence
<220> FEATURE:
<223> OTHER INFORMATION: Seynthetic

<400> SEQUENCE: 102
accaaggggc ugccggaguc 20

<210> SEQ ID NO 103
<211> LENGTH: 20
<212> TYPE: RNA
<213> ORGANISM: Artificial Sequence
<220> FEATURE:
<223> OTHER INFORMATION: Seynthetic

<400> SEQUENCE: 103
accaaggggc ugccugaguc 20

<210> SEQ ID NO 104
<211> LENGTH: 20
<212> TYPE: RNA
<213> ORGANISM: Artificial Sequence
<220> FEATURE:
<223> OTHER INFORMATION: Seynthetic

<400> SEQUENCE: 104
accacaccca gagucaccca 20

<210> SEQ ID NO 105
<211> LENGTH: 20
<212> TYPE: RNA
<213> ORGANISM: Artificial Sequence
<220> FEATURE:
<223> OTHER INFORMATION: Seynthetic

<400> SEQUENCE: 105
accacaccca gaguccccca 20

<210> SEQ ID NO 106
<211> LENGTH: 20
<212> TYPE: RNA
<213> ORGANISM: Artificial Sequence
<220> FEATURE:
<223> OTHER INFORMATION: Seynthetic

<400> SEQUENCE: 106
accagggaac uccugcccug 20

<210> SEQ ID NO 107
<211> LENGTH: 20
<212> TYPE: RNA
<213> ORGANISM: Artificial Sequence
<220> FEATURE:
<223> OTHER INFORMATION: Seynthetic

<400> SEQUENCE: 107
accauguucc agcugcaacg 20

<210> SEQ ID NO 108
<211> LENGTH: 20
<212> TYPE: RNA
<213> ORGANISM: Artificial Sequence
<220> FEATURE:
<223> OTHER INFORMATION: Seynthetic

<400> SEQUENCE: 108
acccacauug auuaucugaa 20

<210> SEQ ID NO 109
<211> LENGTH: 20
<212> TYPE: RNA
<213> ORGANISM: Artificial Sequence
<220> FEATURE:
<223> OTHER INFORMATION: Seynthetic

<400> SEQUENCE: 109
acccacauug auuaucugac 20

<210> SEQ ID NO 110
<211> LENGTH: 20
<212> TYPE: RNA
<213> ORGANISM: Artificial Sequence
<220> FEATURE:
<223> OTHER INFORMATION: Seynthetic

<400> SEQUENCE: 110
acccagaguc acccagggug 20

<210> SEQ ID NO 111

<211> LENGTH: 20
<212> TYPE: RNA
<213> ORGANISM: Artificial Sequence
<220> FEATURE:
<223> OTHER INFORMATION: Seynthetic

<400> SEQUENCE: 111
acccagaguc ccccagggug 20

<210> SEQ ID NO 112
<211> LENGTH: 20
<212> TYPE: RNA
<213> ORGANISM: Artificial Sequence
<220> FEATURE:
<223> OTHER INFORMATION: Seynthetic

<400> SEQUENCE: 112
acccagggug uuucacaauc 20

<210> SEQ ID NO 113
<211> LENGTH: 20
<212> TYPE: RNA
<213> ORGANISM: Artificial Sequence
<220> FEATURE:
<223> OTHER INFORMATION: Seynthetic

<400> SEQUENCE: 113
acccccgcuc cauuaaaaaa 20

<210> SEQ ID NO 114
<211> LENGTH: 20
<212> TYPE: RNA
<213> ORGANISM: Artificial Sequence
<220> FEATURE:
<223> OTHER INFORMATION: Seynthetic

<400> SEQUENCE: 114 accccuucc ugcccaccug 20

<210> SEQ ID NO 115
<211> LENGTH: 20
<212> TYPE: RNA
<213> ORGANISM: Artificial Sequence
<220> FEATURE:
<223> OTHER INFORMATION: Seynthetic

<400> SEQUENCE: 115
acccgcugug accauaacac 20

<210> SEQ ID NO 116
<211> LENGTH: 20
<212> TYPE: RNA
<213> ORGANISM: Artificial Sequence
<220> FEATURE:
<223> OTHER INFORMATION: Seynthetic

<400> SEQUENCE: 116
acccuggggg acucugggug 20

<210> SEQ ID NO 117
<211> LENGTH: 20
<212> TYPE: RNA
<213> ORGANISM: Artificial Sequence
<220> FEATURE:
<223> OTHER INFORMATION: Seynthetic

<400> SEQUENCE: 117
acccugggug acucugggug 20

<210> SEQ ID NO 118
<211> LENGTH: 20
<212> TYPE: RNA
<213> ORGANISM: Artificial Sequence
<220> FEATURE:
<223> OTHER INFORMATION: Seynthetic

<400> SEQUENCE: 118
accugaaggc ggacaucccu 20

<210> SEQ ID NO 119
<211> LENGTH: 20
<212> TYPE: RNA
<213> ORGANISM: Artificial Sequence
<220> FEATURE:
<223> OTHER INFORMATION: Seynthetic

<400> SEQUENCE: 119
accugcugug accauaacac 20

<210> SEQ ID NO 120
<211> LENGTH: 20
<212> TYPE: RNA
<213> ORGANISM: Artificial Sequence
<220> FEATURE:
<223> OTHER INFORMATION: Seynthetic

<400> SEQUENCE: 120
accuggaggg gcuggaggac 20

<210> SEQ ID NO 121
<211> LENGTH: 20
<212> TYPE: RNA
<213> ORGANISM: Artificial Sequence
<220> FEATURE:
<223> OTHER INFORMATION: Seynthetic

<400> SEQUENCE: 121
accuggcggg gcuggaggac 20

<210> SEQ ID NO 122
<211> LENGTH: 20
<212> TYPE: RNA
<213> ORGANISM: Artificial Sequence
<220> FEATURE:
<223> OTHER INFORMATION: Seynthetic

<400> SEQUENCE: 122 accuugucu cugucccugu 20

<210> SEQ ID NO 123
<211> LENGTH: 20
<212> TYPE: RNA
<213> ORGANISM: Artificial Sequence
<220> FEATURE:
<223> OTHER INFORMATION: Seynthetic

<400> SEQUENCE: 123
acgaacguga auuuauuuca 20

<210> SEQ ID NO 124
<211> LENGTH: 20
<212> TYPE: RNA

<213> ORGANISM: Artificial Sequence
<220> FEATURE:
<223> OTHER INFORMATION: Seynthetic

<400> SEQUENCE: 124
acgagguucc cccggcuuuu 20

<210> SEQ ID NO 125
<211> LENGTH: 20
<212> TYPE: RNA
<213> ORGANISM: Artificial Sequence
<220> FEATURE:
<223> OTHER INFORMATION: Seynthetic

<400> SEQUENCE: 125
acgagguucc cccugcuuuu 20

<210> SEQ ID NO 126
<211> LENGTH: 20
<212> TYPE: RNA
<213> ORGANISM: Artificial Sequence
<220> FEATURE:
<223> OTHER INFORMATION: Seynthetic

<400> SEQUENCE: 126
acgauguucc agcugcaacg 20

<210> SEQ ID NO 127
<211> LENGTH: 20
<212> TYPE: RNA
<213> ORGANISM: Artificial Sequence
<220> FEATURE:
<223> OTHER INFORMATION: Seynthetic

<400> SEQUENCE: 127
acgccguauc uuuggaaggg 20

<210> SEQ ID NO 128
<211> LENGTH: 20
<212> TYPE: RNA
<213> ORGANISM: Artificial Sequence
<220> FEATURE:
<223> OTHER INFORMATION: Seynthetic

<400> SEQUENCE: 128
acgcuguauc uuuggaaggg 20

<210> SEQ ID NO 129
<211> LENGTH: 20
<212> TYPE: RNA
<213> ORGANISM: Artificial Sequence
<220> FEATURE:
<223> OTHER INFORMATION: Seynthetic

<400> SEQUENCE: 129
acggacgguc cuccagcccc 20

<210> SEQ ID NO 130
<211> LENGTH: 20
<212> TYPE: RNA
<213> ORGANISM: Artificial Sequence
<220> FEATURE:
<223> OTHER INFORMATION: Seynthetic

<400> SEQUENCE: 130
acggcguccc ccaccccuga 20

<210> SEQ ID NO 131
<211> LENGTH: 20
<212> TYPE: RNA
<213> ORGANISM: Artificial Sequence
<220> FEATURE:
<223> OTHER INFORMATION: Seynthetic

<400> SEQUENCE: 131
acgguccucc agccccgcca 20

<210> SEQ ID NO 132
<211> LENGTH: 20
<212> TYPE: RNA
<213> ORGANISM: Artificial Sequence
<220> FEATURE:
<223> OTHER INFORMATION: Seynthetic

<400> SEQUENCE: 132
acgguccucc agccccucca 20

<210> SEQ ID NO 133
<211> LENGTH: 20
<212> TYPE: RNA
<213> ORGANISM: Artificial Sequence
<220> FEATURE:
<223> OTHER INFORMATION: Seynthetic

<400> SEQUENCE: 133
acgucaagac uccagccugg 20

<210> SEQ ID NO 134
<211> LENGTH: 20
<212> TYPE: RNA
<213> ORGANISM: Artificial Sequence
<220> FEATURE:
<223> OTHER INFORMATION: Seynthetic

<400> SEQUENCE: 134
acgucaggac uccagccugg 20

<210> SEQ ID NO 135
<211> LENGTH: 20
<212> TYPE: RNA
<213> ORGANISM: Artificial Sequence
<220> FEATURE:
<223> OTHER INFORMATION: Seynthetic

<400> SEQUENCE: 135 acguccccu cggagucuac 20

<210> SEQ ID NO 136
<211> LENGTH: 20
<212> TYPE: RNA
<213> ORGANISM: Artificial Sequence
<220> FEATURE:
<223> OTHER INFORMATION: Seynthetic

<400> SEQUENCE: 136
acgugcaguc auuauuaagu 20

<210> SEQ ID NO 137
<211> LENGTH: 20
<212> TYPE: RNA
<213> ORGANISM: Artificial Sequence
<220> FEATURE:

<223> OTHER INFORMATION: Seynthetic

<400> SEQUENCE: 137
acgugcaguc uuuauuaagu 20

<210> SEQ ID NO 138
<211> LENGTH: 20
<212> TYPE: RNA
<213> ORGANISM: Artificial Sequence
<220> FEATURE:
<223> OTHER INFORMATION: Seynthetic

<400> SEQUENCE: 138
acguucauaa aguucuuagc 20

<210> SEQ ID NO 139
<211> LENGTH: 20
<212> TYPE: RNA
<213> ORGANISM: Artificial Sequence
<220> FEATURE:
<223> OTHER INFORMATION: Seynthetic

<400> SEQUENCE: 139
acguucguaa aguucuuagc 20

<210> SEQ ID NO 140
<211> LENGTH: 20
<212> TYPE: RNA
<213> ORGANISM: Artificial Sequence
<220> FEATURE:
<223> OTHER INFORMATION: Seynthetic

<400> SEQUENCE: 140
acguugcauu aauccauggu 20

<210> SEQ ID NO 141
<211> LENGTH: 20
<212> TYPE: RNA
<213> ORGANISM: Artificial Sequence
<220> FEATURE:
<223> OTHER INFORMATION: Seynthetic

<400> SEQUENCE: 141
acuacauucu cacgugcagu 20

<210> SEQ ID NO 142
<211> LENGTH: 20
<212> TYPE: RNA
<213> ORGANISM: Artificial Sequence
<220> FEATURE:
<223> OTHER INFORMATION: Seynthetic

<400> SEQUENCE: 142
acuccggcag ccccuugguc 20

<210> SEQ ID NO 143
<211> LENGTH: 20
<212> TYPE: RNA
<213> ORGANISM: Artificial Sequence
<220> FEATURE:
<223> OTHER INFORMATION: Seynthetic

<400> SEQUENCE: 143
acuuaauaaa gacugcacgu 20

<210> SEQ ID NO 144
<211> LENGTH: 20
<212> TYPE: RNA
<213> ORGANISM: Artificial Sequence
<220> FEATURE:
<223> OTHER INFORMATION: Seynthetic

<400> SEQUENCE: 144
acuuaauaau gacugcacgu 20

<210> SEQ ID NO 145
<211> LENGTH: 20
<212> TYPE: RNA
<213> ORGANISM: Artificial Sequence
<220> FEATURE:
<223> OTHER INFORMATION: Seynthetic

<400> SEQUENCE: 145
acuucaccac acccagaguc 20

<210> SEQ ID NO 146
<211> LENGTH: 20
<212> TYPE: RNA
<213> ORGANISM: Artificial Sequence
<220> FEATURE:
<223> OTHER INFORMATION: Seynthetic

<400> SEQUENCE: 146
acuuccccac auuguauuuu 20

<210> SEQ ID NO 147
<211> LENGTH: 20
<212> TYPE: RNA
<213> ORGANISM: Artificial Sequence
<220> FEATURE:
<223> OTHER INFORMATION: Seynthetic

<400> SEQUENCE: 147
acuuccccac auuguguuuu 20

<210> SEQ ID NO 148
<211> LENGTH: 20
<212> TYPE: RNA
<213> ORGANISM: Artificial Sequence
<220> FEATURE:
<223> OTHER INFORMATION: Seynthetic

<400> SEQUENCE: 148
acuugccugu ggucacguca 20

<210> SEQ ID NO 149
<211> LENGTH: 20
<212> TYPE: RNA
<213> ORGANISM: Artificial Sequence
<220> FEATURE:
<223> OTHER INFORMATION: Seynthetic

<400> SEQUENCE: 149
acuuuacgaa cgugaauuua 20

<210> SEQ ID NO 150
<211> LENGTH: 20
<212> TYPE: RNA
<213> ORGANISM: Artificial Sequence
<220> FEATURE:
<223> OTHER INFORMATION: Seynthetic

<400> SEQUENCE: 150
acuuucuuag cuaagaacuu 20

<210> SEQ ID NO 151
<211> LENGTH: 20
<212> TYPE: RNA
<213> ORGANISM: Artificial Sequence
<220> FEATURE:
<223> OTHER INFORMATION: Seynthetic

<400> SEQUENCE: 151
agaaaaaaac acaaugugggg 20

<210> SEQ ID NO 152
<211> LENGTH: 20
<212> TYPE: RNA
<213> ORGANISM: Artificial Sequence
<220> FEATURE:
<223> OTHER INFORMATION: Seynthetic

<400> SEQUENCE: 152
agaaaagcag ggggaaccuc 20

<210> SEQ ID NO 153
<211> LENGTH: 20
<212> TYPE: RNA
<213> ORGANISM: Artificial Sequence
<220> FEATURE:
<223> OTHER INFORMATION: Seynthetic

<400> SEQUENCE: 153
agaaaagccg ggggaaccuc 20

<210> SEQ ID NO 154
<211> LENGTH: 20
<212> TYPE: RNA
<213> ORGANISM: Artificial Sequence
<220> FEATURE:
<223> OTHER INFORMATION: Seynthetic

<400> SEQUENCE: 154
agaaaguguu gcuuugagag 20

<210> SEQ ID NO 155
<211> LENGTH: 20
<212> TYPE: RNA
<213> ORGANISM: Artificial Sequence
<220> FEATURE:
<223> OTHER INFORMATION: Seynthetic

<400> SEQUENCE: 155
agaacuuuac gaacgugaau 20

<210> SEQ ID NO 156
<211> LENGTH: 20
<212> TYPE: RNA
<213> ORGANISM: Artificial Sequence
<220> FEATURE:
<223> OTHER INFORMATION: Seynthetic

<400> SEQUENCE: 156
agaacuuuau gaacgugaau 20

<210> SEQ ID NO 157
<211> LENGTH: 20

<212> TYPE: RNA
<213> ORGANISM: Artificial Sequence
<220> FEATURE:
<223> OTHER INFORMATION: Seynthetic

<400> SEQUENCE: 157
agaagugacu uccccacauu 20

<210> SEQ ID NO 158
<211> LENGTH: 20
<212> TYPE: RNA
<213> ORGANISM: Artificial Sequence
<220> FEATURE:
<223> OTHER INFORMATION: Seynthetic

<400> SEQUENCE: 158
agaccaaggg gcugccggag 20

<210> SEQ ID NO 159
<211> LENGTH: 20
<212> TYPE: RNA
<213> ORGANISM: Artificial Sequence
<220> FEATURE:
<223> OTHER INFORMATION: Seynthetic

<400> SEQUENCE: 159
agacuccagc cuggcccagg 20

<210> SEQ ID NO 160
<211> LENGTH: 20
<212> TYPE: RNA
<213> ORGANISM: Artificial Sequence
<220> FEATURE:
<223> OTHER INFORMATION: Seynthetic

<400> SEQUENCE: 160
agacugcacg ugagaaugua 20

<210> SEQ ID NO 161
<211> LENGTH: 20
<212> TYPE: RNA
<213> ORGANISM: Artificial Sequence
<220> FEATURE:
<223> OTHER INFORMATION: Seynthetic

<400> SEQUENCE: 161
agagaaaagc agggggaacc 20

<210> SEQ ID NO 162
<211> LENGTH: 20
<212> TYPE: RNA
<213> ORGANISM: Artificial Sequence
<220> FEATURE:
<223> OTHER INFORMATION: Seynthetic

<400> SEQUENCE: 162
agagaaaagc cgggggaacc 20

<210> SEQ ID NO 163
<211> LENGTH: 20
<212> TYPE: RNA
<213> ORGANISM: Artificial Sequence
<220> FEATURE:
<223> OTHER INFORMATION: Seynthetic

<400> SEQUENCE: 163
agagccuggg ccaggcugga 20

<210> SEQ ID NO 164
<211> LENGTH: 20
<212> TYPE: RNA
<213> ORGANISM: Artificial Sequence
<220> FEATURE:
<223> OTHER INFORMATION: Seynthetic

<400> SEQUENCE: 164
agaggccaca gggacagaga 20

<210> SEQ ID NO 165
<211> LENGTH: 20
<212> TYPE: RNA
<213> ORGANISM: Artificial Sequence
<220> FEATURE:
<223> OTHER INFORMATION: Seynthetic

<400> SEQUENCE: 165
agagucaccc aggguguuuc 20

<210> SEQ ID NO 166
<211> LENGTH: 20
<212> TYPE: RNA
<213> ORGANISM: Artificial Sequence
<220> FEATURE:
<223> OTHER INFORMATION: Seynthetic

<400> SEQUENCE: 166
agaguccccc aggguguuuc 20

<210> SEQ ID NO 167
<211> LENGTH: 20
<212> TYPE: RNA
<213> ORGANISM: Artificial Sequence
<220> FEATURE:
<223> OTHER INFORMATION: Seynthetic

<400> SEQUENCE: 167
agauacagcg ucccccaccc 20

<210> SEQ ID NO 168
<211> LENGTH: 20
<212> TYPE: RNA
<213> ORGANISM: Artificial Sequence
<220> FEATURE:
<223> OTHER INFORMATION: Seynthetic

<400> SEQUENCE: 168
agauacggcg ucccccaccc 20

<210> SEQ ID NO 169
<211> LENGTH: 20
<212> TYPE: RNA
<213> ORGANISM: Artificial Sequence
<220> FEATURE:
<223> OTHER INFORMATION: Seynthetic

<400> SEQUENCE: 169
agcacacgag guucccccgg 20

<210> SEQ ID NO 170
<211> LENGTH: 20
<212> TYPE: RNA
<213> ORGANISM: Artificial Sequence
<220> FEATURE:
<223> OTHER INFORMATION: Seynthetic

<400> SEQUENCE: 170
agcacacgag guucccccug 20

<210> SEQ ID NO 171
<211> LENGTH: 20
<212> TYPE: RNA
<213> ORGANISM: Artificial Sequence
<220> FEATURE:
<223> OTHER INFORMATION: Seynthetic

<400> SEQUENCE: 171
agcagcacac gagguucccc 20

<210> SEQ ID NO 172
<211> LENGTH: 20
<212> TYPE: RNA
<213> ORGANISM: Artificial Sequence
<220> FEATURE:
<223> OTHER INFORMATION: Seynthetic

<400> SEQUENCE: 172
agcaggggga accucgugug 20

<210> SEQ ID NO 173
<211> LENGTH: 20
<212> TYPE: RNA
<213> ORGANISM: Artificial Sequence
<220> FEATURE:
<223> OTHER INFORMATION: Seynthetic

<400> SEQUENCE: 173
agcaggugua gacuccgagg 20

<210> SEQ ID NO 174
<211> LENGTH: 20
<212> TYPE: RNA
<213> ORGANISM: Artificial Sequence
<220> FEATURE:
<223> OTHER INFORMATION: Seynthetic

<400> SEQUENCE: 174
agccacaccu gaaggcggac 20

<210> SEQ ID NO 175
<211> LENGTH: 20
<212> TYPE: RNA
<213> ORGANISM: Artificial Sequence
<220> FEATURE:
<223> OTHER INFORMATION: Seynthetic

<400> SEQUENCE: 175
agccccagag gacacaggga 20

<210> SEQ ID NO 176
<211> LENGTH: 20
<212> TYPE: RNA
<213> ORGANISM: Artificial Sequence
<220> FEATURE:
<223> OTHER INFORMATION: Seynthetic

<400> SEQUENCE: 176
agccccuucc aaagauacag 20

<210> SEQ ID NO 177
<211> LENGTH: 20
<212> TYPE: RNA
<213> ORGANISM: Artificial Sequence
<220> FEATURE:
<223> OTHER INFORMATION: Seynthetic

<400> SEQUENCE: 177
agccccuucc aaagauacgg 20

<210> SEQ ID NO 178
<211> LENGTH: 20
<212> TYPE: RNA
<213> ORGANISM: Artificial Sequence
<220> FEATURE:
<223> OTHER INFORMATION: Seynthetic

<400> SEQUENCE: 178
agccggggga accucgugug 20

<210> SEQ ID NO 179
<211> LENGTH: 20
<212> TYPE: RNA
<213> ORGANISM: Artificial Sequence
<220> FEATURE:
<223> OTHER INFORMATION: Seynthetic

<400> SEQUENCE: 179
agccugggcc aggcuggagu 20

<210> SEQ ID NO 180
<211> LENGTH: 20
<212> TYPE: RNA
<213> ORGANISM: Artificial Sequence
<220> FEATURE:
<223> OTHER INFORMATION: Seynthetic

<400> SEQUENCE: 180
agcgggugua gacuccgagg 20

<210> SEQ ID NO 181
<211> LENGTH: 20
<212> TYPE: RNA
<213> ORGANISM: Artificial Sequence
<220> FEATURE:
<223> OTHER INFORMATION: Seynthetic

<400> SEQUENCE: 181 agcgucccccc accccugaaa 20

<210> SEQ ID NO 182
<211> LENGTH: 20
<212> TYPE: RNA
<213> ORGANISM: Artificial Sequence
<220> FEATURE:
<223> OTHER INFORMATION: Seynthetic

<400> SEQUENCE: 182
agcgucggca cacuuaauaa 20

<210> SEQ ID NO 183
<211> LENGTH: 20
<212> TYPE: RNA
<213> ORGANISM: Artificial Sequence
<220> FEATURE:
<223> OTHER INFORMATION: Seynthetic

<400> SEQUENCE: 183
agcuaagaac uuuacgaacg 20

<210> SEQ ID NO 184
<211> LENGTH: 20
<212> TYPE: RNA
<213> ORGANISM: Artificial Sequence
<220> FEATURE:
<223> OTHER INFORMATION: Seynthetic

<400> SEQUENCE: 184
agcuaagaac uuuaugaacg 20

<210> SEQ ID NO 185
<211> LENGTH: 20
<212> TYPE: RNA
<213> ORGANISM: Artificial Sequence
<220> FEATURE:
<223> OTHER INFORMATION: Seynthetic

<400> SEQUENCE: 185
agcucccugg uagaagcaug 20

<210> SEQ ID NO 186
<211> LENGTH: 20
<212> TYPE: RNA
<213> ORGANISM: Artificial Sequence
<220> FEATURE:
<223> OTHER INFORMATION: Seynthetic

<400> SEQUENCE: 186
agcuccugcc cugccuaccc 20

<210> SEQ ID NO 187
<211> LENGTH: 20
<212> TYPE: RNA
<213> ORGANISM: Artificial Sequence
<220> FEATURE:
<223> OTHER INFORMATION: Seynthetic

<400> SEQUENCE: 187
agcugcggga aagggauucc 20

<210> SEQ ID NO 188
<211> LENGTH: 20
<212> TYPE: RNA
<213> ORGANISM: Artificial Sequence
<220> FEATURE:
<223> OTHER INFORMATION: Seynthetic

<400> SEQUENCE: 188
agcugcggga augggauucc 20

<210> SEQ ID NO 189
<211> LENGTH: 20
<212> TYPE: RNA
<213> ORGANISM: Artificial Sequence
<220> FEATURE:
<223> OTHER INFORMATION: Seynthetic

<400> SEQUENCE: 189
agcuggaaca ucguggggga 20

<210> SEQ ID NO 190

<211> LENGTH: 20
<212> TYPE: RNA
<213> ORGANISM: Artificial Sequence
<220> FEATURE:
<223> OTHER INFORMATION: Seynthetic

<400> SEQUENCE: 190
agcuggaaca uggugggga 20

<210> SEQ ID NO 191
<211> LENGTH: 20
<212> TYPE: RNA
<213> ORGANISM: Artificial Sequence
<220> FEATURE:
<223> OTHER INFORMATION: Seynthetic

<400> SEQUENCE: 191
agcuggaguc ccagcugcgg 20

<210> SEQ ID NO 192
<211> LENGTH: 20
<212> TYPE: RNA
<213> ORGANISM: Artificial Sequence
<220> FEATURE:
<223> OTHER INFORMATION: Seynthetic

<400> SEQUENCE: 192
aggacuccag ccuggcccag 20

<210> SEQ ID NO 193
<211> LENGTH: 20
<212> TYPE: RNA
<213> ORGANISM: Artificial Sequence
<220> FEATURE:
<223> OTHER INFORMATION: Seynthetic

<400> SEQUENCE: 193
aggagcuccc ugguagaagc 20

<210> SEQ ID NO 194
<211> LENGTH: 20
<212> TYPE: RNA
<213> ORGANISM: Artificial Sequence
<220> FEATURE:
<223> OTHER INFORMATION: Seynthetic

<400> SEQUENCE: 194
aggaguuccc ugguagaagc 20

<210> SEQ ID NO 195
<211> LENGTH: 20
<212> TYPE: RNA
<213> ORGANISM: Artificial Sequence
<220> FEATURE:
<223> OTHER INFORMATION: Seynthetic

<400> SEQUENCE: 195
aggaugaaau aaauucacgu 20

<210> SEQ ID NO 196
<211> LENGTH: 20
<212> TYPE: RNA
<213> ORGANISM: Artificial Sequence
<220> FEATURE:
<223> OTHER INFORMATION: Seynthetic

<400> SEQUENCE: 196
aggaugcaca aucgcauuca 20

<210> SEQ ID NO 197
<211> LENGTH: 20
<212> TYPE: RNA
<213> ORGANISM: Artificial Sequence
<220> FEATURE:
<223> OTHER INFORMATION: Seynthetic

<400> SEQUENCE: 197
aggauuguga aacacccugg 20

<210> SEQ ID NO 198
<211> LENGTH: 20
<212> TYPE: RNA
<213> ORGANISM: Artificial Sequence
<220> FEATURE:
<223> OTHER INFORMATION: Seynthetic

<400> SEQUENCE: 198
aggcagcccc uuggucugca 20

<210> SEQ ID NO 199
<211> LENGTH: 20
<212> TYPE: RNA
<213> ORGANISM: Artificial Sequence
<220> FEATURE:
<223> OTHER INFORMATION: Seynthetic

<400> SEQUENCE: 199
aggccacagg gacagagaca 20

<210> SEQ ID NO 200
<211> LENGTH: 20
<212> TYPE: RNA
<213> ORGANISM: Artificial Sequence
<220> FEATURE:
<223> OTHER INFORMATION: Seynthetic

<400> SEQUENCE: 200
aggcggacau cccugaacuu 20

<210> SEQ ID NO 201
<211> LENGTH: 20
<212> TYPE: RNA
<213> ORGANISM: Artificial Sequence
<220> FEATURE:
<223> OTHER INFORMATION: Seynthetic

<400> SEQUENCE: 201
aggcuggagu ccugacguga 20

<210> SEQ ID NO 202
<211> LENGTH: 20
<212> TYPE: RNA
<213> ORGANISM: Artificial Sequence
<220> FEATURE:
<223> OTHER INFORMATION: Seynthetic

<400> SEQUENCE: 202
agggaacucc ugcccugccu 20

<210> SEQ ID NO 203
<211> LENGTH: 20
<212> TYPE: RNA

<213> ORGANISM: Artificial Sequence
<220> FEATURE:
<223> OTHER INFORMATION: Seynthetic

<400> SEQUENCE: 203
agggaccaga aggaugggga 20

<210> SEQ ID NO 204
<211> LENGTH: 20
<212> TYPE: RNA
<213> ORGANISM: Artificial Sequence
<220> FEATURE:
<223> OTHER INFORMATION: Seynthetic

<400> SEQUENCE: 204
agggagcucc ugcccugccu 20

<210> SEQ ID NO 205
<211> LENGTH: 20
<212> TYPE: RNA
<213> ORGANISM: Artificial Sequence
<220> FEATURE:
<223> OTHER INFORMATION: Seynthetic

<400> SEQUENCE: 205
agggaugucc gccuucaggu 20

<210> SEQ ID NO 206
<211> LENGTH: 20
<212> TYPE: RNA
<213> ORGANISM: Artificial Sequence
<220> FEATURE:
<223> OTHER INFORMATION: Seynthetic

<400> SEQUENCE: 206
agggauuccc aggacccagc 20

<210> SEQ ID NO 207
<211> LENGTH: 20
<212> TYPE: RNA
<213> ORGANISM: Artificial Sequence
<220> FEATURE:
<223> OTHER INFORMATION: Seynthetic

<400> SEQUENCE: 207
agggcaggag uucccuggua 20

<210> SEQ ID NO 208
<211> LENGTH: 20
<212> TYPE: RNA
<213> ORGANISM: Artificial Sequence
<220> FEATURE:
<223> OTHER INFORMATION: Seynthetic

<400> SEQUENCE: 208
aggggcugga ggaccguccg 20

<210> SEQ ID NO 209
<211> LENGTH: 20
<212> TYPE: RNA
<213> ORGANISM: Artificial Sequence
<220> FEATURE:
<223> OTHER INFORMATION: Seynthetic

<400> SEQUENCE: 209
agggggaacc ucgugugcug 20

<210> SEQ ID NO 210
<211> LENGTH: 20
<212> TYPE: RNA
<213> ORGANISM: Artificial Sequence
<220> FEATURE:
<223> OTHER INFORMATION: Seynthetic

<400> SEQUENCE: 210
agggguaggc agggcaggag 20

<210> SEQ ID NO 211
<211> LENGTH: 20
<212> TYPE: RNA
<213> ORGANISM: Artificial Sequence
<220> FEATURE:
<223> OTHER INFORMATION: Seynthetic

<400> SEQUENCE: 211
aggggugggg gacgccguau 20

<210> SEQ ID NO 212
<211> LENGTH: 20
<212> TYPE: RNA
<213> ORGANISM: Artificial Sequence
<220> FEATURE:
<223> OTHER INFORMATION: Seynthetic

<400> SEQUENCE: 212
aggggugggg gacgcuguau 20

<210> SEQ ID NO 213
<211> LENGTH: 20
<212> TYPE: RNA
<213> ORGANISM: Artificial Sequence
<220> FEATURE:
<223> OTHER INFORMATION: Seynthetic

<400> SEQUENCE: 213 aggggugua uggucacagc 20

<210> SEQ ID NO 214
<211> LENGTH: 20
<212> TYPE: RNA
<213> ORGANISM: Artificial Sequence
<220> FEATURE:
<223> OTHER INFORMATION: Seynthetic

<400> SEQUENCE: 214
agggugucaa gccccagagg 20

<210> SEQ ID NO 215
<211> LENGTH: 20
<212> TYPE: RNA
<213> ORGANISM: Artificial Sequence
<220> FEATURE:
<223> OTHER INFORMATION: Seynthetic

<400> SEQUENCE: 215
agguguagac uccgaggggg 20

<210> SEQ ID NO 216
<211> LENGTH: 20
<212> TYPE: RNA
<213> ORGANISM: Artificial Sequence
<220> FEATURE:

<223> OTHER INFORMATION: Seynthetic

<400> SEQUENCE: 216
agguuccccc ggcuuuucuc 20

<210> SEQ ID NO 217
<211> LENGTH: 20
<212> TYPE: RNA
<213> ORGANISM: Artificial Sequence
<220> FEATURE:
<223> OTHER INFORMATION: Seynthetic

<400> SEQUENCE: 217
agguuccccc ugcuuuucuc 20

<210> SEQ ID NO 218
<211> LENGTH: 20
<212> TYPE: RNA
<213> ORGANISM: Artificial Sequence
<220> FEATURE:
<223> OTHER INFORMATION: Seynthetic

<400> SEQUENCE: 218
agucacccag gguguuucac 20

<210> SEQ ID NO 219
<211> LENGTH: 20
<212> TYPE: RNA
<213> ORGANISM: Artificial Sequence
<220> FEATURE:
<223> OTHER INFORMATION: Seynthetic

<400> SEQUENCE: 219
agucauuauu aagugugccg 20

<210> SEQ ID NO 220
<211> LENGTH: 20
<212> TYPE: RNA
<213> ORGANISM: Artificial Sequence
<220> FEATURE:
<223> OTHER INFORMATION: Seynthetic

<400> SEQUENCE: 220
agucccagcu gcgggaaagg 20

<210> SEQ ID NO 221
<211> LENGTH: 20
<212> TYPE: RNA
<213> ORGANISM: Artificial Sequence
<220> FEATURE:
<223> OTHER INFORMATION: Seynthetic

<400> SEQUENCE: 221
agucccagcu gcgggaaugg 20

<210> SEQ ID NO 222
<211> LENGTH: 20
<212> TYPE: RNA
<213> ORGANISM: Artificial Sequence
<220> FEATURE:
<223> OTHER INFORMATION: Seynthetic

<400> SEQUENCE: 222 aguccccag gguguuucac 20

<210> SEQ ID NO 223
<211> LENGTH: 20
<212> TYPE: RNA
<213> ORGANISM: Artificial Sequence
<220> FEATURE:
<223> OTHER INFORMATION: Seynthetic

<400> SEQUENCE: 223
aguccugacg ugaccacagg 20

<210> SEQ ID NO 224
<211> LENGTH: 20
<212> TYPE: RNA
<213> ORGANISM: Artificial Sequence
<220> FEATURE:
<223> OTHER INFORMATION: Seynthetic

<400> SEQUENCE: 224
agucuacacc cgcugugacc 20

<210> SEQ ID NO 225
<211> LENGTH: 20
<212> TYPE: RNA
<213> ORGANISM: Artificial Sequence
<220> FEATURE:
<223> OTHER INFORMATION: Seynthetic

<400> SEQUENCE: 225
agucuacacc ugcugugacc 20

<210> SEQ ID NO 226
<211> LENGTH: 20
<212> TYPE: RNA
<213> ORGANISM: Artificial Sequence
<220> FEATURE:
<223> OTHER INFORMATION: Seynthetic

<400> SEQUENCE: 226
agucuugacg ugaccacagg 20

<210> SEQ ID NO 227
<211> LENGTH: 20
<212> TYPE: RNA
<213> ORGANISM: Artificial Sequence
<220> FEATURE:
<223> OTHER INFORMATION: Seynthetic

<400> SEQUENCE: 227
agucuuuauu aagugugccg 20

<210> SEQ ID NO 228
<211> LENGTH: 20
<212> TYPE: RNA
<213> ORGANISM: Artificial Sequence
<220> FEATURE:
<223> OTHER INFORMATION: Seynthetic

<400> SEQUENCE: 228
agugacuucc ccacauugua 20

<210> SEQ ID NO 229
<211> LENGTH: 20
<212> TYPE: RNA
<213> ORGANISM: Artificial Sequence
<220> FEATURE:
<223> OTHER INFORMATION: Seynthetic

<400> SEQUENCE: 229
agugacuucc ccacauugug 20

<210> SEQ ID NO 230
<211> LENGTH: 20
<212> TYPE: RNA
<213> ORGANISM: Artificial Sequence
<220> FEATURE:
<223> OTHER INFORMATION: Seynthetic

<400> SEQUENCE: 230
aguucaggga uguccgccuu 20

<210> SEQ ID NO 231
<211> LENGTH: 20
<212> TYPE: RNA
<213> ORGANISM: Artificial Sequence
<220> FEATURE:
<223> OTHER INFORMATION: Seynthetic

<400> SEQUENCE: 231
aguucccugg uagaagcaug 20

<210> SEQ ID NO 232
<211> LENGTH: 20
<212> TYPE: RNA
<213> ORGANISM: Artificial Sequence
<220> FEATURE:
<223> OTHER INFORMATION: Seynthetic

<400> SEQUENCE: 232
auaaagacug cacgugagaa 20

<210> SEQ ID NO 233
<211> LENGTH: 20
<212> TYPE: RNA
<213> ORGANISM: Artificial Sequence
<220> FEATURE:
<223> OTHER INFORMATION: Seynthetic

<400> SEQUENCE: 233
auaaauucac guucguaaag 20

<210> SEQ ID NO 234
<211> LENGTH: 20
<212> TYPE: RNA
<213> ORGANISM: Artificial Sequence
<220> FEATURE:
<223> OTHER INFORMATION: Seynthetic

<400> SEQUENCE: 234
auaaugacug cacgugagaa 20

<210> SEQ ID NO 235
<211> LENGTH: 20
<212> TYPE: RNA
<213> ORGANISM: Artificial Sequence
<220> FEATURE:
<223> OTHER INFORMATION: Seynthetic

<400> SEQUENCE: 235
auacaaugug gggaagucac 20

<210> SEQ ID NO 236
<211> LENGTH: 20

<212> TYPE: RNA
<213> ORGANISM: Artificial Sequence
<220> FEATURE:
<223> OTHER INFORMATION: Seynthetic

<400> SEQUENCE: 236
auacagcguc ccccaccccu 20

<210> SEQ ID NO 237
<211> LENGTH: 20
<212> TYPE: RNA
<213> ORGANISM: Artificial Sequence
<220> FEATURE:
<223> OTHER INFORMATION: Seynthetic

<400> SEQUENCE: 237
auacggcguc ccccaccccu 20

<210> SEQ ID NO 238
<211> LENGTH: 20
<212> TYPE: RNA
<213> ORGANISM: Artificial Sequence
<220> FEATURE:
<223> OTHER INFORMATION: Seynthetic

<400> SEQUENCE: 238
auacuacauu cucacgugca 20

<210> SEQ ID NO 239
<211> LENGTH: 20
<212> TYPE: RNA
<213> ORGANISM: Artificial Sequence
<220> FEATURE:
<223> OTHER INFORMATION: Seynthetic

<400> SEQUENCE: 239
auauggaaag uucagggaug 20

<210> SEQ ID NO 240
<211> LENGTH: 20
<212> TYPE: RNA
<213> ORGANISM: Artificial Sequence
<220> FEATURE:
<223> OTHER INFORMATION: Seynthetic

<400> SEQUENCE: 240
auccauggug aagagaaaag 20

<210> SEQ ID NO 241
<211> LENGTH: 20
<212> TYPE: RNA
<213> ORGANISM: Artificial Sequence
<220> FEATURE:
<223> OTHER INFORMATION: Seynthetic

<400> SEQUENCE: 241
auccauggug cagggaccag 20

<210> SEQ ID NO 242
<211> LENGTH: 20
<212> TYPE: RNA
<213> ORGANISM: Artificial Sequence
<220> FEATURE:
<223> OTHER INFORMATION: Seynthetic

<400> SEQUENCE: 242
auccauggug cggggaccag 20

<210> SEQ ID NO 243
<211> LENGTH: 20
<212> TYPE: RNA
<213> ORGANISM: Artificial Sequence
<220> FEATURE:
<223> OTHER INFORMATION: Seynthetic

<400> SEQUENCE: 243
aucccauucc cgcagcuggg 20

<210> SEQ ID NO 244
<211> LENGTH: 20
<212> TYPE: RNA
<213> ORGANISM: Artificial Sequence
<220> FEATURE:
<223> OTHER INFORMATION: Seynthetic

<400> SEQUENCE: 244
auccccaucc uucugguccc 20

<210> SEQ ID NO 245
<211> LENGTH: 20
<212> TYPE: RNA
<213> ORGANISM: Artificial Sequence
<220> FEATURE:
<223> OTHER INFORMATION: Seynthetic

<400> SEQUENCE: 245
aucccuuucc cgcagcuggg 20

<210> SEQ ID NO 246
<211> LENGTH: 20
<212> TYPE: RNA
<213> ORGANISM: Artificial Sequence
<220> FEATURE:
<223> OTHER INFORMATION: Seynthetic

<400> SEQUENCE: 246
auccuucugg uccccgcacc 20

<210> SEQ ID NO 247
<211> LENGTH: 20
<212> TYPE: RNA
<213> ORGANISM: Artificial Sequence
<220> FEATURE:
<223> OTHER INFORMATION: Seynthetic

<400> SEQUENCE: 247
auccuucugg ucccugcacc 20

<210> SEQ ID NO 248
<211> LENGTH: 20
<212> TYPE: RNA
<213> ORGANISM: Artificial Sequence
<220> FEATURE:
<223> OTHER INFORMATION: Seynthetic

<400> SEQUENCE: 248
aucgcauuca aaugucagau 20

<210> SEQ ID NO 249
<211> LENGTH: 20
<212> TYPE: RNA
<213> ORGANISM: Artificial Sequence
<220> FEATURE:
<223> OTHER INFORMATION: Seynthetic

<400> SEQUENCE: 249
aucguggggg agaugggaag 20

<210> SEQ ID NO 250
<211> LENGTH: 20
<212> TYPE: RNA
<213> ORGANISM: Artificial Sequence
<220> FEATURE:
<223> OTHER INFORMATION: Seynthetic

<400> SEQUENCE: 250
aucuccccca ccauguucca 20

<210> SEQ ID NO 251
<211> LENGTH: 20
<212> TYPE: RNA
<213> ORGANISM: Artificial Sequence
<220> FEATURE:
<223> OTHER INFORMATION: Seynthetic

<400> SEQUENCE: 251
aucuccccca cgauguucca 20

<210> SEQ ID NO 252
<211> LENGTH: 20
<212> TYPE: RNA
<213> ORGANISM: Artificial Sequence
<220> FEATURE:
<223> OTHER INFORMATION: Seynthetic

<400> SEQUENCE: 252
aucugaaauu ugaaugcgau 20

<210> SEQ ID NO 253
<211> LENGTH: 20
<212> TYPE: RNA
<213> ORGANISM: Artificial Sequence
<220> FEATURE:
<223> OTHER INFORMATION: Seynthetic

<400> SEQUENCE: 253
aucugacauu ugaaugcgau 20

<210> SEQ ID NO 254
<211> LENGTH: 20
<212> TYPE: RNA
<213> ORGANISM: Artificial Sequence
<220> FEATURE:
<223> OTHER INFORMATION: Seynthetic

<400> SEQUENCE: 254
augaaauaaa uucacguucg 20

<210> SEQ ID NO 255
<211> LENGTH: 20
<212> TYPE: RNA
<213> ORGANISM: Artificial Sequence
<220> FEATURE:
<223> OTHER INFORMATION: Seynthetic

<400> SEQUENCE: 255
augacugcac gugagaaugu 20

<210> SEQ ID NO 256
<211> LENGTH: 20
<212> TYPE: RNA
<213> ORGANISM: Artificial Sequence
<220> FEATURE:
<223> OTHER INFORMATION: Seynthetic

<400> SEQUENCE: 256
augcacaauc gcauucaaau 20

<210> SEQ ID NO 257
<211> LENGTH: 20
<212> TYPE: RNA
<213> ORGANISM: Artificial Sequence
<220> FEATURE:
<223> OTHER INFORMATION: Seynthetic

<400> SEQUENCE: 257
augccgccuu caggugugge 20

<210> SEQ ID NO 258
<211> LENGTH: 20
<212> TYPE: RNA
<213> ORGANISM: Artificial Sequence
<220> FEATURE:
<223> OTHER INFORMATION: Seynthetic

<400> SEQUENCE: 258
augcuucuac cagggaacuc 20

<210> SEQ ID NO 259
<211> LENGTH: 20
<212> TYPE: RNA
<213> ORGANISM: Artificial Sequence
<220> FEATURE:
<223> OTHER INFORMATION: Seynthetic

<400> SEQUENCE: 259
augcuucuac cagggagcuc 20

<210> SEQ ID NO 260
<211> LENGTH: 20
<212> TYPE: RNA
<213> ORGANISM: Artificial Sequence
<220> FEATURE:
<223> OTHER INFORMATION: Seynthetic

<400> SEQUENCE: 260
auggaaaguu cagggauguc 20

<210> SEQ ID NO 261
<211> LENGTH: 20
<212> TYPE: RNA
<213> ORGANISM: Artificial Sequence
<220> FEATURE:
<223> OTHER INFORMATION: Seynthetic

<400> SEQUENCE: 261
augggauucc caggacccag 20

<210> SEQ ID NO 262
<211> LENGTH: 20
<212> TYPE: RNA
<213> ORGANISM: Artificial Sequence
<220> FEATURE:
<223> OTHER INFORMATION: Seynthetic

<400> SEQUENCE: 262
auggucacag cagguguaga 20

<210> SEQ ID NO 263
<211> LENGTH: 20
<212> TYPE: RNA
<213> ORGANISM: Artificial Sequence
<220> FEATURE:
<223> OTHER INFORMATION: Seynthetic

<400> SEQUENCE: 263
auggucacag cggguguaga 20

<210> SEQ ID NO 264
<211> LENGTH: 20
<212> TYPE: RNA
<213> ORGANISM: Artificial Sequence
<220> FEATURE:
<223> OTHER INFORMATION: Seynthetic

<400> SEQUENCE: 264
auggugaaga gaaaagccgg 20

<210> SEQ ID NO 265
<211> LENGTH: 20
<212> TYPE: RNA
<213> ORGANISM: Artificial Sequence
<220> FEATURE:
<223> OTHER INFORMATION: Seynthetic

<400> SEQUENCE: 265
auggugcagg gaccagaagg 20

<210> SEQ ID NO 266
<211> LENGTH: 20
<212> TYPE: RNA
<213> ORGANISM: Artificial Sequence
<220> FEATURE:
<223> OTHER INFORMATION: Seynthetic

<400> SEQUENCE: 266
auggugcggg gaccagaagg 20

<210> SEQ ID NO 267
<211> LENGTH: 20
<212> TYPE: RNA
<213> ORGANISM: Artificial Sequence
<220> FEATURE:
<223> OTHER INFORMATION: Seynthetic

<400> SEQUENCE: 267
augucagaua aucaaugugg 20

<210> SEQ ID NO 268
<211> LENGTH: 20
<212> TYPE: RNA
<213> ORGANISM: Artificial Sequence
<220> FEATURE:
<223> OTHER INFORMATION: Seynthetic

<400> SEQUENCE: 268
auguccgccu ucaggugugg 20

<210> SEQ ID NO 269

<211> LENGTH: 20
<212> TYPE: RNA
<213> ORGANISM: Artificial Sequence
<220> FEATURE:
<223> OTHER INFORMATION: Seynthetic

<400> SEQUENCE: 269
auuaauccau ggugcaggga 20

<210> SEQ ID NO 270
<211> LENGTH: 20
<212> TYPE: RNA
<213> ORGANISM: Artificial Sequence
<220> FEATURE:
<223> OTHER INFORMATION: Seynthetic

<400> SEQUENCE: 270
auuaauccau ggugcgggga 20

<210> SEQ ID NO 271
<211> LENGTH: 20
<212> TYPE: RNA
<213> ORGANISM: Artificial Sequence
<220> FEATURE:
<223> OTHER INFORMATION: Seynthetic

<400> SEQUENCE: 271
auuaucugac auuugaaugc 20

<210> SEQ ID NO 272
<211> LENGTH: 20
<212> TYPE: RNA
<213> ORGANISM: Artificial Sequence
<220> FEATURE:
<223> OTHER INFORMATION: Seynthetic

<400> SEQUENCE: 272
auuauuaagu gugccgacgc 20

<210> SEQ ID NO 273
<211> LENGTH: 20
<212> TYPE: RNA
<213> ORGANISM: Artificial Sequence
<220> FEATURE:
<223> OTHER INFORMATION: Seynthetic

<400> SEQUENCE: 273
auucacguuc auaaaguucu 20

<210> SEQ ID NO 274
<211> LENGTH: 20
<212> TYPE: RNA
<213> ORGANISM: Artificial Sequence
<220> FEATURE:
<223> OTHER INFORMATION: Seynthetic

<400> SEQUENCE: 274
auucacguuc guaaaguucu 20

<210> SEQ ID NO 275
<211> LENGTH: 20
<212> TYPE: RNA
<213> ORGANISM: Artificial Sequence
<220> FEATURE:
<223> OTHER INFORMATION: Seynthetic

<400> SEQUENCE: 275
auucccgcag cugggacucc 20

<210> SEQ ID NO 276
<211> LENGTH: 20
<212> TYPE: RNA
<213> ORGANISM: Artificial Sequence
<220> FEATURE:
<223> OTHER INFORMATION: Seynthetic

<400> SEQUENCE: 276
auucucacgu gcagucauua 20

<210> SEQ ID NO 277
<211> LENGTH: 20
<212> TYPE: RNA
<213> ORGANISM: Artificial Sequence
<220> FEATURE:
<223> OTHER INFORMATION: Seynthetic

<400> SEQUENCE: 277
auucucacgu gcagucuuua 20

<210> SEQ ID NO 278
<211> LENGTH: 20
<212> TYPE: RNA
<213> ORGANISM: Artificial Sequence
<220> FEATURE:
<223> OTHER INFORMATION: Seynthetic

<400> SEQUENCE: 278
auugcucaug cuucuaccag 20

<210> SEQ ID NO 279
<211> LENGTH: 20
<212> TYPE: RNA
<213> ORGANISM: Artificial Sequence
<220> FEATURE:
<223> OTHER INFORMATION: Seynthetic

<400> SEQUENCE: 279
auugugaaac acccuggggg 20

<210> SEQ ID NO 280
<211> LENGTH: 20
<212> TYPE: RNA
<213> ORGANISM: Artificial Sequence
<220> FEATURE:
<223> OTHER INFORMATION: Seynthetic

<400> SEQUENCE: 280
auugugaaac acccugggug 20

<210> SEQ ID NO 281
<211> LENGTH: 20
<212> TYPE: RNA
<213> ORGANISM: Artificial Sequence
<220> FEATURE:
<223> OTHER INFORMATION: Seynthetic

<400> SEQUENCE: 281
auuucagaua aucaaugugg 20

<210> SEQ ID NO 282
<211> LENGTH: 20
<212> TYPE: RNA

<213> ORGANISM: Artificial Sequence
<220> FEATURE:
<223> OTHER INFORMATION: Seynthetic

<400> SEQUENCE: 282
auuucagggg ugggggacgc 20

<210> SEQ ID NO 283
<211> LENGTH: 20
<212> TYPE: RNA
<213> ORGANISM: Artificial Sequence
<220> FEATURE:
<223> OTHER INFORMATION: Seynthetic

<400> SEQUENCE: 283
auuuuuuuuu aauggagcgg 20

<210> SEQ ID NO 284
<211> LENGTH: 20
<212> TYPE: RNA
<213> ORGANISM: Artificial Sequence
<220> FEATURE:
<223> OTHER INFORMATION: Seynthetic

<400> SEQUENCE: 284
caaaaccccc gcuccauuaa 20

<210> SEQ ID NO 285
<211> LENGTH: 20
<212> TYPE: RNA
<213> ORGANISM: Artificial Sequence
<220> FEATURE:
<223> OTHER INFORMATION: Seynthetic

<400> SEQUENCE: 285
caaagauaca gcgucccccca 20

<210> SEQ ID NO 286
<211> LENGTH: 20
<212> TYPE: RNA
<213> ORGANISM: Artificial Sequence
<220> FEATURE:
<223> OTHER INFORMATION: Seynthetic

<400> SEQUENCE: 286
caaagauacg gcgucccccca 20

<210> SEQ ID NO 287
<211> LENGTH: 20
<212> TYPE: RNA
<213> ORGANISM: Artificial Sequence
<220> FEATURE:
<223> OTHER INFORMATION: Seynthetic

<400> SEQUENCE: 287
caaaugucag auaaucaaug 20

<210> SEQ ID NO 288
<211> LENGTH: 20
<212> TYPE: RNA
<213> ORGANISM: Artificial Sequence
<220> FEATURE:
<223> OTHER INFORMATION: Seynthetic

<400> SEQUENCE: 288
caacuucacc acacccagag 20

<210> SEQ ID NO 289
<211> LENGTH: 20
<212> TYPE: RNA
<213> ORGANISM: Artificial Sequence
<220> FEATURE:
<223> OTHER INFORMATION: Seynthetic

<400> SEQUENCE: 289
caagccacac cugaaggcgg 20

<210> SEQ ID NO 290
<211> LENGTH: 20
<212> TYPE: RNA
<213> ORGANISM: Artificial Sequence
<220> FEATURE:
<223> OTHER INFORMATION: Seynthetic

<400> SEQUENCE: 290
caagccccag aggccacagg 20

<210> SEQ ID NO 291
<211> LENGTH: 20
<212> TYPE: RNA
<213> ORGANISM: Artificial Sequence
<220> FEATURE:
<223> OTHER INFORMATION: Seynthetic

<400> SEQUENCE: 291
caagccccuu ccaaagauac 20

<210> SEQ ID NO 292
<211> LENGTH: 20
<212> TYPE: RNA
<213> ORGANISM: Artificial Sequence
<220> FEATURE:
<223> OTHER INFORMATION: Seynthetic

<400> SEQUENCE: 292
caaggggcug ccggaguccc 20

<210> SEQ ID NO 293
<211> LENGTH: 20
<212> TYPE: RNA
<213> ORGANISM: Artificial Sequence
<220> FEATURE:
<223> OTHER INFORMATION: Seynthetic

<400> SEQUENCE: 293
caaucgcauu caaaugucag 20

<210> SEQ ID NO 294
<211> LENGTH: 20
<212> TYPE: RNA
<213> ORGANISM: Artificial Sequence
<220> FEATURE:
<223> OTHER INFORMATION: Seynthetic

<400> SEQUENCE: 294
caaucgcauu caaauuucag 20

<210> SEQ ID NO 295
<211> LENGTH: 20
<212> TYPE: RNA
<213> ORGANISM: Artificial Sequence
<220> FEATURE:

<223> OTHER INFORMATION: Seynthetic

<400> SEQUENCE: 295
cacaaucgca uucaaauguc 20

<210> SEQ ID NO 296
<211> LENGTH: 20
<212> TYPE: RNA
<213> ORGANISM: Artificial Sequence
<220> FEATURE:
<223> OTHER INFORMATION: Seynthetic

<400> SEQUENCE: 296
cacaaucgca uucaaauuuc 20

<210> SEQ ID NO 297
<211> LENGTH: 20
<212> TYPE: RNA
<213> ORGANISM: Artificial Sequence
<220> FEATURE:
<223> OTHER INFORMATION: Seynthetic

<400> SEQUENCE: 297
cacaaugugg ggaagucacu 20

<210> SEQ ID NO 298
<211> LENGTH: 20
<212> TYPE: RNA
<213> ORGANISM: Artificial Sequence
<220> FEATURE:
<223> OTHER INFORMATION: Seynthetic

<400> SEQUENCE: 298
cacacacagc uauuuucuua 20

<210> SEQ ID NO 299
<211> LENGTH: 20
<212> TYPE: RNA
<213> ORGANISM: Artificial Sequence
<220> FEATURE:
<223> OTHER INFORMATION: Seynthetic

<400> SEQUENCE: 299
cacacccaga gucacccagg 20

<210> SEQ ID NO 300
<211> LENGTH: 20
<212> TYPE: RNA
<213> ORGANISM: Artificial Sequence
<220> FEATURE:
<223> OTHER INFORMATION: Seynthetic

<400> SEQUENCE: 300
cacacccaga gucccccagg 20

<210> SEQ ID NO 301
<211> LENGTH: 20
<212> TYPE: RNA
<213> ORGANISM: Artificial Sequence
<220> FEATURE:
<223> OTHER INFORMATION: Seynthetic

<400> SEQUENCE: 301
cacaccugaa ggcggacauc 20

<210> SEQ ID NO 302
<211> LENGTH: 20
<212> TYPE: RNA
<213> ORGANISM: Artificial Sequence
<220> FEATURE:
<223> OTHER INFORMATION: Seynthetic

<400> SEQUENCE: 302
cacacgaggu ucccccggcu 20

<210> SEQ ID NO 303
<211> LENGTH: 20
<212> TYPE: RNA
<213> ORGANISM: Artificial Sequence
<220> FEATURE:
<223> OTHER INFORMATION: Seynthetic

<400> SEQUENCE: 303
cacacgaggu ucccccugcu 20

<210> SEQ ID NO 304
<211> LENGTH: 20
<212> TYPE: RNA
<213> ORGANISM: Artificial Sequence
<220> FEATURE:
<223> OTHER INFORMATION: Seynthetic

<400> SEQUENCE: 304
cacacggacg guccuccagc 20

<210> SEQ ID NO 305
<211> LENGTH: 20
<212> TYPE: RNA
<213> ORGANISM: Artificial Sequence
<220> FEATURE:
<223> OTHER INFORMATION: Seynthetic

<400> SEQUENCE: 305
cacacuuaau aaagacugca 20

<210> SEQ ID NO 306
<211> LENGTH: 20
<212> TYPE: RNA
<213> ORGANISM: Artificial Sequence
<220> FEATURE:
<223> OTHER INFORMATION: Seynthetic

<400> SEQUENCE: 306
cacacuuaau aaugacugca 20

<210> SEQ ID NO 307
<211> LENGTH: 20
<212> TYPE: RNA
<213> ORGANISM: Artificial Sequence
<220> FEATURE:
<223> OTHER INFORMATION: Seynthetic

<400> SEQUENCE: 307
cacagcaggu guagacuccg 20

<210> SEQ ID NO 308
<211> LENGTH: 20
<212> TYPE: RNA
<213> ORGANISM: Artificial Sequence
<220> FEATURE:
<223> OTHER INFORMATION: Seynthetic

<400> SEQUENCE: 308
cacagcgggu guagacuccg 20

<210> SEQ ID NO 309
<211> LENGTH: 20
<212> TYPE: RNA
<213> ORGANISM: Artificial Sequence
<220> FEATURE:
<223> OTHER INFORMATION: Seynthetic

<400> SEQUENCE: 309
cacagcuauu uucuuaguuu 20

<210> SEQ ID NO 310
<211> LENGTH: 20
<212> TYPE: RNA
<213> ORGANISM: Artificial Sequence
<220> FEATURE:
<223> OTHER INFORMATION: Seynthetic

<400> SEQUENCE: 310
cacaggggga cuccggcagc 20

<210> SEQ ID NO 311
<211> LENGTH: 20
<212> TYPE: RNA
<213> ORGANISM: Artificial Sequence
<220> FEATURE:
<223> OTHER INFORMATION: Seynthetic

<400> SEQUENCE: 311
cacauugauu aucugacauu 20

<210> SEQ ID NO 312
<211> LENGTH: 20
<212> TYPE: RNA
<213> ORGANISM: Artificial Sequence
<220> FEATURE:
<223> OTHER INFORMATION: Seynthetic

<400> SEQUENCE: 312
caccacaccc agagucaccc 20

<210> SEQ ID NO 313
<211> LENGTH: 20
<212> TYPE: RNA
<213> ORGANISM: Artificial Sequence
<220> FEATURE:
<223> OTHER INFORMATION: Seynthetic

<400> SEQUENCE: 313
caccacaccc agaguccccc 20

<210> SEQ ID NO 314
<211> LENGTH: 20
<212> TYPE: RNA
<213> ORGANISM: Artificial Sequence
<220> FEATURE:
<223> OTHER INFORMATION: Seynthetic

<400> SEQUENCE: 314
caccauguuc cagcugcaac 20

<210> SEQ ID NO 315
<211> LENGTH: 20

<212> TYPE: RNA
<213> ORGANISM: Artificial Sequence
<220> FEATURE:
<223> OTHER INFORMATION: Seynthetic

<400> SEQUENCE: 315
cacccagagu cacccagggu 20

<210> SEQ ID NO 316
<211> LENGTH: 20
<212> TYPE: RNA
<213> ORGANISM: Artificial Sequence
<220> FEATURE:
<223> OTHER INFORMATION: Seynthetic

<400> SEQUENCE: 316
cacccagagu cccccagggu 20

<210> SEQ ID NO 317
<211> LENGTH: 20
<212> TYPE: RNA
<213> ORGANISM: Artificial Sequence
<220> FEATURE:
<223> OTHER INFORMATION: Seynthetic

<400> SEQUENCE: 317
cacccagggu guuucacaau 20

<210> SEQ ID NO 318
<211> LENGTH: 20
<212> TYPE: RNA
<213> ORGANISM: Artificial Sequence
<220> FEATURE:
<223> OTHER INFORMATION: Seynthetic

<400> SEQUENCE: 318
cacccccuuc cugcccaccu 20

<210> SEQ ID NO 319
<211> LENGTH: 20
<212> TYPE: RNA
<213> ORGANISM: Artificial Sequence
<220> FEATURE:
<223> OTHER INFORMATION: Seynthetic

<400> SEQUENCE: 319
cacccgcugu gaccauaaca 20

<210> SEQ ID NO 320
<211> LENGTH: 20
<212> TYPE: RNA
<213> ORGANISM: Artificial Sequence
<220> FEATURE:
<223> OTHER INFORMATION: Seynthetic

<400> SEQUENCE: 320
cacccugggg gacucugggu 20

<210> SEQ ID NO 321
<211> LENGTH: 20
<212> TYPE: RNA
<213> ORGANISM: Artificial Sequence
<220> FEATURE:
<223> OTHER INFORMATION: Seynthetic

<400> SEQUENCE: 321
cacccugggu gacucugggu 20

<210> SEQ ID NO 322
<211> LENGTH: 20
<212> TYPE: RNA
<213> ORGANISM: Artificial Sequence
<220> FEATURE:
<223> OTHER INFORMATION: Seynthetic

<400> SEQUENCE: 322
caccugaagg cggacauccc 20

<210> SEQ ID NO 323
<211> LENGTH: 20
<212> TYPE: RNA
<213> ORGANISM: Artificial Sequence
<220> FEATURE:
<223> OTHER INFORMATION: Seynthetic

<400> SEQUENCE: 323
caccugcugu gaccauaaca 20

<210> SEQ ID NO 324
<211> LENGTH: 20
<212> TYPE: RNA
<213> ORGANISM: Artificial Sequence
<220> FEATURE:
<223> OTHER INFORMATION: Seynthetic

<400> SEQUENCE: 324
caccuggagg ggcuggagga 20

<210> SEQ ID NO 325
<211> LENGTH: 20
<212> TYPE: RNA
<213> ORGANISM: Artificial Sequence
<220> FEATURE:
<223> OTHER INFORMATION: Seynthetic

<400> SEQUENCE: 325
caccuggcgg ggcuggagga 20

<210> SEQ ID NO 326
<211> LENGTH: 20
<212> TYPE: RNA
<213> ORGANISM: Artificial Sequence
<220> FEATURE:
<223> OTHER INFORMATION: Seynthetic

<400> SEQUENCE: 326
caccuuuguc ucugucccug 20

<210> SEQ ID NO 327
<211> LENGTH: 20
<212> TYPE: RNA
<213> ORGANISM: Artificial Sequence
<220> FEATURE:
<223> OTHER INFORMATION: Seynthetic

<400> SEQUENCE: 327
cacgagguuc ccccggcuuu 20

<210> SEQ ID NO 328
<211> LENGTH: 20
<212> TYPE: RNA
<213> ORGANISM: Artificial Sequence
<220> FEATURE:
<223> OTHER INFORMATION: Seynthetic

<400> SEQUENCE: 328
cacgagguuc ccccugcuuu 20

<210> SEQ ID NO 329
<211> LENGTH: 20
<212> TYPE: RNA
<213> ORGANISM: Artificial Sequence
<220> FEATURE:
<223> OTHER INFORMATION: Seynthetic

<400> SEQUENCE: 329
cacgauguuc cagcugcaac 20

<210> SEQ ID NO 330
<211> LENGTH: 20
<212> TYPE: RNA
<213> ORGANISM: Artificial Sequence
<220> FEATURE:
<223> OTHER INFORMATION: Seynthetic

<400> SEQUENCE: 330
cacggacggu ccuccagccc 20

<210> SEQ ID NO 331
<211> LENGTH: 20
<212> TYPE: RNA
<213> ORGANISM: Artificial Sequence
<220> FEATURE:
<223> OTHER INFORMATION: Seynthetic

<400> SEQUENCE: 331
cacgucaaga cuccagccug 20

<210> SEQ ID NO 332
<211> LENGTH: 20
<212> TYPE: RNA
<213> ORGANISM: Artificial Sequence
<220> FEATURE:
<223> OTHER INFORMATION: Seynthetic

<400> SEQUENCE: 332
cacgucagga cuccagccug 20

<210> SEQ ID NO 333
<211> LENGTH: 20
<212> TYPE: RNA
<213> ORGANISM: Artificial Sequence
<220> FEATURE:
<223> OTHER INFORMATION: Seynthetic

<400> SEQUENCE: 333
cacgugcagu cauuauuaag 20

<210> SEQ ID NO 334
<211> LENGTH: 20
<212> TYPE: RNA
<213> ORGANISM: Artificial Sequence
<220> FEATURE:
<223> OTHER INFORMATION: Seynthetic

<400> SEQUENCE: 334
cacgugcagu cuuuauuaag 20

<210> SEQ ID NO 335
<211> LENGTH: 20
<212> TYPE: RNA
<213> ORGANISM: Artificial Sequence
<220> FEATURE:
<223> OTHER INFORMATION: Seynthetic

<400> SEQUENCE: 335
cacguucaua aaguucuuag 20

<210> SEQ ID NO 336
<211> LENGTH: 20
<212> TYPE: RNA
<213> ORGANISM: Artificial Sequence
<220> FEATURE:
<223> OTHER INFORMATION: Seynthetic

<400> SEQUENCE: 336
cacguucgua aaguucuuag 20

<210> SEQ ID NO 337
<211> LENGTH: 20
<212> TYPE: RNA
<213> ORGANISM: Artificial Sequence
<220> FEATURE:
<223> OTHER INFORMATION: Seynthetic

<400> SEQUENCE: 337
cacguugcau uaauccaugg 20

<210> SEQ ID NO 338
<211> LENGTH: 20
<212> TYPE: RNA
<213> ORGANISM: Artificial Sequence
<220> FEATURE:
<223> OTHER INFORMATION: Seynthetic

<400> SEQUENCE: 338
cacuuaauaa agacugcacg 20

<210> SEQ ID NO 339
<211> LENGTH: 20
<212> TYPE: RNA
<213> ORGANISM: Artificial Sequence
<220> FEATURE:
<223> OTHER INFORMATION: Seynthetic

<400> SEQUENCE: 339
cacuuaauaa ugacugcacg 20

<210> SEQ ID NO 340
<211> LENGTH: 20
<212> TYPE: RNA
<213> ORGANISM: Artificial Sequence
<220> FEATURE:
<223> OTHER INFORMATION: Seynthetic

<400> SEQUENCE: 340
cacuugccug uggucacguc 20

<210> SEQ ID NO 341
<211> LENGTH: 20
<212> TYPE: RNA
<213> ORGANISM: Artificial Sequence
<220> FEATURE:
<223> OTHER INFORMATION: Seynthetic

<400> SEQUENCE: 341
cacuuucuua gcuaagaacu 20

<210> SEQ ID NO 342
<211> LENGTH: 20
<212> TYPE: RNA
<213> ORGANISM: Artificial Sequence
<220> FEATURE:
<223> OTHER INFORMATION: Seynthetic

<400> SEQUENCE: 342
cagaagugac uuccccacau 20

<210> SEQ ID NO 343
<211> LENGTH: 20
<212> TYPE: RNA
<213> ORGANISM: Artificial Sequence
<220> FEATURE:
<223> OTHER INFORMATION: Seynthetic

<400> SEQUENCE: 343
cagaccaagg ggcugccgga 20

<210> SEQ ID NO 344
<211> LENGTH: 20
<212> TYPE: RNA
<213> ORGANISM: Artificial Sequence
<220> FEATURE:
<223> OTHER INFORMATION: Seynthetic

<400> SEQUENCE: 344
cagaccaagg ggcugccuga 20

<210> SEQ ID NO 345
<211> LENGTH: 20
<212> TYPE: RNA
<213> ORGANISM: Artificial Sequence
<220> FEATURE:
<223> OTHER INFORMATION: Seynthetic

<400> SEQUENCE: 345
cagaggacac agggacagag 20

<210> SEQ ID NO 346
<211> LENGTH: 20
<212> TYPE: RNA
<213> ORGANISM: Artificial Sequence
<220> FEATURE:
<223> OTHER INFORMATION: Seynthetic

<400> SEQUENCE: 346
cagaggccac agggacagag 20

<210> SEQ ID NO 347
<211> LENGTH: 20
<212> TYPE: RNA
<213> ORGANISM: Artificial Sequence
<220> FEATURE:
<223> OTHER INFORMATION: Seynthetic

<400> SEQUENCE: 347
cagagucacc cagggugMuu 20

<210> SEQ ID NO 348

<211> LENGTH: 20
<212> TYPE: RNA
<213> ORGANISM: Artificial Sequence
<220> FEATURE:
<223> OTHER INFORMATION: Seynthetic

<400> SEQUENCE: 348 cagaguccccc cagggguguuu 20

<210> SEQ ID NO 349
<211> LENGTH: 20
<212> TYPE: RNA
<213> ORGANISM: Artificial Sequence
<220> FEATURE:
<223> OTHER INFORMATION: Seynthetic

<400> SEQUENCE: 349
cagcacacga gguucccccg 20

<210> SEQ ID NO 350
<211> LENGTH: 20
<212> TYPE: RNA
<213> ORGANISM: Artificial Sequence
<220> FEATURE:
<223> OTHER INFORMATION: Seynthetic

<400> SEQUENCE: 350
cagcacacga gguuccccccu 20

<210> SEQ ID NO 351
<211> LENGTH: 20
<212> TYPE: RNA
<213> ORGANISM: Artificial Sequence
<220> FEATURE:
<223> OTHER INFORMATION: Seynthetic

<400> SEQUENCE: 351
cagcaggugu agacuccgag 20

<210> SEQ ID NO 352
<211> LENGTH: 20
<212> TYPE: RNA
<213> ORGANISM: Artificial Sequence
<220> FEATURE:
<223> OTHER INFORMATION: Seynthetic

<400> SEQUENCE: 352
cagcgggugu agacuccgag 20

<210> SEQ ID NO 353
<211> LENGTH: 20
<212> TYPE: RNA
<213> ORGANISM: Artificial Sequence
<220> FEATURE:
<223> OTHER INFORMATION: Seynthetic

<400> SEQUENCE: 353
cagcgucccc caccccugaa 20

<210> SEQ ID NO 354
<211> LENGTH: 20
<212> TYPE: RNA
<213> ORGANISM: Artificial Sequence
<220> FEATURE:
<223> OTHER INFORMATION: Seynthetic

<400> SEQUENCE: 354
cagcgucggc acacuuaaua 20

<210> SEQ ID NO 355
<211> LENGTH: 20
<212> TYPE: RNA
<213> ORGANISM: Artificial Sequence
<220> FEATURE:
<223> OTHER INFORMATION: Seynthetic

<400> SEQUENCE: 355
cagcucucaa agcaacacuu 20

<210> SEQ ID NO 356
<211> LENGTH: 20
<212> TYPE: RNA
<213> ORGANISM: Artificial Sequence
<220> FEATURE:
<223> OTHER INFORMATION: Seynthetic

<400> SEQUENCE: 356
cagcugcggg aaagggauuc 20

<210> SEQ ID NO 357
<211> LENGTH: 20
<212> TYPE: RNA
<213> ORGANISM: Artificial Sequence
<220> FEATURE:
<223> OTHER INFORMATION: Seynthetic

<400> SEQUENCE: 357
cagcugcggg aaugggauuc 20

<210> SEQ ID NO 358
<211> LENGTH: 20
<212> TYPE: RNA
<213> ORGANISM: Artificial Sequence
<220> FEATURE:
<223> OTHER INFORMATION: Seynthetic

<400> SEQUENCE: 358
cagcuggaac aucguggggg 20

<210> SEQ ID NO 359
<211> LENGTH: 20
<212> TYPE: RNA
<213> ORGANISM: Artificial Sequence
<220> FEATURE:
<223> OTHER INFORMATION: Seynthetic

<400> SEQUENCE: 359
cagcuggaac augguggggg 20

<210> SEQ ID NO 360
<211> LENGTH: 20
<212> TYPE: RNA
<213> ORGANISM: Artificial Sequence
<220> FEATURE:
<223> OTHER INFORMATION: Seynthetic

<400> SEQUENCE: 360
caggacucca gccuggccca 20

<210> SEQ ID NO 361
<211> LENGTH: 20
<212> TYPE: RNA

<213> ORGANISM: Artificial Sequence
<220> FEATURE:
<223> OTHER INFORMATION: Seynthetic

<400> SEQUENCE: 361
caggagcucc cugguagaag 20

<210> SEQ ID NO 362
<211> LENGTH: 20
<212> TYPE: RNA
<213> ORGANISM: Artificial Sequence
<220> FEATURE:
<223> OTHER INFORMATION: Seynthetic

<400> SEQUENCE: 362
caggaguucc cugguagaag 20

<210> SEQ ID NO 363
<211> LENGTH: 20
<212> TYPE: RNA
<213> ORGANISM: Artificial Sequence
<220> FEATURE:
<223> OTHER INFORMATION: Seynthetic

<400> SEQUENCE: 363
caggcuggag uccugacgug 20

<210> SEQ ID NO 364
<211> LENGTH: 20
<212> TYPE: RNA
<213> ORGANISM: Artificial Sequence
<220> FEATURE:
<223> OTHER INFORMATION: Seynthetic

<400> SEQUENCE: 364
caggcuggag ucuugacgug 20

<210> SEQ ID NO 365
<211> LENGTH: 20
<212> TYPE: RNA
<213> ORGANISM: Artificial Sequence
<220> FEATURE:
<223> OTHER INFORMATION: Seynthetic

<400> SEQUENCE: 365
cagggaacuc cugcccugcc 20

<210> SEQ ID NO 366
<211> LENGTH: 20
<212> TYPE: RNA
<213> ORGANISM: Artificial Sequence
<220> FEATURE:
<223> OTHER INFORMATION: Seynthetic

<400> SEQUENCE: 366
cagggaccag aaggaugggg 20

<210> SEQ ID NO 367
<211> LENGTH: 20
<212> TYPE: RNA
<213> ORGANISM: Artificial Sequence
<220> FEATURE:
<223> OTHER INFORMATION: Seynthetic

<400> SEQUENCE: 367
cagggagcuc cugcccugcc 20

<210> SEQ ID NO 368
<211> LENGTH: 20
<212> TYPE: RNA
<213> ORGANISM: Artificial Sequence
<220> FEATURE:
<223> OTHER INFORMATION: Seynthetic

<400> SEQUENCE: 368
cagggauguc cgccuucagg 20

<210> SEQ ID NO 369
<211> LENGTH: 20
<212> TYPE: RNA
<213> ORGANISM: Artificial Sequence
<220> FEATURE:
<223> OTHER INFORMATION: Seynthetic

<400> SEQUENCE: 369
cagggcagga guucccuggu 20

<210> SEQ ID NO 370
<211> LENGTH: 20
<212> TYPE: RNA
<213> ORGANISM: Artificial Sequence
<220> FEATURE:
<223> OTHER INFORMATION: Seynthetic

<400> SEQUENCE: 370
cagggggaac cucgugugcu 20

<210> SEQ ID NO 371
<211> LENGTH: 20
<212> TYPE: RNA
<213> ORGANISM: Artificial Sequence
<220> FEATURE:
<223> OTHER INFORMATION: Seynthetic

<400> SEQUENCE: 371
caggggaggg ggacgccgua 20

<210> SEQ ID NO 372
<211> LENGTH: 20
<212> TYPE: RNA
<213> ORGANISM: Artificial Sequence
<220> FEATURE:
<223> OTHER INFORMATION: Seynthetic

<400> SEQUENCE: 372
caggggaggg ggacgcugua 20

<210> SEQ ID NO 373
<211> LENGTH: 20
<212> TYPE: RNA
<213> ORGANISM: Artificial Sequence
<220> FEATURE:
<223> OTHER INFORMATION: Seynthetic

<400> SEQUENCE: 373 cagggguguca agccccagag 20

<210> SEQ ID NO 374
<211> LENGTH: 20
<212> TYPE: RNA
<213> ORGANISM: Artificial Sequence
<220> FEATURE:

<223> OTHER INFORMATION: Seynthetic

<400> SEQUENCE: 374
cagguguaga cuccgagggg 20

<210> SEQ ID NO 375
<211> LENGTH: 20
<212> TYPE: RNA
<213> ORGANISM: Artificial Sequence
<220> FEATURE:
<223> OTHER INFORMATION: Seynthetic

<400> SEQUENCE: 375
cagucauuau uaagugugcc 20

<210> SEQ ID NO 376
<211> LENGTH: 20
<212> TYPE: RNA
<213> ORGANISM: Artificial Sequence
<220> FEATURE:
<223> OTHER INFORMATION: Seynthetic

<400> SEQUENCE: 376
cagucuuuau uaagugugcc 20

<210> SEQ ID NO 377
<211> LENGTH: 20
<212> TYPE: RNA
<213> ORGANISM: Artificial Sequence
<220> FEATURE:
<223> OTHER INFORMATION: Seynthetic

<400> SEQUENCE: 377
cauaaaguuc uuagcuaaga 20

<210> SEQ ID NO 378
<211> LENGTH: 20
<212> TYPE: RNA
<213> ORGANISM: Artificial Sequence
<220> FEATURE:
<223> OTHER INFORMATION: Seynthetic

<400> SEQUENCE: 378
cauccuucug guccccgcac 20

<210> SEQ ID NO 379
<211> LENGTH: 20
<212> TYPE: RNA
<213> ORGANISM: Artificial Sequence
<220> FEATURE:
<223> OTHER INFORMATION: Seynthetic

<400> SEQUENCE: 379
cauccuucug gucccugcac 20

<210> SEQ ID NO 380
<211> LENGTH: 20
<212> TYPE: RNA
<213> ORGANISM: Artificial Sequence
<220> FEATURE:
<223> OTHER INFORMATION: Seynthetic

<400> SEQUENCE: 380
caucgugggg gagaugggaa 20

<210> SEQ ID NO 381
<211> LENGTH: 20
<212> TYPE: RNA
<213> ORGANISM: Artificial Sequence
<220> FEATURE:
<223> OTHER INFORMATION: Seynthetic

<400> SEQUENCE: 381
caucuccccc accauguucc 20

<210> SEQ ID NO 382
<211> LENGTH: 20
<212> TYPE: RNA
<213> ORGANISM: Artificial Sequence
<220> FEATURE:
<223> OTHER INFORMATION: Seynthetic

<400> SEQUENCE: 382
caucuccccc acgauguucc 20

<210> SEQ ID NO 383
<211> LENGTH: 20
<212> TYPE: RNA
<213> ORGANISM: Artificial Sequence
<220> FEATURE:
<223> OTHER INFORMATION: Seynthetic

<400> SEQUENCE: 383
caugcuucua ccagggaacu 20

<210> SEQ ID NO 384
<211> LENGTH: 20
<212> TYPE: RNA
<213> ORGANISM: Artificial Sequence
<220> FEATURE:
<223> OTHER INFORMATION: Seynthetic

<400> SEQUENCE: 384
caugcuucua ccagggagcu 20

<210> SEQ ID NO 385
<211> LENGTH: 20
<212> TYPE: RNA
<213> ORGANISM: Artificial Sequence
<220> FEATURE:
<223> OTHER INFORMATION: Seynthetic

<400> SEQUENCE: 385
cauggugaag agaaaagccg 20

<210> SEQ ID NO 386
<211> LENGTH: 20
<212> TYPE: RNA
<213> ORGANISM: Artificial Sequence
<220> FEATURE:
<223> OTHER INFORMATION: Seynthetic

<400> SEQUENCE: 386
cauggugcag ggaccagaag 20

<210> SEQ ID NO 387
<211> LENGTH: 20
<212> TYPE: RNA
<213> ORGANISM: Artificial Sequence
<220> FEATURE:
<223> OTHER INFORMATION: Seynthetic

<400> SEQUENCE: 387
cauggugcgg ggaccagaag 20

<210> SEQ ID NO 388
<211> LENGTH: 20
<212> TYPE: RNA
<213> ORGANISM: Artificial Sequence
<220> FEATURE:
<223> OTHER INFORMATION: Seynthetic

<400> SEQUENCE: 388
cauguuccag cugcaacggc 20

<210> SEQ ID NO 389
<211> LENGTH: 20
<212> TYPE: RNA
<213> ORGANISM: Artificial Sequence
<220> FEATURE:
<223> OTHER INFORMATION: Seynthetic

<400> SEQUENCE: 389
cauuaaucca uggugcaggg 20

<210> SEQ ID NO 390
<211> LENGTH: 20
<212> TYPE: RNA
<213> ORGANISM: Artificial Sequence
<220> FEATURE:
<223> OTHER INFORMATION: Seynthetic

<400> SEQUENCE: 390
cauuaaucca uggugcgggg 20

<210> SEQ ID NO 391
<211> LENGTH: 20
<212> TYPE: RNA
<213> ORGANISM: Artificial Sequence
<220> FEATURE:
<223> OTHER INFORMATION: Seynthetic

<400> SEQUENCE: 391
cauuauuaag ugugccgacg 20

<210> SEQ ID NO 392
<211> LENGTH: 20
<212> TYPE: RNA
<213> ORGANISM: Artificial Sequence
<220> FEATURE:
<223> OTHER INFORMATION: Seynthetic

<400> SEQUENCE: 392
cauucccgca gcugggacuc 20

<210> SEQ ID NO 393
<211> LENGTH: 20
<212> TYPE: RNA
<213> ORGANISM: Artificial Sequence
<220> FEATURE:
<223> OTHER INFORMATION: Seynthetic

<400> SEQUENCE: 393
cauucucacg ugcagucauu 20

<210> SEQ ID NO 394
<211> LENGTH: 20

<212> TYPE: RNA
<213> ORGANISM: Artificial Sequence
<220> FEATURE:
<223> OTHER INFORMATION: Seynthetic

<400> SEQUENCE: 394
cauucucacg ugcagucuuu 20

<210> SEQ ID NO 395
<211> LENGTH: 20
<212> TYPE: RNA
<213> ORGANISM: Artificial Sequence
<220> FEATURE:
<223> OTHER INFORMATION: Seynthetic

<400> SEQUENCE: 395
cauuugaaug cgauugugca 20

<210> SEQ ID NO 396
<211> LENGTH: 20
<212> TYPE: RNA
<213> ORGANISM: Artificial Sequence
<220> FEATURE:
<223> OTHER INFORMATION: Seynthetic

<400> SEQUENCE: 396
ccaaagauac agcguccccc 20

<210> SEQ ID NO 397
<211> LENGTH: 20
<212> TYPE: RNA
<213> ORGANISM: Artificial Sequence
<220> FEATURE:
<223> OTHER INFORMATION: Seynthetic

<400> SEQUENCE: 397
ccaaagauac ggcguccccc 20

<210> SEQ ID NO 398
<211> LENGTH: 20
<212> TYPE: RNA
<213> ORGANISM: Artificial Sequence
<220> FEATURE:
<223> OTHER INFORMATION: Seynthetic

<400> SEQUENCE: 398
ccaacuucac cacacccaga 20

<210> SEQ ID NO 399
<211> LENGTH: 20
<212> TYPE: RNA
<213> ORGANISM: Artificial Sequence
<220> FEATURE:
<223> OTHER INFORMATION: Seynthetic

<400> SEQUENCE: 399
ccaagccccu uccaaagaua 20

<210> SEQ ID NO 400
<211> LENGTH: 20
<212> TYPE: RNA
<213> ORGANISM: Artificial Sequence
<220> FEATURE:
<223> OTHER INFORMATION: Seynthetic

<400> SEQUENCE: 400
ccaaggggcu gccggagucc 20

<210> SEQ ID NO 401
<211> LENGTH: 20
<212> TYPE: RNA
<213> ORGANISM: Artificial Sequence
<220> FEATURE:
<223> OTHER INFORMATION: Seynthetic

<400> SEQUENCE: 401
ccacacccag agucacccag 20

<210> SEQ ID NO 402
<211> LENGTH: 20
<212> TYPE: RNA
<213> ORGANISM: Artificial Sequence
<220> FEATURE:
<223> OTHER INFORMATION: Seynthetic

<400> SEQUENCE: 402
ccacacccag agucccccag 20

<210> SEQ ID NO 403
<211> LENGTH: 20
<212> TYPE: RNA
<213> ORGANISM: Artificial Sequence
<220> FEATURE:
<223> OTHER INFORMATION: Seynthetic

<400> SEQUENCE: 403
ccacaccuga aggcggacau 20

<210> SEQ ID NO 404
<211> LENGTH: 20
<212> TYPE: RNA
<213> ORGANISM: Artificial Sequence
<220> FEATURE:
<223> OTHER INFORMATION: Seynthetic

<400> SEQUENCE: 404
ccacagggac agagacaaag 20

<210> SEQ ID NO 405
<211> LENGTH: 20
<212> TYPE: RNA
<213> ORGANISM: Artificial Sequence
<220> FEATURE:
<223> OTHER INFORMATION: Seynthetic

<400> SEQUENCE: 405
ccacaggggg acuccggcag 20

<210> SEQ ID NO 406
<211> LENGTH: 20
<212> TYPE: RNA
<213> ORGANISM: Artificial Sequence
<220> FEATURE:
<223> OTHER INFORMATION: Seynthetic

<400> SEQUENCE: 406
ccacauugau uaucugaaau 20

<210> SEQ ID NO 407
<211> LENGTH: 20
<212> TYPE: RNA
<213> ORGANISM: Artificial Sequence
<220> FEATURE:
<223> OTHER INFORMATION: Seynthetic

<400> SEQUENCE: 407
ccacauugau uaucugacau 20

<210> SEQ ID NO 408
<211> LENGTH: 20
<212> TYPE: RNA
<213> ORGANISM: Artificial Sequence
<220> FEATURE:
<223> OTHER INFORMATION: Seynthetic

<400> SEQUENCE: 408
ccaccauguu ccagcugcaa 20

<210> SEQ ID NO 409
<211> LENGTH: 20
<212> TYPE: RNA
<213> ORGANISM: Artificial Sequence
<220> FEATURE:
<223> OTHER INFORMATION: Seynthetic

<400> SEQUENCE: 409
ccaccuggag gggcuggagg 20

<210> SEQ ID NO 410
<211> LENGTH: 20
<212> TYPE: RNA
<213> ORGANISM: Artificial Sequence
<220> FEATURE:
<223> OTHER INFORMATION: Seynthetic

<400> SEQUENCE: 410
ccacgauguu ccagcugcaa 20

<210> SEQ ID NO 411
<211> LENGTH: 20
<212> TYPE: RNA
<213> ORGANISM: Artificial Sequence
<220> FEATURE:
<223> OTHER INFORMATION: Seynthetic

<400> SEQUENCE: 411
ccacuugccu guggucacgu 20

<210> SEQ ID NO 412
<211> LENGTH: 20
<212> TYPE: RNA
<213> ORGANISM: Artificial Sequence
<220> FEATURE:
<223> OTHER INFORMATION: Seynthetic

<400> SEQUENCE: 412
ccagaggaca cagggacaga 20

<210> SEQ ID NO 413
<211> LENGTH: 20
<212> TYPE: RNA
<213> ORGANISM: Artificial Sequence
<220> FEATURE:
<223> OTHER INFORMATION: Seynthetic

<400> SEQUENCE: 413
ccagagucac ccaggguguu 20

<210> SEQ ID NO 414
<211> LENGTH: 20
<212> TYPE: RNA
<213> ORGANISM: Artificial Sequence
<220> FEATURE:
<223> OTHER INFORMATION: Seynthetic

<400> SEQUENCE: 414
ccagaguccc ccagggugu u 20

<210> SEQ ID NO 415
<211> LENGTH: 20
<212> TYPE: RNA
<213> ORGANISM: Artificial Sequence
<220> FEATURE:
<223> OTHER INFORMATION: Seynthetic

<400> SEQUENCE: 415
ccagcgucgg cacacuuaau 20

<210> SEQ ID NO 416
<211> LENGTH: 20
<212> TYPE: RNA
<213> ORGANISM: Artificial Sequence
<220> FEATURE:
<223> OTHER INFORMATION: Seynthetic

<400> SEQUENCE: 416
ccagcucuca aagcaacacu 20

<210> SEQ ID NO 417
<211> LENGTH: 20
<212> TYPE: RNA
<213> ORGANISM: Artificial Sequence
<220> FEATURE:
<223> OTHER INFORMATION: Seynthetic

<400> SEQUENCE: 417
ccagcugcgg gaaagggauu 20

<210> SEQ ID NO 418
<211> LENGTH: 20
<212> TYPE: RNA
<213> ORGANISM: Artificial Sequence
<220> FEATURE:
<223> OTHER INFORMATION: Seynthetic

<400> SEQUENCE: 418
ccagcugcgg gaaugggauu 20

<210> SEQ ID NO 419
<211> LENGTH: 20
<212> TYPE: RNA
<213> ORGANISM: Artificial Sequence
<220> FEATURE:
<223> OTHER INFORMATION: Seynthetic

<400> SEQUENCE: 419
ccaggcugga guccugacgu 20

<210> SEQ ID NO 420
<211> LENGTH: 20
<212> TYPE: RNA
<213> ORGANISM: Artificial Sequence
<220> FEATURE:
<223> OTHER INFORMATION: Seynthetic

<400> SEQUENCE: 420
ccaggcugga gucuugacgu 20

<210> SEQ ID NO 421
<211> LENGTH: 20
<212> TYPE: RNA
<213> ORGANISM: Artificial Sequence
<220> FEATURE:
<223> OTHER INFORMATION: Seynthetic

<400> SEQUENCE: 421
ccagggaacu ccugcccugc 20

<210> SEQ ID NO 422
<211> LENGTH: 20
<212> TYPE: RNA
<213> ORGANISM: Artificial Sequence
<220> FEATURE:
<223> OTHER INFORMATION: Seynthetic

<400> SEQUENCE: 422
ccauccuucu gguccccgca 20

<210> SEQ ID NO 423
<211> LENGTH: 20
<212> TYPE: RNA
<213> ORGANISM: Artificial Sequence
<220> FEATURE:
<223> OTHER INFORMATION: Seynthetic

<400> SEQUENCE: 423
ccauccuucu ggucccugca 20

<210> SEQ ID NO 424
<211> LENGTH: 20
<212> TYPE: RNA
<213> ORGANISM: Artificial Sequence
<220> FEATURE:
<223> OTHER INFORMATION: Seynthetic

<400> SEQUENCE: 424
ccaucucccc caccauguuc 20

<210> SEQ ID NO 425
<211> LENGTH: 20
<212> TYPE: RNA
<213> ORGANISM: Artificial Sequence
<220> FEATURE:
<223> OTHER INFORMATION: Seynthetic

<400> SEQUENCE: 425
ccaucucccc cacgauguuc 20

<210> SEQ ID NO 426
<211> LENGTH: 20
<212> TYPE: RNA
<213> ORGANISM: Artificial Sequence
<220> FEATURE:
<223> OTHER INFORMATION: Seynthetic

<400> SEQUENCE: 426
ccauggugaa gagaaaagca 20

<210> SEQ ID NO 427

<211> LENGTH: 20
<212> TYPE: RNA
<213> ORGANISM: Artificial Sequence
<220> FEATURE:
<223> OTHER INFORMATION: Seynthetic

<400> SEQUENCE: 427
ccauggugaa gagaaaagcc 20

<210> SEQ ID NO 428
<211> LENGTH: 20
<212> TYPE: RNA
<213> ORGANISM: Artificial Sequence
<220> FEATURE:
<223> OTHER INFORMATION: Seynthetic

<400> SEQUENCE: 428
ccauggugca gggaccagaa 20

<210> SEQ ID NO 429
<211> LENGTH: 20
<212> TYPE: RNA
<213> ORGANISM: Artificial Sequence
<220> FEATURE:
<223> OTHER INFORMATION: Seynthetic

<400> SEQUENCE: 429
ccauggugcg gggaccagaa 20

<210> SEQ ID NO 430
<211> LENGTH: 20
<212> TYPE: RNA
<213> ORGANISM: Artificial Sequence
<220> FEATURE:
<223> OTHER INFORMATION: Seynthetic

<400> SEQUENCE: 430
ccauguucca gcugcaacgg 20

<210> SEQ ID NO 431
<211> LENGTH: 20
<212> TYPE: RNA
<213> ORGANISM: Artificial Sequence
<220> FEATURE:
<223> OTHER INFORMATION: Seynthetic

<400> SEQUENCE: 431
ccauucccgc agcugggacu 20

<210> SEQ ID NO 432
<211> LENGTH: 20
<212> TYPE: RNA
<213> ORGANISM: Artificial Sequence
<220> FEATURE:
<223> OTHER INFORMATION: Seynthetic

<400> SEQUENCE: 432
cccacauuga uuaucugaca 20

<210> SEQ ID NO 433
<211> LENGTH: 20
<212> TYPE: RNA
<213> ORGANISM: Artificial Sequence
<220> FEATURE:
<223> OTHER INFORMATION: Seynthetic

<400> SEQUENCE: 433
cccaccaugu uccagcugca 20

<210> SEQ ID NO 434
<211> LENGTH: 20
<212> TYPE: RNA
<213> ORGANISM: Artificial Sequence
<220> FEATURE:
<223> OTHER INFORMATION: Seynthetic

<400> SEQUENCE: 434
cccaccugga ggggcuggag 20

<210> SEQ ID NO 435
<211> LENGTH: 20
<212> TYPE: RNA
<213> ORGANISM: Artificial Sequence
<220> FEATURE:
<223> OTHER INFORMATION: Seynthetic

<400> SEQUENCE: 435
cccacgaugu uccagcugca 20

<210> SEQ ID NO 436
<211> LENGTH: 20
<212> TYPE: RNA
<213> ORGANISM: Artificial Sequence
<220> FEATURE:
<223> OTHER INFORMATION: Seynthetic

<400> SEQUENCE: 436
cccagaggac acagggacag 20

<210> SEQ ID NO 437
<211> LENGTH: 20
<212> TYPE: RNA
<213> ORGANISM: Artificial Sequence
<220> FEATURE:
<223> OTHER INFORMATION: Seynthetic

<400> SEQUENCE: 437
cccagaggcc acagggacag 20

<210> SEQ ID NO 438
<211> LENGTH: 20
<212> TYPE: RNA
<213> ORGANISM: Artificial Sequence
<220> FEATURE:
<223> OTHER INFORMATION: Seynthetic

<400> SEQUENCE: 438
cccagaguca cccagggugu 20

<210> SEQ ID NO 439
<211> LENGTH: 20
<212> TYPE: RNA
<213> ORGANISM: Artificial Sequence
<220> FEATURE:
<223> OTHER INFORMATION: Seynthetic

<400> SEQUENCE: 439
cccagagucc cccagggugu 20

<210> SEQ ID NO 440
<211> LENGTH: 20
<212> TYPE: RNA

<213> ORGANISM: Artificial Sequence
<220> FEATURE:
<223> OTHER INFORMATION: Seynthetic

<400> SEQUENCE: 440
cccagcgucg gcacacuuaa 20

<210> SEQ ID NO 441
<211> LENGTH: 20
<212> TYPE: RNA
<213> ORGANISM: Artificial Sequence
<220> FEATURE:
<223> OTHER INFORMATION: Seynthetic

<400> SEQUENCE: 441
cccagcugcg ggaaagggau 20

<210> SEQ ID NO 442
<211> LENGTH: 20
<212> TYPE: RNA
<213> ORGANISM: Artificial Sequence
<220> FEATURE:
<223> OTHER INFORMATION: Seynthetic

<400> SEQUENCE: 442
cccagcugcg ggaaugggau 20

<210> SEQ ID NO 443
<211> LENGTH: 20
<212> TYPE: RNA
<213> ORGANISM: Artificial Sequence
<220> FEATURE:
<223> OTHER INFORMATION: Seynthetic

<400> SEQUENCE: 443
cccauccuuc ugguccccgc 20

<210> SEQ ID NO 444
<211> LENGTH: 20
<212> TYPE: RNA
<213> ORGANISM: Artificial Sequence
<220> FEATURE:
<223> OTHER INFORMATION: Seynthetic

<400> SEQUENCE: 444
cccauccuuc ugguccccugc 20

<210> SEQ ID NO 445
<211> LENGTH: 20
<212> TYPE: RNA
<213> ORGANISM: Artificial Sequence
<220> FEATURE:
<223> OTHER INFORMATION: Seynthetic

<400> SEQUENCE: 445
cccaucuccc ccaccauguu 20

<210> SEQ ID NO 446
<211> LENGTH: 20
<212> TYPE: RNA
<213> ORGANISM: Artificial Sequence
<220> FEATURE:
<223> OTHER INFORMATION: Seynthetic

<400> SEQUENCE: 446
cccaucuccc ccacgauguu 20

<210> SEQ ID NO 447
<211> LENGTH: 20
<212> TYPE: RNA
<213> ORGANISM: Artificial Sequence
<220> FEATURE:
<223> OTHER INFORMATION: Seynthetic

<400> SEQUENCE: 447
cccauucccg cagcugggac 20

<210> SEQ ID NO 448
<211> LENGTH: 20
<212> TYPE: RNA
<213> ORGANISM: Artificial Sequence
<220> FEATURE:
<223> OTHER INFORMATION: Seynthetic

<400> SEQUENCE: 448
ccccacauug uguuuuuuuc 20

<210> SEQ ID NO 449
<211> LENGTH: 20
<212> TYPE: RNA
<213> ORGANISM: Artificial Sequence
<220> FEATURE:
<223> OTHER INFORMATION: Seynthetic

<400> SEQUENCE: 449
ccccaccaug uuccagcugc 20

<210> SEQ ID NO 450
<211> LENGTH: 20
<212> TYPE: RNA
<213> ORGANISM: Artificial Sequence
<220> FEATURE:
<223> OTHER INFORMATION: Seynthetic

<400> SEQUENCE: 450
ccccacgaug uuccagcugc 20

<210> SEQ ID NO 451
<211> LENGTH: 20
<212> TYPE: RNA
<213> ORGANISM: Artificial Sequence
<220> FEATURE:
<223> OTHER INFORMATION: Seynthetic

<400> SEQUENCE: 451
ccccagagga cacagggaca 20

<210> SEQ ID NO 452
<211> LENGTH: 20
<212> TYPE: RNA
<213> ORGANISM: Artificial Sequence
<220> FEATURE:
<223> OTHER INFORMATION: Seynthetic

<400> SEQUENCE: 452
ccccagaggc cacagggaca 20

<210> SEQ ID NO 453
<211> LENGTH: 20
<212> TYPE: RNA
<213> ORGANISM: Artificial Sequence
<220> FEATURE:

<223> OTHER INFORMATION: Seynthetic

<400> SEQUENCE: 453
ccccagggug uuucacaauc 20

<210> SEQ ID NO 454
<211> LENGTH: 20
<212> TYPE: RNA
<213> ORGANISM: Artificial Sequence
<220> FEATURE:
<223> OTHER INFORMATION: Seynthetic

<400> SEQUENCE: 454
ccccauccuu cugguccccg 20

<210> SEQ ID NO 455
<211> LENGTH: 20
<212> TYPE: RNA
<213> ORGANISM: Artificial Sequence
<220> FEATURE:
<223> OTHER INFORMATION: Seynthetic

<400> SEQUENCE: 455
ccccauccuu cugguccccug 20

<210> SEQ ID NO 456
<211> LENGTH: 20
<212> TYPE: RNA
<213> ORGANISM: Artificial Sequence
<220> FEATURE:
<223> OTHER INFORMATION: Seynthetic

<400> SEQUENCE: 456
cccccaccau guuccagcug 20

<210> SEQ ID NO 457
<211> LENGTH: 20
<212> TYPE: RNA
<213> ORGANISM: Artificial Sequence
<220> FEATURE:
<223> OTHER INFORMATION: Seynthetic

<400> SEQUENCE: 457
cccccacgau guuccagcug 20

<210> SEQ ID NO 458
<211> LENGTH: 20
<212> TYPE: RNA
<213> ORGANISM: Artificial Sequence
<220> FEATURE:
<223> OTHER INFORMATION: Seynthetic

<400> SEQUENCE: 458
cccccagggu guuucacaau 20

<210> SEQ ID NO 459
<211> LENGTH: 20
<212> TYPE: RNA
<213> ORGANISM: Artificial Sequence
<220> FEATURE:
<223> OTHER INFORMATION: Seynthetic

<400> SEQUENCE: 459
cccccgcucc auuaaaaaaa 20

<210> SEQ ID NO 460
<211> LENGTH: 20
<212> TYPE: RNA
<213> ORGANISM: Artificial Sequence
<220> FEATURE:
<223> OTHER INFORMATION: Seynthetic

<400> SEQUENCE: 460
cccccggcuu uucucuucac 20

<210> SEQ ID NO 461
<211> LENGTH: 20
<212> TYPE: RNA
<213> ORGANISM: Artificial Sequence
<220> FEATURE:
<223> OTHER INFORMATION: Seynthetic

<400> SEQUENCE: 461
cccccucgga gucuacaccc 20

<210> SEQ ID NO 462
<211> LENGTH: 20
<212> TYPE: RNA
<213> ORGANISM: Artificial Sequence
<220> FEATURE:
<223> OTHER INFORMATION: Seynthetic

<400> SEQUENCE: 462
cccccucgga gucuacaccu 20

<210> SEQ ID NO 463
<211> LENGTH: 20
<212> TYPE: RNA
<213> ORGANISM: Artificial Sequence
<220> FEATURE:
<223> OTHER INFORMATION: Seynthetic

<400> SEQUENCE: 463
cccccuuccu gcccaccugg 20

<210> SEQ ID NO 464
<211> LENGTH: 20
<212> TYPE: RNA
<213> ORGANISM: Artificial Sequence
<220> FEATURE:
<223> OTHER INFORMATION: Seynthetic

<400> SEQUENCE: 464
ccccgcacca uggauuaaug 20

<210> SEQ ID NO 465
<211> LENGTH: 20
<212> TYPE: RNA
<213> ORGANISM: Artificial Sequence
<220> FEATURE:
<223> OTHER INFORMATION: Seynthetic

<400> SEQUENCE: 465
ccccggcuuu ucucuucacc 20

<210> SEQ ID NO 466
<211> LENGTH: 20
<212> TYPE: RNA
<213> ORGANISM: Artificial Sequence
<220> FEATURE:
<223> OTHER INFORMATION: Seynthetic

<400> SEQUENCE: 466
ccccucggag ucuacacccg 20

<210> SEQ ID NO 467
<211> LENGTH: 20
<212> TYPE: RNA
<213> ORGANISM: Artificial Sequence
<220> FEATURE:
<223> OTHER INFORMATION: Seynthetic

<400> SEQUENCE: 467
ccccucggag ucuacaccug 20

<210> SEQ ID NO 468
<211> LENGTH: 20
<212> TYPE: RNA
<213> ORGANISM: Artificial Sequence
<220> FEATURE:
<223> OTHER INFORMATION: Seynthetic

<400> SEQUENCE: 468
ccccugcuuu ucucuucacc 20

<210> SEQ ID NO 469
<211> LENGTH: 20
<212> TYPE: RNA
<213> ORGANISM: Artificial Sequence
<220> FEATURE:
<223> OTHER INFORMATION: Seynthetic

<400> SEQUENCE: 469
ccccuuccaa agauacagcg 20

<210> SEQ ID NO 470
<211> LENGTH: 20
<212> TYPE: RNA
<213> ORGANISM: Artificial Sequence
<220> FEATURE:
<223> OTHER INFORMATION: Seynthetic

<400> SEQUENCE: 470
ccccuuccaa agauacggcg 20

<210> SEQ ID NO 471
<211> LENGTH: 20
<212> TYPE: RNA
<213> ORGANISM: Artificial Sequence
<220> FEATURE:
<223> OTHER INFORMATION: Seynthetic

<400> SEQUENCE: 471
cccgcaccau ggauuaaugc 20

<210> SEQ ID NO 472
<211> LENGTH: 20
<212> TYPE: RNA
<213> ORGANISM: Artificial Sequence
<220> FEATURE:
<223> OTHER INFORMATION: Seynthetic

<400> SEQUENCE: 472
cccgccaggu gggcaggaag 20

<210> SEQ ID NO 473
<211> LENGTH: 20

<212> TYPE: RNA
<213> ORGANISM: Artificial Sequence
<220> FEATURE:
<223> OTHER INFORMATION: Seynthetic

<400> SEQUENCE: 473
cccgcuccau uaaaaaaaaa 20

<210> SEQ ID NO 474
<211> LENGTH: 20
<212> TYPE: RNA
<213> ORGANISM: Artificial Sequence
<220> FEATURE:
<223> OTHER INFORMATION: Seynthetic

<400> SEQUENCE: 474
cccgcuguga ccauaacacc 20

<210> SEQ ID NO 475
<211> LENGTH: 20
<212> TYPE: RNA
<213> ORGANISM: Artificial Sequence
<220> FEATURE:
<223> OTHER INFORMATION: Seynthetic

<400> SEQUENCE: 475
cccggccguu gcagcuggaa 20

<210> SEQ ID NO 476
<211> LENGTH: 20
<212> TYPE: RNA
<213> ORGANISM: Artificial Sequence
<220> FEATURE:
<223> OTHER INFORMATION: Seynthetic

<400> SEQUENCE: 476
cccggcuuuu cucuucacca 20

<210> SEQ ID NO 477
<211> LENGTH: 20
<212> TYPE: RNA
<213> ORGANISM: Artificial Sequence
<220> FEATURE:
<223> OTHER INFORMATION: Seynthetic

<400> SEQUENCE: 477
cccucggagu cuacacccgc 20

<210> SEQ ID NO 478
<211> LENGTH: 20
<212> TYPE: RNA
<213> ORGANISM: Artificial Sequence
<220> FEATURE:
<223> OTHER INFORMATION: Seynthetic

<400> SEQUENCE: 478
cccucggagu cuacaccugc 20

<210> SEQ ID NO 479
<211> LENGTH: 20
<212> TYPE: RNA
<213> ORGANISM: Artificial Sequence
<220> FEATURE:
<223> OTHER INFORMATION: Seynthetic

<400> SEQUENCE: 479
cccugcacca uggauuaaug 20

<210> SEQ ID NO 480
<211> LENGTH: 20
<212> TYPE: RNA
<213> ORGANISM: Artificial Sequence
<220> FEATURE:
<223> OTHER INFORMATION: Seynthetic

<400> SEQUENCE: 480
cccugcuuuu cucuucacca 20

<210> SEQ ID NO 481
<211> LENGTH: 20
<212> TYPE: RNA
<213> ORGANISM: Artificial Sequence
<220> FEATURE:
<223> OTHER INFORMATION: Seynthetic

<400> SEQUENCE: 481
cccuggggga cucugggugu 20

<210> SEQ ID NO 482
<211> LENGTH: 20
<212> TYPE: RNA
<213> ORGANISM: Artificial Sequence
<220> FEATURE:
<223> OTHER INFORMATION: Seynthetic

<400> SEQUENCE: 482
cccuggguga cucugggugu 20

<210> SEQ ID NO 483
<211> LENGTH: 20
<212> TYPE: RNA
<213> ORGANISM: Artificial Sequence
<220> FEATURE:
<223> OTHER INFORMATION: Seynthetic

<400> SEQUENCE: 483
cccuguggcc ucuggggcuu 20

<210> SEQ ID NO 484
<211> LENGTH: 20
<212> TYPE: RNA
<213> ORGANISM: Artificial Sequence
<220> FEATURE:
<223> OTHER INFORMATION: Seynthetic

<400> SEQUENCE: 484
cccugugucc ucuggggcuu 20

<210> SEQ ID NO 485
<211> LENGTH: 20
<212> TYPE: RNA
<213> ORGANISM: Artificial Sequence
<220> FEATURE:
<223> OTHER INFORMATION: Seynthetic

<400> SEQUENCE: 485
cccuuccaaa gauacagcgu 20

<210> SEQ ID NO 486
<211> LENGTH: 20
<212> TYPE: RNA
<213> ORGANISM: Artificial Sequence
<220> FEATURE:
<223> OTHER INFORMATION: Seynthetic

<400> SEQUENCE: 486
cccuuccaaa gauacggcgu 20

<210> SEQ ID NO 487
<211> LENGTH: 20
<212> TYPE: RNA
<213> ORGANISM: Artificial Sequence
<220> FEATURE:
<223> OTHER INFORMATION: Seynthetic

<400> SEQUENCE: 487
cccuuccugc ccaccuggag 20

<210> SEQ ID NO 488
<211> LENGTH: 20
<212> TYPE: RNA
<213> ORGANISM: Artificial Sequence
<220> FEATURE:
<223> OTHER INFORMATION: Seynthetic

<400> SEQUENCE: 488
cccuuucccg cagcugggac 20

<210> SEQ ID NO 489
<211> LENGTH: 20
<212> TYPE: RNA
<213> ORGANISM: Artificial Sequence
<220> FEATURE:
<223> OTHER INFORMATION: Seynthetic

<400> SEQUENCE: 489
ccgcaccaug gauuaaugca 20

<210> SEQ ID NO 490
<211> LENGTH: 20
<212> TYPE: RNA
<213> ORGANISM: Artificial Sequence
<220> FEATURE:
<223> OTHER INFORMATION: Seynthetic

<400> SEQUENCE: 490
ccgccaggug ggcaggaagg 20

<210> SEQ ID NO 491
<211> LENGTH: 20
<212> TYPE: RNA
<213> ORGANISM: Artificial Sequence
<220> FEATURE:
<223> OTHER INFORMATION: Seynthetic

<400> SEQUENCE: 491
ccgcugugac cauaacaccc 20

<210> SEQ ID NO 492
<211> LENGTH: 20
<212> TYPE: RNA
<213> ORGANISM: Artificial Sequence
<220> FEATURE:
<223> OTHER INFORMATION: Seynthetic

<400> SEQUENCE: 492
ccggaguccc ccuguggagg 20

<210> SEQ ID NO 493
<211> LENGTH: 20
<212> TYPE: RNA
<213> ORGANISM: Artificial Sequence
<220> FEATURE:
<223> OTHER INFORMATION: Seynthetic

<400> SEQUENCE: 493
ccggcagccc cuuggucugc 20

<210> SEQ ID NO 494
<211> LENGTH: 20
<212> TYPE: RNA
<213> ORGANISM: Artificial Sequence
<220> FEATURE:
<223> OTHER INFORMATION: Seynthetic

<400> SEQUENCE: 494
ccggccguug cagcuggaac 20

<210> SEQ ID NO 495
<211> LENGTH: 20
<212> TYPE: RNA
<213> ORGANISM: Artificial Sequence
<220> FEATURE:
<223> OTHER INFORMATION: Seynthetic

<400> SEQUENCE: 495
ccggcuuuuc ucuucaccau 20

<210> SEQ ID NO 496
<211> LENGTH: 20
<212> TYPE: RNA
<213> ORGANISM: Artificial Sequence
<220> FEATURE:
<223> OTHER INFORMATION: Seynthetic

<400> SEQUENCE: 496
ccgggggaac cucgugugcu 20

<210> SEQ ID NO 497
<211> LENGTH: 20
<212> TYPE: RNA
<213> ORGANISM: Artificial Sequence
<220> FEATURE:
<223> OTHER INFORMATION: Seynthetic

<400> SEQUENCE: 497
ccguaucuuu ggaaggggcu 20

<210> SEQ ID NO 498
<211> LENGTH: 20
<212> TYPE: RNA
<213> ORGANISM: Artificial Sequence
<220> FEATURE:
<223> OTHER INFORMATION: Seynthetic

<400> SEQUENCE: 498
ccguugcaga ccaaggggcu 20

<210> SEQ ID NO 499
<211> LENGTH: 20
<212> TYPE: RNA
<213> ORGANISM: Artificial Sequence
<220> FEATURE:
<223> OTHER INFORMATION: Seynthetic

<400> SEQUENCE: 499
ccguugcagc uggaacaucg 20

<210> SEQ ID NO 500
<211> LENGTH: 20
<212> TYPE: RNA
<213> ORGANISM: Artificial Sequence
<220> FEATURE:
<223> OTHER INFORMATION: Seynthetic

<400> SEQUENCE: 500
ccguugcagc uggaacaugg 20

<210> SEQ ID NO 501
<211> LENGTH: 20
<212> TYPE: RNA
<213> ORGANISM: Artificial Sequence
<220> FEATURE:
<223> OTHER INFORMATION: Seynthetic

<400> SEQUENCE: 501
ccuccacagg gggacucagg 20

<210> SEQ ID NO 502
<211> LENGTH: 20
<212> TYPE: RNA
<213> ORGANISM: Artificial Sequence
<220> FEATURE:
<223> OTHER INFORMATION: Seynthetic

<400> SEQUENCE: 502
ccuccacagg gggacuccgg 20

<210> SEQ ID NO 503
<211> LENGTH: 20
<212> TYPE: RNA
<213> ORGANISM: Artificial Sequence
<220> FEATURE:
<223> OTHER INFORMATION: Seynthetic

<400> SEQUENCE: 503
ccuccagccc cuccaggugg 20

<210> SEQ ID NO 504
<211> LENGTH: 20
<212> TYPE: RNA
<213> ORGANISM: Artificial Sequence
<220> FEATURE:
<223> OTHER INFORMATION: Seynthetic

<400> SEQUENCE: 504
ccucggaguc uacacccgcu 20

<210> SEQ ID NO 505
<211> LENGTH: 20
<212> TYPE: RNA
<213> ORGANISM: Artificial Sequence
<220> FEATURE:
<223> OTHER INFORMATION: Seynthetic

<400> SEQUENCE: 505
ccucggaguc uacaccugcu 20

<210> SEQ ID NO 506

<211> LENGTH: 20
<212> TYPE: RNA
<213> ORGANISM: Artificial Sequence
<220> FEATURE:
<223> OTHER INFORMATION: Seynthetic

<400> SEQUENCE: 506
ccucuuccca ucucccccac 20

<210> SEQ ID NO 507
<211> LENGTH: 20
<212> TYPE: RNA
<213> ORGANISM: Artificial Sequence
<220> FEATURE:
<223> OTHER INFORMATION: Seynthetic

<400> SEQUENCE: 507
ccugaaggcg gacaucccug 20

<210> SEQ ID NO 508
<211> LENGTH: 20
<212> TYPE: RNA
<213> ORGANISM: Artificial Sequence
<220> FEATURE:
<223> OTHER INFORMATION: Seynthetic

<400> SEQUENCE: 508
ccugacguga ccacaggcaa 20

<210> SEQ ID NO 509
<211> LENGTH: 20
<212> TYPE: RNA
<213> ORGANISM: Artificial Sequence
<220> FEATURE:
<223> OTHER INFORMATION: Seynthetic

<400> SEQUENCE: 509
ccugaguccc ccuguggagg 20

<210> SEQ ID NO 510
<211> LENGTH: 20
<212> TYPE: RNA
<213> ORGANISM: Artificial Sequence
<220> FEATURE:
<223> OTHER INFORMATION: Seynthetic

<400> SEQUENCE: 510
ccugcaccau ggauuaaugc 20

<210> SEQ ID NO 511
<211> LENGTH: 20
<212> TYPE: RNA
<213> ORGANISM: Artificial Sequence
<220> FEATURE:
<223> OTHER INFORMATION: Seynthetic

<400> SEQUENCE: 511
ccugcuuuuc ucuucaccau 20

<210> SEQ ID NO 512
<211> LENGTH: 20
<212> TYPE: RNA
<213> ORGANISM: Artificial Sequence
<220> FEATURE:
<223> OTHER INFORMATION: Seynthetic

<400> SEQUENCE: 512
ccuggagggg cuggaggacc 20

<210> SEQ ID NO 513
<211> LENGTH: 20
<212> TYPE: RNA
<213> ORGANISM: Artificial Sequence
<220> FEATURE:
<223> OTHER INFORMATION: Seynthetic

<400> SEQUENCE: 513
ccugggaauc ccauucccgc 20

<210> SEQ ID NO 514
<211> LENGTH: 20
<212> TYPE: RNA
<213> ORGANISM: Artificial Sequence
<220> FEATURE:
<223> OTHER INFORMATION: Seynthetic

<400> SEQUENCE: 514
ccugggaauc ccuuucccgc 20

<210> SEQ ID NO 515
<211> LENGTH: 20
<212> TYPE: RNA
<213> ORGANISM: Artificial Sequence
<220> FEATURE:
<223> OTHER INFORMATION: Seynthetic

<400> SEQUENCE: 515
ccugggggac ucugggugug 20

<210> SEQ ID NO 516
<211> LENGTH: 20
<212> TYPE: RNA
<213> ORGANISM: Artificial Sequence
<220> FEATURE:
<223> OTHER INFORMATION: Seynthetic

<400> SEQUENCE: 516
ccugggugac ucugggugug 20

<210> SEQ ID NO 517
<211> LENGTH: 20
<212> TYPE: RNA
<213> ORGANISM: Artificial Sequence
<220> FEATURE:
<223> OTHER INFORMATION: Seynthetic

<400> SEQUENCE: 517
ccuguggccu cuggggcuug 20

<210> SEQ ID NO 518
<211> LENGTH: 20
<212> TYPE: RNA
<213> ORGANISM: Artificial Sequence
<220> FEATURE:
<223> OTHER INFORMATION: Seynthetic

<400> SEQUENCE: 518
ccugugguca cgucaagacu 20

<210> SEQ ID NO 519
<211> LENGTH: 20
<212> TYPE: RNA

<213> ORGANISM: Artificial Sequence
<220> FEATURE:
<223> OTHER INFORMATION: Seynthetic

<400> SEQUENCE: 519
ccugugguca cgucaggacu 20

<210> SEQ ID NO 520
<211> LENGTH: 20
<212> TYPE: RNA
<213> ORGANISM: Artificial Sequence
<220> FEATURE:
<223> OTHER INFORMATION: Seynthetic

<400> SEQUENCE: 520
ccuguguccu cuggggcuug 20

<210> SEQ ID NO 521
<211> LENGTH: 20
<212> TYPE: RNA
<213> ORGANISM: Artificial Sequence
<220> FEATURE:
<223> OTHER INFORMATION: Seynthetic

<400> SEQUENCE: 521
ccuuccaaag auacagcguc 20

<210> SEQ ID NO 522
<211> LENGTH: 20
<212> TYPE: RNA
<213> ORGANISM: Artificial Sequence
<220> FEATURE:
<223> OTHER INFORMATION: Seynthetic

<400> SEQUENCE: 522
ccuuccaaag auacggcguc 20

<210> SEQ ID NO 523
<211> LENGTH: 20
<212> TYPE: RNA
<213> ORGANISM: Artificial Sequence
<220> FEATURE:
<223> OTHER INFORMATION: Seynthetic

<400> SEQUENCE: 523
ccuucugguc cccgcaccau 20

<210> SEQ ID NO 524
<211> LENGTH: 20
<212> TYPE: RNA
<213> ORGANISM: Artificial Sequence
<220> FEATURE:
<223> OTHER INFORMATION: Seynthetic

<400> SEQUENCE: 524
ccuucugguc ccugcaccau 20

<210> SEQ ID NO 525
<211> LENGTH: 20
<212> TYPE: RNA
<213> ORGANISM: Artificial Sequence
<220> FEATURE:
<223> OTHER INFORMATION: Seynthetic

<400> SEQUENCE: 525
ccuuugucuc ugucccugug 20

<210> SEQ ID NO 526
<211> LENGTH: 20
<212> TYPE: RNA
<213> ORGANISM: Artificial Sequence
<220> FEATURE:
<223> OTHER INFORMATION: Seynthetic

<400> SEQUENCE: 526
cgaacgugaa uuuauuucau 20

<210> SEQ ID NO 527
<211> LENGTH: 20
<212> TYPE: RNA
<213> ORGANISM: Artificial Sequence
<220> FEATURE:
<223> OTHER INFORMATION: Seynthetic

<400> SEQUENCE: 527
cgagguuccc ccggcuuuuc 20

<210> SEQ ID NO 528
<211> LENGTH: 20
<212> TYPE: RNA
<213> ORGANISM: Artificial Sequence
<220> FEATURE:
<223> OTHER INFORMATION: Seynthetic

<400> SEQUENCE: 528
cgagguuccc ccugcuuuuc 20

<210> SEQ ID NO 529
<211> LENGTH: 20
<212> TYPE: RNA
<213> ORGANISM: Artificial Sequence
<220> FEATURE:
<223> OTHER INFORMATION: Seynthetic

<400> SEQUENCE: 529
cgauguucca gcugcaacgg 20

<210> SEQ ID NO 530
<211> LENGTH: 20
<212> TYPE: RNA
<213> ORGANISM: Artificial Sequence
<220> FEATURE:
<223> OTHER INFORMATION: Seynthetic

<400> SEQUENCE: 530
cgcaccaugg auuaaugcaa 20

<210> SEQ ID NO 531
<211> LENGTH: 20
<212> TYPE: RNA
<213> ORGANISM: Artificial Sequence
<220> FEATURE:
<223> OTHER INFORMATION: Seynthetic

<400> SEQUENCE: 531
cgcauucaaa ugucagauaa 20

<210> SEQ ID NO 532
<211> LENGTH: 20
<212> TYPE: RNA
<213> ORGANISM: Artificial Sequence
<220> FEATURE:

<223> OTHER INFORMATION: Seynthetic

<400> SEQUENCE: 532
cgccguaucu uuggaagggg 20

<210> SEQ ID NO 533
<211> LENGTH: 20
<212> TYPE: RNA
<213> ORGANISM: Artificial Sequence
<220> FEATURE:
<223> OTHER INFORMATION: Seynthetic

<400> SEQUENCE: 533
cgcugugacc auaacacccc 20

<210> SEQ ID NO 534
<211> LENGTH: 20
<212> TYPE: RNA
<213> ORGANISM: Artificial Sequence
<220> FEATURE:
<223> OTHER INFORMATION: Seynthetic

<400> SEQUENCE: 534
cggacauccc ugaacuuucc 20

<210> SEQ ID NO 535
<211> LENGTH: 20
<212> TYPE: RNA
<213> ORGANISM: Artificial Sequence
<220> FEATURE:
<223> OTHER INFORMATION: Seynthetic

<400> SEQUENCE: 535
cggacggucc uccagccccu 20

<210> SEQ ID NO 536
<211> LENGTH: 20
<212> TYPE: RNA
<213> ORGANISM: Artificial Sequence
<220> FEATURE:
<223> OTHER INFORMATION: Seynthetic

<400> SEQUENCE: 536
cggagucccc cuguggaggc 20

<210> SEQ ID NO 537
<211> LENGTH: 20
<212> TYPE: RNA
<213> ORGANISM: Artificial Sequence
<220> FEATURE:
<223> OTHER INFORMATION: Seynthetic

<400> SEQUENCE: 537
cggagucuac acccgcugug 20

<210> SEQ ID NO 538
<211> LENGTH: 20
<212> TYPE: RNA
<213> ORGANISM: Artificial Sequence
<220> FEATURE:
<223> OTHER INFORMATION: Seynthetic

<400> SEQUENCE: 538
cggagucuac accugcugug 20

<210> SEQ ID NO 539
<211> LENGTH: 20
<212> TYPE: RNA
<213> ORGANISM: Artificial Sequence
<220> FEATURE:
<223> OTHER INFORMATION: Seynthetic

<400> SEQUENCE: 539
cggcacacuu aauaaagacu 20

<210> SEQ ID NO 540
<211> LENGTH: 20
<212> TYPE: RNA
<213> ORGANISM: Artificial Sequence
<220> FEATURE:
<223> OTHER INFORMATION: Seynthetic

<400> SEQUENCE: 540
cggcacacuu aauaaugacu 20

<210> SEQ ID NO 541
<211> LENGTH: 20
<212> TYPE: RNA
<213> ORGANISM: Artificial Sequence
<220> FEATURE:
<223> OTHER INFORMATION: Seynthetic

<400> SEQUENCE: 541
cggcagcccc uuggucugca 20

<210> SEQ ID NO 542
<211> LENGTH: 20
<212> TYPE: RNA
<213> ORGANISM: Artificial Sequence
<220> FEATURE:
<223> OTHER INFORMATION: Seynthetic

<400> SEQUENCE: 542
cggccguugc agcuggaaca 20

<210> SEQ ID NO 543
<211> LENGTH: 20
<212> TYPE: RNA
<213> ORGANISM: Artificial Sequence
<220> FEATURE:
<223> OTHER INFORMATION: Seynthetic

<400> SEQUENCE: 543
cggcgucccc caccccugaa 20

<210> SEQ ID NO 544
<211> LENGTH: 20
<212> TYPE: RNA
<213> ORGANISM: Artificial Sequence
<220> FEATURE:
<223> OTHER INFORMATION: Seynthetic

<400> SEQUENCE: 544
cggcuuuucu cuucaccaug 20

<210> SEQ ID NO 545
<211> LENGTH: 20
<212> TYPE: RNA
<213> ORGANISM: Artificial Sequence
<220> FEATURE:
<223> OTHER INFORMATION: Seynthetic

<400> SEQUENCE: 545
cgggaaaggg auucccagga 20

<210> SEQ ID NO 546
<211> LENGTH: 20
<212> TYPE: RNA
<213> ORGANISM: Artificial Sequence
<220> FEATURE:
<223> OTHER INFORMATION: Seynthetic

<400> SEQUENCE: 546
cgggaauggg auucccagga 20

<210> SEQ ID NO 547
<211> LENGTH: 20
<212> TYPE: RNA
<213> ORGANISM: Artificial Sequence
<220> FEATURE:
<223> OTHER INFORMATION: Seynthetic

<400> SEQUENCE: 547
cggggaccag aaggaugggg 20

<210> SEQ ID NO 548
<211> LENGTH: 20
<212> TYPE: RNA
<213> ORGANISM: Artificial Sequence
<220> FEATURE:
<223> OTHER INFORMATION: Seynthetic

<400> SEQUENCE: 548
cggggcuggg uccugggaau 20

<210> SEQ ID NO 549
<211> LENGTH: 20
<212> TYPE: RNA
<213> ORGANISM: Artificial Sequence
<220> FEATURE:
<223> OTHER INFORMATION: Seynthetic

<400> SEQUENCE: 549
cgggggaacc ucgugugcug 20

<210> SEQ ID NO 550
<211> LENGTH: 20
<212> TYPE: RNA
<213> ORGANISM: Artificial Sequence
<220> FEATURE:
<223> OTHER INFORMATION: Seynthetic

<400> SEQUENCE: 550
cggguguaga cuccgagggg 20

<210> SEQ ID NO 551
<211> LENGTH: 20
<212> TYPE: RNA
<213> ORGANISM: Artificial Sequence
<220> FEATURE:
<223> OTHER INFORMATION: Seynthetic

<400> SEQUENCE: 551
cgguccucca gccccuccag 20

<210> SEQ ID NO 552
<211> LENGTH: 20

<212> TYPE: RNA
<213> ORGANISM: Artificial Sequence
<220> FEATURE:
<223> OTHER INFORMATION: Seynthetic

<400> SEQUENCE: 552
cguaaaguuc uuagcuaaga 20

<210> SEQ ID NO 553
<211> LENGTH: 20
<212> TYPE: RNA
<213> ORGANISM: Artificial Sequence
<220> FEATURE:
<223> OTHER INFORMATION: Seynthetic

<400> SEQUENCE: 553
cguaucuuug gaaggggcuu 20

<210> SEQ ID NO 554
<211> LENGTH: 20
<212> TYPE: RNA
<213> ORGANISM: Artificial Sequence
<220> FEATURE:
<223> OTHER INFORMATION: Seynthetic

<400> SEQUENCE: 554
cgucaagacu ccagccuggc 20

<210> SEQ ID NO 555
<211> LENGTH: 20
<212> TYPE: RNA
<213> ORGANISM: Artificial Sequence
<220> FEATURE:
<223> OTHER INFORMATION: Seynthetic

<400> SEQUENCE: 555
cgucaggacu ccagccuggc 20

<210> SEQ ID NO 556
<211> LENGTH: 20
<212> TYPE: RNA
<213> ORGANISM: Artificial Sequence
<220> FEATURE:
<223> OTHER INFORMATION: Seynthetic

<400> SEQUENCE: 556 cguccccuc ggagucuaca 20

<210> SEQ ID NO 557
<211> LENGTH: 20
<212> TYPE: RNA
<213> ORGANISM: Artificial Sequence
<220> FEATURE:
<223> OTHER INFORMATION: Seynthetic

<400> SEQUENCE: 557
cgucggcaca cuuaauaaag 20

<210> SEQ ID NO 558
<211> LENGTH: 20
<212> TYPE: RNA
<213> ORGANISM: Artificial Sequence
<220> FEATURE:
<223> OTHER INFORMATION: Seynthetic

<400> SEQUENCE: 558
cgucggcaca cuuaauaaug 20

<210> SEQ ID NO 559
<211> LENGTH: 20
<212> TYPE: RNA
<213> ORGANISM: Artificial Sequence
<220> FEATURE:
<223> OTHER INFORMATION: Seynthetic

<400> SEQUENCE: 559
cgugcaguca uuauuaagug 20

<210> SEQ ID NO 560
<211> LENGTH: 20
<212> TYPE: RNA
<213> ORGANISM: Artificial Sequence
<220> FEATURE:
<223> OTHER INFORMATION: Seynthetic

<400> SEQUENCE: 560
cgugcagucu uuauuaagug 20

<210> SEQ ID NO 561
<211> LENGTH: 20
<212> TYPE: RNA
<213> ORGANISM: Artificial Sequence
<220> FEATURE:
<223> OTHER INFORMATION: Seynthetic

<400> SEQUENCE: 561 cguggggag augggaagag 20

<210> SEQ ID NO 562
<211> LENGTH: 20
<212> TYPE: RNA
<213> ORGANISM: Artificial Sequence
<220> FEATURE:
<223> OTHER INFORMATION: Seynthetic

<400> SEQUENCE: 562
cguucguaaa guucuuagcu 20

<210> SEQ ID NO 563
<211> LENGTH: 20
<212> TYPE: RNA
<213> ORGANISM: Artificial Sequence
<220> FEATURE:
<223> OTHER INFORMATION: Seynthetic

<400> SEQUENCE: 563
cguugcagac caaggggcug 20

<210> SEQ ID NO 564
<211> LENGTH: 20
<212> TYPE: RNA
<213> ORGANISM: Artificial Sequence
<220> FEATURE:
<223> OTHER INFORMATION: Seynthetic

<400> SEQUENCE: 564
cguugcagcu ggaacaucgu 20

<210> SEQ ID NO 565
<211> LENGTH: 20
<212> TYPE: RNA
<213> ORGANISM: Artificial Sequence
<220> FEATURE:
<223> OTHER INFORMATION: Seynthetic

<400> SEQUENCE: 565
cguugcagcu ggaacauggu 20

<210> SEQ ID NO 566
<211> LENGTH: 20
<212> TYPE: RNA
<213> ORGANISM: Artificial Sequence
<220> FEATURE:
<223> OTHER INFORMATION: Seynthetic

<400> SEQUENCE: 566
cguugcauua auccauggug 20

<210> SEQ ID NO 567
<211> LENGTH: 20
<212> TYPE: RNA
<213> ORGANISM: Artificial Sequence
<220> FEATURE:
<223> OTHER INFORMATION: Seynthetic

<400> SEQUENCE: 567
cuaagaacuu uacgaacgug 20

<210> SEQ ID NO 568
<211> LENGTH: 20
<212> TYPE: RNA
<213> ORGANISM: Artificial Sequence
<220> FEATURE:
<223> OTHER INFORMATION: Seynthetic

<400> SEQUENCE: 568
cuaagaacuu uaugaacgug 20

<210> SEQ ID NO 569
<211> LENGTH: 20
<212> TYPE: RNA
<213> ORGANISM: Artificial Sequence
<220> FEATURE:
<223> OTHER INFORMATION: Seynthetic

<400> SEQUENCE: 569
cuacacccgc ugugaccaua 20

<210> SEQ ID NO 570
<211> LENGTH: 20
<212> TYPE: RNA
<213> ORGANISM: Artificial Sequence
<220> FEATURE:
<223> OTHER INFORMATION: Seynthetic

<400> SEQUENCE: 570
cuacaccugc ugugaccaua 20

<210> SEQ ID NO 571
<211> LENGTH: 20
<212> TYPE: RNA
<213> ORGANISM: Artificial Sequence
<220> FEATURE:
<223> OTHER INFORMATION: Seynthetic

<400> SEQUENCE: 571
cuacauucuc acgugcaguc 20

<210> SEQ ID NO 572
<211> LENGTH: 20
<212> TYPE: RNA
<213> ORGANISM: Artificial Sequence
<220> FEATURE:
<223> OTHER INFORMATION: Seynthetic

<400> SEQUENCE: 572
cuaggauugu gaaacacccu 20

<210> SEQ ID NO 573
<211> LENGTH: 20
<212> TYPE: RNA
<213> ORGANISM: Artificial Sequence
<220> FEATURE:
<223> OTHER INFORMATION: Seynthetic

<400> SEQUENCE: 573
cucacgugca gucauuauua 20

<210> SEQ ID NO 574
<211> LENGTH: 20
<212> TYPE: RNA
<213> ORGANISM: Artificial Sequence
<220> FEATURE:
<223> OTHER INFORMATION: Seynthetic

<400> SEQUENCE: 574
cucacgugca gucuuuauua 20

<210> SEQ ID NO 575
<211> LENGTH: 20
<212> TYPE: RNA
<213> ORGANISM: Artificial Sequence
<220> FEATURE:
<223> OTHER INFORMATION: Seynthetic

<400> SEQUENCE: 575
cucaugcuuc uaccagggaa 20

<210> SEQ ID NO 576
<211> LENGTH: 20
<212> TYPE: RNA
<213> ORGANISM: Artificial Sequence
<220> FEATURE:
<223> OTHER INFORMATION: Seynthetic

<400> SEQUENCE: 576
cucaugcuuc uaccagggag 20

<210> SEQ ID NO 577
<211> LENGTH: 20
<212> TYPE: RNA
<213> ORGANISM: Artificial Sequence
<220> FEATURE:
<223> OTHER INFORMATION: Seynthetic

<400> SEQUENCE: 577
cuccacaggg ggacuccggc 20

<210> SEQ ID NO 578
<211> LENGTH: 20
<212> TYPE: RNA
<213> ORGANISM: Artificial Sequence
<220> FEATURE:
<223> OTHER INFORMATION: Seynthetic

<400> SEQUENCE: 578
cuccaggugg gcaggaaggg 20

<210> SEQ ID NO 579
<211> LENGTH: 20
<212> TYPE: RNA
<213> ORGANISM: Artificial Sequence
<220> FEATURE:
<223> OTHER INFORMATION: Seynthetic

<400> SEQUENCE: 579
cucccccacc auguuccagc 20

<210> SEQ ID NO 580
<211> LENGTH: 20
<212> TYPE: RNA
<213> ORGANISM: Artificial Sequence
<220> FEATURE:
<223> OTHER INFORMATION: Seynthetic

<400> SEQUENCE: 580
cucccccacg auguuccagc 20

<210> SEQ ID NO 581
<211> LENGTH: 20
<212> TYPE: RNA
<213> ORGANISM: Artificial Sequence
<220> FEATURE:
<223> OTHER INFORMATION: Seynthetic

<400> SEQUENCE: 581
cucccuggua gaagcaugag 20

<210> SEQ ID NO 582
<211> LENGTH: 20
<212> TYPE: RNA
<213> ORGANISM: Artificial Sequence
<220> FEATURE:
<223> OTHER INFORMATION: Seynthetic

<400> SEQUENCE: 582
cuccggcagc cccuuggucu 20

<210> SEQ ID NO 583
<211> LENGTH: 20
<212> TYPE: RNA
<213> ORGANISM: Artificial Sequence
<220> FEATURE:
<223> OTHER INFORMATION: Seynthetic

<400> SEQUENCE: 583
cucggagucu acacccgcug 20

<210> SEQ ID NO 584
<211> LENGTH: 20
<212> TYPE: RNA
<213> ORGANISM: Artificial Sequence
<220> FEATURE:
<223> OTHER INFORMATION: Seynthetic

<400> SEQUENCE: 584
cucggagucu acaccugcug 20

<210> SEQ ID NO 585

<211> LENGTH: 20
<212> TYPE: RNA
<213> ORGANISM: Artificial Sequence
<220> FEATURE:
<223> OTHER INFORMATION: Seynthetic

<400> SEQUENCE: 585
cucucaaagc aacacuuucu 20

<210> SEQ ID NO 586
<211> LENGTH: 20
<212> TYPE: RNA
<213> ORGANISM: Artificial Sequence
<220> FEATURE:
<223> OTHER INFORMATION: Seynthetic

<400> SEQUENCE: 586
cucuucccau cucccccacc 20

<210> SEQ ID NO 587
<211> LENGTH: 20
<212> TYPE: RNA
<213> ORGANISM: Artificial Sequence
<220> FEATURE:
<223> OTHER INFORMATION: Seynthetic

<400> SEQUENCE: 587
cucuucccau cucccccacg 20

<210> SEQ ID NO 588
<211> LENGTH: 20
<212> TYPE: RNA
<213> ORGANISM: Artificial Sequence
<220> FEATURE:
<223> OTHER INFORMATION: Seynthetic

<400> SEQUENCE: 588
cugaaauuug aaugcgauug 20

<210> SEQ ID NO 589
<211> LENGTH: 20
<212> TYPE: RNA
<213> ORGANISM: Artificial Sequence
<220> FEATURE:
<223> OTHER INFORMATION: Seynthetic

<400> SEQUENCE: 589
cugaaggcgg acaucccuga 20

<210> SEQ ID NO 590
<211> LENGTH: 20
<212> TYPE: RNA
<213> ORGANISM: Artificial Sequence
<220> FEATURE:
<223> OTHER INFORMATION: Seynthetic

<400> SEQUENCE: 590
cugacauuug aaugcgauug 20

<210> SEQ ID NO 591
<211> LENGTH: 20
<212> TYPE: RNA
<213> ORGANISM: Artificial Sequence
<220> FEATURE:
<223> OTHER INFORMATION: Seynthetic

<400> SEQUENCE: 591
cugacgugac cacaggcaag 20

<210> SEQ ID NO 592
<211> LENGTH: 20
<212> TYPE: RNA
<213> ORGANISM: Artificial Sequence
<220> FEATURE:
<223> OTHER INFORMATION: Seynthetic

<400> SEQUENCE: 592
cugagucccc cuguggaggc 20

<210> SEQ ID NO 593
<211> LENGTH: 20
<212> TYPE: RNA
<213> ORGANISM: Artificial Sequence
<220> FEATURE:
<223> OTHER INFORMATION: Seynthetic

<400> SEQUENCE: 593
cugcaccaug gauuaaugca 20

<210> SEQ ID NO 594
<211> LENGTH: 20
<212> TYPE: RNA
<213> ORGANISM: Artificial Sequence
<220> FEATURE:
<223> OTHER INFORMATION: Seynthetic

<400> SEQUENCE: 594
cugcccaccu ggaggggcug 20

<210> SEQ ID NO 595
<211> LENGTH: 20
<212> TYPE: RNA
<213> ORGANISM: Artificial Sequence
<220> FEATURE:
<223> OTHER INFORMATION: Seynthetic

<400> SEQUENCE: 595
cugccggagu cccccugugg 20

<210> SEQ ID NO 596
<211> LENGTH: 20
<212> TYPE: RNA
<213> ORGANISM: Artificial Sequence
<220> FEATURE:
<223> OTHER INFORMATION: Seynthetic

<400> SEQUENCE: 596
cugccuccac agggggacuc 20

<210> SEQ ID NO 597
<211> LENGTH: 20
<212> TYPE: RNA
<213> ORGANISM: Artificial Sequence
<220> FEATURE:
<223> OTHER INFORMATION: Seynthetic

<400> SEQUENCE: 597
cugccugagu cccccugugg 20

<210> SEQ ID NO 598
<211> LENGTH: 20
<212> TYPE: RNA

<213> ORGANISM: Artificial Sequence
<220> FEATURE:
<223> OTHER INFORMATION: Seynthetic

<400> SEQUENCE: 598
cugcgggaaa gggauuccca 20

<210> SEQ ID NO 599
<211> LENGTH: 20
<212> TYPE: RNA
<213> ORGANISM: Artificial Sequence
<220> FEATURE:
<223> OTHER INFORMATION: Seynthetic

<400> SEQUENCE: 599
cugcgggaau gggauuccca 20

<210> SEQ ID NO 600
<211> LENGTH: 20
<212> TYPE: RNA
<213> ORGANISM: Artificial Sequence
<220> FEATURE:
<223> OTHER INFORMATION: Seynthetic

<400> SEQUENCE: 600
cugcuuuucu cuucaccaug 20

<210> SEQ ID NO 601
<211> LENGTH: 20
<212> TYPE: RNA
<213> ORGANISM: Artificial Sequence
<220> FEATURE:
<223> OTHER INFORMATION: Seynthetic

<400> SEQUENCE: 601
cuggaacauc gugggggaga 20

<210> SEQ ID NO 602
<211> LENGTH: 20
<212> TYPE: RNA
<213> ORGANISM: Artificial Sequence
<220> FEATURE:
<223> OTHER INFORMATION: Seynthetic

<400> SEQUENCE: 602
cuggaacaug gugggggaga 20

<210> SEQ ID NO 603
<211> LENGTH: 20
<212> TYPE: RNA
<213> ORGANISM: Artificial Sequence
<220> FEATURE:
<223> OTHER INFORMATION: Seynthetic

<400> SEQUENCE: 603
cuggaggggc uggaggaccg 20

<210> SEQ ID NO 604
<211> LENGTH: 20
<212> TYPE: RNA
<213> ORGANISM: Artificial Sequence
<220> FEATURE:
<223> OTHER INFORMATION: Seynthetic

<400> SEQUENCE: 604
cuggaguccc agcugcggga 20

<210> SEQ ID NO 605
<211> LENGTH: 20
<212> TYPE: RNA
<213> ORGANISM: Artificial Sequence
<220> FEATURE:
<223> OTHER INFORMATION: Seynthetic

<400> SEQUENCE: 605
cuggaguccu gacgugacca 20

<210> SEQ ID NO 606
<211> LENGTH: 20
<212> TYPE: RNA
<213> ORGANISM: Artificial Sequence
<220> FEATURE:
<223> OTHER INFORMATION: Seynthetic

<400> SEQUENCE: 606
cuggagucuu gacgugacca 20

<210> SEQ ID NO 607
<211> LENGTH: 20
<212> TYPE: RNA
<213> ORGANISM: Artificial Sequence
<220> FEATURE:
<223> OTHER INFORMATION: Seynthetic

<400> SEQUENCE: 607
cugggaaucc cauucccgca 20

<210> SEQ ID NO 608
<211> LENGTH: 20
<212> TYPE: RNA
<213> ORGANISM: Artificial Sequence
<220> FEATURE:
<223> OTHER INFORMATION: Seynthetic

<400> SEQUENCE: 608
cugggaaucc cuuucccgca 20

<210> SEQ ID NO 609
<211> LENGTH: 20
<212> TYPE: RNA
<213> ORGANISM: Artificial Sequence
<220> FEATURE:
<223> OTHER INFORMATION: Seynthetic

<400> SEQUENCE: 609
cugggccagg cuggaguccu 20

<210> SEQ ID NO 610
<211> LENGTH: 20
<212> TYPE: RNA
<213> ORGANISM: Artificial Sequence
<220> FEATURE:
<223> OTHER INFORMATION: Seynthetic

<400> SEQUENCE: 610
cugggccagg cuggagucuu 20

<210> SEQ ID NO 611
<211> LENGTH: 20
<212> TYPE: RNA
<213> ORGANISM: Artificial Sequence
<220> FEATURE:

<223> OTHER INFORMATION: Seynthetic

<400> SEQUENCE: 611
cugggggacu cugggugugg 20

<210> SEQ ID NO 612
<211> LENGTH: 20
<212> TYPE: RNA
<213> ORGANISM: Artificial Sequence
<220> FEATURE:
<223> OTHER INFORMATION: Seynthetic

<400> SEQUENCE: 612
cuggguccug ggaaucccau 20

<210> SEQ ID NO 613
<211> LENGTH: 20
<212> TYPE: RNA
<213> ORGANISM: Artificial Sequence
<220> FEATURE:
<223> OTHER INFORMATION: Seynthetic

<400> SEQUENCE: 613
cuggguccug ggaaucccuu 20

<210> SEQ ID NO 614
<211> LENGTH: 20
<212> TYPE: RNA
<213> ORGANISM: Artificial Sequence
<220> FEATURE:
<223> OTHER INFORMATION: Seynthetic

<400> SEQUENCE: 614
cugguccccg caccauggau 20

<210> SEQ ID NO 615
<211> LENGTH: 20
<212> TYPE: RNA
<213> ORGANISM: Artificial Sequence
<220> FEATURE:
<223> OTHER INFORMATION: Seynthetic

<400> SEQUENCE: 615
cuggucccug caccauggau 20

<210> SEQ ID NO 616
<211> LENGTH: 20
<212> TYPE: RNA
<213> ORGANISM: Artificial Sequence
<220> FEATURE:
<223> OTHER INFORMATION: Seynthetic

<400> SEQUENCE: 616
cuguaucuuu ggaaggggcu 20

<210> SEQ ID NO 617
<211> LENGTH: 20
<212> TYPE: RNA
<213> ORGANISM: Artificial Sequence
<220> FEATURE:
<223> OTHER INFORMATION: Seynthetic

<400> SEQUENCE: 617
cugucccugu ggccucuggg 20

<210> SEQ ID NO 618
<211> LENGTH: 20
<212> TYPE: RNA
<213> ORGANISM: Artificial Sequence
<220> FEATURE:
<223> OTHER INFORMATION: Seynthetic

<400> SEQUENCE: 618
cuguggccuc uggggcuuga 20

<210> SEQ ID NO 619
<211> LENGTH: 20
<212> TYPE: RNA
<213> ORGANISM: Artificial Sequence
<220> FEATURE:
<223> OTHER INFORMATION: Seynthetic

<400> SEQUENCE: 619
cuguggucac gucaagacuc 20

<210> SEQ ID NO 620
<211> LENGTH: 20
<212> TYPE: RNA
<213> ORGANISM: Artificial Sequence
<220> FEATURE:
<223> OTHER INFORMATION: Seynthetic

<400> SEQUENCE: 620
cuguggucac gucaggacuc 20

<210> SEQ ID NO 621
<211> LENGTH: 20
<212> TYPE: RNA
<213> ORGANISM: Artificial Sequence
<220> FEATURE:
<223> OTHER INFORMATION: Seynthetic

<400> SEQUENCE: 621
cuguguccuc uggggcuuga 20

<210> SEQ ID NO 622
<211> LENGTH: 20
<212> TYPE: RNA
<213> ORGANISM: Artificial Sequence
<220> FEATURE:
<223> OTHER INFORMATION: Seynthetic

<400> SEQUENCE: 622
cuuaauaaag acugcacgug 20

<210> SEQ ID NO 623
<211> LENGTH: 20
<212> TYPE: RNA
<213> ORGANISM: Artificial Sequence
<220> FEATURE:
<223> OTHER INFORMATION: Seynthetic

<400> SEQUENCE: 623
cuuaauaaug acugcacgug 20

<210> SEQ ID NO 624
<211> LENGTH: 20
<212> TYPE: RNA
<213> ORGANISM: Artificial Sequence
<220> FEATURE:
<223> OTHER INFORMATION: Seynthetic

<400> SEQUENCE: 624
cuuagcuaag aacuuuacga 20

<210> SEQ ID NO 625
<211> LENGTH: 20
<212> TYPE: RNA
<213> ORGANISM: Artificial Sequence
<220> FEATURE:
<223> OTHER INFORMATION: Seynthetic

<400> SEQUENCE: 625
cuuagcuaag aacuuuauga 20

<210> SEQ ID NO 626
<211> LENGTH: 20
<212> TYPE: RNA
<213> ORGANISM: Artificial Sequence
<220> FEATURE:
<223> OTHER INFORMATION: Seynthetic

<400> SEQUENCE: 626
cuucaccaca cccagaguca 20

<210> SEQ ID NO 627
<211> LENGTH: 20
<212> TYPE: RNA
<213> ORGANISM: Artificial Sequence
<220> FEATURE:
<223> OTHER INFORMATION: Seynthetic

<400> SEQUENCE: 627
cuucaccaca cccagagucc 20

<210> SEQ ID NO 628
<211> LENGTH: 20
<212> TYPE: RNA
<213> ORGANISM: Artificial Sequence
<220> FEATURE:
<223> OTHER INFORMATION: Seynthetic

<400> SEQUENCE: 628
cuuccaaaga uacagcgucc 20

<210> SEQ ID NO 629
<211> LENGTH: 20
<212> TYPE: RNA
<213> ORGANISM: Artificial Sequence
<220> FEATURE:
<223> OTHER INFORMATION: Seynthetic

<400> SEQUENCE: 629
cuuccaaaga uacggcgucc 20

<210> SEQ ID NO 630
<211> LENGTH: 20
<212> TYPE: RNA
<213> ORGANISM: Artificial Sequence
<220> FEATURE:
<223> OTHER INFORMATION: Seynthetic

<400> SEQUENCE: 630
cuucccaucu cccccacgau 20

<210> SEQ ID NO 631
<211> LENGTH: 20

<212> TYPE: RNA
<213> ORGANISM: Artificial Sequence
<220> FEATURE:
<223> OTHER INFORMATION: Seynthetic

<400> SEQUENCE: 631
cuuccccaca uuguguuuuu 20

<210> SEQ ID NO 632
<211> LENGTH: 20
<212> TYPE: RNA
<213> ORGANISM: Artificial Sequence
<220> FEATURE:
<223> OTHER INFORMATION: Seynthetic

<400> SEQUENCE: 632
cuucuaccag ggaacuccug 20

<210> SEQ ID NO 633
<211> LENGTH: 20
<212> TYPE: RNA
<213> ORGANISM: Artificial Sequence
<220> FEATURE:
<223> OTHER INFORMATION: Seynthetic

<400> SEQUENCE: 633
cuucuggucc ccgcaccaug 20

<210> SEQ ID NO 634
<211> LENGTH: 20
<212> TYPE: RNA
<213> ORGANISM: Artificial Sequence
<220> FEATURE:
<223> OTHER INFORMATION: Seynthetic

<400> SEQUENCE: 634
cuugacguga ccacaggcaa 20

<210> SEQ ID NO 635
<211> LENGTH: 20
<212> TYPE: RNA
<213> ORGANISM: Artificial Sequence
<220> FEATURE:
<223> OTHER INFORMATION: Seynthetic

<400> SEQUENCE: 635
cuugccugug gucacgucaa 20

<210> SEQ ID NO 636
<211> LENGTH: 20
<212> TYPE: RNA
<213> ORGANISM: Artificial Sequence
<220> FEATURE:
<223> OTHER INFORMATION: Seynthetic

<400> SEQUENCE: 636
cuugccugug gucacgucag 20

<210> SEQ ID NO 637
<211> LENGTH: 20
<212> TYPE: RNA
<213> ORGANISM: Artificial Sequence
<220> FEATURE:
<223> OTHER INFORMATION: Seynthetic

<400> SEQUENCE: 637
cuuuacgaac gugaauuuau 20

<210> SEQ ID NO 638
<211> LENGTH: 20
<212> TYPE: RNA
<213> ORGANISM: Artificial Sequence
<220> FEATURE:
<223> OTHER INFORMATION: Seynthetic

<400> SEQUENCE: 638
cuuuauuaag ugugccgacg 20

<210> SEQ ID NO 639
<211> LENGTH: 20
<212> TYPE: RNA
<213> ORGANISM: Artificial Sequence
<220> FEATURE:
<223> OTHER INFORMATION: Seynthetic

<400> SEQUENCE: 639
cuuucccgca gcugggacuc 20

<210> SEQ ID NO 640
<211> LENGTH: 20
<212> TYPE: RNA
<213> ORGANISM: Artificial Sequence
<220> FEATURE:
<223> OTHER INFORMATION: Seynthetic

<400> SEQUENCE: 640
cuuucuuagc uaagaacuuu 20

<210> SEQ ID NO 641
<211> LENGTH: 20
<212> TYPE: RNA
<213> ORGANISM: Artificial Sequence
<220> FEATURE:
<223> OTHER INFORMATION: Seynthetic

<400> SEQUENCE: 641
cuuugucucu gucccugugg 20

<210> SEQ ID NO 642
<211> LENGTH: 20
<212> TYPE: RNA
<213> ORGANISM: Artificial Sequence
<220> FEATURE:
<223> OTHER INFORMATION: Seynthetic

<400> SEQUENCE: 642
gaaaaaaaca caaugugggg 20

<210> SEQ ID NO 643
<211> LENGTH: 20
<212> TYPE: RNA
<213> ORGANISM: Artificial Sequence
<220> FEATURE:
<223> OTHER INFORMATION: Seynthetic

<400> SEQUENCE: 643
gaaaaaaaua caaugugggg 20

<210> SEQ ID NO 644
<211> LENGTH: 20
<212> TYPE: RNA
<213> ORGANISM: Artificial Sequence
<220> FEATURE:
<223> OTHER INFORMATION: Seynthetic

<400> SEQUENCE: 644
gaaaagcagg gggaaccucg 20

<210> SEQ ID NO 645
<211> LENGTH: 20
<212> TYPE: RNA
<213> ORGANISM: Artificial Sequence
<220> FEATURE:
<223> OTHER INFORMATION: Seynthetic

<400> SEQUENCE: 645
gaaaagccgg gggaaccucg 20

<210> SEQ ID NO 646
<211> LENGTH: 20
<212> TYPE: RNA
<213> ORGANISM: Artificial Sequence
<220> FEATURE:
<223> OTHER INFORMATION: Seynthetic

<400> SEQUENCE: 646
gaaacacccu gggggacucu 20

<210> SEQ ID NO 647
<211> LENGTH: 20
<212> TYPE: RNA
<213> ORGANISM: Artificial Sequence
<220> FEATURE:
<223> OTHER INFORMATION: Seynthetic

<400> SEQUENCE: 647
gaaacacccu gggugacucu 20

<210> SEQ ID NO 648
<211> LENGTH: 20
<212> TYPE: RNA
<213> ORGANISM: Artificial Sequence
<220> FEATURE:
<223> OTHER INFORMATION: Seynthetic

<400> SEQUENCE: 648
gaaagggauu cccaggaccc 20

<210> SEQ ID NO 649
<211> LENGTH: 20
<212> TYPE: RNA
<213> ORGANISM: Artificial Sequence
<220> FEATURE:
<223> OTHER INFORMATION: Seynthetic

<400> SEQUENCE: 649
gaaaguucag ggauguccgc 20

<210> SEQ ID NO 650
<211> LENGTH: 20
<212> TYPE: RNA
<213> ORGANISM: Artificial Sequence
<220> FEATURE:
<223> OTHER INFORMATION: Seynthetic

<400> SEQUENCE: 650
gaaauaaauu cacguucgua 20

<210> SEQ ID NO 651
<211> LENGTH: 20
<212> TYPE: RNA
<213> ORGANISM: Artificial Sequence
<220> FEATURE:
<223> OTHER INFORMATION: Seynthetic

<400> SEQUENCE: 651
gaaauuugaa ugcgauugug 20

<210> SEQ ID NO 652
<211> LENGTH: 20
<212> TYPE: RNA
<213> ORGANISM: Artificial Sequence
<220> FEATURE:
<223> OTHER INFORMATION: Seynthetic

<400> SEQUENCE: 652
gaacaucgug ggggagaugg 20

<210> SEQ ID NO 653
<211> LENGTH: 20
<212> TYPE: RNA
<213> ORGANISM: Artificial Sequence
<220> FEATURE:
<223> OTHER INFORMATION: Seynthetic

<400> SEQUENCE: 653
gaacuuuacg aacgugaauu 20

<210> SEQ ID NO 654
<211> LENGTH: 20
<212> TYPE: RNA
<213> ORGANISM: Artificial Sequence
<220> FEATURE:
<223> OTHER INFORMATION: Seynthetic

<400> SEQUENCE: 654
gaacuuuaug aacgugaauu 20

<210> SEQ ID NO 655
<211> LENGTH: 20
<212> TYPE: RNA
<213> ORGANISM: Artificial Sequence
<220> FEATURE:
<223> OTHER INFORMATION: Seynthetic

<400> SEQUENCE: 655
gaagagaaaa gccgggggaa 20

<210> SEQ ID NO 656
<211> LENGTH: 20
<212> TYPE: RNA
<213> ORGANISM: Artificial Sequence
<220> FEATURE:
<223> OTHER INFORMATION: Seynthetic

<400> SEQUENCE: 656
gaaggcggac aucccugaac 20

<210> SEQ ID NO 657
<211> LENGTH: 20
<212> TYPE: RNA
<213> ORGANISM: Artificial Sequence
<220> FEATURE:
<223> OTHER INFORMATION: Seynthetic

<400> SEQUENCE: 657
gaagugacuu ccccacauug 20

<210> SEQ ID NO 658
<211> LENGTH: 20
<212> TYPE: RNA
<213> ORGANISM: Artificial Sequence
<220> FEATURE:
<223> OTHER INFORMATION: Seynthetic

<400> SEQUENCE: 658
gaaucccauu cccgcagcug 20

<210> SEQ ID NO 659
<211> LENGTH: 20
<212> TYPE: RNA
<213> ORGANISM: Artificial Sequence
<220> FEATURE:
<223> OTHER INFORMATION: Seynthetic

<400> SEQUENCE: 659
gaaucccuuu cccgcagcug 20

<210> SEQ ID NO 660
<211> LENGTH: 20
<212> TYPE: RNA
<213> ORGANISM: Artificial Sequence
<220> FEATURE:
<223> OTHER INFORMATION: Seynthetic

<400> SEQUENCE: 660
gaaugggauu cccaggaccc 20

<210> SEQ ID NO 661
<211> LENGTH: 20
<212> TYPE: RNA
<213> ORGANISM: Artificial Sequence
<220> FEATURE:
<223> OTHER INFORMATION: Seynthetic

<400> SEQUENCE: 661
gacacaggga cagagacaaa 20

<210> SEQ ID NO 662
<211> LENGTH: 20
<212> TYPE: RNA
<213> ORGANISM: Artificial Sequence
<220> FEATURE:
<223> OTHER INFORMATION: Seynthetic

<400> SEQUENCE: 662
gacaucccug aacuuuccau 20

<210> SEQ ID NO 663
<211> LENGTH: 20
<212> TYPE: RNA
<213> ORGANISM: Artificial Sequence
<220> FEATURE:
<223> OTHER INFORMATION: Seynthetic

<400> SEQUENCE: 663
gaccaagggg cugccggagu 20

<210> SEQ ID NO 664

<211> LENGTH: 20
<212> TYPE: RNA
<213> ORGANISM: Artificial Sequence
<220> FEATURE:
<223> OTHER INFORMATION: Seynthetic

<400> SEQUENCE: 664
gacgccguau cuuuggaagg 20

<210> SEQ ID NO 665
<211> LENGTH: 20
<212> TYPE: RNA
<213> ORGANISM: Artificial Sequence
<220> FEATURE:
<223> OTHER INFORMATION: Seynthetic

<400> SEQUENCE: 665
gacgcuguau cuuuggaagg 20

<210> SEQ ID NO 666
<211> LENGTH: 20
<212> TYPE: RNA
<213> ORGANISM: Artificial Sequence
<220> FEATURE:
<223> OTHER INFORMATION: Seynthetic

<400> SEQUENCE: 666
gacgguccuc cagccccucc 20

<210> SEQ ID NO 667
<211> LENGTH: 20
<212> TYPE: RNA
<213> ORGANISM: Artificial Sequence
<220> FEATURE:
<223> OTHER INFORMATION: Seynthetic

<400> SEQUENCE: 667
gacuccggca gccccuuggu 20

<210> SEQ ID NO 668
<211> LENGTH: 20
<212> TYPE: RNA
<213> ORGANISM: Artificial Sequence
<220> FEATURE:
<223> OTHER INFORMATION: Seynthetic

<400> SEQUENCE: 668
gacuucccca cauuguauuu 20

<210> SEQ ID NO 669
<211> LENGTH: 20
<212> TYPE: RNA
<213> ORGANISM: Artificial Sequence
<220> FEATURE:
<223> OTHER INFORMATION: Seynthetic

<400> SEQUENCE: 669
gacuucccca cauuguguuu 20

<210> SEQ ID NO 670
<211> LENGTH: 20
<212> TYPE: RNA
<213> ORGANISM: Artificial Sequence
<220> FEATURE:
<223> OTHER INFORMATION: Seynthetic

<400> SEQUENCE: 670
gagaaaagca gggggaaccu 20

<210> SEQ ID NO 671
<211> LENGTH: 20
<212> TYPE: RNA
<213> ORGANISM: Artificial Sequence
<220> FEATURE:
<223> OTHER INFORMATION: Seynthetic

<400> SEQUENCE: 671
gagaaaagcc gggggaaccu 20

<210> SEQ ID NO 672
<211> LENGTH: 20
<212> TYPE: RNA
<213> ORGANISM: Artificial Sequence
<220> FEATURE:
<223> OTHER INFORMATION: Seynthetic

<400> SEQUENCE: 672
gagcagcaca cgagguuccc 20

<210> SEQ ID NO 673
<211> LENGTH: 20
<212> TYPE: RNA
<213> ORGANISM: Artificial Sequence
<220> FEATURE:
<223> OTHER INFORMATION: Seynthetic

<400> SEQUENCE: 673
gagccugggc caggcuggag 20

<210> SEQ ID NO 674
<211> LENGTH: 20
<212> TYPE: RNA
<213> ORGANISM: Artificial Sequence
<220> FEATURE:
<223> OTHER INFORMATION: Seynthetic

<400> SEQUENCE: 674
gagcucccug guagaagcau 20

<210> SEQ ID NO 675
<211> LENGTH: 20
<212> TYPE: RNA
<213> ORGANISM: Artificial Sequence
<220> FEATURE:
<223> OTHER INFORMATION: Seynthetic

<400> SEQUENCE: 675
gaggaugaaa uaaauucacg 20

<210> SEQ ID NO 676
<211> LENGTH: 20
<212> TYPE: RNA
<213> ORGANISM: Artificial Sequence
<220> FEATURE:
<223> OTHER INFORMATION: Seynthetic

<400> SEQUENCE: 676
gaggccacag ggacagagac 20

<210> SEQ ID NO 677
<211> LENGTH: 20
<212> TYPE: RNA

<213> ORGANISM: Artificial Sequence
<220> FEATURE:
<223> OTHER INFORMATION: Seynthetic

<400> SEQUENCE: 677
gaggggcugg aggaccgucc 20

<210> SEQ ID NO 678
<211> LENGTH: 20
<212> TYPE: RNA
<213> ORGANISM: Artificial Sequence
<220> FEATURE:
<223> OTHER INFORMATION: Seynthetic

<400> SEQUENCE: 678
gagguucccc cggcuuuucu 20

<210> SEQ ID NO 679
<211> LENGTH: 20
<212> TYPE: RNA
<213> ORGANISM: Artificial Sequence
<220> FEATURE:
<223> OTHER INFORMATION: Seynthetic

<400> SEQUENCE: 679
gagucaccca ggguguuuca 20

<210> SEQ ID NO 680
<211> LENGTH: 20
<212> TYPE: RNA
<213> ORGANISM: Artificial Sequence
<220> FEATURE:
<223> OTHER INFORMATION: Seynthetic

<400> SEQUENCE: 680
gagucccagc ugcgggaaag 20

<210> SEQ ID NO 681
<211> LENGTH: 20
<212> TYPE: RNA
<213> ORGANISM: Artificial Sequence
<220> FEATURE:
<223> OTHER INFORMATION: Seynthetic

<400> SEQUENCE: 681
gagucccagc ugcgggaaug 20

<210> SEQ ID NO 682
<211> LENGTH: 20
<212> TYPE: RNA
<213> ORGANISM: Artificial Sequence
<220> FEATURE:
<223> OTHER INFORMATION: Seynthetic

<400> SEQUENCE: 682
gaguccccca ggguguuuca 20

<210> SEQ ID NO 683
<211> LENGTH: 20
<212> TYPE: RNA
<213> ORGANISM: Artificial Sequence
<220> FEATURE:
<223> OTHER INFORMATION: Seynthetic

<400> SEQUENCE: 683
gaguccugac gugaccacag 20

<210> SEQ ID NO 684
<211> LENGTH: 20
<212> TYPE: RNA
<213> ORGANISM: Artificial Sequence
<220> FEATURE:
<223> OTHER INFORMATION: Seynthetic

<400> SEQUENCE: 684
gagucuacac ccgcugugac 20

<210> SEQ ID NO 685
<211> LENGTH: 20
<212> TYPE: RNA
<213> ORGANISM: Artificial Sequence
<220> FEATURE:
<223> OTHER INFORMATION: Seynthetic

<400> SEQUENCE: 685
gagucuacac cugcugugac 20

<210> SEQ ID NO 686
<211> LENGTH: 20
<212> TYPE: RNA
<213> ORGANISM: Artificial Sequence
<220> FEATURE:
<223> OTHER INFORMATION: Seynthetic

<400> SEQUENCE: 686
gagucuugac gugaccacag 20

<210> SEQ ID NO 687
<211> LENGTH: 20
<212> TYPE: RNA
<213> ORGANISM: Artificial Sequence
<220> FEATURE:
<223> OTHER INFORMATION: Seynthetic

<400> SEQUENCE: 687
gaguucccug guagaagcau 20

<210> SEQ ID NO 688
<211> LENGTH: 20
<212> TYPE: RNA
<213> ORGANISM: Artificial Sequence
<220> FEATURE:
<223> OTHER INFORMATION: Seynthetic

<400> SEQUENCE: 688
gauacagcgu cccccacccc 20

<210> SEQ ID NO 689
<211> LENGTH: 20
<212> TYPE: RNA
<213> ORGANISM: Artificial Sequence
<220> FEATURE:
<223> OTHER INFORMATION: Seynthetic

<400> SEQUENCE: 689
gauacggcgu cccccacccc 20

<210> SEQ ID NO 690
<211> LENGTH: 20
<212> TYPE: RNA
<213> ORGANISM: Artificial Sequence
<220> FEATURE:

<223> OTHER INFORMATION: Seynthetic

<400> SEQUENCE: 690
gauccauggu gaagagaaaa 20

<210> SEQ ID NO 691
<211> LENGTH: 20
<212> TYPE: RNA
<213> ORGANISM: Artificial Sequence
<220> FEATURE:
<223> OTHER INFORMATION: Seynthetic

<400> SEQUENCE: 691
gaugaaauaa auucacguuc 20

<210> SEQ ID NO 692
<211> LENGTH: 20
<212> TYPE: RNA
<213> ORGANISM: Artificial Sequence
<220> FEATURE:
<223> OTHER INFORMATION: Seynthetic

<400> SEQUENCE: 692
gaugcacaau cgcauucaaa 20

<210> SEQ ID NO 693
<211> LENGTH: 20
<212> TYPE: RNA
<213> ORGANISM: Artificial Sequence
<220> FEATURE:
<223> OTHER INFORMATION: Seynthetic

<400> SEQUENCE: 693
gauguccgcc uucaggugug 20

<210> SEQ ID NO 694
<211> LENGTH: 20
<212> TYPE: RNA
<213> ORGANISM: Artificial Sequence
<220> FEATURE:
<223> OTHER INFORMATION: Seynthetic

<400> SEQUENCE: 694
gauguuccag cugcaacggc 20

<210> SEQ ID NO 695
<211> LENGTH: 20
<212> TYPE: RNA
<213> ORGANISM: Artificial Sequence
<220> FEATURE:
<223> OTHER INFORMATION: Seynthetic

<400> SEQUENCE: 695
gauuaucuga cauuugaaug 20

<210> SEQ ID NO 696
<211> LENGTH: 20
<212> TYPE: RNA
<213> ORGANISM: Artificial Sequence
<220> FEATURE:
<223> OTHER INFORMATION: Seynthetic

<400> SEQUENCE: 696
gauugugaaa cacccugggg 20

<210> SEQ ID NO 697
<211> LENGTH: 20
<212> TYPE: RNA
<213> ORGANISM: Artificial Sequence
<220> FEATURE:
<223> OTHER INFORMATION: Seynthetic

<400> SEQUENCE: 697
gauugugaaa cacccugggu 20

<210> SEQ ID NO 698
<211> LENGTH: 20
<212> TYPE: RNA
<213> ORGANISM: Artificial Sequence
<220> FEATURE:
<223> OTHER INFORMATION: Seynthetic

<400> SEQUENCE: 698
gauuucaggg gugggggacg 20

<210> SEQ ID NO 699
<211> LENGTH: 20
<212> TYPE: RNA
<213> ORGANISM: Artificial Sequence
<220> FEATURE:
<223> OTHER INFORMATION: Seynthetic

<400> SEQUENCE: 699
gcaaaacccc cgcuccauua 20

<210> SEQ ID NO 700
<211> LENGTH: 20
<212> TYPE: RNA
<213> ORGANISM: Artificial Sequence
<220> FEATURE:
<223> OTHER INFORMATION: Seynthetic

<400> SEQUENCE: 700
gcacaaucgc auucaaaugu 20

<210> SEQ ID NO 701
<211> LENGTH: 20
<212> TYPE: RNA
<213> ORGANISM: Artificial Sequence
<220> FEATURE:
<223> OTHER INFORMATION: Seynthetic

<400> SEQUENCE: 701
gcacaaucgc auucaaauuu 20

<210> SEQ ID NO 702
<211> LENGTH: 20
<212> TYPE: RNA
<213> ORGANISM: Artificial Sequence
<220> FEATURE:
<223> OTHER INFORMATION: Seynthetic

<400> SEQUENCE: 702
gcacacgagg uucccccggc 20

<210> SEQ ID NO 703
<211> LENGTH: 20
<212> TYPE: RNA
<213> ORGANISM: Artificial Sequence
<220> FEATURE:
<223> OTHER INFORMATION: Seynthetic

<400> SEQUENCE: 703
gcacacgagg uucccccugc 20

<210> SEQ ID NO 704
<211> LENGTH: 20
<212> TYPE: RNA
<213> ORGANISM: Artificial Sequence
<220> FEATURE:
<223> OTHER INFORMATION: Seynthetic

<400> SEQUENCE: 704
gcacacuuaa uaaagacugc 20

<210> SEQ ID NO 705
<211> LENGTH: 20
<212> TYPE: RNA
<213> ORGANISM: Artificial Sequence
<220> FEATURE:
<223> OTHER INFORMATION: Seynthetic

<400> SEQUENCE: 705
gcacacuuaa uaaugacugc 20

<210> SEQ ID NO 706
<211> LENGTH: 20
<212> TYPE: RNA
<213> ORGANISM: Artificial Sequence
<220> FEATURE:
<223> OTHER INFORMATION: Seynthetic

<400> SEQUENCE: 706
gcagaccaag gggcugccgg 20

<210> SEQ ID NO 707
<211> LENGTH: 20
<212> TYPE: RNA
<213> ORGANISM: Artificial Sequence
<220> FEATURE:
<223> OTHER INFORMATION: Seynthetic

<400> SEQUENCE: 707
gcagcacacg agguuccccc 20

<210> SEQ ID NO 708
<211> LENGTH: 20
<212> TYPE: RNA
<213> ORGANISM: Artificial Sequence
<220> FEATURE:
<223> OTHER INFORMATION: Seynthetic

<400> SEQUENCE: 708
gcagcuggaa caucgugggg 20

<210> SEQ ID NO 709
<211> LENGTH: 20
<212> TYPE: RNA
<213> ORGANISM: Artificial Sequence
<220> FEATURE:
<223> OTHER INFORMATION: Seynthetic

<400> SEQUENCE: 709
gcagcuggaa cauggugggg 20

<210> SEQ ID NO 710
<211> LENGTH: 20

<212> TYPE: RNA
<213> ORGANISM: Artificial Sequence
<220> FEATURE:
<223> OTHER INFORMATION: Seynthetic

<400> SEQUENCE: 710
gcaggagcuc ccugguagaa 20

<210> SEQ ID NO 711
<211> LENGTH: 20
<212> TYPE: RNA
<213> ORGANISM: Artificial Sequence
<220> FEATURE:
<223> OTHER INFORMATION: Seynthetic

<400> SEQUENCE: 711
gcaggaguuc ccugguagaa 20

<210> SEQ ID NO 712
<211> LENGTH: 20
<212> TYPE: RNA
<213> ORGANISM: Artificial Sequence
<220> FEATURE:
<223> OTHER INFORMATION: Seynthetic

<400> SEQUENCE: 712
gcagggacca gaaggauggg 20

<210> SEQ ID NO 713
<211> LENGTH: 20
<212> TYPE: RNA
<213> ORGANISM: Artificial Sequence
<220> FEATURE:
<223> OTHER INFORMATION: Seynthetic

<400> SEQUENCE: 713
gcagggggaa ccucgugugc 20

<210> SEQ ID NO 714
<211> LENGTH: 20
<212> TYPE: RNA
<213> ORGANISM: Artificial Sequence
<220> FEATURE:
<223> OTHER INFORMATION: Seynthetic

<400> SEQUENCE: 714
gcagguguag acuccgaggg 20

<210> SEQ ID NO 715
<211> LENGTH: 20
<212> TYPE: RNA
<213> ORGANISM: Artificial Sequence
<220> FEATURE:
<223> OTHER INFORMATION: Seynthetic

<400> SEQUENCE: 715
gcagucauua uuaagugugc 20

<210> SEQ ID NO 716
<211> LENGTH: 20
<212> TYPE: RNA
<213> ORGANISM: Artificial Sequence
<220> FEATURE:
<223> OTHER INFORMATION: Seynthetic

<400> SEQUENCE: 716
gcagucuuua uuaagugugc 20

<210> SEQ ID NO 717
<211> LENGTH: 20
<212> TYPE: RNA
<213> ORGANISM: Artificial Sequence
<220> FEATURE:
<223> OTHER INFORMATION: Seynthetic

<400> SEQUENCE: 717
gcaucccuga acuuuccaua 20

<210> SEQ ID NO 718
<211> LENGTH: 20
<212> TYPE: RNA
<213> ORGANISM: Artificial Sequence
<220> FEATURE:
<223> OTHER INFORMATION: Seynthetic

<400> SEQUENCE: 718
gcauuaaucc auggugcagg 20

<210> SEQ ID NO 719
<211> LENGTH: 20
<212> TYPE: RNA
<213> ORGANISM: Artificial Sequence
<220> FEATURE:
<223> OTHER INFORMATION: Seynthetic

<400> SEQUENCE: 719
gcauuaaucc auggugcggg 20

<210> SEQ ID NO 720
<211> LENGTH: 20
<212> TYPE: RNA
<213> ORGANISM: Artificial Sequence
<220> FEATURE:
<223> OTHER INFORMATION: Seynthetic

<400> SEQUENCE: 720
gccaagcccc uuccaaagau 20

<210> SEQ ID NO 721
<211> LENGTH: 20
<212> TYPE: RNA
<213> ORGANISM: Artificial Sequence
<220> FEATURE:
<223> OTHER INFORMATION: Seynthetic

<400> SEQUENCE: 721
gccacaccug aaggcggaca 20

<210> SEQ ID NO 722
<211> LENGTH: 20
<212> TYPE: RNA
<213> ORGANISM: Artificial Sequence
<220> FEATURE:
<223> OTHER INFORMATION: Seynthetic

<400> SEQUENCE: 722
gccacaggga cagagacaaa 20

<210> SEQ ID NO 723
<211> LENGTH: 20
<212> TYPE: RNA
<213> ORGANISM: Artificial Sequence
<220> FEATURE:
<223> OTHER INFORMATION: Seynthetic

<400> SEQUENCE: 723
gccaggcugg aguccugacg 20

<210> SEQ ID NO 724
<211> LENGTH: 20
<212> TYPE: RNA
<213> ORGANISM: Artificial Sequence
<220> FEATURE:
<223> OTHER INFORMATION: Seynthetic

<400> SEQUENCE: 724
gccaggcugg agucuugacg 20

<210> SEQ ID NO 725
<211> LENGTH: 20
<212> TYPE: RNA
<213> ORGANISM: Artificial Sequence
<220> FEATURE:
<223> OTHER INFORMATION: Seynthetic

<400> SEQUENCE: 725
gccagguggg caggaagggg 20

<210> SEQ ID NO 726
<211> LENGTH: 20
<212> TYPE: RNA
<213> ORGANISM: Artificial Sequence
<220> FEATURE:
<223> OTHER INFORMATION: Seynthetic

<400> SEQUENCE: 726
gccccuccag gugggcagga 20

<210> SEQ ID NO 727
<211> LENGTH: 20
<212> TYPE: RNA
<213> ORGANISM: Artificial Sequence
<220> FEATURE:
<223> OTHER INFORMATION: Seynthetic

<400> SEQUENCE: 727
gccccuucca aagauacagc 20

<210> SEQ ID NO 728
<211> LENGTH: 20
<212> TYPE: RNA
<213> ORGANISM: Artificial Sequence
<220> FEATURE:
<223> OTHER INFORMATION: Seynthetic

<400> SEQUENCE: 728
gccccuucca aagauacggc 20

<210> SEQ ID NO 729
<211> LENGTH: 20
<212> TYPE: RNA
<213> ORGANISM: Artificial Sequence
<220> FEATURE:
<223> OTHER INFORMATION: Seynthetic

<400> SEQUENCE: 729
gccggagucc cccuguggag 20

<210> SEQ ID NO 730
<211> LENGTH: 20
<212> TYPE: RNA
<213> ORGANISM: Artificial Sequence
<220> FEATURE:
<223> OTHER INFORMATION: Seynthetic

<400> SEQUENCE: 730
gccgggggaa ccucgugugc 20

<210> SEQ ID NO 731
<211> LENGTH: 20
<212> TYPE: RNA
<213> ORGANISM: Artificial Sequence
<220> FEATURE:
<223> OTHER INFORMATION: Seynthetic

<400> SEQUENCE: 731
gccguaucuu uggaaggggc 20

<210> SEQ ID NO 732
<211> LENGTH: 20
<212> TYPE: RNA
<213> ORGANISM: Artificial Sequence
<220> FEATURE:
<223> OTHER INFORMATION: Seynthetic

<400> SEQUENCE: 732
gccguugcag cuggaacauc 20

<210> SEQ ID NO 733
<211> LENGTH: 20
<212> TYPE: RNA
<213> ORGANISM: Artificial Sequence
<220> FEATURE:
<223> OTHER INFORMATION: Seynthetic

<400> SEQUENCE: 733
gccguugcag cuggaacaug 20

<210> SEQ ID NO 734
<211> LENGTH: 20
<212> TYPE: RNA
<213> ORGANISM: Artificial Sequence
<220> FEATURE:
<223> OTHER INFORMATION: Seynthetic

<400> SEQUENCE: 734
gccuccacag ggggacucag 20

<210> SEQ ID NO 735
<211> LENGTH: 20
<212> TYPE: RNA
<213> ORGANISM: Artificial Sequence
<220> FEATURE:
<223> OTHER INFORMATION: Seynthetic

<400> SEQUENCE: 735
gccuccacag ggggacuccg 20

<210> SEQ ID NO 736
<211> LENGTH: 20
<212> TYPE: RNA
<213> ORGANISM: Artificial Sequence
<220> FEATURE:
<223> OTHER INFORMATION: Seynthetic

<400> SEQUENCE: 736
gccucugggg cuugacaccc 20

<210> SEQ ID NO 737
<211> LENGTH: 20
<212> TYPE: RNA
<213> ORGANISM: Artificial Sequence
<220> FEATURE:
<223> OTHER INFORMATION: Seynthetic

<400> SEQUENCE: 737
gccugagucc cccuguggag 20

<210> SEQ ID NO 738
<211> LENGTH: 20
<212> TYPE: RNA
<213> ORGANISM: Artificial Sequence
<220> FEATURE:
<223> OTHER INFORMATION: Seynthetic

<400> SEQUENCE: 738
gccugggcca ggcuggaguc 20

<210> SEQ ID NO 739
<211> LENGTH: 20
<212> TYPE: RNA
<213> ORGANISM: Artificial Sequence
<220> FEATURE:
<223> OTHER INFORMATION: Seynthetic

<400> SEQUENCE: 739
gccugugguc acgucaagac 20

<210> SEQ ID NO 740
<211> LENGTH: 20
<212> TYPE: RNA
<213> ORGANISM: Artificial Sequence
<220> FEATURE:
<223> OTHER INFORMATION: Seynthetic

<400> SEQUENCE: 740
gccugugguc acgucaggac 20

<210> SEQ ID NO 741
<211> LENGTH: 20
<212> TYPE: RNA
<213> ORGANISM: Artificial Sequence
<220> FEATURE:
<223> OTHER INFORMATION: Seynthetic

<400> SEQUENCE: 741
gcggacaucc cugaacuuuc 20

<210> SEQ ID NO 742
<211> LENGTH: 20
<212> TYPE: RNA
<213> ORGANISM: Artificial Sequence
<220> FEATURE:
<223> OTHER INFORMATION: Seynthetic

<400> SEQUENCE: 742
gcgggaaagg gauucccagg 20

<210> SEQ ID NO 743

<211> LENGTH: 20
<212> TYPE: RNA
<213> ORGANISM: Artificial Sequence
<220> FEATURE:
<223> OTHER INFORMATION: Seynthetic

<400> SEQUENCE: 743
gcgggaaugg gauucccagg 20

<210> SEQ ID NO 744
<211> LENGTH: 20
<212> TYPE: RNA
<213> ORGANISM: Artificial Sequence
<220> FEATURE:
<223> OTHER INFORMATION: Seynthetic

<400> SEQUENCE: 744
gcggggacca gaaggauggg 20

<210> SEQ ID NO 745
<211> LENGTH: 20
<212> TYPE: RNA
<213> ORGANISM: Artificial Sequence
<220> FEATURE:
<223> OTHER INFORMATION: Seynthetic

<400> SEQUENCE: 745
gcggguguag acuccgaggg 20

<210> SEQ ID NO 746
<211> LENGTH: 20
<212> TYPE: RNA
<213> ORGANISM: Artificial Sequence
<220> FEATURE:
<223> OTHER INFORMATION: Seynthetic

<400> SEQUENCE: 746
gcgucggcac acuuaauaaa 20

<210> SEQ ID NO 747
<211> LENGTH: 20
<212> TYPE: RNA
<213> ORGANISM: Artificial Sequence
<220> FEATURE:
<223> OTHER INFORMATION: Seynthetic

<400> SEQUENCE: 747
gcgucggcac acuuaauaau 20

<210> SEQ ID NO 748
<211> LENGTH: 20
<212> TYPE: RNA
<213> ORGANISM: Artificial Sequence
<220> FEATURE:
<223> OTHER INFORMATION: Seynthetic

<400> SEQUENCE: 748
gcuaagaacu uuacgaacgu 20

<210> SEQ ID NO 749
<211> LENGTH: 20
<212> TYPE: RNA
<213> ORGANISM: Artificial Sequence
<220> FEATURE:
<223> OTHER INFORMATION: Seynthetic

<400> SEQUENCE: 749
gcuaagaacu uuaugaacgu 20

<210> SEQ ID NO 750
<211> LENGTH: 20
<212> TYPE: RNA
<213> ORGANISM: Artificial Sequence
<220> FEATURE:
<223> OTHER INFORMATION: Seynthetic

<400> SEQUENCE: 750
gcucaugcuu cuaccaggga 20

<210> SEQ ID NO 751
<211> LENGTH: 20
<212> TYPE: RNA
<213> ORGANISM: Artificial Sequence
<220> FEATURE:
<223> OTHER INFORMATION: Seynthetic

<400> SEQUENCE: 751
gcucccuggu agaagcauga 20

<210> SEQ ID NO 752
<211> LENGTH: 20
<212> TYPE: RNA
<213> ORGANISM: Artificial Sequence
<220> FEATURE:
<223> OTHER INFORMATION: Seynthetic

<400> SEQUENCE: 752
gcucucaaag caacacuuuc 20

<210> SEQ ID NO 753
<211> LENGTH: 20
<212> TYPE: RNA
<213> ORGANISM: Artificial Sequence
<220> FEATURE:
<223> OTHER INFORMATION: Seynthetic

<400> SEQUENCE: 753
gcugccggag ucccccugug 20

<210> SEQ ID NO 754
<211> LENGTH: 20
<212> TYPE: RNA
<213> ORGANISM: Artificial Sequence
<220> FEATURE:
<223> OTHER INFORMATION: Seynthetic

<400> SEQUENCE: 754
gcugccugag ucccccugug 20

<210> SEQ ID NO 755
<211> LENGTH: 20
<212> TYPE: RNA
<213> ORGANISM: Artificial Sequence
<220> FEATURE:
<223> OTHER INFORMATION: Seynthetic

<400> SEQUENCE: 755
gcugcgggaa agggauuccc 20

<210> SEQ ID NO 756
<211> LENGTH: 20
<212> TYPE: RNA

<213> ORGANISM: Artificial Sequence
<220> FEATURE:
<223> OTHER INFORMATION: Seynthetic

<400> SEQUENCE: 756
gcugcgggaa ugggauuccc 20

<210> SEQ ID NO 757
<211> LENGTH: 20
<212> TYPE: RNA
<213> ORGANISM: Artificial Sequence
<220> FEATURE:
<223> OTHER INFORMATION: Seynthetic

<400> SEQUENCE: 757
gcuggaacau cgugggggag 20

<210> SEQ ID NO 758
<211> LENGTH: 20
<212> TYPE: RNA
<213> ORGANISM: Artificial Sequence
<220> FEATURE:
<223> OTHER INFORMATION: Seynthetic

<400> SEQUENCE: 758
gcuggaacau ggugggggag 20

<210> SEQ ID NO 759
<211> LENGTH: 20
<212> TYPE: RNA
<213> ORGANISM: Artificial Sequence
<220> FEATURE:
<223> OTHER INFORMATION: Seynthetic

<400> SEQUENCE: 759
gcuggagucc cagcugcggg 20

<210> SEQ ID NO 760
<211> LENGTH: 20
<212> TYPE: RNA
<213> ORGANISM: Artificial Sequence
<220> FEATURE:
<223> OTHER INFORMATION: Seynthetic

<400> SEQUENCE: 760
gcuggagucc ugacgugacc 20

<210> SEQ ID NO 761
<211> LENGTH: 20
<212> TYPE: RNA
<213> ORGANISM: Artificial Sequence
<220> FEATURE:
<223> OTHER INFORMATION: Seynthetic

<400> SEQUENCE: 761
gcuggagucu ugacgugacc 20

<210> SEQ ID NO 762
<211> LENGTH: 20
<212> TYPE: RNA
<213> ORGANISM: Artificial Sequence
<220> FEATURE:
<223> OTHER INFORMATION: Seynthetic

<400> SEQUENCE: 762 gcugggucccu gggaauccca 20

<210> SEQ ID NO 763
<211> LENGTH: 20
<212> TYPE: RNA
<213> ORGANISM: Artificial Sequence
<220> FEATURE:
<223> OTHER INFORMATION: Seynthetic

<400> SEQUENCE: 763
gcuggguccu gggaaucccu 20

<210> SEQ ID NO 764
<211> LENGTH: 20
<212> TYPE: RNA
<213> ORGANISM: Artificial Sequence
<220> FEATURE:
<223> OTHER INFORMATION: Seynthetic

<400> SEQUENCE: 764
gcuguaucuu uggaaggggc 20

<210> SEQ ID NO 765
<211> LENGTH: 20
<212> TYPE: RNA
<213> ORGANISM: Artificial Sequence
<220> FEATURE:
<223> OTHER INFORMATION: Seynthetic

<400> SEQUENCE: 765
gcuucuacca gggaacuccu 20

<210> SEQ ID NO 766
<211> LENGTH: 20
<212> TYPE: RNA
<213> ORGANISM: Artificial Sequence
<220> FEATURE:
<223> OTHER INFORMATION: Seynthetic

<400> SEQUENCE: 766
gcuucuacca gggagcuccu 20

<210> SEQ ID NO 767
<211> LENGTH: 20
<212> TYPE: RNA
<213> ORGANISM: Artificial Sequence
<220> FEATURE:
<223> OTHER INFORMATION: Seynthetic

<400> SEQUENCE: 767
ggaaagggau ucccaggacc 20

<210> SEQ ID NO 768
<211> LENGTH: 20
<212> TYPE: RNA
<213> ORGANISM: Artificial Sequence
<220> FEATURE:
<223> OTHER INFORMATION: Seynthetic

<400> SEQUENCE: 768
ggaaaguuca gggauguccg 20

<210> SEQ ID NO 769
<211> LENGTH: 20
<212> TYPE: RNA
<213> ORGANISM: Artificial Sequence
<220> FEATURE:

<223> OTHER INFORMATION: Seynthetic

<400> SEQUENCE: 769
ggaacaucgu gggggagaug 20

<210> SEQ ID NO 770
<211> LENGTH: 20
<212> TYPE: RNA
<213> ORGANISM: Artificial Sequence
<220> FEATURE:
<223> OTHER INFORMATION: Seynthetic

<400> SEQUENCE: 770
ggaacauggu gggggagaug 20

<210> SEQ ID NO 771
<211> LENGTH: 20
<212> TYPE: RNA
<213> ORGANISM: Artificial Sequence
<220> FEATURE:
<223> OTHER INFORMATION: Seynthetic

<400> SEQUENCE: 771
ggaaucccau ucccgcagcu 20

<210> SEQ ID NO 772
<211> LENGTH: 20
<212> TYPE: RNA
<213> ORGANISM: Artificial Sequence
<220> FEATURE:
<223> OTHER INFORMATION: Seynthetic

<400> SEQUENCE: 772
ggaaucccuu ucccgcagcu 20

<210> SEQ ID NO 773
<211> LENGTH: 20
<212> TYPE: RNA
<213> ORGANISM: Artificial Sequence
<220> FEATURE:
<223> OTHER INFORMATION: Seynthetic

<400> SEQUENCE: 773
ggaaugggau ucccaggacc 20

<210> SEQ ID NO 774
<211> LENGTH: 20
<212> TYPE: RNA
<213> ORGANISM: Artificial Sequence
<220> FEATURE:
<223> OTHER INFORMATION: Seynthetic

<400> SEQUENCE: 774
ggacaucccu gaacuuucca 20

<210> SEQ ID NO 775
<211> LENGTH: 20
<212> TYPE: RNA
<213> ORGANISM: Artificial Sequence
<220> FEATURE:
<223> OTHER INFORMATION: Seynthetic

<400> SEQUENCE: 775
ggacgccgua ucuuuggaag 20

<210> SEQ ID NO 776
<211> LENGTH: 20
<212> TYPE: RNA
<213> ORGANISM: Artificial Sequence
<220> FEATURE:
<223> OTHER INFORMATION: Seynthetic

<400> SEQUENCE: 776
ggacgcugua ucuuuggaag 20

<210> SEQ ID NO 777
<211> LENGTH: 20
<212> TYPE: RNA
<213> ORGANISM: Artificial Sequence
<220> FEATURE:
<223> OTHER INFORMATION: Seynthetic

<400> SEQUENCE: 777
ggacgguccu ccagccccuc 20

<210> SEQ ID NO 778
<211> LENGTH: 20
<212> TYPE: RNA
<213> ORGANISM: Artificial Sequence
<220> FEATURE:
<223> OTHER INFORMATION: Seynthetic

<400> SEQUENCE: 778
ggacucaggc agccccuugg 20

<210> SEQ ID NO 779
<211> LENGTH: 20
<212> TYPE: RNA
<213> ORGANISM: Artificial Sequence
<220> FEATURE:
<223> OTHER INFORMATION: Seynthetic

<400> SEQUENCE: 779
ggacuccagc cuggcccagg 20

<210> SEQ ID NO 780
<211> LENGTH: 20
<212> TYPE: RNA
<213> ORGANISM: Artificial Sequence
<220> FEATURE:
<223> OTHER INFORMATION: Seynthetic

<400> SEQUENCE: 780
ggacuccggc agccccuugg 20

<210> SEQ ID NO 781
<211> LENGTH: 20
<212> TYPE: RNA
<213> ORGANISM: Artificial Sequence
<220> FEATURE:
<223> OTHER INFORMATION: Seynthetic

<400> SEQUENCE: 781
ggagcagcac acgagguucc 20

<210> SEQ ID NO 782
<211> LENGTH: 20
<212> TYPE: RNA
<213> ORGANISM: Artificial Sequence
<220> FEATURE:
<223> OTHER INFORMATION: Seynthetic

<400> SEQUENCE: 782
ggagcucccu gguagaagca 20

<210> SEQ ID NO 783
<211> LENGTH: 20
<212> TYPE: RNA
<213> ORGANISM: Artificial Sequence
<220> FEATURE:
<223> OTHER INFORMATION: Seynthetic

<400> SEQUENCE: 783
ggagcuccug cccugccuac 20

<210> SEQ ID NO 784
<211> LENGTH: 20
<212> TYPE: RNA
<213> ORGANISM: Artificial Sequence
<220> FEATURE:
<223> OTHER INFORMATION: Seynthetic

<400> SEQUENCE: 784
ggaggggcug gaggaccguc 20

<210> SEQ ID NO 785
<211> LENGTH: 20
<212> TYPE: RNA
<213> ORGANISM: Artificial Sequence
<220> FEATURE:
<223> OTHER INFORMATION: Seynthetic

<400> SEQUENCE: 785 ggaggguag gcagggcagg 20

<210> SEQ ID NO 786
<211> LENGTH: 20
<212> TYPE: RNA
<213> ORGANISM: Artificial Sequence
<220> FEATURE:
<223> OTHER INFORMATION: Seynthetic

<400> SEQUENCE: 786
ggagucccag cugcgggaaa 20

<210> SEQ ID NO 787
<211> LENGTH: 20
<212> TYPE: RNA
<213> ORGANISM: Artificial Sequence
<220> FEATURE:
<223> OTHER INFORMATION: Seynthetic

<400> SEQUENCE: 787
ggagucccag cugcgggaau 20

<210> SEQ ID NO 788
<211> LENGTH: 20
<212> TYPE: RNA
<213> ORGANISM: Artificial Sequence
<220> FEATURE:
<223> OTHER INFORMATION: Seynthetic

<400> SEQUENCE: 788
ggaguccccc uguggaggca 20

<210> SEQ ID NO 789
<211> LENGTH: 20

<212> TYPE: RNA
<213> ORGANISM: Artificial Sequence
<220> FEATURE:
<223> OTHER INFORMATION: Seynthetic

<400> SEQUENCE: 789
ggaguccuga cgugaccaca 20

<210> SEQ ID NO 790
<211> LENGTH: 20
<212> TYPE: RNA
<213> ORGANISM: Artificial Sequence
<220> FEATURE:
<223> OTHER INFORMATION: Seynthetic

<400> SEQUENCE: 790
ggagucuaca cccgcuguga 20

<210> SEQ ID NO 791
<211> LENGTH: 20
<212> TYPE: RNA
<213> ORGANISM: Artificial Sequence
<220> FEATURE:
<223> OTHER INFORMATION: Seynthetic

<400> SEQUENCE: 791
ggagucuaca ccugcuguga 20

<210> SEQ ID NO 792
<211> LENGTH: 20
<212> TYPE: RNA
<213> ORGANISM: Artificial Sequence
<220> FEATURE:
<223> OTHER INFORMATION: Seynthetic

<400> SEQUENCE: 792
ggagucuuga cgugaccaca 20

<210> SEQ ID NO 793
<211> LENGTH: 20
<212> TYPE: RNA
<213> ORGANISM: Artificial Sequence
<220> FEATURE:
<223> OTHER INFORMATION: Seynthetic

<400> SEQUENCE: 793
ggaguucccu gguagaagca 20

<210> SEQ ID NO 794
<211> LENGTH: 20
<212> TYPE: RNA
<213> ORGANISM: Artificial Sequence
<220> FEATURE:
<223> OTHER INFORMATION: Seynthetic

<400> SEQUENCE: 794
ggaugaaaua aauucacguu 20

<210> SEQ ID NO 795
<211> LENGTH: 20
<212> TYPE: RNA
<213> ORGANISM: Artificial Sequence
<220> FEATURE:
<223> OTHER INFORMATION: Seynthetic

<400> SEQUENCE: 795
ggaugcacaa ucgcauucaa 20

<210> SEQ ID NO 796
<211> LENGTH: 20
<212> TYPE: RNA
<213> ORGANISM: Artificial Sequence
<220> FEATURE:
<223> OTHER INFORMATION: Seynthetic

<400> SEQUENCE: 796
ggauguccgc cuucaggugu 20

<210> SEQ ID NO 797
<211> LENGTH: 20
<212> TYPE: RNA
<213> ORGANISM: Artificial Sequence
<220> FEATURE:
<223> OTHER INFORMATION: Seynthetic

<400> SEQUENCE: 797
ggauugugaa acacccuggg 20

<210> SEQ ID NO 798
<211> LENGTH: 20
<212> TYPE: RNA
<213> ORGANISM: Artificial Sequence
<220> FEATURE:
<223> OTHER INFORMATION: Seynthetic

<400> SEQUENCE: 798
ggauuucagg gguggggac 20

<210> SEQ ID NO 799
<211> LENGTH: 20
<212> TYPE: RNA
<213> ORGANISM: Artificial Sequence
<220> FEATURE:
<223> OTHER INFORMATION: Seynthetic

<400> SEQUENCE: 799
ggcaaaaccc ccgcuccauu 20

<210> SEQ ID NO 800
<211> LENGTH: 20
<212> TYPE: RNA
<213> ORGANISM: Artificial Sequence
<220> FEATURE:
<223> OTHER INFORMATION: Seynthetic

<400> SEQUENCE: 800
ggcacacuua auaaagacug 20

<210> SEQ ID NO 801
<211> LENGTH: 20
<212> TYPE: RNA
<213> ORGANISM: Artificial Sequence
<220> FEATURE:
<223> OTHER INFORMATION: Seynthetic

<400> SEQUENCE: 801
ggcacacuua auaaugacug 20

<210> SEQ ID NO 802
<211> LENGTH: 20
<212> TYPE: RNA
<213> ORGANISM: Artificial Sequence
<220> FEATURE:
<223> OTHER INFORMATION: Seynthetic

<400> SEQUENCE: 802
ggcaggagcu cccugguaga 20

<210> SEQ ID NO 803
<211> LENGTH: 20
<212> TYPE: RNA
<213> ORGANISM: Artificial Sequence
<220> FEATURE:
<223> OTHER INFORMATION: Seynthetic

<400> SEQUENCE: 803
ggcaggaguu cccugguaga 20

<210> SEQ ID NO 804
<211> LENGTH: 20
<212> TYPE: RNA
<213> ORGANISM: Artificial Sequence
<220> FEATURE:
<223> OTHER INFORMATION: Seynthetic

<400> SEQUENCE: 804
ggcaucccug aacuuuccau 20

<210> SEQ ID NO 805
<211> LENGTH: 20
<212> TYPE: RNA
<213> ORGANISM: Artificial Sequence
<220> FEATURE:
<223> OTHER INFORMATION: Seynthetic

<400> SEQUENCE: 805
ggccaagccc cuuccaaaga 20

<210> SEQ ID NO 806
<211> LENGTH: 20
<212> TYPE: RNA
<213> ORGANISM: Artificial Sequence
<220> FEATURE:
<223> OTHER INFORMATION: Seynthetic

<400> SEQUENCE: 806
ggccacaggg acagagacaa 20

<210> SEQ ID NO 807
<211> LENGTH: 20
<212> TYPE: RNA
<213> ORGANISM: Artificial Sequence
<220> FEATURE:
<223> OTHER INFORMATION: Seynthetic

<400> SEQUENCE: 807
ggccaggcug gaguccugac 20

<210> SEQ ID NO 808
<211> LENGTH: 20
<212> TYPE: RNA
<213> ORGANISM: Artificial Sequence
<220> FEATURE:
<223> OTHER INFORMATION: Seynthetic

<400> SEQUENCE: 808
ggccaggcug gagucuugac 20

<210> SEQ ID NO 809
<211> LENGTH: 20
<212> TYPE: RNA
<213> ORGANISM: Artificial Sequence
<220> FEATURE:
<223> OTHER INFORMATION: Seynthetic

<400> SEQUENCE: 809
ggccguugca gcuggaacau 20

<210> SEQ ID NO 810
<211> LENGTH: 20
<212> TYPE: RNA
<213> ORGANISM: Artificial Sequence
<220> FEATURE:
<223> OTHER INFORMATION: Seynthetic

<400> SEQUENCE: 810
ggcggacauc ccugaacuuu 20

<210> SEQ ID NO 811
<211> LENGTH: 20
<212> TYPE: RNA
<213> ORGANISM: Artificial Sequence
<220> FEATURE:
<223> OTHER INFORMATION: Seynthetic

<400> SEQUENCE: 811
ggcguccccc accccugaaa 20

<210> SEQ ID NO 812
<211> LENGTH: 20
<212> TYPE: RNA
<213> ORGANISM: Artificial Sequence
<220> FEATURE:
<223> OTHER INFORMATION: Seynthetic

<400> SEQUENCE: 812
ggcugccgga gucccccugu 20

<210> SEQ ID NO 813
<211> LENGTH: 20
<212> TYPE: RNA
<213> ORGANISM: Artificial Sequence
<220> FEATURE:
<223> OTHER INFORMATION: Seynthetic

<400> SEQUENCE: 813
ggcuggaguc cugacgugac 20

<210> SEQ ID NO 814
<211> LENGTH: 20
<212> TYPE: RNA
<213> ORGANISM: Artificial Sequence
<220> FEATURE:
<223> OTHER INFORMATION: Seynthetic

<400> SEQUENCE: 814
ggcuggaguc uugacgugac 20

<210> SEQ ID NO 815
<211> LENGTH: 20
<212> TYPE: RNA
<213> ORGANISM: Artificial Sequence
<220> FEATURE:
<223> OTHER INFORMATION: Seynthetic

<400> SEQUENCE: 815
ggcugggucc ugggaauccc 20

<210> SEQ ID NO 816
<211> LENGTH: 20
<212> TYPE: RNA
<213> ORGANISM: Artificial Sequence
<220> FEATURE:
<223> OTHER INFORMATION: Seynthetic

<400> SEQUENCE: 816
gggaaaggga uucccaggac 20

<210> SEQ ID NO 817
<211> LENGTH: 20
<212> TYPE: RNA
<213> ORGANISM: Artificial Sequence
<220> FEATURE:
<223> OTHER INFORMATION: Seynthetic

<400> SEQUENCE: 817
gggaacuccu gcccugccua 20

<210> SEQ ID NO 818
<211> LENGTH: 20
<212> TYPE: RNA
<213> ORGANISM: Artificial Sequence
<220> FEATURE:
<223> OTHER INFORMATION: Seynthetic

<400> SEQUENCE: 818
gggaauccca uucccgcagc 20

<210> SEQ ID NO 819
<211> LENGTH: 20
<212> TYPE: RNA
<213> ORGANISM: Artificial Sequence
<220> FEATURE:
<223> OTHER INFORMATION: Seynthetic

<400> SEQUENCE: 819
gggaaucccu uucccgcagc 20

<210> SEQ ID NO 820
<211> LENGTH: 20
<212> TYPE: RNA
<213> ORGANISM: Artificial Sequence
<220> FEATURE:
<223> OTHER INFORMATION: Seynthetic

<400> SEQUENCE: 820
gggaauggga uucccaggac 20

<210> SEQ ID NO 821
<211> LENGTH: 20
<212> TYPE: RNA
<213> ORGANISM: Artificial Sequence
<220> FEATURE:
<223> OTHER INFORMATION: Seynthetic

<400> SEQUENCE: 821
gggacgccgu aucuuuggaa 20

<210> SEQ ID NO 822

<211> LENGTH: 20
<212> TYPE: RNA
<213> ORGANISM: Artificial Sequence
<220> FEATURE:
<223> OTHER INFORMATION: Seynthetic

<400> SEQUENCE: 822
gggacgcugu aucuuuggaa 20

<210> SEQ ID NO 823
<211> LENGTH: 20
<212> TYPE: RNA
<213> ORGANISM: Artificial Sequence
<220> FEATURE:
<223> OTHER INFORMATION: Seynthetic

<400> SEQUENCE: 823
gggacuccgg cagccccuug 20

<210> SEQ ID NO 824
<211> LENGTH: 20
<212> TYPE: RNA
<213> ORGANISM: Artificial Sequence
<220> FEATURE:
<223> OTHER INFORMATION: Seynthetic

<400> SEQUENCE: 824
gggagcuccu gcccugccua 20

<210> SEQ ID NO 825
<211> LENGTH: 20
<212> TYPE: RNA
<213> ORGANISM: Artificial Sequence
<220> FEATURE:
<223> OTHER INFORMATION: Seynthetic

<400> SEQUENCE: 825
gggauguccg ccuucaggug 20

<210> SEQ ID NO 826
<211> LENGTH: 20
<212> TYPE: RNA
<213> ORGANISM: Artificial Sequence
<220> FEATURE:
<223> OTHER INFORMATION: Seynthetic

<400> SEQUENCE: 826
gggauuucag gggugggga 20

<210> SEQ ID NO 827
<211> LENGTH: 20
<212> TYPE: RNA
<213> ORGANISM: Artificial Sequence
<220> FEATURE:
<223> OTHER INFORMATION: Seynthetic

<400> SEQUENCE: 827
gggcaggagc ucccugguag 20

<210> SEQ ID NO 828
<211> LENGTH: 20
<212> TYPE: RNA
<213> ORGANISM: Artificial Sequence
<220> FEATURE:
<223> OTHER INFORMATION: Seynthetic

<400> SEQUENCE: 828
gggcaggagu ucccugguag 20

<210> SEQ ID NO 829
<211> LENGTH: 20
<212> TYPE: RNA
<213> ORGANISM: Artificial Sequence
<220> FEATURE:
<223> OTHER INFORMATION: Seynthetic

<400> SEQUENCE: 829
gggccaggcu ggaguccuga 20

<210> SEQ ID NO 830
<211> LENGTH: 20
<212> TYPE: RNA
<213> ORGANISM: Artificial Sequence
<220> FEATURE:
<223> OTHER INFORMATION: Seynthetic

<400> SEQUENCE: 830
gggccaggcu ggagucuuga 20

<210> SEQ ID NO 831
<211> LENGTH: 20
<212> TYPE: RNA
<213> ORGANISM: Artificial Sequence
<220> FEATURE:
<223> OTHER INFORMATION: Seynthetic

<400> SEQUENCE: 831
gggcuggguc cugggaaucc 20

<210> SEQ ID NO 832
<211> LENGTH: 20
<212> TYPE: RNA
<213> ORGANISM: Artificial Sequence
<220> FEATURE:
<223> OTHER INFORMATION: Seynthetic

<400> SEQUENCE: 832
ggggaccaga aggaugggga 20

<210> SEQ ID NO 833
<211> LENGTH: 20
<212> TYPE: RNA
<213> ORGANISM: Artificial Sequence
<220> FEATURE:
<223> OTHER INFORMATION: Seynthetic

<400> SEQUENCE: 833
ggggacgccg uaucuuugga 20

<210> SEQ ID NO 834
<211> LENGTH: 20
<212> TYPE: RNA
<213> ORGANISM: Artificial Sequence
<220> FEATURE:
<223> OTHER INFORMATION: Seynthetic

<400> SEQUENCE: 834
ggggacgcug uaucuuugga 20

<210> SEQ ID NO 835
<211> LENGTH: 20
<212> TYPE: RNA

<213> ORGANISM: Artificial Sequence
<220> FEATURE:
<223> OTHER INFORMATION: Seynthetic

<400> SEQUENCE: 835 gggacuccg gcagccccuu 20

<210> SEQ ID NO 836
<211> LENGTH: 20
<212> TYPE: RNA
<213> ORGANISM: Artificial Sequence
<220> FEATURE:
<223> OTHER INFORMATION: Seynthetic

<400> SEQUENCE: 836
ggggcugggu ccugggaauc 20

<210> SEQ ID NO 837
<211> LENGTH: 20
<212> TYPE: RNA
<213> ORGANISM: Artificial Sequence
<220> FEATURE:
<223> OTHER INFORMATION: Seynthetic

<400> SEQUENCE: 837
gggggacgcc guaucuuugg 20

<210> SEQ ID NO 838
<211> LENGTH: 20
<212> TYPE: RNA
<213> ORGANISM: Artificial Sequence
<220> FEATURE:
<223> OTHER INFORMATION: Seynthetic

<400> SEQUENCE: 838
gggggacgcu guaucuuugg 20

<210> SEQ ID NO 839
<211> LENGTH: 20
<212> TYPE: RNA
<213> ORGANISM: Artificial Sequence
<220> FEATURE:
<223> OTHER INFORMATION: Seynthetic

<400> SEQUENCE: 839
gggggacuca ggcagccccu 20

<210> SEQ ID NO 840
<211> LENGTH: 20
<212> TYPE: RNA
<213> ORGANISM: Artificial Sequence
<220> FEATURE:
<223> OTHER INFORMATION: Seynthetic

<400> SEQUENCE: 840
gggggacucu gggugugcug 20

<210> SEQ ID NO 841
<211> LENGTH: 20
<212> TYPE: RNA
<213> ORGANISM: Artificial Sequence
<220> FEATURE:
<223> OTHER INFORMATION: Seynthetic

<400> SEQUENCE: 841
gggguaggca gggcaggagc 20

<210> SEQ ID NO 842
<211> LENGTH: 20
<212> TYPE: RNA
<213> ORGANISM: Artificial Sequence
<220> FEATURE:
<223> OTHER INFORMATION: Seynthetic

<400> SEQUENCE: 842
gggguaggca gggcaggagu 20

<210> SEQ ID NO 843
<211> LENGTH: 20
<212> TYPE: RNA
<213> ORGANISM: Artificial Sequence
<220> FEATURE:
<223> OTHER INFORMATION: Seynthetic

<400> SEQUENCE: 843 ggggugggggg acgccguauc 20

<210> SEQ ID NO 844
<211> LENGTH: 20
<212> TYPE: RNA
<213> ORGANISM: Artificial Sequence
<220> FEATURE:
<223> OTHER INFORMATION: Seynthetic

<400> SEQUENCE: 844
gggguggggg acgcuguauc 20

<210> SEQ ID NO 845
<211> LENGTH: 20
<212> TYPE: RNA
<213> ORGANISM: Artificial Sequence
<220> FEATURE:
<223> OTHER INFORMATION: Seynthetic

<400> SEQUENCE: 845
gggguguuau ggucacagca 20

<210> SEQ ID NO 846
<211> LENGTH: 20
<212> TYPE: RNA
<213> ORGANISM: Artificial Sequence
<220> FEATURE:
<223> OTHER INFORMATION: Seynthetic

<400> SEQUENCE: 846
gggguguuau ggucacagcg 20

<210> SEQ ID NO 847
<211> LENGTH: 20
<212> TYPE: RNA
<213> ORGANISM: Artificial Sequence
<220> FEATURE:
<223> OTHER INFORMATION: Seynthetic

<400> SEQUENCE: 847
ggguaggcag ggcaggagcu 20

<210> SEQ ID NO 848
<211> LENGTH: 20
<212> TYPE: RNA
<213> ORGANISM: Artificial Sequence
<220> FEATURE:

<223> OTHER INFORMATION: Seynthetic

<400> SEQUENCE: 848
ggguaggcag ggcaggaguu 20

<210> SEQ ID NO 849
<211> LENGTH: 20
<212> TYPE: RNA
<213> ORGANISM: Artificial Sequence
<220> FEATURE:
<223> OTHER INFORMATION: Seynthetic

<400> SEQUENCE: 849
ggguccuggg aaucccauuc 20

<210> SEQ ID NO 850
<211> LENGTH: 20
<212> TYPE: RNA
<213> ORGANISM: Artificial Sequence
<220> FEATURE:
<223> OTHER INFORMATION: Seynthetic

<400> SEQUENCE: 850
ggguccuggg aaucccuuuc 20

<210> SEQ ID NO 851
<211> LENGTH: 20
<212> TYPE: RNA
<213> ORGANISM: Artificial Sequence
<220> FEATURE:
<223> OTHER INFORMATION: Seynthetic

<400> SEQUENCE: 851
gggugacucu gggugugqug 20

<210> SEQ ID NO 852
<211> LENGTH: 20
<212> TYPE: RNA
<213> ORGANISM: Artificial Sequence
<220> FEATURE:
<223> OTHER INFORMATION: Seynthetic

<400> SEQUENCE: 852 gggugggga cgccguaucu 20

<210> SEQ ID NO 853
<211> LENGTH: 20
<212> TYPE: RNA
<213> ORGANISM: Artificial Sequence
<220> FEATURE:
<223> OTHER INFORMATION: Seynthetic

<400> SEQUENCE: 853 gggugggga cgcuguaucu 20

<210> SEQ ID NO 854
<211> LENGTH: 20
<212> TYPE: RNA
<213> ORGANISM: Artificial Sequence
<220> FEATURE:
<223> OTHER INFORMATION: Seynthetic

<400> SEQUENCE: 854
ggguguagac uccgaggggg 20

<210> SEQ ID NO 855
<211> LENGTH: 20
<212> TYPE: RNA
<213> ORGANISM: Artificial Sequence
<220> FEATURE:
<223> OTHER INFORMATION: Seynthetic

<400> SEQUENCE: 855
gggugucaag ccccagagga 20

<210> SEQ ID NO 856
<211> LENGTH: 20
<212> TYPE: RNA
<213> ORGANISM: Artificial Sequence
<220> FEATURE:
<223> OTHER INFORMATION: Seynthetic

<400> SEQUENCE: 856
gggugucaag ccccagaggc 20

<210> SEQ ID NO 857
<211> LENGTH: 20
<212> TYPE: RNA
<213> ORGANISM: Artificial Sequence
<220> FEATURE:
<223> OTHER INFORMATION: Seynthetic

<400> SEQUENCE: 857
ggguguuaug gucacagcag 20

<210> SEQ ID NO 858
<211> LENGTH: 20
<212> TYPE: RNA
<213> ORGANISM: Artificial Sequence
<220> FEATURE:
<223> OTHER INFORMATION: Seynthetic

<400> SEQUENCE: 858
ggguguuaug gucacagcgg 20

<210> SEQ ID NO 859
<211> LENGTH: 20
<212> TYPE: RNA
<213> ORGANISM: Artificial Sequence
<220> FEATURE:
<223> OTHER INFORMATION: Seynthetic

<400> SEQUENCE: 859
gguaggcagg gcaggagcuc 20

<210> SEQ ID NO 860
<211> LENGTH: 20
<212> TYPE: RNA
<213> ORGANISM: Artificial Sequence
<220> FEATURE:
<223> OTHER INFORMATION: Seynthetic

<400> SEQUENCE: 860
gguaggcagg gcaggaguuc 20

<210> SEQ ID NO 861
<211> LENGTH: 20
<212> TYPE: RNA
<213> ORGANISM: Artificial Sequence
<220> FEATURE:
<223> OTHER INFORMATION: Seynthetic

<400> SEQUENCE: 861
gguaggggug uuauggucac 20

<210> SEQ ID NO 862
<211> LENGTH: 20
<212> TYPE: RNA
<213> ORGANISM: Artificial Sequence
<220> FEATURE:
<223> OTHER INFORMATION: Seynthetic

<400> SEQUENCE: 862
gguaucccca uccuucuggu 20

<210> SEQ ID NO 863
<211> LENGTH: 20
<212> TYPE: RNA
<213> ORGANISM: Artificial Sequence
<220> FEATURE:
<223> OTHER INFORMATION: Seynthetic

<400> SEQUENCE: 863
ggucacagca gguguagacu 20

<210> SEQ ID NO 864
<211> LENGTH: 20
<212> TYPE: RNA
<213> ORGANISM: Artificial Sequence
<220> FEATURE:
<223> OTHER INFORMATION: Seynthetic

<400> SEQUENCE: 864
ggucacagcg gguguagacu 20

<210> SEQ ID NO 865
<211> LENGTH: 20
<212> TYPE: RNA
<213> ORGANISM: Artificial Sequence
<220> FEATURE:
<223> OTHER INFORMATION: Seynthetic

<400> SEQUENCE: 865
ggucacguca agacuccagc 20

<210> SEQ ID NO 866
<211> LENGTH: 20
<212> TYPE: RNA
<213> ORGANISM: Artificial Sequence
<220> FEATURE:
<223> OTHER INFORMATION: Seynthetic

<400> SEQUENCE: 866
ggucacguca ggacuccagc 20

<210> SEQ ID NO 867
<211> LENGTH: 20
<212> TYPE: RNA
<213> ORGANISM: Artificial Sequence
<220> FEATURE:
<223> OTHER INFORMATION: Seynthetic

<400> SEQUENCE: 867
gguccccgca ccauggauua 20

<210> SEQ ID NO 868
<211> LENGTH: 20

<212> TYPE: RNA
<213> ORGANISM: Artificial Sequence
<220> FEATURE:
<223> OTHER INFORMATION: Seynthetic

<400> SEQUENCE: 868
ggucccugca ccauggauua 20

<210> SEQ ID NO 869
<211> LENGTH: 20
<212> TYPE: RNA
<213> ORGANISM: Artificial Sequence
<220> FEATURE:
<223> OTHER INFORMATION: Seynthetic

<400> SEQUENCE: 869
gguccuccag ccccuccagg 20

<210> SEQ ID NO 870
<211> LENGTH: 20
<212> TYPE: RNA
<213> ORGANISM: Artificial Sequence
<220> FEATURE:
<223> OTHER INFORMATION: Seynthetic

<400> SEQUENCE: 870
gguccuggga aucccauucc 20

<210> SEQ ID NO 871
<211> LENGTH: 20
<212> TYPE: RNA
<213> ORGANISM: Artificial Sequence
<220> FEATURE:
<223> OTHER INFORMATION: Seynthetic

<400> SEQUENCE: 871
gguccuggga aucccuuucc 20

<210> SEQ ID NO 872
<211> LENGTH: 20
<212> TYPE: RNA
<213> ORGANISM: Artificial Sequence
<220> FEATURE:
<223> OTHER INFORMATION: Seynthetic

<400> SEQUENCE: 872
ggugaagaga aaagccgggg 20

<210> SEQ ID NO 873
<211> LENGTH: 20
<212> TYPE: RNA
<213> ORGANISM: Artificial Sequence
<220> FEATURE:
<223> OTHER INFORMATION: Seynthetic

<400> SEQUENCE: 873
ggugacucug ggugugguga 20

<210> SEQ ID NO 874
<211> LENGTH: 20
<212> TYPE: RNA
<213> ORGANISM: Artificial Sequence
<220> FEATURE:
<223> OTHER INFORMATION: Seynthetic

<400> SEQUENCE: 874
ggugcaggga ccagaaggau 20

<210> SEQ ID NO 875
<211> LENGTH: 20
<212> TYPE: RNA
<213> ORGANISM: Artificial Sequence
<220> FEATURE:
<223> OTHER INFORMATION: Seynthetic

<400> SEQUENCE: 875
ggugcgggga ccagaaggau 20

<210> SEQ ID NO 876
<211> LENGTH: 20
<212> TYPE: RNA
<213> ORGANISM: Artificial Sequence
<220> FEATURE:
<223> OTHER INFORMATION: Seynthetic

<400> SEQUENCE: 876
ggugggggac gccguaucuu 20

<210> SEQ ID NO 877
<211> LENGTH: 20
<212> TYPE: RNA
<213> ORGANISM: Artificial Sequence
<220> FEATURE:
<223> OTHER INFORMATION: Seynthetic

<400> SEQUENCE: 877
ggugggggac gcuguaucuu 20

<210> SEQ ID NO 878
<211> LENGTH: 20
<212> TYPE: RNA
<213> ORGANISM: Artificial Sequence
<220> FEATURE:
<223> OTHER INFORMATION: Seynthetic

<400> SEQUENCE: 878
ggugucaagc cccagaggac 20

<210> SEQ ID NO 879
<211> LENGTH: 20
<212> TYPE: RNA
<213> ORGANISM: Artificial Sequence
<220> FEATURE:
<223> OTHER INFORMATION: Seynthetic

<400> SEQUENCE: 879
ggugucaagc cccagaggcc 20

<210> SEQ ID NO 880
<211> LENGTH: 20
<212> TYPE: RNA
<213> ORGANISM: Artificial Sequence
<220> FEATURE:
<223> OTHER INFORMATION: Seynthetic

<400> SEQUENCE: 880
gguguuaugg ucacagcagg 20

<210> SEQ ID NO 881
<211> LENGTH: 20
<212> TYPE: RNA
<213> ORGANISM: Artificial Sequence
<220> FEATURE:
<223> OTHER INFORMATION: Seynthetic

<400> SEQUENCE: 881
gguguuaugg ucacagcggg 20

<210> SEQ ID NO 882
<211> LENGTH: 20
<212> TYPE: RNA
<213> ORGANISM: Artificial Sequence
<220> FEATURE:
<223> OTHER INFORMATION: Seynthetic

<400> SEQUENCE: 882
gguucccccg gcuuuucucu 20

<210> SEQ ID NO 883
<211> LENGTH: 20
<212> TYPE: RNA
<213> ORGANISM: Artificial Sequence
<220> FEATURE:
<223> OTHER INFORMATION: Seynthetic

<400> SEQUENCE: 883 gguuccccu gcuuuucucu 20

<210> SEQ ID NO 884
<211> LENGTH: 20
<212> TYPE: RNA
<213> ORGANISM: Artificial Sequence
<220> FEATURE:
<223> OTHER INFORMATION: Seynthetic

<400> SEQUENCE: 884
guaaaguucu uagcuaagaa 20

<210> SEQ ID NO 885
<211> LENGTH: 20
<212> TYPE: RNA
<213> ORGANISM: Artificial Sequence
<220> FEATURE:
<223> OTHER INFORMATION: Seynthetic

<400> SEQUENCE: 885
guaggcaggg caggaguucc 20

<210> SEQ ID NO 886
<211> LENGTH: 20
<212> TYPE: RNA
<213> ORGANISM: Artificial Sequence
<220> FEATURE:
<223> OTHER INFORMATION: Seynthetic

<400> SEQUENCE: 886
guaggggugu uauggucaca 20

<210> SEQ ID NO 887
<211> LENGTH: 20
<212> TYPE: RNA
<213> ORGANISM: Artificial Sequence
<220> FEATURE:
<223> OTHER INFORMATION: Seynthetic

<400> SEQUENCE: 887
guauccccau ccuucugguc 20

<210> SEQ ID NO 888
<211> LENGTH: 20
<212> TYPE: RNA
<213> ORGANISM: Artificial Sequence
<220> FEATURE:
<223> OTHER INFORMATION: Seynthetic

<400> SEQUENCE: 888
gucaagcccc agaggacaca 20

<210> SEQ ID NO 889
<211> LENGTH: 20
<212> TYPE: RNA
<213> ORGANISM: Artificial Sequence
<220> FEATURE:
<223> OTHER INFORMATION: Seynthetic

<400> SEQUENCE: 889
gucaagcccc agaggccaca 20

<210> SEQ ID NO 890
<211> LENGTH: 20
<212> TYPE: RNA
<213> ORGANISM: Artificial Sequence
<220> FEATURE:
<223> OTHER INFORMATION: Seynthetic

<400> SEQUENCE: 890
gucacagcag guguagacuc 20

<210> SEQ ID NO 891
<211> LENGTH: 20
<212> TYPE: RNA
<213> ORGANISM: Artificial Sequence
<220> FEATURE:
<223> OTHER INFORMATION: Seynthetic

<400> SEQUENCE: 891
gucacagcgg guguagacuc 20

<210> SEQ ID NO 892
<211> LENGTH: 20
<212> TYPE: RNA
<213> ORGANISM: Artificial Sequence
<220> FEATURE:
<223> OTHER INFORMATION: Seynthetic

<400> SEQUENCE: 892
gucacccagg guguuucaca 20

<210> SEQ ID NO 893
<211> LENGTH: 20
<212> TYPE: RNA
<213> ORGANISM: Artificial Sequence
<220> FEATURE:
<223> OTHER INFORMATION: Seynthetic

<400> SEQUENCE: 893
gucacgucaa gacuccagcc 20

<210> SEQ ID NO 894
<211> LENGTH: 20
<212> TYPE: RNA
<213> ORGANISM: Artificial Sequence
<220> FEATURE:
<223> OTHER INFORMATION: Seynthetic

<400> SEQUENCE: 894
gucacgucag gacuccagcc 20

<210> SEQ ID NO 895
<211> LENGTH: 20
<212> TYPE: RNA
<213> ORGANISM: Artificial Sequence
<220> FEATURE:
<223> OTHER INFORMATION: Seynthetic

<400> SEQUENCE: 895
gucagauaau caaugugggu 20

<210> SEQ ID NO 896
<211> LENGTH: 20
<212> TYPE: RNA
<213> ORGANISM: Artificial Sequence
<220> FEATURE:
<223> OTHER INFORMATION: Seynthetic

<400> SEQUENCE: 896
gucagggugu caagccccag 20

<210> SEQ ID NO 897
<211> LENGTH: 20
<212> TYPE: RNA
<213> ORGANISM: Artificial Sequence
<220> FEATURE:
<223> OTHER INFORMATION: Seynthetic

<400> SEQUENCE: 897
gucauuauua agugugccga 20

<210> SEQ ID NO 898
<211> LENGTH: 20
<212> TYPE: RNA
<213> ORGANISM: Artificial Sequence
<220> FEATURE:
<223> OTHER INFORMATION: Seynthetic

<400> SEQUENCE: 898
gucccagcug cgggaaaggg 20

<210> SEQ ID NO 899
<211> LENGTH: 20
<212> TYPE: RNA
<213> ORGANISM: Artificial Sequence
<220> FEATURE:
<223> OTHER INFORMATION: Seynthetic

<400> SEQUENCE: 899
gucccagcug cgggaauggg 20

<210> SEQ ID NO 900
<211> LENGTH: 20
<212> TYPE: RNA
<213> ORGANISM: Artificial Sequence
<220> FEATURE:
<223> OTHER INFORMATION: Seynthetic

<400> SEQUENCE: 900
gucccccagg guguuucaca 20

<210> SEQ ID NO 901

<211> LENGTH: 20
<212> TYPE: RNA
<213> ORGANISM: Artificial Sequence
<220> FEATURE:
<223> OTHER INFORMATION: Seynthetic

<400> SEQUENCE: 901 guccccucg gagucuacac 20

<210> SEQ ID NO 902
<211> LENGTH: 20
<212> TYPE: RNA
<213> ORGANISM: Artificial Sequence
<220> FEATURE:
<223> OTHER INFORMATION: Seynthetic

<400> SEQUENCE: 902
gucccugcac cauggauuaa 20

<210> SEQ ID NO 903
<211> LENGTH: 20
<212> TYPE: RNA
<213> ORGANISM: Artificial Sequence
<220> FEATURE:
<223> OTHER INFORMATION: Seynthetic

<400> SEQUENCE: 903
gucccugugg ccucuggggc 20

<210> SEQ ID NO 904
<211> LENGTH: 20
<212> TYPE: RNA
<213> ORGANISM: Artificial Sequence
<220> FEATURE:
<223> OTHER INFORMATION: Seynthetic

<400> SEQUENCE: 904
guccuccagc cccgccaggu 20

<210> SEQ ID NO 905
<211> LENGTH: 20
<212> TYPE: RNA
<213> ORGANISM: Artificial Sequence
<220> FEATURE:
<223> OTHER INFORMATION: Seynthetic

<400> SEQUENCE: 905
guccucuggg gcuugacacc 20

<210> SEQ ID NO 906
<211> LENGTH: 20
<212> TYPE: RNA
<213> ORGANISM: Artificial Sequence
<220> FEATURE:
<223> OTHER INFORMATION: Seynthetic

<400> SEQUENCE: 906
guccugacgu gaccacaggc 20

<210> SEQ ID NO 907
<211> LENGTH: 20
<212> TYPE: RNA
<213> ORGANISM: Artificial Sequence
<220> FEATURE:
<223> OTHER INFORMATION: Seynthetic

<400> SEQUENCE: 907
guccugggaa ucccauuccc 20

<210> SEQ ID NO 908
<211> LENGTH: 20
<212> TYPE: RNA
<213> ORGANISM: Artificial Sequence
<220> FEATURE:
<223> OTHER INFORMATION: Seynthetic

<400> SEQUENCE: 908
guccugggaa ucccuuuccc 20

<210> SEQ ID NO 909
<211> LENGTH: 20
<212> TYPE: RNA
<213> ORGANISM: Artificial Sequence
<220> FEATURE:
<223> OTHER INFORMATION: Seynthetic

<400> SEQUENCE: 909
gucggcacac uuaauaaaga 20

<210> SEQ ID NO 910
<211> LENGTH: 20
<212> TYPE: RNA
<213> ORGANISM: Artificial Sequence
<220> FEATURE:
<223> OTHER INFORMATION: Seynthetic

<400> SEQUENCE: 910
gucggcacac uuaauaauga 20

<210> SEQ ID NO 911
<211> LENGTH: 20
<212> TYPE: RNA
<213> ORGANISM: Artificial Sequence
<220> FEATURE:
<223> OTHER INFORMATION: Seynthetic

<400> SEQUENCE: 911
gucuacaccc gcugugacca 20

<210> SEQ ID NO 912
<211> LENGTH: 20
<212> TYPE: RNA
<213> ORGANISM: Artificial Sequence
<220> FEATURE:
<223> OTHER INFORMATION: Seynthetic

<400> SEQUENCE: 912
gucuacaccu gcugugacca 20

<210> SEQ ID NO 913
<211> LENGTH: 20
<212> TYPE: RNA
<213> ORGANISM: Artificial Sequence
<220> FEATURE:
<223> OTHER INFORMATION: Seynthetic

<400> SEQUENCE: 913
gucucugucc cuguggccuc 20

<210> SEQ ID NO 914
<211> LENGTH: 20
<212> TYPE: RNA

<213> ORGANISM: Artificial Sequence
<220> FEATURE:
<223> OTHER INFORMATION: Seynthetic

<400> SEQUENCE: 914
gucucugucc cuguguccuc 20

<210> SEQ ID NO 915
<211> LENGTH: 20
<212> TYPE: RNA
<213> ORGANISM: Artificial Sequence
<220> FEATURE:
<223> OTHER INFORMATION: Seynthetic

<400> SEQUENCE: 915
gucugccucc acagggggac 20

<210> SEQ ID NO 916
<211> LENGTH: 20
<212> TYPE: RNA
<213> ORGANISM: Artificial Sequence
<220> FEATURE:
<223> OTHER INFORMATION: Seynthetic

<400> SEQUENCE: 916
gucuugacgu gaccacaggc 20

<210> SEQ ID NO 917
<211> LENGTH: 20
<212> TYPE: RNA
<213> ORGANISM: Artificial Sequence
<220> FEATURE:
<223> OTHER INFORMATION: Seynthetic

<400> SEQUENCE: 917
gucuuuauua agugugccga 20

<210> SEQ ID NO 918
<211> LENGTH: 20
<212> TYPE: RNA
<213> ORGANISM: Artificial Sequence
<220> FEATURE:
<223> OTHER INFORMATION: Seynthetic

<400> SEQUENCE: 918
gugaaacacc cugggggacu 20

<210> SEQ ID NO 919
<211> LENGTH: 20
<212> TYPE: RNA
<213> ORGANISM: Artificial Sequence
<220> FEATURE:
<223> OTHER INFORMATION: Seynthetic

<400> SEQUENCE: 919
gugaaacacc cugggugacu 20

<210> SEQ ID NO 920
<211> LENGTH: 20
<212> TYPE: RNA
<213> ORGANISM: Artificial Sequence
<220> FEATURE:
<223> OTHER INFORMATION: Seynthetic

<400> SEQUENCE: 920
gugaagagaa aagcaggggg 20

<210> SEQ ID NO 921
<211> LENGTH: 20
<212> TYPE: RNA
<213> ORGANISM: Artificial Sequence
<220> FEATURE:
<223> OTHER INFORMATION: Seynthetic

<400> SEQUENCE: 921
gugaagagaa aagccggggg 20

<210> SEQ ID NO 922
<211> LENGTH: 20
<212> TYPE: RNA
<213> ORGANISM: Artificial Sequence
<220> FEATURE:
<223> OTHER INFORMATION: Seynthetic

<400> SEQUENCE: 922
gugacucugg guguggugaa 20

<210> SEQ ID NO 923
<211> LENGTH: 20
<212> TYPE: RNA
<213> ORGANISM: Artificial Sequence
<220> FEATURE:
<223> OTHER INFORMATION: Seynthetic

<400> SEQUENCE: 923
gugacuuccc cacauuguau 20

<210> SEQ ID NO 924
<211> LENGTH: 20
<212> TYPE: RNA
<213> ORGANISM: Artificial Sequence
<220> FEATURE:
<223> OTHER INFORMATION: Seynthetic

<400> SEQUENCE: 924
gugacuuccc cacauugugu 20

<210> SEQ ID NO 925
<211> LENGTH: 20
<212> TYPE: RNA
<213> ORGANISM: Artificial Sequence
<220> FEATURE:
<223> OTHER INFORMATION: Seynthetic

<400> SEQUENCE: 925
gugcagggac cagaaggaug 20

<210> SEQ ID NO 926
<211> LENGTH: 20
<212> TYPE: RNA
<213> ORGANISM: Artificial Sequence
<220> FEATURE:
<223> OTHER INFORMATION: Seynthetic

<400> SEQUENCE: 926
gugcagucau uauuaagugu 20

<210> SEQ ID NO 927
<211> LENGTH: 20
<212> TYPE: RNA
<213> ORGANISM: Artificial Sequence
<220> FEATURE:

<223> OTHER INFORMATION: Seynthetic

<400> SEQUENCE: 927
gugcagucuu uauuaagugu 20

<210> SEQ ID NO 928
<211> LENGTH: 20
<212> TYPE: RNA
<213> ORGANISM: Artificial Sequence
<220> FEATURE:
<223> OTHER INFORMATION: Seynthetic

<400> SEQUENCE: 928
gugcggggac cagaaggaug 20

<210> SEQ ID NO 929
<211> LENGTH: 20
<212> TYPE: RNA
<213> ORGANISM: Artificial Sequence
<220> FEATURE:
<223> OTHER INFORMATION: Seynthetic

<400> SEQUENCE: 929
guggccucug gggcuugaca 20

<210> SEQ ID NO 930
<211> LENGTH: 20
<212> TYPE: RNA
<213> ORGANISM: Artificial Sequence
<220> FEATURE:
<223> OTHER INFORMATION: Seynthetic

<400> SEQUENCE: 930 guggggacg ccguaucuuu 20

<210> SEQ ID NO 931
<211> LENGTH: 20
<212> TYPE: RNA
<213> ORGANISM: Artificial Sequence
<220> FEATURE:
<223> OTHER INFORMATION: Seynthetic

<400> SEQUENCE: 931 guggggacg cuguaucuuu 20

<210> SEQ ID NO 932
<211> LENGTH: 20
<212> TYPE: RNA
<213> ORGANISM: Artificial Sequence
<220> FEATURE:
<223> OTHER INFORMATION: Seynthetic

<400> SEQUENCE: 932
guggucacgu caggacucca 20

<210> SEQ ID NO 933
<211> LENGTH: 20
<212> TYPE: RNA
<213> ORGANISM: Artificial Sequence
<220> FEATURE:
<223> OTHER INFORMATION: Seynthetic

<400> SEQUENCE: 933
gugucaagcc ccagaggaca 20

<210> SEQ ID NO 934
<211> LENGTH: 20
<212> TYPE: RNA
<213> ORGANISM: Artificial Sequence
<220> FEATURE:
<223> OTHER INFORMATION: Seynthetic

<400> SEQUENCE: 934
gugucaagcc ccagaggcca 20

<210> SEQ ID NO 935
<211> LENGTH: 20
<212> TYPE: RNA
<213> ORGANISM: Artificial Sequence
<220> FEATURE:
<223> OTHER INFORMATION: Seynthetic

<400> SEQUENCE: 935
guguccucug gggcuugaca 20

<210> SEQ ID NO 936
<211> LENGTH: 20
<212> TYPE: RNA
<213> ORGANISM: Artificial Sequence
<220> FEATURE:
<223> OTHER INFORMATION: Seynthetic

<400> SEQUENCE: 936
guguuauggu cacagcaggu 20

<210> SEQ ID NO 937
<211> LENGTH: 20
<212> TYPE: RNA
<213> ORGANISM: Artificial Sequence
<220> FEATURE:
<223> OTHER INFORMATION: Seynthetic

<400> SEQUENCE: 937
guguuauggu cacagcgggu 20

<210> SEQ ID NO 938
<211> LENGTH: 20
<212> TYPE: RNA
<213> ORGANISM: Artificial Sequence
<220> FEATURE:
<223> OTHER INFORMATION: Seynthetic

<400> SEQUENCE: 938
guuauaugga aaguucaggg 20

<210> SEQ ID NO 939
<211> LENGTH: 20
<212> TYPE: RNA
<213> ORGANISM: Artificial Sequence
<220> FEATURE:
<223> OTHER INFORMATION: Seynthetic

<400> SEQUENCE: 939
guuaugguca cagcaggugu 20

<210> SEQ ID NO 940
<211> LENGTH: 20
<212> TYPE: RNA
<213> ORGANISM: Artificial Sequence
<220> FEATURE:
<223> OTHER INFORMATION: Seynthetic

<400> SEQUENCE: 940
guuaugguca cagcgggugu 20

<210> SEQ ID NO 941
<211> LENGTH: 20
<212> TYPE: RNA
<213> ORGANISM: Artificial Sequence
<220> FEATURE:
<223> OTHER INFORMATION: Seynthetic

<400> SEQUENCE: 941
guucagggau guccgccuuc 20

<210> SEQ ID NO 942
<211> LENGTH: 20
<212> TYPE: RNA
<213> ORGANISM: Artificial Sequence
<220> FEATURE:
<223> OTHER INFORMATION: Seynthetic

<400> SEQUENCE: 942
guucauaaag uucuuagcua 20

<210> SEQ ID NO 943
<211> LENGTH: 20
<212> TYPE: RNA
<213> ORGANISM: Artificial Sequence
<220> FEATURE:
<223> OTHER INFORMATION: Seynthetic

<400> SEQUENCE: 943
guucccccgg cuuuucucuu 20

<210> SEQ ID NO 944
<211> LENGTH: 20
<212> TYPE: RNA
<213> ORGANISM: Artificial Sequence
<220> FEATURE:
<223> OTHER INFORMATION: Seynthetic

<400> SEQUENCE: 944
guucccuggu agaagcauga 20

<210> SEQ ID NO 945
<211> LENGTH: 20
<212> TYPE: RNA
<213> ORGANISM: Artificial Sequence
<220> FEATURE:
<223> OTHER INFORMATION: Seynthetic

<400> SEQUENCE: 945
guuccucuuc ccaucucccc 20

<210> SEQ ID NO 946
<211> LENGTH: 20
<212> TYPE: RNA
<213> ORGANISM: Artificial Sequence
<220> FEATURE:
<223> OTHER INFORMATION: Seynthetic

<400> SEQUENCE: 946
guucguaaag uucuuagcua 20

<210> SEQ ID NO 947
<211> LENGTH: 20

<212> TYPE: RNA
<213> ORGANISM: Artificial Sequence
<220> FEATURE:
<223> OTHER INFORMATION: Seynthetic

<400> SEQUENCE: 947
guugcagacc aaggggcugc 20

<210> SEQ ID NO 948
<211> LENGTH: 20
<212> TYPE: RNA
<213> ORGANISM: Artificial Sequence
<220> FEATURE:
<223> OTHER INFORMATION: Seynthetic

<400> SEQUENCE: 948
guugcagcug gaacaucgug 20

<210> SEQ ID NO 949
<211> LENGTH: 20
<212> TYPE: RNA
<213> ORGANISM: Artificial Sequence
<220> FEATURE:
<223> OTHER INFORMATION: Seynthetic

<400> SEQUENCE: 949
guugcagcug gaacauggug 20

<210> SEQ ID NO 950
<211> LENGTH: 20
<212> TYPE: RNA
<213> ORGANISM: Artificial Sequence
<220> FEATURE:
<223> OTHER INFORMATION: Seynthetic

<400> SEQUENCE: 950
guugcauuaa uccauggugc 20

<210> SEQ ID NO 951
<211> LENGTH: 20
<212> TYPE: RNA
<213> ORGANISM: Artificial Sequence
<220> FEATURE:
<223> OTHER INFORMATION: Seynthetic

<400> SEQUENCE: 951
uaaagacugc acgugagaau 20

<210> SEQ ID NO 952
<211> LENGTH: 20
<212> TYPE: RNA
<213> ORGANISM: Artificial Sequence
<220> FEATURE:
<223> OTHER INFORMATION: Seynthetic

<400> SEQUENCE: 952
uaaauucacg uucguaaagu 20

<210> SEQ ID NO 953
<211> LENGTH: 20
<212> TYPE: RNA
<213> ORGANISM: Artificial Sequence
<220> FEATURE:
<223> OTHER INFORMATION: Seynthetic

<400> SEQUENCE: 953
uaagaacuuu acgaacguga 20

<210> SEQ ID NO 954
<211> LENGTH: 20
<212> TYPE: RNA
<213> ORGANISM: Artificial Sequence
<220> FEATURE:
<223> OTHER INFORMATION: Seynthetic

<400> SEQUENCE: 954
uaagaacuuu augaacguga 20

<210> SEQ ID NO 955
<211> LENGTH: 20
<212> TYPE: RNA
<213> ORGANISM: Artificial Sequence
<220> FEATURE:
<223> OTHER INFORMATION: Seynthetic

<400> SEQUENCE: 955
uaauaaagac ugcacgugag 20

<210> SEQ ID NO 956
<211> LENGTH: 20
<212> TYPE: RNA
<213> ORGANISM: Artificial Sequence
<220> FEATURE:
<223> OTHER INFORMATION: Seynthetic

<400> SEQUENCE: 956
uaauaaugac ugcacgugag 20

<210> SEQ ID NO 957
<211> LENGTH: 20
<212> TYPE: RNA
<213> ORGANISM: Artificial Sequence
<220> FEATURE:
<223> OTHER INFORMATION: Seynthetic

<400> SEQUENCE: 957
uaauccaugg ugcggggacc 20

<210> SEQ ID NO 958
<211> LENGTH: 20
<212> TYPE: RNA
<213> ORGANISM: Artificial Sequence
<220> FEATURE:
<223> OTHER INFORMATION: Seynthetic

<400> SEQUENCE: 958
uaaugacugc acgugagaau 20

<210> SEQ ID NO 959
<211> LENGTH: 20
<212> TYPE: RNA
<213> ORGANISM: Artificial Sequence
<220> FEATURE:
<223> OTHER INFORMATION: Seynthetic

<400> SEQUENCE: 959
uacaaugugg ggaagucacu 20

<210> SEQ ID NO 960
<211> LENGTH: 20
<212> TYPE: RNA
<213> ORGANISM: Artificial Sequence
<220> FEATURE:
<223> OTHER INFORMATION: Seynthetic

<400> SEQUENCE: 960
uacacccgcu gugaccauaa 20

<210> SEQ ID NO 961
<211> LENGTH: 20
<212> TYPE: RNA
<213> ORGANISM: Artificial Sequence
<220> FEATURE:
<223> OTHER INFORMATION: Seynthetic

<400> SEQUENCE: 961
uacaccugcu gugaccauaa 20

<210> SEQ ID NO 962
<211> LENGTH: 20
<212> TYPE: RNA
<213> ORGANISM: Artificial Sequence
<220> FEATURE:
<223> OTHER INFORMATION: Seynthetic

<400> SEQUENCE: 962
uacagcgucc cccaccccug 20

<210> SEQ ID NO 963
<211> LENGTH: 20
<212> TYPE: RNA
<213> ORGANISM: Artificial Sequence
<220> FEATURE:
<223> OTHER INFORMATION: Seynthetic

<400> SEQUENCE: 963
uacauucuca cgugcaguca 20

<210> SEQ ID NO 964
<211> LENGTH: 20
<212> TYPE: RNA
<213> ORGANISM: Artificial Sequence
<220> FEATURE:
<223> OTHER INFORMATION: Seynthetic

<400> SEQUENCE: 964
uacauucuca cgugcagucu 20

<210> SEQ ID NO 965
<211> LENGTH: 20
<212> TYPE: RNA
<213> ORGANISM: Artificial Sequence
<220> FEATURE:
<223> OTHER INFORMATION: Seynthetic

<400> SEQUENCE: 965
uacgaacgug aauuuauuuc 20

<210> SEQ ID NO 966
<211> LENGTH: 20
<212> TYPE: RNA
<213> ORGANISM: Artificial Sequence
<220> FEATURE:
<223> OTHER INFORMATION: Seynthetic

<400> SEQUENCE: 966
uacggcgucc cccaccccug 20

<210> SEQ ID NO 967
<211> LENGTH: 20
<212> TYPE: RNA
<213> ORGANISM: Artificial Sequence
<220> FEATURE:
<223> OTHER INFORMATION: Seynthetic

<400> SEQUENCE: 967
uacuacauuc ucacgugcag 20

<210> SEQ ID NO 968
<211> LENGTH: 20
<212> TYPE: RNA
<213> ORGANISM: Artificial Sequence
<220> FEATURE:
<223> OTHER INFORMATION: Seynthetic

<400> SEQUENCE: 968
uagcuaagaa cuuuacgaac 20

<210> SEQ ID NO 969
<211> LENGTH: 20
<212> TYPE: RNA
<213> ORGANISM: Artificial Sequence
<220> FEATURE:
<223> OTHER INFORMATION: Seynthetic

<400> SEQUENCE: 969
uagcuaagaa cuuuaugaac 20

<210> SEQ ID NO 970
<211> LENGTH: 20
<212> TYPE: RNA
<213> ORGANISM: Artificial Sequence
<220> FEATURE:
<223> OTHER INFORMATION: Seynthetic

<400> SEQUENCE: 970
uaggauugug aaacacccug 20

<210> SEQ ID NO 971
<211> LENGTH: 20
<212> TYPE: RNA
<213> ORGANISM: Artificial Sequence
<220> FEATURE:
<223> OTHER INFORMATION: Seynthetic

<400> SEQUENCE: 971
uaggcagggc aggaguuccc 20

<210> SEQ ID NO 972
<211> LENGTH: 20
<212> TYPE: RNA
<213> ORGANISM: Artificial Sequence
<220> FEATURE:
<223> OTHER INFORMATION: Seynthetic

<400> SEQUENCE: 972 uaggggüguu auggucacag 20

<210> SEQ ID NO 973
<211> LENGTH: 20
<212> TYPE: RNA
<213> ORGANISM: Artificial Sequence
<220> FEATURE:
<223> OTHER INFORMATION: Seynthetic

<400> SEQUENCE: 973
uauauggaaa guucagggau 20

<210> SEQ ID NO 974
<211> LENGTH: 20
<212> TYPE: RNA
<213> ORGANISM: Artificial Sequence
<220> FEATURE:
<223> OTHER INFORMATION: Seynthetic

<400> SEQUENCE: 974
uauccccauc cuucuggucc 20

<210> SEQ ID NO 975
<211> LENGTH: 20
<212> TYPE: RNA
<213> ORGANISM: Artificial Sequence
<220> FEATURE:
<223> OTHER INFORMATION: Seynthetic

<400> SEQUENCE: 975
uaucugaaau uugaaugcga 20

<210> SEQ ID NO 976
<211> LENGTH: 20
<212> TYPE: RNA
<213> ORGANISM: Artificial Sequence
<220> FEATURE:
<223> OTHER INFORMATION: Seynthetic

<400> SEQUENCE: 976
uaucugacau uugaaugcga 20

<210> SEQ ID NO 977
<211> LENGTH: 20
<212> TYPE: RNA
<213> ORGANISM: Artificial Sequence
<220> FEATURE:
<223> OTHER INFORMATION: Seynthetic

<400> SEQUENCE: 977
uauggaaagu ucagggaugu 20

<210> SEQ ID NO 978
<211> LENGTH: 20
<212> TYPE: RNA
<213> ORGANISM: Artificial Sequence
<220> FEATURE:
<223> OTHER INFORMATION: Seynthetic

<400> SEQUENCE: 978
uauggucaca gcagguguag 20

<210> SEQ ID NO 979
<211> LENGTH: 20
<212> TYPE: RNA
<213> ORGANISM: Artificial Sequence
<220> FEATURE:
<223> OTHER INFORMATION: Seynthetic

<400> SEQUENCE: 979
uauggucaca gcggguguag 20

<210> SEQ ID NO 980

<211> LENGTH: 20
<212> TYPE: RNA
<213> ORGANISM: Artificial Sequence
<220> FEATURE:
<223> OTHER INFORMATION: Seynthetic

<400> SEQUENCE: 980
ucaaagcaac acuuucuuuu 20

<210> SEQ ID NO 981
<211> LENGTH: 20
<212> TYPE: RNA
<213> ORGANISM: Artificial Sequence
<220> FEATURE:
<223> OTHER INFORMATION: Seynthetic

<400> SEQUENCE: 981
ucaagccaca ccugaaggcg 20

<210> SEQ ID NO 982
<211> LENGTH: 20
<212> TYPE: RNA
<213> ORGANISM: Artificial Sequence
<220> FEATURE:
<223> OTHER INFORMATION: Seynthetic

<400> SEQUENCE: 982
ucaagcccca gaggccacag 20

<210> SEQ ID NO 983
<211> LENGTH: 20
<212> TYPE: RNA
<213> ORGANISM: Artificial Sequence
<220> FEATURE:
<223> OTHER INFORMATION: Seynthetic

<400> SEQUENCE: 983
ucacagcagg uguagacucc 20

<210> SEQ ID NO 984
<211> LENGTH: 20
<212> TYPE: RNA
<213> ORGANISM: Artificial Sequence
<220> FEATURE:
<223> OTHER INFORMATION: Seynthetic

<400> SEQUENCE: 984
ucacagcggg uguagacucc 20

<210> SEQ ID NO 985
<211> LENGTH: 20
<212> TYPE: RNA
<213> ORGANISM: Artificial Sequence
<220> FEATURE:
<223> OTHER INFORMATION: Seynthetic

<400> SEQUENCE: 985
ucaccacacc cagagucacc 20

<210> SEQ ID NO 986
<211> LENGTH: 20
<212> TYPE: RNA
<213> ORGANISM: Artificial Sequence
<220> FEATURE:
<223> OTHER INFORMATION: Seynthetic

<400> SEQUENCE: 986
ucaccacacc cagagucccc 20

<210> SEQ ID NO 987
<211> LENGTH: 20
<212> TYPE: RNA
<213> ORGANISM: Artificial Sequence
<220> FEATURE:
<223> OTHER INFORMATION: Seynthetic

<400> SEQUENCE: 987
ucacccaggg uguuucacaa 20

<210> SEQ ID NO 988
<211> LENGTH: 20
<212> TYPE: RNA
<213> ORGANISM: Artificial Sequence
<220> FEATURE:
<223> OTHER INFORMATION: Seynthetic

<400> SEQUENCE: 988
ucacgucaag acuccagccu 20

<210> SEQ ID NO 989
<211> LENGTH: 20
<212> TYPE: RNA
<213> ORGANISM: Artificial Sequence
<220> FEATURE:
<223> OTHER INFORMATION: Seynthetic

<400> SEQUENCE: 989
ucacgucagg acuccagccu 20

<210> SEQ ID NO 990
<211> LENGTH: 20
<212> TYPE: RNA
<213> ORGANISM: Artificial Sequence
<220> FEATURE:
<223> OTHER INFORMATION: Seynthetic

<400> SEQUENCE: 990
ucacgugcag ucauuauuaa 20

<210> SEQ ID NO 991
<211> LENGTH: 20
<212> TYPE: RNA
<213> ORGANISM: Artificial Sequence
<220> FEATURE:
<223> OTHER INFORMATION: Seynthetic

<400> SEQUENCE: 991
ucacgugcag ucuuuauuaa 20

<210> SEQ ID NO 992
<211> LENGTH: 20
<212> TYPE: RNA
<213> ORGANISM: Artificial Sequence
<220> FEATURE:
<223> OTHER INFORMATION: Seynthetic

<400> SEQUENCE: 992
ucacguucau aaaguucuua 20

<210> SEQ ID NO 993
<211> LENGTH: 20
<212> TYPE: RNA

<213> ORGANISM: Artificial Sequence
<220> FEATURE:
<223> OTHER INFORMATION: Seynthetic

<400> SEQUENCE: 993
ucacguucgu aaaguucuua 20

<210> SEQ ID NO 994
<211> LENGTH: 20
<212> TYPE: RNA
<213> ORGANISM: Artificial Sequence
<220> FEATURE:
<223> OTHER INFORMATION: Seynthetic

<400> SEQUENCE: 994
ucaggacucc agccuggccc 20

<210> SEQ ID NO 995
<211> LENGTH: 20
<212> TYPE: RNA
<213> ORGANISM: Artificial Sequence
<220> FEATURE:
<223> OTHER INFORMATION: Seynthetic

<400> SEQUENCE: 995
ucagggaugu ccgccuucag 20

<210> SEQ ID NO 996
<211> LENGTH: 20
<212> TYPE: RNA
<213> ORGANISM: Artificial Sequence
<220> FEATURE:
<223> OTHER INFORMATION: Seynthetic

<400> SEQUENCE: 996
ucaggggugg gggacgccgu 20

<210> SEQ ID NO 997
<211> LENGTH: 20
<212> TYPE: RNA
<213> ORGANISM: Artificial Sequence
<220> FEATURE:
<223> OTHER INFORMATION: Seynthetic

<400> SEQUENCE: 997
ucaggggugg gggacgcugu 20

<210> SEQ ID NO 998
<211> LENGTH: 20
<212> TYPE: RNA
<213> ORGANISM: Artificial Sequence
<220> FEATURE:
<223> OTHER INFORMATION: Seynthetic

<400> SEQUENCE: 998 ucagggugu caagccccaga 20

<210> SEQ ID NO 999
<211> LENGTH: 20
<212> TYPE: RNA
<213> ORGANISM: Artificial Sequence
<220> FEATURE:
<223> OTHER INFORMATION: Seynthetic

<400> SEQUENCE: 999
ucaugcuucu accagggaac 20

<210> SEQ ID NO 1000
<211> LENGTH: 20
<212> TYPE: RNA
<213> ORGANISM: Artificial Sequence
<220> FEATURE:
<223> OTHER INFORMATION: Seynthetic

<400> SEQUENCE: 1000
ucaugcuucu accagggagc 20

<210> SEQ ID NO 1001
<211> LENGTH: 20
<212> TYPE: RNA
<213> ORGANISM: Artificial Sequence
<220> FEATURE:
<223> OTHER INFORMATION: Seynthetic

<400> SEQUENCE: 1001
ucauuauuaa gugugccgac 20

<210> SEQ ID NO 1002
<211> LENGTH: 20
<212> TYPE: RNA
<213> ORGANISM: Artificial Sequence
<220> FEATURE:
<223> OTHER INFORMATION: Seynthetic

<400> SEQUENCE: 1002
uccaaagaua cagcgucccc 20

<210> SEQ ID NO 1003
<211> LENGTH: 20
<212> TYPE: RNA
<213> ORGANISM: Artificial Sequence
<220> FEATURE:
<223> OTHER INFORMATION: Seynthetic

<400> SEQUENCE: 1003
uccaaagaua cggcgucccc 20

<210> SEQ ID NO 1004
<211> LENGTH: 20
<212> TYPE: RNA
<213> ORGANISM: Artificial Sequence
<220> FEATURE:
<223> OTHER INFORMATION: Seynthetic

<400> SEQUENCE: 1004
uccacagggg gacuccggca 20

<210> SEQ ID NO 1005
<211> LENGTH: 20
<212> TYPE: RNA
<213> ORGANISM: Artificial Sequence
<220> FEATURE:
<223> OTHER INFORMATION: Seynthetic

<400> SEQUENCE: 1005
uccacuugcc uguggucacg 20

<210> SEQ ID NO 1006
<211> LENGTH: 20
<212> TYPE: RNA
<213> ORGANISM: Artificial Sequence
<220> FEATURE:

<223> OTHER INFORMATION: Seynthetic

<400> SEQUENCE: 1006
uccaugguga agagaaaagc 20

<210> SEQ ID NO 1007
<211> LENGTH: 20
<212> TYPE: RNA
<213> ORGANISM: Artificial Sequence
<220> FEATURE:
<223> OTHER INFORMATION: Seynthetic

<400> SEQUENCE: 1007
uccauggugc agggaccaga 20

<210> SEQ ID NO 1008
<211> LENGTH: 20
<212> TYPE: RNA
<213> ORGANISM: Artificial Sequence
<220> FEATURE:
<223> OTHER INFORMATION: Seynthetic

<400> SEQUENCE: 1008
uccauggugc ggggaccaga 20

<210> SEQ ID NO 1009
<211> LENGTH: 20
<212> TYPE: RNA
<213> ORGANISM: Artificial Sequence
<220> FEATURE:
<223> OTHER INFORMATION: Seynthetic

<400> SEQUENCE: 1009
ucccagcugc gggaaaggga 20

<210> SEQ ID NO 1010
<211> LENGTH: 20
<212> TYPE: RNA
<213> ORGANISM: Artificial Sequence
<220> FEATURE:
<223> OTHER INFORMATION: Seynthetic

<400> SEQUENCE: 1010
ucccagcugc gggaauggga 20

<210> SEQ ID NO 1011
<211> LENGTH: 20
<212> TYPE: RNA
<213> ORGANISM: Artificial Sequence
<220> FEATURE:
<223> OTHER INFORMATION: Seynthetic

<400> SEQUENCE: 1011
ucccaucucc cccaccaugu 20

<210> SEQ ID NO 1012
<211> LENGTH: 20
<212> TYPE: RNA
<213> ORGANISM: Artificial Sequence
<220> FEATURE:
<223> OTHER INFORMATION: Seynthetic

<400> SEQUENCE: 1012
ucccaucucc cccacgaugu 20

<210> SEQ ID NO 1013
<211> LENGTH: 20
<212> TYPE: RNA
<213> ORGANISM: Artificial Sequence
<220> FEATURE:
<223> OTHER INFORMATION: Seynthetic

<400> SEQUENCE: 1013
ucccauuccc gcagcuggga 20

<210> SEQ ID NO 1014
<211> LENGTH: 20
<212> TYPE: RNA
<213> ORGANISM: Artificial Sequence
<220> FEATURE:
<223> OTHER INFORMATION: Seynthetic

<400> SEQUENCE: 1014
uccccauccu ucuggucccc 20

<210> SEQ ID NO 1015
<211> LENGTH: 20
<212> TYPE: RNA
<213> ORGANISM: Artificial Sequence
<220> FEATURE:
<223> OTHER INFORMATION: Seynthetic

<400> SEQUENCE: 1015
uccccauccu ucugguccccu 20

<210> SEQ ID NO 1016
<211> LENGTH: 20
<212> TYPE: RNA
<213> ORGANISM: Artificial Sequence
<220> FEATURE:
<223> OTHER INFORMATION: Seynthetic

<400> SEQUENCE: 1016
ucccccaggg uguuucacaa 20

<210> SEQ ID NO 1017
<211> LENGTH: 20
<212> TYPE: RNA
<213> ORGANISM: Artificial Sequence
<220> FEATURE:
<223> OTHER INFORMATION: Seynthetic

<400> SEQUENCE: 1017
ucccccggcu uuucucuuca 20

<210> SEQ ID NO 1018
<211> LENGTH: 20
<212> TYPE: RNA
<213> ORGANISM: Artificial Sequence
<220> FEATURE:
<223> OTHER INFORMATION: Seynthetic

<400> SEQUENCE: 1018
ucccccucgg agucuacacc 20

<210> SEQ ID NO 1019
<211> LENGTH: 20
<212> TYPE: RNA
<213> ORGANISM: Artificial Sequence
<220> FEATURE:
<223> OTHER INFORMATION: Seynthetic

<400> SEQUENCE: 1019
uccccgcacc auggauuaau 20

<210> SEQ ID NO 1020
<211> LENGTH: 20
<212> TYPE: RNA
<213> ORGANISM: Artificial Sequence
<220> FEATURE:
<223> OTHER INFORMATION: Seynthetic

<400> SEQUENCE: 1020
ucccugcacc auggauuaau 20

<210> SEQ ID NO 1021
<211> LENGTH: 20
<212> TYPE: RNA
<213> ORGANISM: Artificial Sequence
<220> FEATURE:
<223> OTHER INFORMATION: Seynthetic

<400> SEQUENCE: 1021
ucccuguggc cucuggggcu 20

<210> SEQ ID NO 1022
<211> LENGTH: 20
<212> TYPE: RNA
<213> ORGANISM: Artificial Sequence
<220> FEATURE:
<223> OTHER INFORMATION: Seynthetic

<400> SEQUENCE: 1022
ucccuguguc cucuggggcu 20

<210> SEQ ID NO 1023
<211> LENGTH: 20
<212> TYPE: RNA
<213> ORGANISM: Artificial Sequence
<220> FEATURE:
<223> OTHER INFORMATION: Seynthetic

<400> SEQUENCE: 1023
ucccuuuccc gcagcuggga 20

<210> SEQ ID NO 1024
<211> LENGTH: 20
<212> TYPE: RNA
<213> ORGANISM: Artificial Sequence
<220> FEATURE:
<223> OTHER INFORMATION: Seynthetic

<400> SEQUENCE: 1024
uccggcagcc ccuuggucug 20

<210> SEQ ID NO 1025
<211> LENGTH: 20
<212> TYPE: RNA
<213> ORGANISM: Artificial Sequence
<220> FEATURE:
<223> OTHER INFORMATION: Seynthetic

<400> SEQUENCE: 1025
uccuccagcc ccgccaggug 20

<210> SEQ ID NO 1026
<211> LENGTH: 20

<212> TYPE: RNA
<213> ORGANISM: Artificial Sequence
<220> FEATURE:
<223> OTHER INFORMATION: Seynthetic

<400> SEQUENCE: 1026
uccucugggg cuugacaccc 20

<210> SEQ ID NO 1027
<211> LENGTH: 20
<212> TYPE: RNA
<213> ORGANISM: Artificial Sequence
<220> FEATURE:
<223> OTHER INFORMATION: Seynthetic

<400> SEQUENCE: 1027
uccucuuccc aucuccccca 20

<210> SEQ ID NO 1028
<211> LENGTH: 20
<212> TYPE: RNA
<213> ORGANISM: Artificial Sequence
<220> FEATURE:
<223> OTHER INFORMATION: Seynthetic

<400> SEQUENCE: 1028
uccugacgug accacaggca 20

<210> SEQ ID NO 1029
<211> LENGTH: 20
<212> TYPE: RNA
<213> ORGANISM: Artificial Sequence
<220> FEATURE:
<223> OTHER INFORMATION: Seynthetic

<400> SEQUENCE: 1029
uccugggaau cccauucccg 20

<210> SEQ ID NO 1030
<211> LENGTH: 20
<212> TYPE: RNA
<213> ORGANISM: Artificial Sequence
<220> FEATURE:
<223> OTHER INFORMATION: Seynthetic

<400> SEQUENCE: 1030
uccugggaau cccuuucccg 20

<210> SEQ ID NO 1031
<211> LENGTH: 20
<212> TYPE: RNA
<213> ORGANISM: Artificial Sequence
<220> FEATURE:
<223> OTHER INFORMATION: Seynthetic

<400> SEQUENCE: 1031
uccuucuggu ccccgcacca 20

<210> SEQ ID NO 1032
<211> LENGTH: 20
<212> TYPE: RNA
<213> ORGANISM: Artificial Sequence
<220> FEATURE:
<223> OTHER INFORMATION: Seynthetic

<400> SEQUENCE: 1032
uccuucuggu cccugcacca 20

<210> SEQ ID NO 1033
<211> LENGTH: 20
<212> TYPE: RNA
<213> ORGANISM: Artificial Sequence
<220> FEATURE:
<223> OTHER INFORMATION: Seynthetic

<400> SEQUENCE: 1033
ucgcauucaa augucagaua 20

<210> SEQ ID NO 1034
<211> LENGTH: 20
<212> TYPE: RNA
<213> ORGANISM: Artificial Sequence
<220> FEATURE:
<223> OTHER INFORMATION: Seynthetic

<400> SEQUENCE: 1034
ucggagucua cacccgcugu 20

<210> SEQ ID NO 1035
<211> LENGTH: 20
<212> TYPE: RNA
<213> ORGANISM: Artificial Sequence
<220> FEATURE:
<223> OTHER INFORMATION: Seynthetic

<400> SEQUENCE: 1035
ucggagucua caccugcugu 20

<210> SEQ ID NO 1036
<211> LENGTH: 20
<212> TYPE: RNA
<213> ORGANISM: Artificial Sequence
<220> FEATURE:
<223> OTHER INFORMATION: Seynthetic

<400> SEQUENCE: 1036
ucggcacacu uaauaaagac 20

<210> SEQ ID NO 1037
<211> LENGTH: 20
<212> TYPE: RNA
<213> ORGANISM: Artificial Sequence
<220> FEATURE:
<223> OTHER INFORMATION: Seynthetic

<400> SEQUENCE: 1037
ucggcacacu uaauaaugac 20

<210> SEQ ID NO 1038
<211> LENGTH: 20
<212> TYPE: RNA
<213> ORGANISM: Artificial Sequence
<220> FEATURE:
<223> OTHER INFORMATION: Seynthetic

<400> SEQUENCE: 1038
ucguaaaguu cuuagcuaag 20

<210> SEQ ID NO 1039
<211> LENGTH: 20
<212> TYPE: RNA
<213> ORGANISM: Artificial Sequence
<220> FEATURE:
<223> OTHER INFORMATION: Seynthetic

<400> SEQUENCE: 1039
ucguggggga gaugggaaga 20

<210> SEQ ID NO 1040
<211> LENGTH: 20
<212> TYPE: RNA
<213> ORGANISM: Artificial Sequence
<220> FEATURE:
<223> OTHER INFORMATION: Seynthetic

<400> SEQUENCE: 1040
ucuacacccg cugugaccau 20

<210> SEQ ID NO 1041
<211> LENGTH: 20
<212> TYPE: RNA
<213> ORGANISM: Artificial Sequence
<220> FEATURE:
<223> OTHER INFORMATION: Seynthetic

<400> SEQUENCE: 1041
ucucaaagca acacuuucuu 20

<210> SEQ ID NO 1042
<211> LENGTH: 20
<212> TYPE: RNA
<213> ORGANISM: Artificial Sequence
<220> FEATURE:
<223> OTHER INFORMATION: Seynthetic

<400> SEQUENCE: 1042
ucucacgugc agucauuauu 20

<210> SEQ ID NO 1043
<211> LENGTH: 20
<212> TYPE: RNA
<213> ORGANISM: Artificial Sequence
<220> FEATURE:
<223> OTHER INFORMATION: Seynthetic

<400> SEQUENCE: 1043
ucucacgugc agucuuuauu 20

<210> SEQ ID NO 1044
<211> LENGTH: 20
<212> TYPE: RNA
<213> ORGANISM: Artificial Sequence
<220> FEATURE:
<223> OTHER INFORMATION: Seynthetic

<400> SEQUENCE: 1044
ucucccccac cauguuccag 20

<210> SEQ ID NO 1045
<211> LENGTH: 20
<212> TYPE: RNA
<213> ORGANISM: Artificial Sequence
<220> FEATURE:
<223> OTHER INFORMATION: Seynthetic

<400> SEQUENCE: 1045
ucucccccac gauguuccag 20

<210> SEQ ID NO 1046
<211> LENGTH: 20
<212> TYPE: RNA
<213> ORGANISM: Artificial Sequence
<220> FEATURE:
<223> OTHER INFORMATION: Seynthetic

<400> SEQUENCE: 1046
ucucuguccc uguggccucu 20

<210> SEQ ID NO 1047
<211> LENGTH: 20
<212> TYPE: RNA
<213> ORGANISM: Artificial Sequence
<220> FEATURE:
<223> OTHER INFORMATION: Seynthetic

<400> SEQUENCE: 1047
ucucuguccc uguguccucu 20

<210> SEQ ID NO 1048
<211> LENGTH: 20
<212> TYPE: RNA
<213> ORGANISM: Artificial Sequence
<220> FEATURE:
<223> OTHER INFORMATION: Seynthetic

<400> SEQUENCE: 1048
ucugaaauuu gaaugcgauu 20

<210> SEQ ID NO 1049
<211> LENGTH: 20
<212> TYPE: RNA
<213> ORGANISM: Artificial Sequence
<220> FEATURE:
<223> OTHER INFORMATION: Seynthetic

<400> SEQUENCE: 1049
ucugacauuu gaaugcgauu 20

<210> SEQ ID NO 1050
<211> LENGTH: 20
<212> TYPE: RNA
<213> ORGANISM: Artificial Sequence
<220> FEATURE:
<223> OTHER INFORMATION: Seynthetic

<400> SEQUENCE: 1050
ucugccucca cagggggacu 20

<210> SEQ ID NO 1051
<211> LENGTH: 20
<212> TYPE: RNA
<213> ORGANISM: Artificial Sequence
<220> FEATURE:
<223> OTHER INFORMATION: Seynthetic

<400> SEQUENCE: 1051
ucuggucccc gcaccaugga 20

<210> SEQ ID NO 1052
<211> LENGTH: 20
<212> TYPE: RNA
<213> ORGANISM: Artificial Sequence
<220> FEATURE:
<223> OTHER INFORMATION: Seynthetic

<400> SEQUENCE: 1052
ucuggucccu gcaccaugga 20

<210> SEQ ID NO 1053
<211> LENGTH: 20
<212> TYPE: RNA
<213> ORGANISM: Artificial Sequence
<220> FEATURE:
<223> OTHER INFORMATION: Seynthetic

<400> SEQUENCE: 1053
ucugucccug uguccucugg 20

<210> SEQ ID NO 1054
<211> LENGTH: 20
<212> TYPE: RNA
<213> ORGANISM: Artificial Sequence
<220> FEATURE:
<223> OTHER INFORMATION: Seynthetic

<400> SEQUENCE: 1054
ucuuagcuaa gaacuuuacg 20

<210> SEQ ID NO 1055
<211> LENGTH: 20
<212> TYPE: RNA
<213> ORGANISM: Artificial Sequence
<220> FEATURE:
<223> OTHER INFORMATION: Seynthetic

<400> SEQUENCE: 1055
ucuucccauc ucccccacca 20

<210> SEQ ID NO 1056
<211> LENGTH: 20
<212> TYPE: RNA
<213> ORGANISM: Artificial Sequence
<220> FEATURE:
<223> OTHER INFORMATION: Seynthetic

<400> SEQUENCE: 1056
ucuucccauc ucccccacga 20

<210> SEQ ID NO 1057
<211> LENGTH: 20
<212> TYPE: RNA
<213> ORGANISM: Artificial Sequence
<220> FEATURE:
<223> OTHER INFORMATION: Seynthetic

<400> SEQUENCE: 1057
ucuugacgug accacaggca 20

<210> SEQ ID NO 1058
<211> LENGTH: 20
<212> TYPE: RNA
<213> ORGANISM: Artificial Sequence
<220> FEATURE:
<223> OTHER INFORMATION: Seynthetic

<400> SEQUENCE: 1058
ucuuuauuaa gugugccgac 20

<210> SEQ ID NO 1059

<211> LENGTH: 20
<212> TYPE: RNA
<213> ORGANISM: Artificial Sequence
<220> FEATURE:
<223> OTHER INFORMATION: Seynthetic

<400> SEQUENCE: 1059
ugaaacaccc ugggggacuc 20

<210> SEQ ID NO 1060
<211> LENGTH: 20
<212> TYPE: RNA
<213> ORGANISM: Artificial Sequence
<220> FEATURE:
<223> OTHER INFORMATION: Seynthetic

<400> SEQUENCE: 1060
ugaaacaccc ugggugacuc 20

<210> SEQ ID NO 1061
<211> LENGTH: 20
<212> TYPE: RNA
<213> ORGANISM: Artificial Sequence
<220> FEATURE:
<223> OTHER INFORMATION: Seynthetic

<400> SEQUENCE: 1061
ugaaauaaau ucacguucgu 20

<210> SEQ ID NO 1062
<211> LENGTH: 20
<212> TYPE: RNA
<213> ORGANISM: Artificial Sequence
<220> FEATURE:
<223> OTHER INFORMATION: Seynthetic

<400> SEQUENCE: 1062
ugaaauuuga augcgauugu 20

<210> SEQ ID NO 1063
<211> LENGTH: 20
<212> TYPE: RNA
<213> ORGANISM: Artificial Sequence
<220> FEATURE:
<223> OTHER INFORMATION: Seynthetic

<400> SEQUENCE: 1063
ugaagagaaa agcaggggga 20

<210> SEQ ID NO 1064
<211> LENGTH: 20
<212> TYPE: RNA
<213> ORGANISM: Artificial Sequence
<220> FEATURE:
<223> OTHER INFORMATION: Seynthetic

<400> SEQUENCE: 1064
ugaagagaaa agccggggga 20

<210> SEQ ID NO 1065
<211> LENGTH: 20
<212> TYPE: RNA
<213> ORGANISM: Artificial Sequence
<220> FEATURE:
<223> OTHER INFORMATION: Seynthetic

<400> SEQUENCE: 1065
ugaaggcgga caucccugaa 20

<210> SEQ ID NO 1066
<211> LENGTH: 20
<212> TYPE: RNA
<213> ORGANISM: Artificial Sequence
<220> FEATURE:
<223> OTHER INFORMATION: Seynthetic

<400> SEQUENCE: 1066
ugacucuggg uguggugaag 20

<210> SEQ ID NO 1067
<211> LENGTH: 20
<212> TYPE: RNA
<213> ORGANISM: Artificial Sequence
<220> FEATURE:
<223> OTHER INFORMATION: Seynthetic

<400> SEQUENCE: 1067
ugacuucccc acauuguauu 20

<210> SEQ ID NO 1068
<211> LENGTH: 20
<212> TYPE: RNA
<213> ORGANISM: Artificial Sequence
<220> FEATURE:
<223> OTHER INFORMATION: Seynthetic

<400> SEQUENCE: 1068
ugacuucccc acauuguguu 20

<210> SEQ ID NO 1069
<211> LENGTH: 20
<212> TYPE: RNA
<213> ORGANISM: Artificial Sequence
<220> FEATURE:
<223> OTHER INFORMATION: Seynthetic

<400> SEQUENCE: 1069
ugaguccccc uguggaggca 20

<210> SEQ ID NO 1070
<211> LENGTH: 20
<212> TYPE: RNA
<213> ORGANISM: Artificial Sequence
<220> FEATURE:
<223> OTHER INFORMATION: Seynthetic

<400> SEQUENCE: 1070
ugcacaaucg cauucaaaug 20

<210> SEQ ID NO 1071
<211> LENGTH: 20
<212> TYPE: RNA
<213> ORGANISM: Artificial Sequence
<220> FEATURE:
<223> OTHER INFORMATION: Seynthetic

<400> SEQUENCE: 1071
ugcacaaucg cauucaaauu 20

<210> SEQ ID NO 1072
<211> LENGTH: 20
<212> TYPE: RNA

<213> ORGANISM: Artificial Sequence
<220> FEATURE:
<223> OTHER INFORMATION: Seynthetic

<400> SEQUENCE: 1072
ugcaccaugg auuaaugcaa 20

<210> SEQ ID NO 1073
<211> LENGTH: 20
<212> TYPE: RNA
<213> ORGANISM: Artificial Sequence
<220> FEATURE:
<223> OTHER INFORMATION: Seynthetic

<400> SEQUENCE: 1073
ugcagaccaa ggggcugccg 20

<210> SEQ ID NO 1074
<211> LENGTH: 20
<212> TYPE: RNA
<213> ORGANISM: Artificial Sequence
<220> FEATURE:
<223> OTHER INFORMATION: Seynthetic

<400> SEQUENCE: 1074
ugcagcugga acaucguggg 20

<210> SEQ ID NO 1075
<211> LENGTH: 20
<212> TYPE: RNA
<213> ORGANISM: Artificial Sequence
<220> FEATURE:
<223> OTHER INFORMATION: Seynthetic

<400> SEQUENCE: 1075
ugcagcugga acauggguggg 20

<210> SEQ ID NO 1076
<211> LENGTH: 20
<212> TYPE: RNA
<213> ORGANISM: Artificial Sequence
<220> FEATURE:
<223> OTHER INFORMATION: Seynthetic

<400> SEQUENCE: 1076
ugcagggacc agaaggaugg 20

<210> SEQ ID NO 1077
<211> LENGTH: 20
<212> TYPE: RNA
<213> ORGANISM: Artificial Sequence
<220> FEATURE:
<223> OTHER INFORMATION: Seynthetic

<400> SEQUENCE: 1077
ugcagucauu auuaagugug 20

<210> SEQ ID NO 1078
<211> LENGTH: 20
<212> TYPE: RNA
<213> ORGANISM: Artificial Sequence
<220> FEATURE:
<223> OTHER INFORMATION: Seynthetic

<400> SEQUENCE: 1078
ugcagucuuu auuaagugug 20

<210> SEQ ID NO 1079
<211> LENGTH: 20
<212> TYPE: RNA
<213> ORGANISM: Artificial Sequence
<220> FEATURE:
<223> OTHER INFORMATION: Seynthetic

<400> SEQUENCE: 1079
ugcauuaauc cauggugcag 20

<210> SEQ ID NO 1080
<211> LENGTH: 20
<212> TYPE: RNA
<213> ORGANISM: Artificial Sequence
<220> FEATURE:
<223> OTHER INFORMATION: Seynthetic

<400> SEQUENCE: 1080
ugccuguggu cacgucaaga 20

<210> SEQ ID NO 1081
<211> LENGTH: 20
<212> TYPE: RNA
<213> ORGANISM: Artificial Sequence
<220> FEATURE:
<223> OTHER INFORMATION: Seynthetic

<400> SEQUENCE: 1081
ugccuguggu cacgucagga 20

<210> SEQ ID NO 1082
<211> LENGTH: 20
<212> TYPE: RNA
<213> ORGANISM: Artificial Sequence
<220> FEATURE:
<223> OTHER INFORMATION: Seynthetic

<400> SEQUENCE: 1082
ugcgggaaag ggauucccag 20

<210> SEQ ID NO 1083
<211> LENGTH: 20
<212> TYPE: RNA
<213> ORGANISM: Artificial Sequence
<220> FEATURE:
<223> OTHER INFORMATION: Seynthetic

<400> SEQUENCE: 1083
ugcgggaaug ggauucccag 20

<210> SEQ ID NO 1084
<211> LENGTH: 20
<212> TYPE: RNA
<213> ORGANISM: Artificial Sequence
<220> FEATURE:
<223> OTHER INFORMATION: Seynthetic

<400> SEQUENCE: 1084
ugcggggacc agaaggaugg 20

<210> SEQ ID NO 1085
<211> LENGTH: 20
<212> TYPE: RNA
<213> ORGANISM: Artificial Sequence
<220> FEATURE:

<223> OTHER INFORMATION: Seynthetic

<400> SEQUENCE: 1085
ugcucaugcu ucuaccaggg 20

<210> SEQ ID NO 1086
<211> LENGTH: 20
<212> TYPE: RNA
<213> ORGANISM: Artificial Sequence
<220> FEATURE:
<223> OTHER INFORMATION: Seynthetic

<400> SEQUENCE: 1086
ugcugugacc auaacacccc 20

<210> SEQ ID NO 1087
<211> LENGTH: 20
<212> TYPE: RNA
<213> ORGANISM: Artificial Sequence
<220> FEATURE:
<223> OTHER INFORMATION: Seynthetic

<400> SEQUENCE: 1087
ugcuucuacc agggaacucc 20

<210> SEQ ID NO 1088
<211> LENGTH: 20
<212> TYPE: RNA
<213> ORGANISM: Artificial Sequence
<220> FEATURE:
<223> OTHER INFORMATION: Seynthetic

<400> SEQUENCE: 1088
ugcuucuacc agggagcucc 20

<210> SEQ ID NO 1089
<211> LENGTH: 20
<212> TYPE: RNA
<213> ORGANISM: Artificial Sequence
<220> FEATURE:
<223> OTHER INFORMATION: Seynthetic

<400> SEQUENCE: 1089
uggaaaguuc agggaugucc 20

<210> SEQ ID NO 1090
<211> LENGTH: 20
<212> TYPE: RNA
<213> ORGANISM: Artificial Sequence
<220> FEATURE:
<223> OTHER INFORMATION: Seynthetic

<400> SEQUENCE: 1090
uggaacaucg ugggggagau 20

<210> SEQ ID NO 1091
<211> LENGTH: 20
<212> TYPE: RNA
<213> ORGANISM: Artificial Sequence
<220> FEATURE:
<223> OTHER INFORMATION: Seynthetic

<400> SEQUENCE: 1091
uggaacaugg ugggggagau 20

<210> SEQ ID NO 1092
<211> LENGTH: 20
<212> TYPE: RNA
<213> ORGANISM: Artificial Sequence
<220> FEATURE:
<223> OTHER INFORMATION: Seynthetic

<400> SEQUENCE: 1092
uggaggggcu ggaggaccgu 20

<210> SEQ ID NO 1093
<211> LENGTH: 20
<212> TYPE: RNA
<213> ORGANISM: Artificial Sequence
<220> FEATURE:
<223> OTHER INFORMATION: Seynthetic

<400> SEQUENCE: 1093
uggaguccca gcugcgggaa 20

<210> SEQ ID NO 1094
<211> LENGTH: 20
<212> TYPE: RNA
<213> ORGANISM: Artificial Sequence
<220> FEATURE:
<223> OTHER INFORMATION: Seynthetic

<400> SEQUENCE: 1094
uggaguccug acgugaccac 20

<210> SEQ ID NO 1095
<211> LENGTH: 20
<212> TYPE: RNA
<213> ORGANISM: Artificial Sequence
<220> FEATURE:
<223> OTHER INFORMATION: Seynthetic

<400> SEQUENCE: 1095
uggagucuug acgugaccac 20

<210> SEQ ID NO 1096
<211> LENGTH: 20
<212> TYPE: RNA
<213> ORGANISM: Artificial Sequence
<220> FEATURE:
<223> OTHER INFORMATION: Seynthetic

<400> SEQUENCE: 1096
uggauucuag uuuguuguuu 20

<210> SEQ ID NO 1097
<211> LENGTH: 20
<212> TYPE: RNA
<213> ORGANISM: Artificial Sequence
<220> FEATURE:
<223> OTHER INFORMATION: Seynthetic

<400> SEQUENCE: 1097
uggccucugg ggcuugacac 20

<210> SEQ ID NO 1098
<211> LENGTH: 20
<212> TYPE: RNA
<213> ORGANISM: Artificial Sequence
<220> FEATURE:
<223> OTHER INFORMATION: Seynthetic

<400> SEQUENCE: 1098
uggcggggcu ggaggaccgu 20

<210> SEQ ID NO 1099
<211> LENGTH: 20
<212> TYPE: RNA
<213> ORGANISM: Artificial Sequence
<220> FEATURE:
<223> OTHER INFORMATION: Seynthetic

<400> SEQUENCE: 1099
ugggaauccc auucccgcag 20

<210> SEQ ID NO 1100
<211> LENGTH: 20
<212> TYPE: RNA
<213> ORGANISM: Artificial Sequence
<220> FEATURE:
<223> OTHER INFORMATION: Seynthetic

<400> SEQUENCE: 1100
ugggaauccc uuucccgcag 20

<210> SEQ ID NO 1101
<211> LENGTH: 20
<212> TYPE: RNA
<213> ORGANISM: Artificial Sequence
<220> FEATURE:
<223> OTHER INFORMATION: Seynthetic

<400> SEQUENCE: 1101
ugggauuccc aggacccagc 20

<210> SEQ ID NO 1102
<211> LENGTH: 20
<212> TYPE: RNA
<213> ORGANISM: Artificial Sequence
<220> FEATURE:
<223> OTHER INFORMATION: Seynthetic

<400> SEQUENCE: 1102
ugggccaggc uggaguccug 20

<210> SEQ ID NO 1103
<211> LENGTH: 20
<212> TYPE: RNA
<213> ORGANISM: Artificial Sequence
<220> FEATURE:
<223> OTHER INFORMATION: Seynthetic

<400> SEQUENCE: 1103
ugggccaggc uggagucuug 20

<210> SEQ ID NO 1104
<211> LENGTH: 20
<212> TYPE: RNA
<213> ORGANISM: Artificial Sequence
<220> FEATURE:
<223> OTHER INFORMATION: Seynthetic

<400> SEQUENCE: 1104
ugggggacgc cguaucuuug 20

<210> SEQ ID NO 1105
<211> LENGTH: 20

<212> TYPE: RNA
<213> ORGANISM: Artificial Sequence
<220> FEATURE:
<223> OTHER INFORMATION: Seynthetic

<400> SEQUENCE: 1105
ugggggacgc uguaucuuug 20

<210> SEQ ID NO 1106
<211> LENGTH: 20
<212> TYPE: RNA
<213> ORGANISM: Artificial Sequence
<220> FEATURE:
<223> OTHER INFORMATION: Seynthetic

<400> SEQUENCE: 1106
ugggggacuc ugggguguggu 20

<210> SEQ ID NO 1107
<211> LENGTH: 20
<212> TYPE: RNA
<213> ORGANISM: Artificial Sequence
<220> FEATURE:
<223> OTHER INFORMATION: Seynthetic

<400> SEQUENCE: 1107
uggguccugg gaaucccauu 20

<210> SEQ ID NO 1108
<211> LENGTH: 20
<212> TYPE: RNA
<213> ORGANISM: Artificial Sequence
<220> FEATURE:
<223> OTHER INFORMATION: Seynthetic

<400> SEQUENCE: 1108
uggguccugg gaaucccuuu 20

<210> SEQ ID NO 1109
<211> LENGTH: 20
<212> TYPE: RNA
<213> ORGANISM: Artificial Sequence
<220> FEATURE:
<223> OTHER INFORMATION: Seynthetic

<400> SEQUENCE: 1109
ugggugacuc ugggguguggu 20

<210> SEQ ID NO 1110
<211> LENGTH: 20
<212> TYPE: RNA
<213> ORGANISM: Artificial Sequence
<220> FEATURE:
<223> OTHER INFORMATION: Seynthetic

<400> SEQUENCE: 1110
uggucacagc agguguagac 20

<210> SEQ ID NO 1111
<211> LENGTH: 20
<212> TYPE: RNA
<213> ORGANISM: Artificial Sequence
<220> FEATURE:
<223> OTHER INFORMATION: Seynthetic

<400> SEQUENCE: 1111
uggucacagc ggguguagac 20

<210> SEQ ID NO 1112
<211> LENGTH: 20
<212> TYPE: RNA
<213> ORGANISM: Artificial Sequence
<220> FEATURE:
<223> OTHER INFORMATION: Seynthetic

<400> SEQUENCE: 1112
uggucacguc aagacuccag 20

<210> SEQ ID NO 1113
<211> LENGTH: 20
<212> TYPE: RNA
<213> ORGANISM: Artificial Sequence
<220> FEATURE:
<223> OTHER INFORMATION: Seynthetic

<400> SEQUENCE: 1113
uggucacguc aggacuccag 20

<210> SEQ ID NO 1114
<211> LENGTH: 20
<212> TYPE: RNA
<213> ORGANISM: Artificial Sequence
<220> FEATURE:
<223> OTHER INFORMATION: Seynthetic

<400> SEQUENCE: 1114
ugguccccgc accauggauu 20

<210> SEQ ID NO 1115
<211> LENGTH: 20
<212> TYPE: RNA
<213> ORGANISM: Artificial Sequence
<220> FEATURE:
<223> OTHER INFORMATION: Seynthetic

<400> SEQUENCE: 1115 ugguccugc accauggauu 20

<210> SEQ ID NO 1116
<211> LENGTH: 20
<212> TYPE: RNA
<213> ORGANISM: Artificial Sequence
<220> FEATURE:
<223> OTHER INFORMATION: Seynthetic

<400> SEQUENCE: 1116
uggugaagag aaaagcaggg 20

<210> SEQ ID NO 1117
<211> LENGTH: 20
<212> TYPE: RNA
<213> ORGANISM: Artificial Sequence
<220> FEATURE:
<223> OTHER INFORMATION: Seynthetic

<400> SEQUENCE: 1117
uggugaagag aaaagccggg 20

<210> SEQ ID NO 1118
<211> LENGTH: 20
<212> TYPE: RNA
<213> ORGANISM: Artificial Sequence
<220> FEATURE:
<223> OTHER INFORMATION: Seynthetic

<400> SEQUENCE: 1118
uggugcaggg accagaagga 20

<210> SEQ ID NO 1119
<211> LENGTH: 20
<212> TYPE: RNA
<213> ORGANISM: Artificial Sequence
<220> FEATURE:
<223> OTHER INFORMATION: Seynthetic

<400> SEQUENCE: 1119
uggugcgggg accagaagga 20

<210> SEQ ID NO 1120
<211> LENGTH: 20
<212> TYPE: RNA
<213> ORGANISM: Artificial Sequence
<220> FEATURE:
<223> OTHER INFORMATION: Seynthetic

<400> SEQUENCE: 1120
uguaucuuug gaaggggcuu 20

<210> SEQ ID NO 1121
<211> LENGTH: 20
<212> TYPE: RNA
<213> ORGANISM: Artificial Sequence
<220> FEATURE:
<223> OTHER INFORMATION: Seynthetic

<400> SEQUENCE: 1121
ugucaagccc cagaggacac 20

<210> SEQ ID NO 1122
<211> LENGTH: 20
<212> TYPE: RNA
<213> ORGANISM: Artificial Sequence
<220> FEATURE:
<223> OTHER INFORMATION: Seynthetic

<400> SEQUENCE: 1122
ugucaagccc cagaggccac 20

<210> SEQ ID NO 1123
<211> LENGTH: 20
<212> TYPE: RNA
<213> ORGANISM: Artificial Sequence
<220> FEATURE:
<223> OTHER INFORMATION: Seynthetic

<400> SEQUENCE: 1123
ugucagauaa ucaauguggg 20

<210> SEQ ID NO 1124
<211> LENGTH: 20
<212> TYPE: RNA
<213> ORGANISM: Artificial Sequence
<220> FEATURE:
<223> OTHER INFORMATION: Seynthetic

<400> SEQUENCE: 1124
ugucccugug gccucugggg 20

<210> SEQ ID NO 1125
<211> LENGTH: 20
<212> TYPE: RNA
<213> ORGANISM: Artificial Sequence
<220> FEATURE:
<223> OTHER INFORMATION: Seynthetic

<400> SEQUENCE: 1125
uguccgccuu caggugugge 20

<210> SEQ ID NO 1126
<211> LENGTH: 20
<212> TYPE: RNA
<213> ORGANISM: Artificial Sequence
<220> FEATURE:
<223> OTHER INFORMATION: Seynthetic

<400> SEQUENCE: 1126 ugucccucugg ggcuugacac 20

<210> SEQ ID NO 1127
<211> LENGTH: 20
<212> TYPE: RNA
<213> ORGANISM: Artificial Sequence
<220> FEATURE:
<223> OTHER INFORMATION: Seynthetic

<400> SEQUENCE: 1127
ugucucuguc ccuguguccu 20

<210> SEQ ID NO 1128
<211> LENGTH: 20
<212> TYPE: RNA
<213> ORGANISM: Artificial Sequence
<220> FEATURE:
<223> OTHER INFORMATION: Seynthetic

<400> SEQUENCE: 1128
ugucugccuc cacaggggga 20

<210> SEQ ID NO 1129
<211> LENGTH: 20
<212> TYPE: RNA
<213> ORGANISM: Artificial Sequence
<220> FEATURE:
<223> OTHER INFORMATION: Seynthetic

<400> SEQUENCE: 1129
ugugaaacac ccugggggac 20

<210> SEQ ID NO 1130
<211> LENGTH: 20
<212> TYPE: RNA
<213> ORGANISM: Artificial Sequence
<220> FEATURE:
<223> OTHER INFORMATION: Seynthetic

<400> SEQUENCE: 1130
ugugaaacac ccugggugac 20

<210> SEQ ID NO 1131
<211> LENGTH: 20
<212> TYPE: RNA
<213> ORGANISM: Artificial Sequence
<220> FEATURE:
<223> OTHER INFORMATION: Seynthetic

<400> SEQUENCE: 1131
uguggccucu ggggcuugac 20

<210> SEQ ID NO 1132
<211> LENGTH: 20
<212> TYPE: RNA
<213> ORGANISM: Artificial Sequence
<220> FEATURE:
<223> OTHER INFORMATION: Seynthetic

<400> SEQUENCE: 1132
uguggucacg ucaagacucc 20

<210> SEQ ID NO 1133
<211> LENGTH: 20
<212> TYPE: RNA
<213> ORGANISM: Artificial Sequence
<220> FEATURE:
<223> OTHER INFORMATION: Seynthetic

<400> SEQUENCE: 1133
uguggucacg ucaggacucc 20

<210> SEQ ID NO 1134
<211> LENGTH: 20
<212> TYPE: RNA
<213> ORGANISM: Artificial Sequence
<220> FEATURE:
<223> OTHER INFORMATION: Seynthetic

<400> SEQUENCE: 1134
uguguccucu ggggcuugac 20

<210> SEQ ID NO 1135
<211> LENGTH: 20
<212> TYPE: RNA
<213> ORGANISM: Artificial Sequence
<220> FEATURE:
<223> OTHER INFORMATION: Seynthetic

<400> SEQUENCE: 1135
uguuaugguc acagcgggug 20

<210> SEQ ID NO 1136
<211> LENGTH: 20
<212> TYPE: RNA
<213> ORGANISM: Artificial Sequence
<220> FEATURE:
<223> OTHER INFORMATION: Seynthetic

<400> SEQUENCE: 1136
uuaauaaaga cugcacguga 20

<210> SEQ ID NO 1137
<211> LENGTH: 20
<212> TYPE: RNA
<213> ORGANISM: Artificial Sequence
<220> FEATURE:
<223> OTHER INFORMATION: Seynthetic

<400> SEQUENCE: 1137
uuaauaauga cugcacguga 20

<210> SEQ ID NO 1138

<211> LENGTH: 20
<212> TYPE: RNA
<213> ORGANISM: Artificial Sequence
<220> FEATURE:
<223> OTHER INFORMATION: Seynthetic

<400> SEQUENCE: 1138
uuaauccaug gugcagggac 20

<210> SEQ ID NO 1139
<211> LENGTH: 20
<212> TYPE: RNA
<213> ORGANISM: Artificial Sequence
<220> FEATURE:
<223> OTHER INFORMATION: Seynthetic

<400> SEQUENCE: 1139
uuaauccaug gugcggggac 20

<210> SEQ ID NO 1140
<211> LENGTH: 20
<212> TYPE: RNA
<213> ORGANISM: Artificial Sequence
<220> FEATURE:
<223> OTHER INFORMATION: Seynthetic

<400> SEQUENCE: 1140
uuagcuaaga acuuuacgaa 20

<210> SEQ ID NO 1141
<211> LENGTH: 20
<212> TYPE: RNA
<213> ORGANISM: Artificial Sequence
<220> FEATURE:
<223> OTHER INFORMATION: Seynthetic

<400> SEQUENCE: 1141
uuauauggaa aguucaggga 20

<210> SEQ ID NO 1142
<211> LENGTH: 20
<212> TYPE: RNA
<213> ORGANISM: Artificial Sequence
<220> FEATURE:
<223> OTHER INFORMATION: Seynthetic

<400> SEQUENCE: 1142
uuaucugaaa uuugaaugcg 20

<210> SEQ ID NO 1143
<211> LENGTH: 20
<212> TYPE: RNA
<213> ORGANISM: Artificial Sequence
<220> FEATURE:
<223> OTHER INFORMATION: Seynthetic

<400> SEQUENCE: 1143
uuaucugaca uuugaaugcg 20

<210> SEQ ID NO 1144
<211> LENGTH: 20
<212> TYPE: RNA
<213> ORGANISM: Artificial Sequence
<220> FEATURE:
<223> OTHER INFORMATION: Seynthetic

<400> SEQUENCE: 1144
uuauggucac agcaggugua 20

<210> SEQ ID NO 1145
<211> LENGTH: 20
<212> TYPE: RNA
<213> ORGANISM: Artificial Sequence
<220> FEATURE:
<223> OTHER INFORMATION: Seynthetic

<400> SEQUENCE: 1145
uuauggucac agcgggugua 20

<210> SEQ ID NO 1146
<211> LENGTH: 20
<212> TYPE: RNA
<213> ORGANISM: Artificial Sequence
<220> FEATURE:
<223> OTHER INFORMATION: Seynthetic

<400> SEQUENCE: 1146
uucaccacac ccagaguccc 20

<210> SEQ ID NO 1147
<211> LENGTH: 20
<212> TYPE: RNA
<213> ORGANISM: Artificial Sequence
<220> FEATURE:
<223> OTHER INFORMATION: Seynthetic

<400> SEQUENCE: 1147
uucacguuca uaaaguucuu 20

<210> SEQ ID NO 1148
<211> LENGTH: 20
<212> TYPE: RNA
<213> ORGANISM: Artificial Sequence
<220> FEATURE:
<223> OTHER INFORMATION: Seynthetic

<400> SEQUENCE: 1148
uucacguucg uaaaguucuu 20

<210> SEQ ID NO 1149
<211> LENGTH: 20
<212> TYPE: RNA
<213> ORGANISM: Artificial Sequence
<220> FEATURE:
<223> OTHER INFORMATION: Seynthetic

<400> SEQUENCE: 1149
uucagauaau caaugugggu 20

<210> SEQ ID NO 1150
<211> LENGTH: 20
<212> TYPE: RNA
<213> ORGANISM: Artificial Sequence
<220> FEATURE:
<223> OTHER INFORMATION: Seynthetic

<400> SEQUENCE: 1150
uucagggaug uccgccuuca 20

<210> SEQ ID NO 1151
<211> LENGTH: 20
<212> TYPE: RNA

<213> ORGANISM: Artificial Sequence
<220> FEATURE:
<223> OTHER INFORMATION: Seynthetic

<400> SEQUENCE: 1151
uucaggggug ggggacgccg 20

<210> SEQ ID NO 1152
<211> LENGTH: 20
<212> TYPE: RNA
<213> ORGANISM: Artificial Sequence
<220> FEATURE:
<223> OTHER INFORMATION: Seynthetic

<400> SEQUENCE: 1152
uucaggggug ggggacgcug 20

<210> SEQ ID NO 1153
<211> LENGTH: 20
<212> TYPE: RNA
<213> ORGANISM: Artificial Sequence
<220> FEATURE:
<223> OTHER INFORMATION: Seynthetic

<400> SEQUENCE: 1153
uuccaaagau acagcguccc 20

<210> SEQ ID NO 1154
<211> LENGTH: 20
<212> TYPE: RNA
<213> ORGANISM: Artificial Sequence
<220> FEATURE:
<223> OTHER INFORMATION: Seynthetic

<400> SEQUENCE: 1154
uuccaaagau acggcguccc 20

<210> SEQ ID NO 1155
<211> LENGTH: 20
<212> TYPE: RNA
<213> ORGANISM: Artificial Sequence
<220> FEATURE:
<223> OTHER INFORMATION: Seynthetic

<400> SEQUENCE: 1155
uucccaucuc ccccaccaug 20

<210> SEQ ID NO 1156
<211> LENGTH: 20
<212> TYPE: RNA
<213> ORGANISM: Artificial Sequence
<220> FEATURE:
<223> OTHER INFORMATION: Seynthetic

<400> SEQUENCE: 1156
uucccaucuc ccccacgaug 20

<210> SEQ ID NO 1157
<211> LENGTH: 20
<212> TYPE: RNA
<213> ORGANISM: Artificial Sequence
<220> FEATURE:
<223> OTHER INFORMATION: Seynthetic

<400> SEQUENCE: 1157
uuccccacau uguguuuuuu 20

<210> SEQ ID NO 1158
<211> LENGTH: 20
<212> TYPE: RNA
<213> ORGANISM: Artificial Sequence
<220> FEATURE:
<223> OTHER INFORMATION: Seynthetic

<400> SEQUENCE: 1158
uucccccggc uuuucucuuc 20

<210> SEQ ID NO 1159
<211> LENGTH: 20
<212> TYPE: RNA
<213> ORGANISM: Artificial Sequence
<220> FEATURE:
<223> OTHER INFORMATION: Seynthetic

<400> SEQUENCE: 1159
uucccccugc uuuucucuuc 20

<210> SEQ ID NO 1160
<211> LENGTH: 20
<212> TYPE: RNA
<213> ORGANISM: Artificial Sequence
<220> FEATURE:
<223> OTHER INFORMATION: Seynthetic

<400> SEQUENCE: 1160
uuccucuucc caucuccccc 20

<210> SEQ ID NO 1161
<211> LENGTH: 20
<212> TYPE: RNA
<213> ORGANISM: Artificial Sequence
<220> FEATURE:
<223> OTHER INFORMATION: Seynthetic

<400> SEQUENCE: 1161
uuccugccca ccuggcgggg 20

<210> SEQ ID NO 1162
<211> LENGTH: 20
<212> TYPE: RNA
<213> ORGANISM: Artificial Sequence
<220> FEATURE:
<223> OTHER INFORMATION: Seynthetic

<400> SEQUENCE: 1162
uucguaaagu ucuuagcuaa 20

<210> SEQ ID NO 1163
<211> LENGTH: 20
<212> TYPE: RNA
<213> ORGANISM: Artificial Sequence
<220> FEATURE:
<223> OTHER INFORMATION: Seynthetic

<400> SEQUENCE: 1163
uucuaccagg gaacuccugc 20

<210> SEQ ID NO 1164
<211> LENGTH: 20
<212> TYPE: RNA
<213> ORGANISM: Artificial Sequence
<220> FEATURE:

<223> OTHER INFORMATION: Seynthetic

<400> SEQUENCE: 1164
uucucacgug cagucauuau 20

<210> SEQ ID NO 1165
<211> LENGTH: 20
<212> TYPE: RNA
<213> ORGANISM: Artificial Sequence
<220> FEATURE:
<223> OTHER INFORMATION: Seynthetic

<400> SEQUENCE: 1165
uucucacgug cagucuuuau 20

<210> SEQ ID NO 1166
<211> LENGTH: 20
<212> TYPE: RNA
<213> ORGANISM: Artificial Sequence
<220> FEATURE:
<223> OTHER INFORMATION: Seynthetic

<400> SEQUENCE: 1166 uucuggucce cgcaccaugg 20

<210> SEQ ID NO 1167
<211> LENGTH: 20
<212> TYPE: RNA
<213> ORGANISM: Artificial Sequence
<220> FEATURE:
<223> OTHER INFORMATION: Seynthetic

<400> SEQUENCE: 1167
uucuuagcua agaacuuuac 20

<210> SEQ ID NO 1168
<211> LENGTH: 20
<212> TYPE: RNA
<213> ORGANISM: Artificial Sequence
<220> FEATURE:
<223> OTHER INFORMATION: Seynthetic

<400> SEQUENCE: 1168
uugacgugac cacaggcaag 20

<210> SEQ ID NO 1169
<211> LENGTH: 20
<212> TYPE: RNA
<213> ORGANISM: Artificial Sequence
<220> FEATURE:
<223> OTHER INFORMATION: Seynthetic

<400> SEQUENCE: 1169
uugcagacca aggggcugcc 20

<210> SEQ ID NO 1170
<211> LENGTH: 20
<212> TYPE: RNA
<213> ORGANISM: Artificial Sequence
<220> FEATURE:
<223> OTHER INFORMATION: Seynthetic

<400> SEQUENCE: 1170
uugcauuaau ccauggugca 20

<210> SEQ ID NO 1171
<211> LENGTH: 20
<212> TYPE: RNA
<213> ORGANISM: Artificial Sequence
<220> FEATURE:
<223> OTHER INFORMATION: Seynthetic

<400> SEQUENCE: 1171
uugcauuaau ccauggugcg 20

<210> SEQ ID NO 1172
<211> LENGTH: 20
<212> TYPE: RNA
<213> ORGANISM: Artificial Sequence
<220> FEATURE:
<223> OTHER INFORMATION: Seynthetic

<400> SEQUENCE: 1172
uugccugugg ucacgucaag 20

<210> SEQ ID NO 1173
<211> LENGTH: 20
<212> TYPE: RNA
<213> ORGANISM: Artificial Sequence
<220> FEATURE:
<223> OTHER INFORMATION: Seynthetic

<400> SEQUENCE: 1173
uugccugugg ucacgucagg 20

<210> SEQ ID NO 1174
<211> LENGTH: 20
<212> TYPE: RNA
<213> ORGANISM: Artificial Sequence
<220> FEATURE:
<223> OTHER INFORMATION: Seynthetic

<400> SEQUENCE: 1174
uugcucaugc uucuaccagg 20

<210> SEQ ID NO 1175
<211> LENGTH: 20
<212> TYPE: RNA
<213> ORGANISM: Artificial Sequence
<220> FEATURE:
<223> OTHER INFORMATION: Seynthetic

<400> SEQUENCE: 1175
uugucucugu cccuguggcc 20

<210> SEQ ID NO 1176
<211> LENGTH: 20
<212> TYPE: RNA
<213> ORGANISM: Artificial Sequence
<220> FEATURE:
<223> OTHER INFORMATION: Seynthetic

<400> SEQUENCE: 1176
uugucucugu cccugugucc 20

<210> SEQ ID NO 1177
<211> LENGTH: 20
<212> TYPE: RNA
<213> ORGANISM: Artificial Sequence
<220> FEATURE:
<223> OTHER INFORMATION: Seynthetic

<400> SEQUENCE: 1177
uugugaaaca cccuggggga 20

<210> SEQ ID NO 1178
<211> LENGTH: 20
<212> TYPE: RNA
<213> ORGANISM: Artificial Sequence
<220> FEATURE:
<223> OTHER INFORMATION: Seynthetic

<400> SEQUENCE: 1178
uugugaaaca cccuggguga 20

<210> SEQ ID NO 1179
<211> LENGTH: 20
<212> TYPE: RNA
<213> ORGANISM: Artificial Sequence
<220> FEATURE:
<223> OTHER INFORMATION: Seynthetic

<400> SEQUENCE: 1179
uuuauuaagu gugccgacgc 20

<210> SEQ ID NO 1180
<211> LENGTH: 20
<212> TYPE: RNA
<213> ORGANISM: Artificial Sequence
<220> FEATURE:
<223> OTHER INFORMATION: Seynthetic

<400> SEQUENCE: 1180
uuucaggggu gggggacgcc 20

<210> SEQ ID NO 1181
<211> LENGTH: 20
<212> TYPE: RNA
<213> ORGANISM: Artificial Sequence
<220> FEATURE:
<223> OTHER INFORMATION: Seynthetic

<400> SEQUENCE: 1181
uuucaggggu gggggacgcu 20

<210> SEQ ID NO 1182
<211> LENGTH: 20
<212> TYPE: RNA
<213> ORGANISM: Artificial Sequence
<220> FEATURE:
<223> OTHER INFORMATION: Seynthetic

<400> SEQUENCE: 1182
uuucccgcag cugggacucc 20

<210> SEQ ID NO 1183
<211> LENGTH: 20
<212> TYPE: RNA
<213> ORGANISM: Artificial Sequence
<220> FEATURE:
<223> OTHER INFORMATION: Seynthetic

<400> SEQUENCE: 1183
uuugucucug ucccuguggc 20

<210> SEQ ID NO 1184
<211> LENGTH: 20

<212> TYPE: RNA
<213> ORGANISM: Artificial Sequence
<220> FEATURE:
<223> OTHER INFORMATION: Seynthetic

<400> SEQUENCE: 1184
uuuuaaugga gcgggggguuu 20

<210> SEQ ID NO 1185
<211> LENGTH: 20
<212> TYPE: RNA
<213> ORGANISM: Artificial Sequence
<220> FEATURE:
<223> OTHER INFORMATION: Seynthetic

<400> SEQUENCE: 1185
uuuuuaaugg agcgggggguu 20

<210> SEQ ID NO 1186
<211> LENGTH: 20
<212> TYPE: RNA
<213> ORGANISM: Artificial Sequence
<220> FEATURE:
<223> OTHER INFORMATION: Seynthetic

<400> SEQUENCE: 1186
uuuuuuaaug gagcgggggu 20

<210> SEQ ID NO 1187
<211> LENGTH: 20
<212> TYPE: RNA
<213> ORGANISM: Artificial Sequence
<220> FEATURE:
<223> OTHER INFORMATION: Seynthetic

<400> SEQUENCE: 1187
uuuuuuuaau ggagcggggg 20

<210> SEQ ID NO 1188
<211> LENGTH: 20
<212> TYPE: RNA
<213> ORGANISM: Artificial Sequence
<220> FEATURE:
<223> OTHER INFORMATION: Seynthetic

<400> SEQUENCE: 1188
uuuuuuuuua auggagcggg 20

<210> SEQ ID NO 1189
<211> LENGTH: 20
<212> TYPE: RNA
<213> ORGANISM: Artificial Sequence
<220> FEATURE:
<223> OTHER INFORMATION: Seynthetic

<400> SEQUENCE: 1189
uuuuuuuuuu aauggagcgg 20

<210> SEQ ID NO 1190
<211> LENGTH: 20
<212> TYPE: RNA
<213> ORGANISM: Artificial Sequence
<220> FEATURE:
<223> OTHER INFORMATION: Seynthetic

<400> SEQUENCE: 1190
cucugucccu guggccucug 20

<210> SEQ ID NO 1191
<211> LENGTH: 20
<212> TYPE: RNA
<213> ORGANISM: Artificial Sequence
<220> FEATURE:
<223> OTHER INFORMATION: Seynthetic

<400> SEQUENCE: 1191
aaaugucaga uaaucaaugu 20

<210> SEQ ID NO 1192
<211> LENGTH: 20
<212> TYPE: RNA
<213> ORGANISM: Artificial Sequence
<220> FEATURE:
<223> OTHER INFORMATION: Seynthetic

<400> SEQUENCE: 1192
uugcagcugg aacaucgugg 20

<210> SEQ ID NO 1193
<211> LENGTH: 20
<212> TYPE: RNA
<213> ORGANISM: Artificial Sequence
<220> FEATURE:
<223> OTHER INFORMATION: Seynthetic

<400> SEQUENCE: 1193
accaaggcuc agggcguugg 20

<210> SEQ ID NO 1194
<211> LENGTH: 20
<212> TYPE: RNA
<213> ORGANISM: Artificial Sequence
<220> FEATURE:
<223> OTHER INFORMATION: Seynthetic

<400> SEQUENCE: 1194
ccuguugcug caguccgggc 20

<210> SEQ ID NO 1195
<211> LENGTH: 20
<212> TYPE: RNA
<213> ORGANISM: Artificial Sequence
<220> FEATURE:
<223> OTHER INFORMATION: Seynthetic

<400> SEQUENCE: 1195
ccagcccgga cugcagcaac 20

<210> SEQ ID NO 1196
<211> LENGTH: 20
<212> TYPE: RNA
<213> ORGANISM: Artificial Sequence
<220> FEATURE:
<223> OTHER INFORMATION: Seynthetic

<400> SEQUENCE: 1196
ucccuccuag ggucuagcca 20

<210> SEQ ID NO 1197
<211> LENGTH: 20
<212> TYPE: RNA
<213> ORGANISM: Artificial Sequence
<220> FEATURE:
<223> OTHER INFORMATION: Seynthetic

<400> SEQUENCE: 1197
aguccgggcu gggagcgggu 20

<210> SEQ ID NO 1198
<211> LENGTH: 20
<212> TYPE: RNA
<213> ORGANISM: Artificial Sequence
<220> FEATURE:
<223> OTHER INFORMATION: Seynthetic

<400> SEQUENCE: 1198
auguuuauug ugccagaugc 20

<210> SEQ ID NO 1199
<211> LENGTH: 20
<212> TYPE: RNA
<213> ORGANISM: Artificial Sequence
<220> FEATURE:
<223> OTHER INFORMATION: Seynthetic

<400> SEQUENCE: 1199
gugggcagcu gaggugaccc 20

<210> SEQ ID NO 1200
<211> LENGTH: 20
<212> TYPE: RNA
<213> ORGANISM: Artificial Sequence
<220> FEATURE:
<223> OTHER INFORMATION: Seynthetic

<400> SEQUENCE: 1200
cacccacacu cuccagcauc 20

<210> SEQ ID NO 1201
<211> LENGTH: 17
<212> TYPE: RNA
<213> ORGANISM: Artificial Sequence
<220> FEATURE:
<223> OTHER INFORMATION: Seynthetic

<400> SEQUENCE: 1201
aaaacacaau gugggga 17

<210> SEQ ID NO 1202
<211> LENGTH: 17
<212> TYPE: RNA
<213> ORGANISM: Artificial Sequence
<220> FEATURE:
<223> OTHER INFORMATION: Seynthetic

<400> SEQUENCE: 1202
aaaaacacaa ugugggg 17

<210> SEQ ID NO 1203
<211> LENGTH: 17
<212> TYPE: RNA
<213> ORGANISM: Artificial Sequence
<220> FEATURE:
<223> OTHER INFORMATION: Seynthetic

<400> SEQUENCE: 1203
aaaaaacaca auguggg 17

-continued

```
<210> SEQ ID NO 1204
<211> LENGTH: 17
<212> TYPE: RNA
<213> ORGANISM: Artificial Sequence
<220> FEATURE:
<223> OTHER INFORMATION: Seynthetic

<400> SEQUENCE: 1204

aaaaaaacac aaugugg                                                   17
```